United States Patent
Suciu-Foca

(12) 
(10) Patent No.: US 6,667,175 B1
(45) Date of Patent: Dec. 23, 2003

(54) GENERATION OF ANTIGEN SPECIFIC T SUPPRESSOR CELLS FOR TREATMENT OF REJECTION

(75) Inventor: Nicole Suciu-Foca, Cliffside Park, NJ (US)

(73) Assignee: The Trustees of Columbia University, New York, NY (US)

( * ) Notice: Subject to any disclaimer, the term of this patent is extended or adjusted under 35 U.S.C. 154(b) by 0 days.

(21) Appl. No.: 09/333,809

(22) Filed: Jun. 15, 1999

(51) Int. Cl.[7] .............................. C12N 5/00; C12N 5/08; C12N 5/02
(52) U.S. Cl. .................... 435/325; 435/372.3; 435/373; 435/375; 435/376; 435/377
(58) Field of Search .............................. 435/325, 372.3, 435/373, 375, 376, 377

(56) References Cited

PUBLICATIONS

Banchereau J, Steinman, R. M., (1998) "Dendritic cells and the control of immunity," *Nature* 392:245–252.

Bennett, S. R. M., Carbone, F. R., Karamalis, F., Flavell, R. A., Miller, J., and Heath, W R. (1998) "Help for cytotoxic–T–cell responses is mediated by CD40 signaling," *Nature* 393:478–480.

Barker, T. D., Weisman, D., Daucher, J. A., Roche, K. M., and Fauci, A. S. (1996) "Identification of multiple and distinct CD8+ T cell supressor activities: Dichotomy between infected and uninfected individuals, evolution with progression of disease and sensitivity to gamma radiation," *J. Immunol.* 156:4476–4483.

Ciubotariu, R., Colovai, A. I., Pennesi, G., Liu, Z., Smith, D., Berlocco, P., Cortesini, R., Suciu–Foca, N. (1998) "Specific supression of human CD4+ Th cell responses to pig MHC antigens by CD8+CD28– regulatory T cells," *J. Immuno.* 161(10):5193–5202.

Damle, N. K., Mohagheghpour, N., Hansen, J. A., and Engleman, E. G. (1993) "Alloantigen–specific cytotoxic and supressor T lymphocytes are derived from phenotypically distinct precursors," *J. Immunol.* 131:2296–2300.

Groux, H., O'Garra, A., Bigler, M., Rouleau, M., Antonenko, S., de Vires, J. E., and Roncarolo, M. G. (1997) "A CD4+ T–cell subset inhibits antigen–specific T–cell responses and prevents colitis," *Nature* 389:737–742.

Jiang S., Tugulea, S., Pennesi, G., Liu, Z., Mulder, A., Lederman, S., Harris, P., Cortesini, R., and Suciu–Foca, N. (1998) Induction of MHC–class I restricted human supressor T cells by peptide priming in vitro. *Hum. Immunol.* 59:690–699.

Lanier, L. L., O'Fallon, S., Somoza, C., Philips, J. H., Linsey, P. S., Okumura, K., Ito, D., and Azuma, M. (1995) "CD80 (B7) and CD86 (B70) provide similar costimulatory signals for T cell proliferation, cytokine production and generation of CTL," *J. Immunol.* 154:97–105.

Liu, Z., Tugulea, S., Cortesini, R., Suciu–Foca, N. (1998) "Specific suppression of T helper alloreactivity by allo–MHC class I–restricted CD8+CD28– T cells," *Int. Immunol.* 10(6):775–783.

Lombardi, G., Sidhu, S., Batchelor, R., Lechler, R. (1994) "Anergic T cells as supressor cells in vitro," *Science* 264:1587–1589.

Noble, A., Zhao, Z., and Cantor, H. (1998) "Supression of immune responses by CD8 cells. II. Qa–1 on activated B cells stimulates CD8 cell suppression of T helper 2 Responses," *J. Immunol.* 160:556–571.

Qin, S., Cobbold, S. P., Pope, H., Elliott, J., Kioussis, D., Davies, J., and Waldman, H. (1993) "Infectious' transplantation tolerance," *Science* 259:974–977.

Ridge, J. P., Di Rosa, F., and Matzinger, P. (1998) "A conditioned dendritic cell can be a temporal bridge between a CD4+ T–helper cell and a T–killer cell," *Nature* 393:474–478.

Schoenberger, S. P., Toes, R. E. M., (1998) "T–cell help for cytotoxic T lymphocytes is mediated by CD40–CD40L interactions," *Nature* 393:480–483.

Swartz, R. H. (1992) "Costimulation of T lymphocytes: The role of CD28, CTLA–4, and B7/BB1 in interleuken–2 production and immunotherapy," *Cell* 71:1065–1068.

Tan, P., Anasetti, C., Hansen, J. A., Melrose, J., Brunvard, M., Bradshaw, J., Ledbetter, J. A., and Linsey, P. S. (1993) "Induction of alloantigen–specific hyporesponsiveness in human T lymphocytes by blocking interaction of CD28 with its natural ligand B7/BB1," *J. Exp. Med.* 177:165–173.

Yang, Y., Wilson, J. M. (1996) "CD40 ligand–dependant T cell activation: Requirement of B7–CD28 signaling through CD40," *Science* 273:1862–1864.

Primary Examiner—Christina Chan
Assistant Examiner—Michail A Belyavskyi
(74) Attorney, Agent, or Firm—John P. White; Cooper & Dunham LLP

(57) ABSTRACT

This invention provides a method of generating antigen specific allospecific human suppressor CD8+CD28– T cells. This invention also provides a method of generating xenospecific human suppressor CD8+CD28– T cells. This invention further provides a method of generating allopeptide antigen specific human suppressor CD8+CD28– T cells. Methods of treatment for reduction of risk of rejection of allografts and xenografts and autoimmune diseases using the human suppressor CD8+CD28– T cells so produced are also provides, as are methods of preventing rejection and autoimmune diseases, and vaccines comprising the produced suppressor T cells. Methods of diagnosis to determine whether a level of immuno-suppressant therapy requires a reduction are provided.

4 Claims, 67 Drawing Sheets

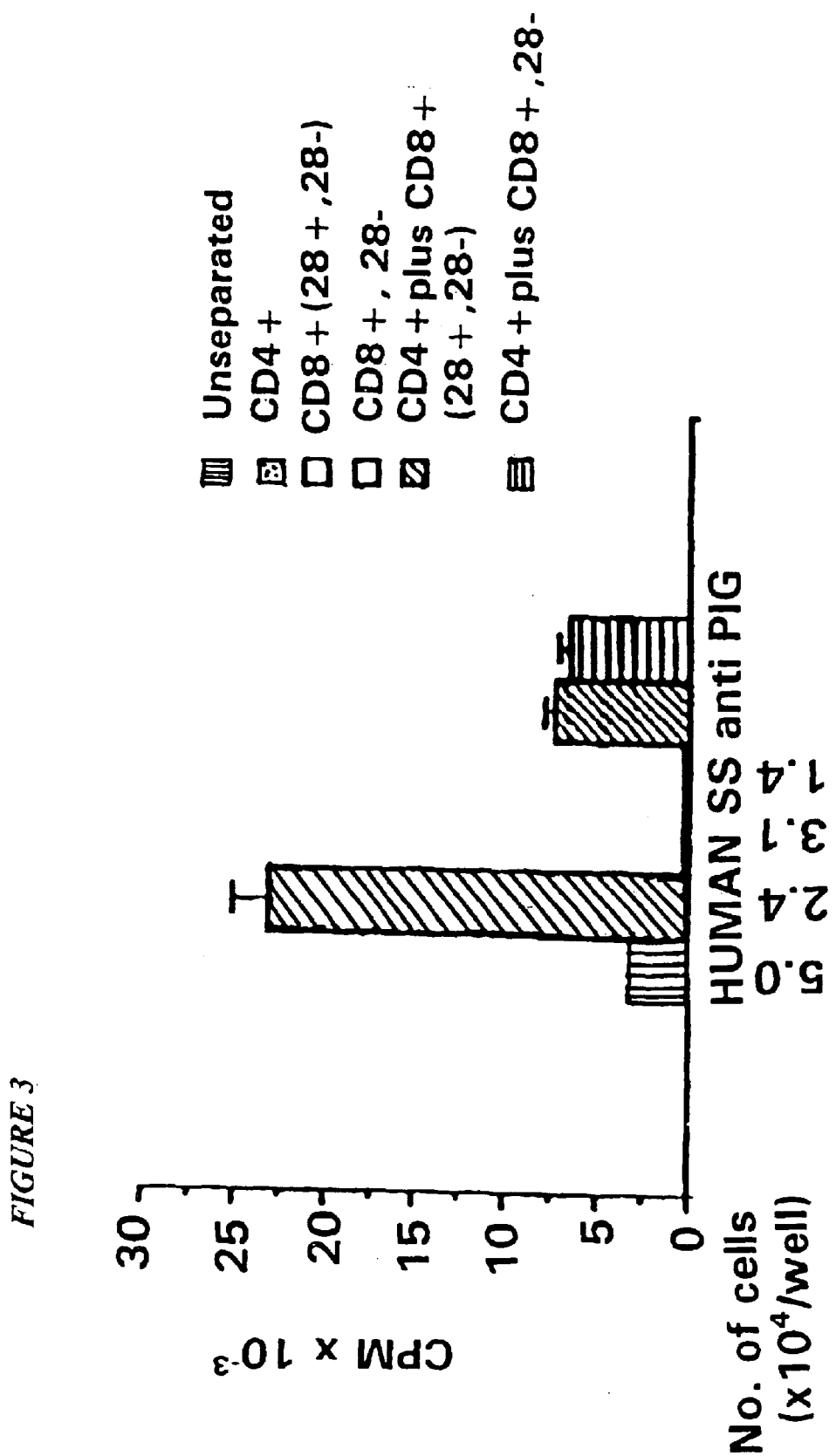

% Pos  MFI
40    47

% Pos  MFI
8     59

% Pos  MFI
73    123

% Pos  MFI
27    144

% Pos MFI 63   78

% Pos MFI 13   128

% Pos MFI 61   74

% Pos MFI 17   110

T helper cells

T suppressor cells

IL-2

IFN-g

IL-4

IL-10

FIGURE 20C   CD40
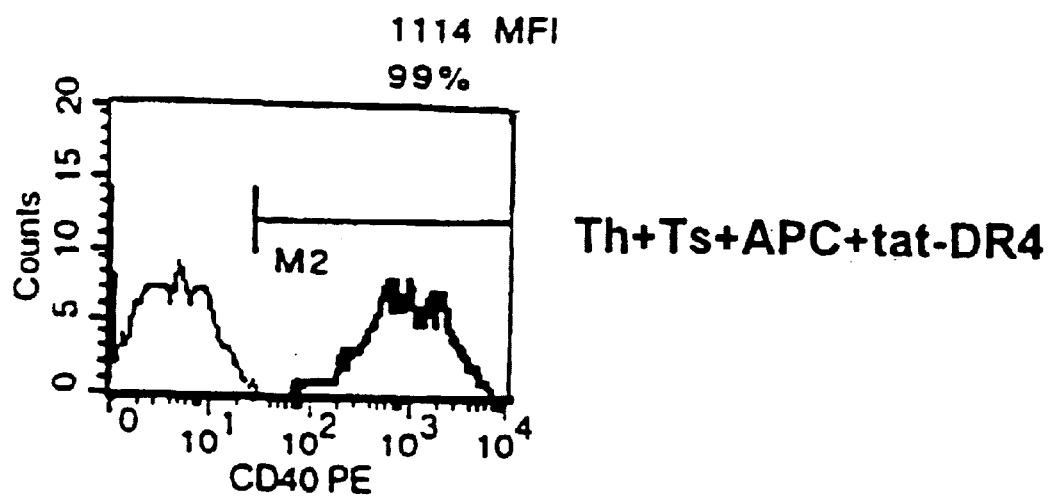
FIGURE 20D
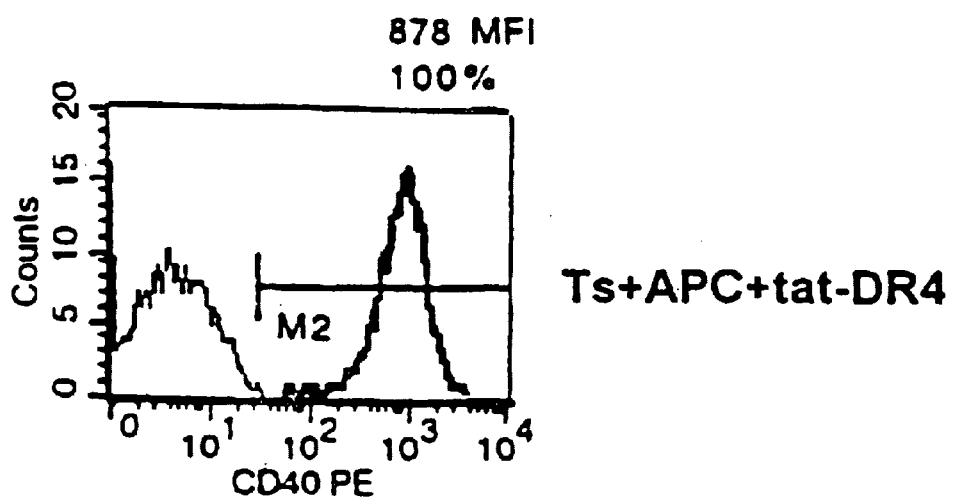

CD54

CD58

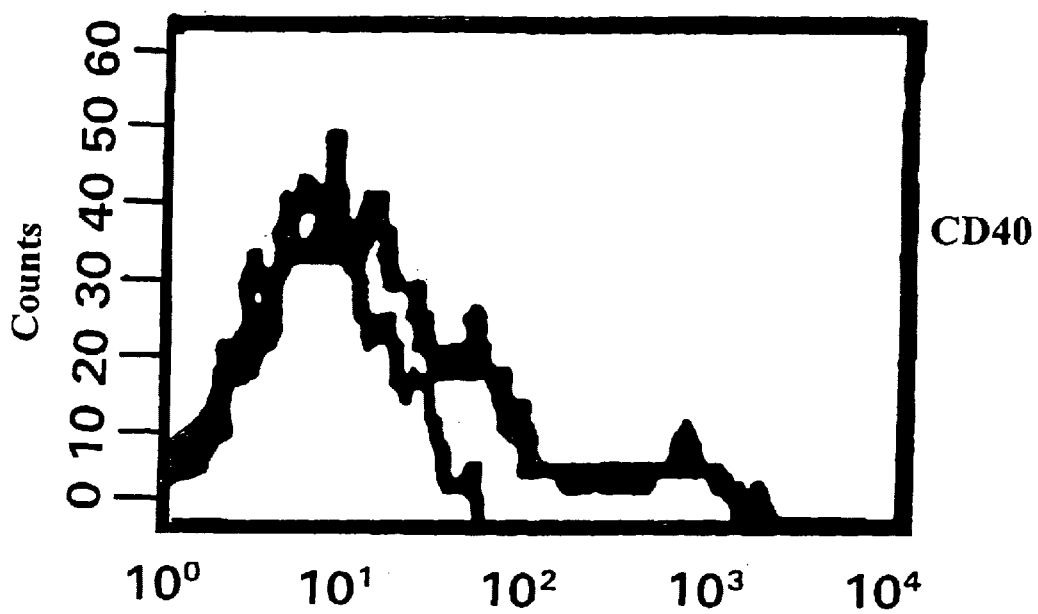
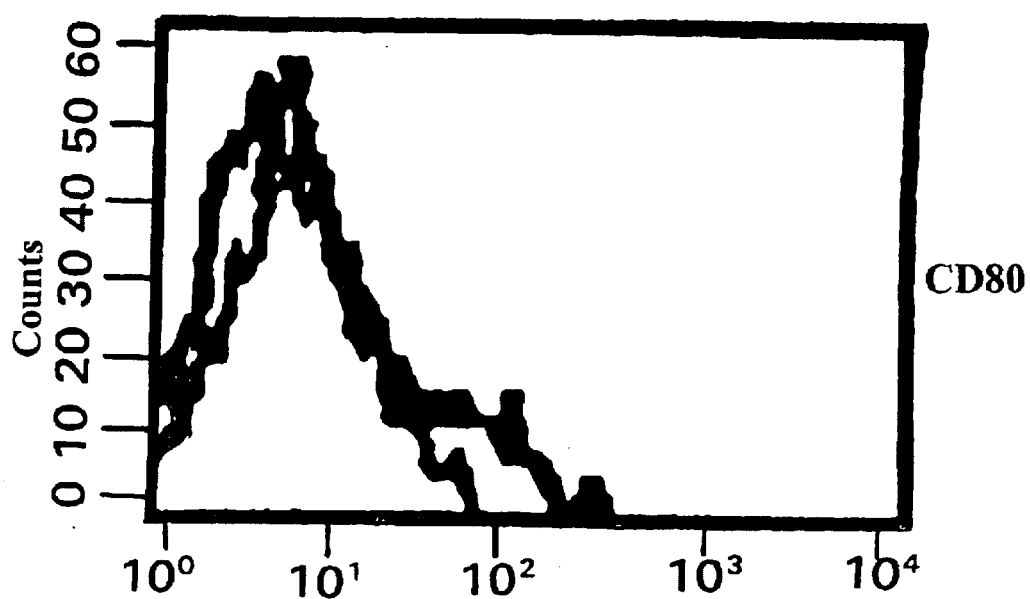

CD54

CD58

CD80

CD86

CD54

CD58

CD40

CD80

CD86

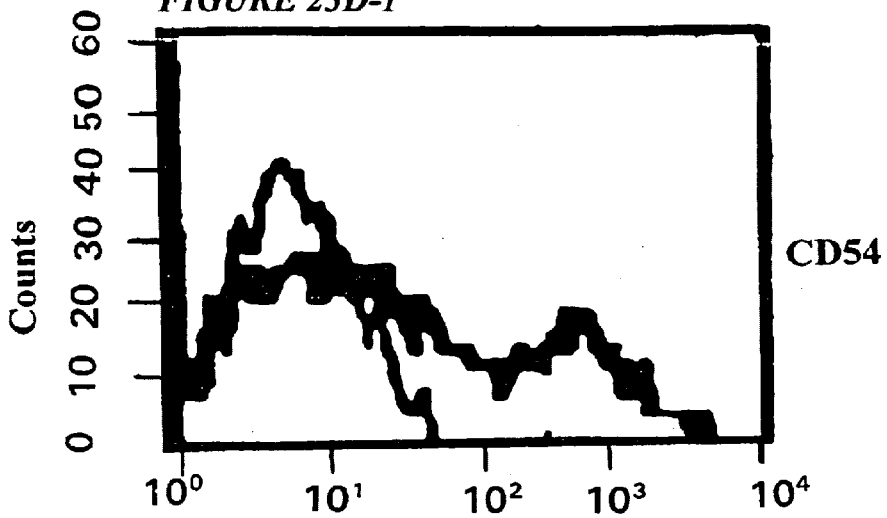
*FIGURE 23D-1* CD54
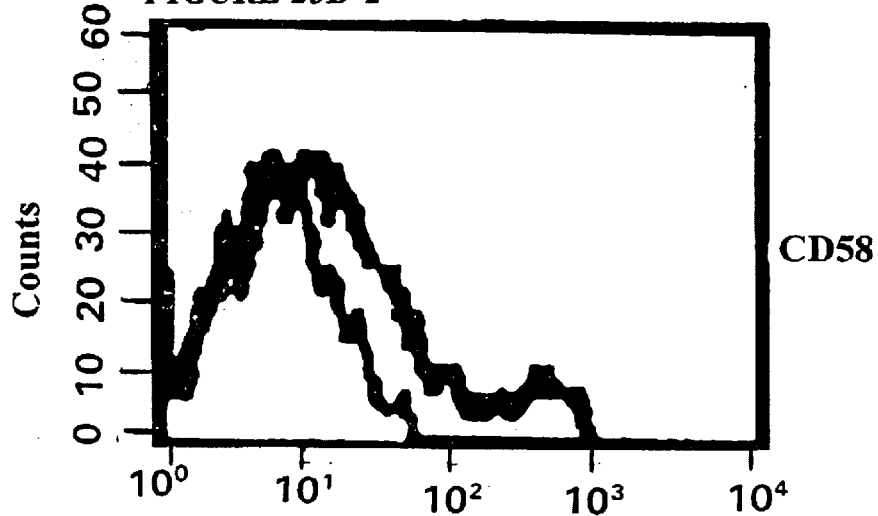
*FIGURE 23D-2* CD58
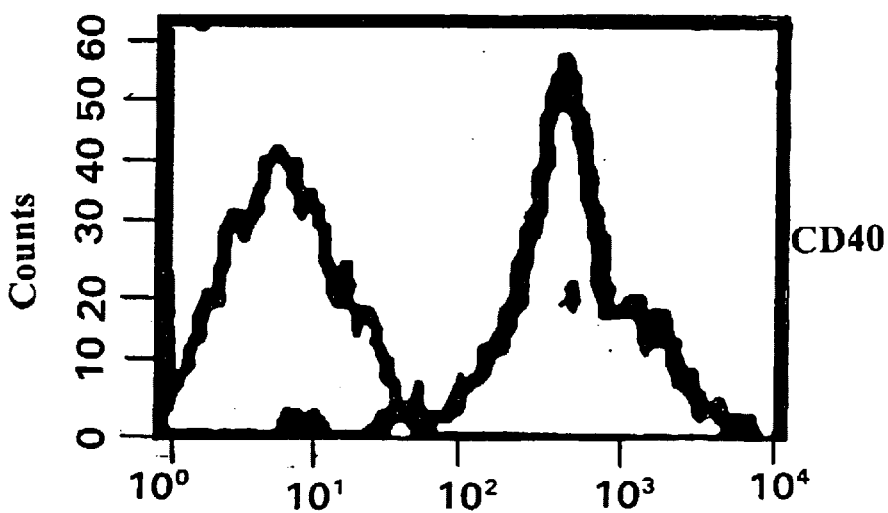
*FIGURE 23D-3* CD40

CD80

CD86

CD54

CD58

CD40

CD80

CD86

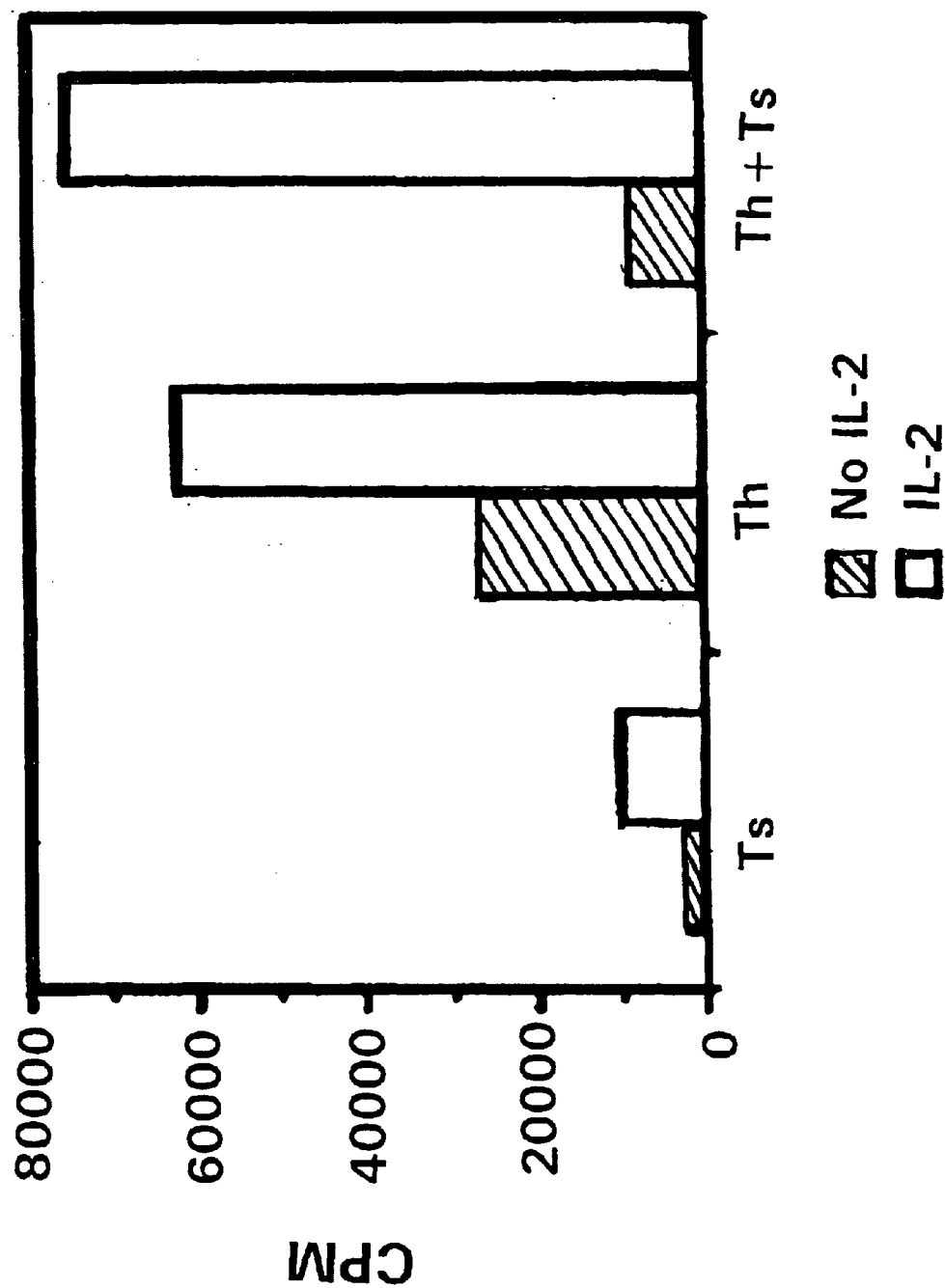

FIG. 26

HLA A, B and DR Antigen Values and Split Equivalences

| A LOCUS | EQUIVALENT | B LOCUS | EQUIVALENT | DR LOCUS | EQUIVALENT |
|---|---|---|---|---|---|
| 1 | 1 | 5 | 5 | 1 | 1 |
| 2 | 2 | 7 | 7 | 2 | 2,15,16 |
| 3 | 3 | 8 | 8 | 3 | 3,17,18 |
| 9 | 9 | 12 | 12 | 4 | 4 |
| 10 | 10,66 | 13 | 13 | 5 | 5,11,12 |
| 11 | 11 | 14 | 14,64,65 | 6 | 6,13,14 |
| 19 | 19,74 | 15 | 15,75,76,77 | 7 | 7 |
| 23 | 23 | 16 | 16 | 8 | 8 |
| 24 | 24 | 17 | 17,58 | 9 | 9 |
| 25 | 25 | 18 | 18 | 10 | 10 |
| 26 | 26 | 21 | 21 | 11 | 11,5 |
| 28 | 28,68,69 | 22 | 22,54,55,56 | 12 | 12,5 |
| 29 | 29 | 27 | 27 | 13 | 13,6 |
| 30 | 30 | 35 | 35 | 14 | 14,6 |
| 31 | 31 | 37 | 37 | 15 | 15,2 |
| 32 | 32 | 38 | 38 | 16 | 16,2 |
| 33 | 33 | 39 | 39 | 17 | 17,3 |
| 34 | 34 | 40 | 40,61 | 18 | 18,3 |
| 36 | 36 | 41 | 41 | 51 | 51 |
| 43 | 43 | 42 | 42 | 52 | 52 |
| 66 | 66,10 | 44 | 44 | 53 | 53 |
| 68 | 68,28 | 45 | 45 | *103 | 103 |
| 69 | 69,28 | 46 | 46 | *1403 | 1403 |
| 74 | 74,19 | 47 | 47 | *1404 | 1404 |
| 80 | 80 | 48 | 48 | --99 | 99 |
| *203 | 203 | 49 | 49 | | |
| *210 | 210 | 50 | 50 | | |
| *2403 | 2403 | 51 | 51 | | |
| --99 | 99 | 52 | 52 | | |
| | | 53 | 53 | | |
| | | 54 | 54,22 | | |
| | | 55 | 55,22 | | |
| | | 56 | 56,22 | | |
| | | 57 | 57 | | |
| | | 58 | 58,17 | | |
| | | 59 | 59 | | |
| | | 60 | 60 | | |
| | | 61 | 61,40 | | |
| | | 62 | 62 | | |
| | | 63 | 63 | | |
| | | 64 | 64,14 | | |
| | | 65 | 65,14 | | |
| | | 67 | 67 | | |
| | | 70 | 70,71,72 | | |
| | | 71 | 71,70 | | |
| | | 72 | 72,70 | | |
| | | 73 | 73 | | |
| | | 75 | 75,15 | | |
| | | 76 | 76,15 | | |
| | | 77 | 77,15 | | |
| | | *703 | 703 | | |
| | | *3901 | 3901 | | |
| | | *3902 | 3902 | | |
| | | *4005 | 4005 | | |
| | | *5102 | 5102 | | |
| | | *5103 | 5103 | | |
| | | *7801 | 7801 | | |
| | | *8101 | 8101 | | |
| | | --99 | 99 | | |

-- Code 99 means not tested

FIG. 27A

DRB Protein Sequences - 20th March 1998 - SGE Marsh ANRI

```
              1    10    20    30    40    50    60    70    80    90    100
              .    .     .     .     .     .     .     .     .     .     .

DRB1*0101
GDTRPRFLWQLKFECHFFNGTERVRLLERCIYNQEESVRFDSDVGEYRAVTELGRPDAEYWNSQK
DLLEQRRAAVDTYCRHNYGVGESFTVQRRVEPKVTVY
DRB1*01021   ---------------------------------------------------------------AV----------
DRB1*01022   *****-------------------------------------------------------------------
AV***************
DRB1*0103    -----------------------------------------------------I--DE-----------------
DRB1*0104    -----------------------------------------------------N-------V-------------
DRB1*15011   ---------P-R-----------F-D-YF---------------F-----------------I---A-----------V---------Q---
--
DRB1*15012   *****-----P-R-----------F-D-YF---------------F-----------------I---A-----------V---------
*********
DRB1*15021   ---------P-R-----------F-D-YF---------------F-----------------I---A-----------------Q----
-
DRB1*15022   **************----------F-D-YF---------------F-----------------I---A-----------
****************
DRB1*15023   *****-----P-R-----------F-D-YF---------------F-----------------I---A-----------
****************
DRB1*1503    ---------P-R-----------F-D-HF---------------F-----------------I---A-----------V---------Q--
****
DRB1*1504    ******-----P-R-----------F-D-YF---------------F-----------------F---A-----------V-----
***********
DRB1*1505    ******-----P-R-----------F-D-YF---------------F-----------------------A-----------V------
*********
DRB1*1506    ********--P-R-----------F-D-YF---------------F--A-----------------I---A-----------V-
***************
DRB1*16011   ---------P-R-----------F-D-YF-----------------------------F--D----------------Q----
-
DRB1*16012   *****-----P-R-----------F-D-YF-----------------------------F--D--------------------
***********
DRB1*16021   ---------P-R-----------F-D-YF-------------------------------D------------------Q----
DRB1*16022   ******-----P-R-----------F-D-YF-------------------------------D-----------------
****************
DRB1*1603    ---------P-R-----------F-D-YF-----------------------------F--D-A----------------Q----
-
DRB1*1604    ********--P-R-----------F-D-YF-----------------------------F--D---L-----------
****************
DRB1*1605    *******----P-R-----------F-D-YF------------------------------I--D--------------
****************
DRB1*1607    *****------P-R-----------FPD-YF------------------------------I--D--------------
***********
DRB1*1608    *****------P-R-----------F-D-YF-----N-----------------F--D---------------
********
DRB1*03011   ---------EYSTS-----------Y-D-YFH----N---------F---------------------K-GR--N---------V--------
--H-----
DRB1*03012   *****---EYSTS-----------Y-D-YFH----N---------F---------------------K-GR--N---------V---
_**********
```

FIG. 27B

```
DRB1*03021    --------EYSTS-----------F---YFH----N-----------------------K-GR--N-------------
              H------
DRB1*03022    --------EYSTS-----------F---YFH----N-----------------------K-GR--N-------------
              H----**
DRB1*0303     *********YSTS-----------F---YFH----N-----------------------K-GR--N--------V-----
              --********
DRB1*0304     *******-EYSTS-----------Y-D-YFH-------------F---------------K-GR--N--------V-
              ***************
DRB1*0305     *****---EYSTS-----------Y-D-YFH----N--------F---------------K-GR--N------------
              --********
DRB1*0306     ******--EYSTS-----------Y-D-YFH----N------------------------K-GR--N--------V-----
              -*********
DRB1*0307     --------EYSTS-----------F-D-YFH----N--------F---------------K-GR--N--------V--------
              -H------
DRB1*0308     --------EYSTS-----------Y-D-YFH----N--------F-------E-------K-GR--N--------V--------
              --H-----
DRB1*0309     *******-EYSTS-----------Y-D-YFH-R--N--------F---------------K-GR--N-------------
              ---********
DRB1*0310     --------EYSTS-----------Y-D-YFH----N--------F--------A--H---K-GR--N--------V----
              ----H------
DRB1*0311     *****---EYSTS-----------Y-D-YFH----N--------F---------------K-GQ--N--------V-----
              --********
DRB1*04011    --------E-V-H-----------F-D-YF-H---Y------------------------K-----------------Y-
              E----
DRB1*04012    *****---E-V-H-----------F-D-YF-H---Y------------------------K-------------------
              ********
DRB1*0402     --------E-V-H-----------F-D-YF-H---Y-------------I--DE-----------V-----
              ********
DRB1*0403     --------E-V-H-----------F-D-YF-H---Y--------------E---------V----------Y-
              E---
DRB1*0404     --------E-V-H-----------F-D-YF-H---Y----------------------------V----------Y-
              E---
DRB1*04051    --------E-V-H-----------F-D-YF-H---Y-----------S-----------------------
              ********
DRB1*04052    ******--E-V-H-----------F-D-YF-H---Y-----------S-----------------------
              ********
DRB1*0406     --------E-V-H-----------F-D-YF-H----------------------E---------V----------Y-
              E---
DRB1*0407     --------E-V-H-----------F-D-YF-H---Y------------------E-------------------
              ********
DRB1*0408     ******--E-V-H-----------F-D-YF-H---Y----------------------------------
              ********
DRB1*0409     *************-----------F-D-YF-H---Y-----------S----------K----------
              ***************
DRB1*0410     ******--E-V-H-----------F-D-YF-H---Y-----------S-----------------V---
              ************
DRB1*0411     --------E-V-H-----------F-D-YF-H---Y-----------S------E---------V----------Y-
              E---
DRB1*0412     ******--E-V-H-----------F-D-YF-H---Y-----------S--------I--D---L-----------V------
              *********
DRB1*0413     *************H----------F-D-YF-H---Y-----------------------K------------V---
              ************
DRB1*0414     **************----------F-D-YF-H---Y-------------------I--DE----------------
              ***************
```

FIG. 27C

```
DRB1*0415   *****---E-V-H----------F-D-YF-H---Y--------------E-------F--D-------------V-
            **************
DRB1*0416   **************---------F-D-YF-H---Y--------------Q--------K--------
            ****************
DRB1*0417   **************---------F-D-YF-H---Y--------------S--------E--------
            ****************
DRB1*0418   **************---------F-D-YF-H---Y--------------I--D---L--------V----
            **********
DRB1*0419   ************H----------F-D-YF-H----------------------------------
            **********
DRB1*0420   *************----------F-D-YF-H--------------------E-----------
            ****************
DRB1*0421   ********E-V-H----------F-D-YF-H---------------------K-----------
            **********
DRB1*0422   ********E-V-H----------F-D-YF-H---Y---------------K-GR--N-------V---
            ************
DRB1*0423   *****---E-V-H----------F-D-YF-H---Y------------------------V-R------
            ********
DRB1*0424   *****---E-V-H----------F-D-YF-H---Y--------------S-----R-----------
            ********
DRB1*0425   *******-E-V-H----------F-D-YF-H---Y--------------F--D---L--------V-
            ***************
DRB1*0426   *****---E-V-H----------F-D-YF-H---Y--------------T------K-----------
            ****************
DRB1*0427   *****---E-V-H----------F-D-YF-H---Y---------------E--------AV---
            **********
DRB1*11011  ------EYSTS----------F-D-YF-----Y--------F---------E-------F--D-------------
            H-----
DRB1*11012  ------EYSTS----------F-D-YF-----Y--------F---------E-------F--D-------------
            H-----*
DRB1*11013  *****---EYSTS----------F-D-YF-----Y--------F---------E-------F--D-------------
            ********
DRB1*1102   ------EYSTS----------F-D-YF-----Y--------F---------E-------I--DE--------V---------
            H-----
DRB1*1103   ------EYSTS----------F-D-YF-----Y--------F---------E-------F--DE--------V---------
            H-----
DRB1*11041  ------EYSTS----------F-D-YF-----Y--------F---------E-------F--D---------V---------
            ********
DRB1*11042  ------EYSTS----------F-D-YF-----Y--------F---------E-------F--D---------V---------
            H-----
DRB1*1105   ****---EYSTG----------F-D-YF-----Y--------F---------E-------F--D---------V---------
            ********
DRB1*1106   *****---EYSTS----------F-D-YF-----Y--------F---------E-------F--D----------AV---
            ************
DRB1*1107   *******-EYSTS----------F-D-YF-----Y--------F---------E-------K-GR--N--------V-----
            ---********
DRB1*11081  ************S----------F-D-YF-----Y--------F---------E----------D---------------
            **********
DRB1*11082  ************S----------F-D-YF-----Y--------F---------E----------D---------------
            **********
DRB1*1109   ****************-------F-D-YFH---N--------F---------E--------F--D----------
            **********
DRB1*1110   *************----------F-D-YFH---F--------F---------E--------F--D-----------
            ***************
```

FIG. 27D

```
DRB1*1111   ************S-----------F-D-YF-----Y---------F----------E--------F--DE-----------------
            ***********
DRB1*1112   **************---------F-D-YF-----F---------F----------E--------F--D--------------
            ****************
DRB1*1113   ------EYSTS-----------F-D-YFH----F----------F----------E----------R---------------V--------
            ********
DRB1*1114   ------EYSTS-----------F-D-YF-----Y---------F----------E--------I--DE-----------------
            *********
DRB1*1115   ------EYSTS-----------F-D-YF-----DL---------F----------E--------F--D--------------------
            H-----
DRB1*1116   *****---EYSTS-----------F-D-YFH----N---------F----------E--------I--DE--------------V------
            -********
DRB1*1117   ------EYSTS-----------F-D-YFH----F----------E----------R---E----------V---------
            H------
DRB1*1118   ******--EYSTS-----------F-D-YF-----Y---------F----------E--------I--D---------------V--------
            ********
DRB1*1119   ******--EYSTS-----------F-D-YF-----Y---------F----------E--------I--D---------------
            ********
DRB1*1120   *******-EYSTS-----------F-D-YFH----N---------F----------E--------I--DE-----------------
            **********
DRB1*1121   *******-EYSTS-----------F-D-YF-----Y---------F----------E--------I--DE-------------AV-
            ***************
DRB1*1122   *****---E-V-H-----------F-D-YF-----Y---------F----------E--------F--D--------------
            ****************
DRB1*1123   ****-----EYSTS-----------F-D-YF-----Y---------F----------E--------F--D---L-------------
            ****************
DRB1*1124   ******--EYSTS-----------F-D-YF-----D---------F----------E--------F--D---------------
            *************
DRB1*1125   *****---EYSTS-----------F-D-YF-----Y---------F----------E--------F--D---L-------------V--------
            -********
DRB1*1126   *******-EYSTS-----------F-D-YF-----Y---------F----------E--------------------
            ****************
DRB1*1127   ******--EYSTS-----------F-D-YF-----Y---------F----------E--------F--D------N-----------
            ******************
DRB1*1128   *****---EYSTS-----------F-D-YF-----N---------F----------E--------F--D---------------
            ********
DRB1*1129   *****---EYSTS-----------F-D-YF-----------F----------E--------F--D--------------
            ****************
DRB1*1130   *****---EL--S-----------F-D-YF-----Y---------F----------E--------F--D--------------
            ********
DRB1*1131   ------EYSTS-----------F-D-YF-----Y---------F----------E-H------I--D-----------------
            H-----
DRB1*1201   ------EYSTG--Y-----------HFH----LL---------F----------V--S-------I--D-------------AV--------
            -H-----
DRB1*12021  *****---EYSTG--Y-----------HFH----LL---------F----------V--S-------F--D--------------
            AV****************
DRB1*12022  ******--EYSTG--Y-----------HFH----LL---------F----------V--S-------F--D-------------AV-
            **************
DRB1*12032  *****---EYSTG--Y-----------HFH----LL---------F----------V--S-------I--D-------------V------
            -********
DRB1*1204   ********EYSTG--Y-----------HFH----LL---------F----------E--------I--D--------------
            AV****************
DRB1*1205   *****---EYSTG--Y-----------HFH----FL---------F----------V--S-------I--D-------------AV-----
            --********
```

FIG. 27E

```
DRB1*1301   ------EYSTS----------F-D-YFH----N---------F----------------I--DE--------------V---------
H-----
DRB1*1302   ------EYSTS----------F-D-YFH----N---------F----------------I--DE---------------------
H-----
DRB1*13031  ------EYSTS----------F-D-YF-----Y-----------------S---------I--DK---------------------
H-----*
DRB1*13032  *******-EYSTS----------F-D-YF-----Y-----------------S---------I--DK---------------------
********
DRB1*1304   ------EYSTS----------F-D-YF-----Y---------F--------S---------I--DE--------------V---------
H-----*
DRB1*1305   *****---EYSTS----------F-D-YFH----N---------F----------------F--D-----------------------
********
DRB1*1306   **************----------F-D-YFH----N---------F----------------I--D--------------V---
************
DRB1*13071  ******--EYSTS----------F-D-YF-----Y-------------------------F--D----------------
************
DRB1*1308   ******--EYSTS----------F-D-YFH----F---------------------------I--DE------------V-----
***********
DRB1*1309   ******--EYSTS----------F-D-YFH----N---------F----------------I---A--------------V-----
***********
DRB1*1310   *******-EYSTS----------F-D-YFH----N---------F----------------I--DK--------------V-
***************
DRB1*1311   *******-EYSTS----------F-D-YF-----Y---------F----------------F--D---------------V------
*********
DRB1*1312   *****---EYSTS----------F-D-YF-----Y-----------------S---------I--D----------------------
********
DRB1*1313   *****---EYSTS----------F-D-YF-----Y-----------------S---------I--D---L-----------------
***********
DRB1*1314   ***********TS----------F-D-YF-----Y---------F----------------F--D----------------
****************
DRB1*1315   ******--EYSTS----------F---YFH----N---------F----------------I--DE--------------V----
************
DRB1*1316   ********EYSTS----------F-D-YFH----N---------F----------------I--DE--------------D----
************
DRB1*1317   ------EYSTG--Y---------F-D-YF-----Y---------F----------------I--DE--------------V---------
H-----
DRB1*1318   *****---EYSTS----------F-D-YFH----N---------F----------------F--D---L-----------V--------
.********
DRB1*1319   ------EYSTS----------F---YFH----F------------------------------I--DE--------------V---------H-
----
DRB1*1320   *****---EYSTS----------F-D-YFH----N---------F----------------DE--------------V--------
*********
DRB1*1321   ------EYSTS----------F-D-YF-----Y---------F--------S---------F--D--------------------H-
----
DRB1*1322   ****----EYSTS----------F-D-YF-----Y---------F----------------I--DE--------------V---------
********
DRB1*1323   *****---EYSTS----------F-D-YF-----Y---------F----------------I--DE---------------------
*********
DRB1*1324   *****---EYSTS----------F-D-YF-----Y---------F----------------F--DE--------------V---------
*********
DRB1*1325   *****---EYSTS----------F-D-YF-----Y---------F----------------D--------------------
***************
DRB1*1326   *****---EYSTS----------F---YFH----N---------------------------F--D---------------------
********
```

FIG. 27F

```
DRB1*1327  *****---EYSTS----------Y-D-YFH----N---------F---------------I--DE-------------V-----
           -********
DRB1*1328  *******-EYSTS----------F-D-YFH----N---------F---------------I--DE-----------R-V---
           *************
DRB1*1329  *****---EYSTS----------F-D-YFH----N---------F------------------DE-----------------
           ********
DRB1*1330  ******--EYSTS----------F-D-YF-----Y---------F--------S---------I--D----------------
           ************
DRB1*1331  *****---EYSTS----------F-D-YFH----N---------F--------V---------I--DE---------------
           ********
DRB1*1332  *****---EYSTS----------F-D-YFH----N------------------S---------I--DE-----------V-----
           ********
DRB1*1333  *****---EYSTS----------F-D-YF-----Y------------------S---------I--DK----N---------
           ****************
DRB1*1401  --------EYSTS----------F-D-YFH----F--------------A--H--------R---E-------------V-----
           ********
DRB1*1402  --------EYSTS----------F---YFH----N---------------------------------------------
           ********
DRB1*1403  --------EYSTS----------F---YFH----N-----------------------------D---L------------
           ********
DRB1*1404  *****---EYSTG--Y-------F-D-YFH----F--------------A--H--------R---E-----------V-----
           ___********
DRB1*1405  ******--EYSTS-Q--------F-D-YFH----F-----------------------R---E-------------V-----
           -********
DRB1*1406  ******--EYSTS----------F---YFH----N--------------------------------------V---------
           ********
DRB1*1407  ********EYSTS----------F-D-YFH----F--------------A--H--------R---E-----------
           ****************
DRB1*1408  ******--EYSTS----------F-D-YFH----F-----------------H--------R---E-----------V-----
           *********
DRB1*1409  ******--EYSTS----------F-D-YFH----N---------------------------------------------
           *********
DRB1*1410  ******--E-V-H----------F-D-YFH----F--------------A--H--------R---E-----------V-----
           *********
DRB1*1411  ********EYSTG--Y-------F-D-YFH----F--------------E-----------R---E-----------
           V****************
DRB1*1412  ************S----------F---YFH----N------------------------D---L----------
           V****************
DRB1*1413  ********EYSTS----------F---YFH----N--------S---------------------------
           ****************
DRB1*1414  ******--EYSTS----------F-D-YFH----F-----------------------R---E-----------
           **********
DRB1*1415  **********STG--Y-------F-D-YFH----F--------------F--D---L-----------V-----
           *********
DRB1*1416  *******-EYSTS----------F-D-YFH----F--------------A--H------I--DE-----------V-
           ****************
DRB1*1417  *****---EYSTS----------F-D-YFH----N---------F-----------------------V--------
           *********
DRB1*1418  ********EYSTS----------F---YFH----N----------------------R---E-----------V---------
           ********
DRB1*1419  --------EYSTS----------F---YFH----N-----------------K--------------------
           ************
DRB1*1420  *******-EYSTS----------F---YFH----F-------------------------------V-
           ***************
```

FIG. 27G

```
DRB1*1421  *******-EYSTS----------F-D-YFH----N--------F-----------------K------------V-
***************
DRB1*1422  *****---EYSTS----------F-D-YFH----F----------------A--H------F--D------------
********
DRB1*1423  *****---EYSTS----------F-D-YFH----F---------------------R---E----------V-------
********
DRB1*1424  ******--EYSTS----------F---YFH----N-----------------I---A-------------------
H------
DRB1*1425  ********EYSTS----------F-D-YF-----Y-----------------A--H------F--D------------
****************
DRB1*1426  *****---EYSTS----------QF-D-YFH----F----------------A--H---------R---E----------V------
--********
DRB1*1427  *****---EYSTS----------F---YFH----N-----------------F--D---L-----------
********
DRB1*1428  *****---EYSTG--Y--------F-D-YFH----F----------------A--H---------R---E---------
AV****************
DRB1*1429  *****---EYSTS----------F---YFH----N-----------------------------AV--------
********
DRB1*1430  ******--EYSTS----------F-D-YFH----N--------F-----------------------
************
DRB1*1431  ******--EYSTG--Y--------F-D-YFH----F----------------A--H---------R---------------V----
************
DRB1*0701  ---Q-----G-YK----------QF--LF-----F----------------V--S------I--D--GQ---V---------
H-E----
DRB1*0703  *****-----G-YK----------QF--SLF-----F----------------V--S------I--D--GQ---V--------
****************
DRB1*0801  --------EYSTG--Y--------F-D-YF-----Y----------------S---------F--D---L------------------
********
DRB1*08021 --------EYSTG--Y--------F-D-YF-----Y--------------------------F--D---L---------------
H------
DRB1*08022 *****---EYSTG--Y--------F-D-YF-----Y--------------------------F--D---L---------------
-H------
DRB1*08032 --------EYSTG--Y--------F-D-YF-----Y----------------S---------I--D---L--------------
H------
DRB1*08041 --------EYSTG--Y--------F-D-YF-----Y--------------------------F--D---L----------V--------
H------*
DRB1*08042 *****************-------F-D-YF-----Y--------------------------F--D---L----------V------
-********
DRB1*08043 *****---EYSTG--Y--------F-D-YF-----Y--------------------------F--D---L----------V------
-********
DRB1*0805  *****---EYSTG--Y--------F-D-YF-----Y----------------S---------F--D--------------
****************
DRB1*0806  ****----EYSTG--Y--------F-D-YF-----Y----------------S---------F--D---L----------V------
-********
DRB1*0807  *****---EYSTG--Y--------F-D-YF-----Y----------------V---------F--D---L------------
************
DRB1*0808  *******-EYSTG--Y--------F-D-YF-----Y----------------A--H------F--D---L------------
****************
DRB1*0809  *************--Y--------F-D-YFH----F--------------------------F--D---L-----------
****************
DRB1*0810  *****---EYSTG--Y--------F-D-YF-----Y----------------S---------I--D---L----------V------
-********
DRB1*0811  *****---EYSTG--Y--------F-D-YF-----Y----------------A---------F--D---L------------
************
```

FIG. 27H

```
DRB1*0812   *****—EYSTG--Y———F-D-YF----Y———————S——————I--D---L————AV————
—********
DRB1*0813   *******-EYSTG--Y———F-D-YF----Y———————————————D---L————
***************
DRB1*0814   *****—EYSRG--Y———F-D-YF----Y———————S——————I-D---L————
**********
DRB1*0815   ******--EYSTG--Y———F-D-YF----Y———————H——————I--D---L————
************
DRB1*0816   *****—EYSTG--Y———F-D-YF----D———————S——————F--D---L————
****************
DRB1*0817   *****—EYSTG--Y———F-D-YF----Y————F————S——————F--D---L————
****************
DRB1*0818   *****—EYSTG--Y———F-D-YF----Y———————S——————I--D————————
********
DRB1*0819   ******--EYSTG--Y———F-D-YF----Y———————I————————I--D---L————
***********
DRB1*09012  —Q---K-D————————Y-H-G----N—————————V-S—————F--R---E--V————
H-E---
DRB1*1001   ——————EEV————————————RVH—YA-Y————————————————R——————————————Q--
———
```

FIG. 29

```
               1                                                        50
Sladra-0102    ----------  ----------  ----------  ----------  ----------
Sladra-0202    ----------  ----------  ----------  ----------  ----------
Sladra-0203    ----------  ----------  ----------  ----------  ----------
Sladra-0101    ----------  ----------  ----------  ----------  ----------
Sladra-02011   ----------  ----------  ----------  ----------  ----------
Sladra-02012   ----------  ----------  ----------  ----------  ----------
Consensus      VENHVIIQAE  FYLSPDKSGE  FMFDFDGDEI  FHVDMEKRET  VWRLEEFGHF 51                                                       100
Sladra-0102    ----------  ----------  ----------  ----------  ----------
Sladra-0202    ----------  ----------  -m--------  ----------  ----------
Sladra-0203    ----------  ----------  ----------  ----------  ----------
Sladra-0101    ----------  ----------  ----------  ----------  ----------
Sladra-02011   ----------  ----------  -m--------  ----------  ----------
Sladra-02012   ----------  ----------  -m--------  ----------  ----------
Consensus      ASFEAQGALA  NIAVDKANLE  ILIKRSNNTP  NTNVPPEVTV  LSDKPVELGE 101                                                      150
Sladra-0102    ----------  ----------  ----------  ----------  ----------
Sladra-0202    ----------  ----------  ----------  ----------  ----------
Sladra-0203    ----------  ----------  ----------  ----------  ----------
Sladra-0101    ----------  ----------  ----------  ----------  ----------
Sladra-02011   ----------  ----------  ----------  ----------  ----------
Sladra-02012   ----------  ----------  ----------  ----------  ----------
Consensus      PNILICFIDK  FSPPVVNVTW  LRNGSPVTRG  VSETVFLPRE  DHLFRKFHYL 151                                                      200
Sladra-0102    ----------  ----------  ----------  -r--------  ----------
Sladra-0202    ----------  ----------  ----------  ----------  ----------
Sladra-0203    ----------  ----------  ----------  ----------  ----------
Sladra-0101    ----------  ----------  ----------  ----------  ----------
Sladra-02011   ----------  ----------  ----------  ----------  ----------
Sladra-02012   ----------  ----------  ----------  ----------  ----------
Consensus      PFMPSTEDVY  DCQVEHWGLD  KPLLKHWEFE  AQTPLPETTE  NTVCALGLIV 201         228
Sladra-0102    ----------  --------
Sladra-0202    ----------  ---h----
Sladra-0203    ----------  ---h----
Sladra-0101    ----------  --------
Sladra-02011   ----------  --------
Sladra-02012   ----------  --------
Consensus      ALVGIIVGTV  LIIKGVRKGN  ATERRGPL
```

Group 01 has a leucine at residue 72 and Group 02 has a methionine.
No other polymorphisms have been found in the alpha 1 domain.

Amino Acid Sequences of SLA DRA Alleles

FIG. 30

```
           1                     21                           41         50
Sladrb-T   --iaq--ffm  g-s-------  ------y-qky  l---------  ---l--f---
Sladrb-N   --------f-  g-a-------  -------d-y   f---d-y---  ------f-e-
Sladrb-M   --------f-  g---------  --q-------   ----------  ----------
Sladrb-Z   -------y-   ----------  ----------   ------y---  ----------
Sladrb-AD  ----------  ----------  ----------   ------l--   ----------
Sladrb-C   --i------q  ----------  -------q-n   c-----y---  ----------
Sladrb-WX  ----------  v-h--r----  ----l--d-y   f---------  ------f---
Sladrb-Y   --i----ffm  g-s-------  -----y-lky   l---------  ---l----e-
Consensus  RDTPPHFLHL  LKFECHFFNG  TERVRLLERQ   YYNGEEFVRF  DSDVGEYRAV 51         64                        81                    100
Sladrb-T   ----------  -------m--  k--v------   ----------  ----------
Sladrb-N   --f-------  ------fm--  k------v--   ---e--e---  -------r--
Sladrb-M   ---------n  y---------  ----------   ----ts----  -------r--
Sladrb-Z   ------v--d  ----------  ----------   ----ts----  -------r--
Sladrb-AD  ---------d  ----------  ----------   ----------  ----------
Sladrb-C   ----------  r---------  ---a------   ----------  ----------
Sladrb-WX  ----------  ------i--d  s--s-----i   ----------  ----------
Sladrb-Y   ----------  ----------  --ek------   ---gvs-s--  ----------
Consensus  TELGRPDAKY  WNSQKDLLEQ  RRAEVDTYCR   HNYRILDTFL  VPRRAEPTVT 101                                                        150
Sladrb-T   ----------  ----------  ----------   ----------  ----------
Sladrb-N   ----------  ----------  ----------   ----------  ----------
Sladrb-M   ----------  ----------  ----------   ----------  ----------
Sladrb-Z   ----------  ----------  ----------   ----------  ----------
Sladrb-AD  ----------  ----------  ----------   ----------  ----------
Sladrb-C   ----------  ----------  ----------   ----------  ----------
Sladrb-WX  ----------  ----------  ----------   ----------  ----------
Sladrb-Y   ----------  ----------  ----------   ----------  ----------
Consensus  VYPAKTQPLQ  HHNLLVCSVT  GFYPGHVEVR   WFRNGQEEAA  GVVSTGLIPN 151                                                        200
Sladrb-T   ----------  ----------  ----------   ----------  ----------
Sladrb-N   ----------  ----------  -t-------i   ----------  ----------
Sladrb-M   ----------  ----------  ----------   ----------  ----------
Sladrb-Z   ----------  ----------  ----------   ----------  ----------
Sladrb-AD  ----------  ----------  ----------   ----------  ----------
Sladrb-C   ----------  ----------  ----------   ----------  ----------
Sladrb-WX  ----------  ----------  ----------   ----------  ----------
Sladrb-Y   ----------  ----------  ----------   ----------  ----------
Consensus  GDWTFQTMVM  LETVPQSGEV  YSCRVEHPSL   TSPVTVEWRA  RSESAQGKMM 201                               237
Sladrb-T   --v-------  ----------  ----------  -------
Sladrb-N   ----------  ----------  ----------  -------
Sladrb-M   ----------  ----------  ----------  -------
Sladrb-Z   --v-------  ----------  ----------  -------
Sladrb-AD  ----------  ----------  ----------  -------
Sladrb-C   --v-------  ----------  ----------  -------
Sladrb-WX  ----------  ----------  ----------  -------
Sladrb-Y   --v-------  ----------  ----------  -------
Consensus  SGIGGFVLGL  LFVAVGLFIY  FKNQKGRPAL  QPTGLLS
```

Amino Acid Sequence of SLA-DRB Alleles

FIG. 31

```
                    1                                                       50
Sladqa-02021   ----------  ----------  ----------  ---------g  ----------
Sladqa-02022   ----------  ----------  ----------  ---------g  ----------
Sladqa-02023   ----------  ----------  ----------  ---------g  ----------
Sladqa-0201    ----------  ----------  ----------  ----------  ----------
Sladqa-0101    ----------  ----------  -r--------  ---q------  -------r---
Sladqa-0103    ----------  ----------  -r--f-----  ---q------  -------r---
Sladqa-0102    ----------  ----------  ----f-----  ----------  -------r---
Consensus      EDIAADHVAS  YGLNVYQSYG  PSGYYTHEFD  GDEEFYVDLE  KKETVWQLPL 51                                                      100
Sladqa-02021   ----r-----  ----------  ----------  ----------  ----------
Sladqa-02022   ----r-----  ----------  ----------  ----------  ----------
Sladqa-02023   ----r-----  ----------  ----------  ----------  ----------
Sladqa--201    ----------  ----------  ----------  ----------  ----------
Sladqa-0101    --e-------  --------l-  -----vt---  --------k--  -----s----
Sladqa-0103    --e-------  --------l-  -----vt---  --------k--  -----s----
Sladqa-0102    --e-------  --------l-  -----vt---  ----------  -----s----
Consensus      FSKFTSFDPQ  GALRNIATAK  HNLNILIKRS  NNTAAVNQVP  EVTVFPKSPV 101                                                     150
Sladqa-02021   ----------  ----------  ----------  ----------  ----------
Sladqa-02022   ----------  ----------  ----------  ----------  ----------
Sladqa-02023   ----------  ----------  ----------  ----------  ----------
Sladqa-0201    ----------  ----------  ----------  ----------  ----------
Sladqa-0101    i---------  ---s------  ----------  -.k-------  ----------
Sladqa-0103    i---------  ---s------  ----------  -.k-------  ----------
Sladqa-0102    i---------  ---s------  ----------  -.k-------  ----------
Consensus      MLGQPNTLIC  HVDNIFPPVI  NITWLKNGHS  VTEGFSETSF  LSKNDHSFLK 151                                                     200
Sladqa-02021   ----------  ----------  ----------  ----------  ----------
Sladqa-02022   ----------  ----------  ----------  ----------  ----------
Sladqa-02023   ----------  ----------  ----------  ----------  ----------
Sladqa-0201    ----------  ----------  ----------  ----------  ----------
Sladqa-0101    ----------  ----------  --------t-  ----------  ----------
Sladqa-0103    ----------  ----------  ----------  ----------  ----------
Sladqa-0102    ----------  ----------  ----------  ----------  ----------
Consensus      ISYLTFLPSD  DDFYDCKVEH  WGLDKPLLKH  WEPEIPAPMS  ELTETVVCAL 201                    232
Sladqa-02021   ----------  ----------  ----------  --
Sladqa-02022   ----------  ----------  ----------  --
Sladqa-02023   ----------  ----------  ----------  --
Sladqa-0201    ----------  ----------  ----------  --
Sladqa-0101    ----------  ----------  ----------  --
Sladqa-0103    ----------  ----------  ----------  --
Sladqa-0102    ----------  ----------  l---------  --
Consensus      GLIVGLVGIV  VGTVFIIQGL  RSGGPSRHQG  SL
```

Group 01 is 231 amino acids (deletion at 132) and Group 02 is 232 amino acids

Amino Acid Sequences of SLA-DQA Alleles

FIG. 32

```
              1                                                              50
Sladqb-D     ----------v ---g----y- -----ws-d- --------fl- ----m--y--
Sladqb-D2    ----------f ---g----y- -----ws-d- --------fl- ----m--y--
Sladqb-XA    ----------- ---------- ------g--- wv--------- ----------
Sladqb-Z     ----------- --------y- ------l--- wv--r----- ----------
Sladqb-W     ----------- ---------- ------i-t- --------ya- -------y--
Sladqb-T     ----------- ---------- ------llt- ---------- ---n---y--
Sladqb-Y     ----------- ---g------ ------h-t- ---------- ----------
Sladqb-C     ----------f ---g----y- ------g--- ---------l- ----------
Consensus    GRDSPQDFVY  QFKFECYFFN GTQRVR-VAR YIYNQEEHVR  FDSDVGEFRA 51                                                            100
Sladqb-D     ---------- -l----ea-- ---------- ---------- ----------
Sladqb-D2    ---------- -l----ea-- ---------- ---------- ----------
Sladqb-XA    -------t-- ---------- -----v---- ---------- ----------
Sladqb-Z     ---------- ------e--- ---------- ---------- ----------
Sladqb-W     -------a-- ---s---i-- -t-------- ---------- ----------
Sladqb-T     ---------- ---------- -t-------- ---------- ----------
Sladqb-Y     ---------- -------f-- -t-------- ---------- ----------
Sladqb-C     ------e--- s--s------ -m---v-r-- ---------- ----------
Consensus    VTPLGRPDAD YWNGQKDVLE QKRAELDTVC KHNYQIEEGT TLQRRVQPTV 101                                                           150
Sladqb-D     ---------- ---------- ---------- ---------- ----------
Sladqb-D2    ---------- ---------- ---------- ---------- ----------
Sladqb-XA    ---------- ---------- ---------- ---------- ----------
Sladqb-Z     ---------- ---------- ---------- ---------- ----------
Sladqb-W     ---------- ---------- ---------- ---------- ----------
Sladqb-T     ---------- ---------- ---------- ---------- ----------
Sladqb-Y     ---------- ---------- ---------- ---------- ----------
Sladqb-C     ---------- ---------- ---------- ---------- ----------
Consensus    TISPSKAEAL NHHNLLVCAV TDFYPSQVKV QWFRNGQEET AGVVSTPLIR 151                                                           200
Sladqb-D     ---------- ---------- ---------- ---------- ----------
Sladqb-D2    ---------- ---------- ---------- ---------- ----------
Sladqb-XA    ---------- ---------- ---------- --n------- ----------
Sladqb-Z     ---------- ---------- ---------- ---------- ----------
Sladqb-W     ---------- ---------- ---------- ---------- ----------
Sladqb-T     ---------- ---------- ---------- ---------- ----------
Sladqb-Y     ---------- ---------- ---------- ---------- ----------
Sladqb-C     ---------- ---------- ---------- --n------- ----------
Consensus    NGDWTYQVLV MLEMNLQRGD VYTCRVEHSS LQSPILVEWR AQSESAQSKM 201            230
Sladqb-D     ---------- ---------- ----------
Sladqb-D2    ---------- ---------- ----------
Sladqb-XA    ---------- ---------- ----------
Sladqb-Z     ---------- ---------- ----------
Sladqb-W     ---------- ---------- ----------
Sladqb-T     ---------- ---------- ----------
Sladqb-Y     ---------- ---------- ----------
Sladqb-C     ---------- ---------- ----------
Consensus    LSGVGGFVLG LIFLGLGLFI RHRSQKGLVR
```

Amino Acid Sequences of SLA-DQB Alleles

GENERATION OF ANTIGEN SPECIFIC T SUPPRESSOR CELLS FOR TREATMENT OF REJECTION

This invention was made with support under Grant Nos. 5-RO1-A125210-11, RO1A125210-10, and 5-RO1-A125210-12 from the National Institutes of Health. Accordingly, the United States Government has certain rights in the invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Specific suppression of the host's immune response to donor HLA antigens remains the ultimate goal for clinical transplantation. In spite of considerable effort, however, allospecific human suppressor T cells (Ts) have been difficult to generate. The studies herein (first series of experiments) show that allospecific and xenospecific $T_s$ can be raised by multiple priming of human T cells in mixed lymphocyte cultures (MLC). $T_s$ derive from the $CD8^+CD28^-$ subset and recognize specifically the MHC class I antigens expressed by Antigen-Presenting Cells (APC) used for in vitro immunization. Allospecific $T_s$ prevent the upregulation of B7 molecules on target APCs, interfering with the CD28-B7 interaction required for T helper ($T_h$) activation. These findings provide a basis for the development of specific immunosuppressive therapy.

The induction of donor-specific tolerance remains the ultimate goal for clinical transplantation. Immunosuppressive treatments that have been developed so far act non-specifically, placing the recipient at increased risk for infections and malignancies.

Transplant tolerance has been induced in adult animals by inactivation or depletion of mature T lymphocytes prior to transplantation using cyclosporine (CsA) (1), total lymphoid irradiation (2,3), anti-lymphocyte serum (4), antibodies against CD4+ and CD8+ T cells (5), or donor-specific transfusions (6,7). Studies of peripheral graft tolerance have suggested the existence of an active mechanism of suppression which is donor-specific and can be transferred adoptively to secondary hosts (1, 7–10). However, there is still controversy concerning the phenotypic characteristics of these regulatory T cells and their MHC restriction, as both CD8+ and CD4+ T cells were reported to display suppressive activity (11). This controversy lead to the speculation that no distinctive $T_s$ lineage actually exists. It has been suggested that suppression may result from antagonistic effects of (Th)2-type lymphokines (such as IL-4 and IL-10) on the response of $T_h1$ cells (2,12), or from recognition by $T_s$ of either idiotypic determinants of the TCR of alloreactive T cells or of MHC antigens expressed on stimulating cells (10,13). The generation of $T_s$ lines has proven, however, to be a difficult task rendering the characterization of these cells hard to achieve.

The aim of the present study (first series of experiments) was to develop and characterize suppressor T cell lines which inhibit specifically the alloimmune response. This study established for the first time the existence of a population of $CD8^+CD28^-$ $T_s$ which are allorestricted by HLA-class I antigens expressed by the cells used for priming. The mechanism of suppression is based on the capacity of $T_s$ to prevent the upregulation of B7 molecules (CD80 and CD86) induced by Th on the stimulating APC. Allorestricted $T_s$ can be easily and reproducibly expanded in cultures facilitating the in vitro study of immunoregulatory networks and the development of new strategies for specific immunosuppression.

Evidence that T cells can down-regulate the immune response by producing or consuming certain cytokines or by lysing APCs or T helper cells has been provided in various systems. However, the generation and characterization of suppressor T cell lines have met with limited success. In the second series of experiments herein it is shown that xenospecific suppressor T cells can be generated by in vitro stimulation of human T cells with pig APCs. Similar to allospecific suppressors, these xenospecific suppressor T cells carry the $CD8^+CD28^-$ phenotype and react to MHC class I antigens expressed by the APCs used for priming. TCR spectratyping of T suppressor cells showed oligoclonal usage of TCR-Vβ families, indicating that xenostimulation of $CD8^+CD28^-$ T cells results in antigen-driven selection of a limited Vβ repertoire. Xenospecific T suppressor cells prevent the up-regulation of CD154 molecules on the membrane of T helper (Th) cells, inhibiting their ability to react against the immunizing MHC-class II xenoantigens. The mechanism of this suppression, therefore, appears to be blockade of CD154/CD40 interaction required for efficient costimulation of activated T cells.

The induction of regulatory T cells may offer an effective means for specific immunosuppression of autoimmune disease and allograft rejection. The existence of suppressor T cells has been previously documented, yet their mechanism of action remains poorly characterized. The third series of studies herein demonstrate that T suppressor (Ts) cell lines can be generated by in vitro immunization of human PBMCs, with synthetic peptides or soluble proteins coupled to beads. Such Ts cells express the $CD8^+CD28^-$ phenotype and show the following characteristics: a) antigen specificity and restriction by self MHC Class I molecules, b) limited TCR V beta gene usage, c) ability to inhibit antigen-specific, MHC Class II restricted, Th proliferative responses, and d) capacity to downregulate and/or inhibit the upregulation by Th of CD40, CD80, and CD86 molecules on APCs. The inhibitory activity of Ts on Th proliferation requires the tripartite interaction between Th, Ts, and APCs and results from inefficient costimulation of Th.

Understanding the mechanism which underlies the induction of immunologic tolerance is crucial to the development of strategies for treatment of auto-immune diseases and allograft rejection. Although the concept that T suppressor cells (Ts) downregulate the immune response has long been accepted, the existence of a distinct population of lymphocytes that mediates suppression has not been convincingly demonstrated. In previous studies, human T cell lines (TCLs) were utilized to analyze the suppressive effects of $CD8^+CD28^-$ T cells in allogeneic, peptide specific and xeno-specific responses. In each case, $CD8^+CD28^-$ T cells inhibit proliferation of CD4+ T helper lymphocytes (Th) with cognate antigen specificity. These $CD8^+CD28^-$ T cells display the critical functional characteristics of T suppressor cells. Similar to the induction of $CD8^+$ cytotoxic T cells (Tc) by Th, this process depends on antigen presenting cells (APC) acting as a "bridge" between MHC-class I specific $CD8^+$ and class II specific CD4+ T cells. A possible explanation of Ts-mediated suppression is their ability to modulate the function of APCs. The fourth series of studies herein show that $CD8^+CD28^-$ Ts directly inhibit the CD40 signaling pathway of APC by a contact-dependent mechanism that renders bridging APCs incapable of inducing CD4+ The activation. The effects of Ts on the functional state of APC supports the concept that the order in which Ts and The cells interact with cognate APCs determines the functional outcome of immune responses.

SUMMARY OF THE INVENTION

This invention provides a method of generating antigen specific allospecific human suppressor CD8+CD28− T cells which comprises: a) obtaining peripheral blood T cells from a subject; b) stimulating by multiple priming a T cell line from the T cells obtained in step (a) with allogeneic antigen presenting cells (APCs), said APCs expressing an MHC class I antigen recognized by the primed T cell line and an MHC class II antigen recognized by CD4+ T helper cells from said primed T cell line; c) isolating primed CD8+ T cells and CD4+ T helper cells from the T cell line stimulated in step (b); d) isolating primed CD8+CD28− T cells from the isolated primed CD8+ T cells of step (c); e) detecting suppression by the primed CD8+CD28− T cells isolated in step (d) of interaction between the CD4+ T helper cells isolated in step (c) and allogeneic antigen presenting cells (APCs) expressing the same MHC class I antigen and the same MHC class II antigen expressed by the APCs used to stimulate the T cell line of step (b), thereby identifying antigen specific allospecific human suppressor CD8+CD28− T cells; and f) expanding the antigen specific allospecific human suppressor CD8+CD28− T cells identified in step (e), thereby generating the antigen specific allospecific human suppressor CD8+CD28− T cells.

This invention provides antigen specific allospecific human suppressor CD8+CD28+ T cells produced by the method of generating antigen specific allospecific human suppressor CD8+CD28− T cells which comprises: a) obtaining peripheral blood T cells from a subject; b) stimulating by multiple priming a T cell line from the T cells obtained in step (a) with allogeneic antigen presenting cells (APCs), said APCs expressing an MHC class I antigen recognized by the primed T cell line and an MHC class II antigen recognized by CD4+ T helper cells from said primed T cell line; c) isolating primed CD8+ T cells and CD4+T helper cells from the T cell line stimulated in step (b); d) isolating primed CD8+CD28− T cells from the isolated primed CD8+ T cells of step (c); e) detecting suppression by the primed CD8+CD28− T cells isolated in step (d) of interaction between the CD4+ T helper cells isolated in step (c) and allogeneic antigen presenting cells (APCs) expressing the same MHC class I antigen and the same MHC class II antigen expressed by the APCs used to stimulate the T cell line of step (b), thereby identifying antigen specific allospecific human suppressor CD8+CD28− T cells; and f) expanding the antigen specific allospecific human suppressor CD8+CD28− T cells identified in step (e).

This invention provides a method of generating xenospecific human suppressor CD8+CD28− T cells which comprises: a) obtaining peripheral blood T cells from a human subject; b) stimulating by multiple priming a human T cell line from the T cells obtained in step (a) with xenogeneic mammalian antigen presenting cells (APCs), said APCs expressing a xenogeneic MHC class I antigen and a xenogeneic MHC class II antigen; c) isolating primed human CD8+ T cells and human CD4+ T helper cells from the T cell line stimulated in step (b); d) isolating primed human CD8+CD28− T cells from the isolated primed human CD8+ T cells of step (c); e) detecting suppression by the primed human CD8+CD28− T cells isolated in step (d) of interaction between the human CD4+ T helper cells isolated in step (c) and xenogeneic antigen presenting cells (APCs) expressing the same xenogeneic MHC class I antigen and xenogeneic MHC class II antigen expressed by the xenogeneic APCs used to stimulate the human T cell line of step (b), thereby identifying xenospecific human suppressor CD8+CD28− T cells; f) expanding the xenospecific human suppressor CD8+CD28− T cells identified in step (e), thereby generating the xenospecific human suppressor CD8+CD28− T cells.

This invention provides xenospecific human suppressor CD8+CD28+ T cells produced by the method of generating xenospecific human suppressor CD8+CD28− T cells which comprises: a) obtaining peripheral blood T cells from a human subject; b) stimulating by multiple priming a human T cell line from the T cells obtained in step (a) with xenogeneic mammalian antigen presenting cells (APCs), said APCs expressing a xenogeneic MHC class I antigen and a xenogeneic MHC class II antigen; c) isolating primed human CD8+ T cells and human CD4+ T helper cells from the T cell line stimulated in step (b); d) isolating primed human CD8+CD28− T cells from the isolated primed human CD8+ T cells of step (c); e) detecting suppression by the primed human CD8+CD28− T cells isolated in step (d) of interaction between the human CD4+ T helper cells isolated in step (c) and xenogeneic antigen presenting cells (APCs) expressing the same xenogeneic MHC class I antigen and xenogeneic MHC class II antigen expressed by the xenogeneic APCs used to stimulate the human T cell line of step (b), thereby identifying xenospecific human suppressor CD8+CD28− T cells; and f) expanding the xenospecific human suppressor CD8+CD28− T cells identified in step (e).

This invention provides a method of generating allopeptide antigen specific human suppressor CD8+CD28− T cells which comprises: a) obtaining peripheral blood T cells from a subject; b) stimulating by multiple priming a T cell line from the T cells obtained in step (a) with autologous antigen presenting cells (APCs) pulsed with an allopeptide, said allopeptide comprising an amino acid sequence comprising both MHC class I and MHC class II amino acid sequences wherein the amino acid sequences are binding sequences (motifs) and are recognized by the primed T cell line; c) isolating primed CD8+ T cells and CD4+ T helper cells from the T cell line stimulated in step (b); d) isolating primed CD8+CD28− T cells from the isolated primed CD8+ T cells of step (c); e) detecting suppression by the primed CD8+ CD28− T cells isolated in step (d) of interaction between the CD4+ T helper cells isolated in step (c) and autologous antigen presenting cells (APCs) expressing the same MHC class I and MHC class II binding motifs as expressed by the APCs used to stimulate the T cell line of step (b), thereby identifying allopeptide antigen specific human suppressor CD8+CD28− T cells; and f) expanding the allopeptide antigen specific human suppressor CD8+CD28− T cells identified in step (e), thereby generating the antigen specific human suppressor CD8+CD28− T cells.

This invention provides an antigen specific human suppressor CD8+CD28− T cells produced by the above-described method of generating the antigen specific human suppressor CD8+CD28− T cells.

This invention provides a method of determining whether a level of immunosuppresant therapy given to a subject undergoing the level immunosuppression therapy requires a reduction which comprises: a) obtaining a blood sample from the subject; and b) determining the presence of T suppressor cells present in the sample, the presence of T suppressor cells indicating that the subject requires the reduction of immunosuppresant therapy.

This invention provides a method of reducing the risk of rejection of an allograft in a subject undergoing immunosuppression therapy which comprises: a) obtaining a blood sample from the subject; b) removing T suppressor cells from the blood sample; c) expanding the T suppressor cells of step (b); and d) reintroducing the expanded T suppressor cells of step (b) into the subject.

This invention provides a method of reducing the level of rejection of an allograft in a subject undergoing immunosuppression therapy which comprises administering to the subject the T suppressor cells produced by the above-described method of generating antigen specific allospecific human suppressor CD8+CD28− T cells, thereby preventing rejection of the tissue or organ transplant in the subject.

This invention provides a method of reducing the level of rejection of an allograft in a subject undergoing immunosuppression therapy which comprises administering to the subject the T suppressor cells produced by the above-described method of generating allopeptide antigen specific human suppressor CD8+CD28− T cells, thereby preventing rejection of the tissue or organ transplant in the subject.

This invention provides a method of preventing rejection of an allograft in a subject which comprises: a) obtaining a blood sample from the subject; b) removing T suppressor cells from the blood sample; c) expanding the T suppressor cells of step (b); and d) reintroducing the expanded T suppressor cells of step (b) into the subject, thereby preventing the rejection of the allograft in the subject.

This invention provides a method of preventing rejection of an allograft in a subject which comprises administering the T suppressor cells produced by the above-described method of generating antigen specific allospecific human suppressor CD8+CD28− T cells to the subject, thereby preventing rejection of the allograft in the subject.

This invention provides a method of preventing rejection of an allograft in a subject which comprises administering the T suppressor cells produced by the above-described method of generating allopeptide antigen specific human suppressor CD8+CD28− T cells to the subject, thereby preventing rejection of the allograft in the subject.

This invention provides a method of preventing rejection of a xenograft in a subject which comprises: a) obtaining a blood sample from the subject; b) removing T suppressor cells from the blood sample; c) expanding the T suppressor cells of step (b); and d) reintroducing the expanded T suppressor cells of step (b) into the subject, thereby preventing the rejection of the xenograft in the subject.

This invention provides a method of preventing rejection of a xenograft in a subject which comprises administering the T suppressor cells produced by the above-described method of generating xenospecific human suppressor CD8+CD28− T cells to the subject, thereby preventing rejection of the xenograft in the subject.

This invention provides a method of preventing autoimmune disease in a subject which comprises: a) obtaining a blood sample from the subject; b) removing T suppressor cells from the blood sample; c) expanding the T suppressor cells of step (b); and d) reintroducing the expanded T suppressor cells of step (b) into the subject, thereby preventing autoimmune disease in the subject.

This invention provides a method of preventing autoimmune disease in a subject which comprises administering the T suppressor cells produced by the above-described method of generating antigen specific allospecific human suppressor CD8+CD28− T cells to the subject, thereby preventing autoimmune disease in the subject.

This invention provides a method of preventing autoimmune disease in a subject which comprises administering the T suppressor cells produced by above-described method of generating allopeptide antigen specific human suppressor CD8+CD28− T cells to the subject, thereby preventing autoimmune disease in the subject.

This invention provides a vaccine comprising allospecific T suppressor cells stimulated by APCs expressing an MHC class I antigen and an MHC class II antigen which T suppressor cells suppress an interaction between CD4+ T helper cells and allogeneic antigen presenting cells (APCs) expressing the same MHC class I antigen and the same MHC class II antigen expressed by the APCs used to stimulate the allospecific T suppressor cells.

This invention provides a vaccine comprising xenospecific T suppressor cells stimulated by APCs expressing a xenogeneic MHC class I antigen and a xenogeneic MHC class II antigen which xenospecific T suppressor cells suppress an interaction between CD4+ T helper cells and xenogeneic antigen presenting cells (APCs) expressing the same xenogeneic MHC class I antigen and xenogeneic MHC class II antigen expressed by the APCs used to stimulate the xenospecific T suppressor cells.

BRIEF DESCRIPTION OF THE FIGURES

FIG. 1A. Reactivity of unseparated TCL, separated $CD4^+$ and $CD8^+$ T cell subsets, and mixtures of $CD4^+$ and $CD8^+$ T cells to the specific allostimulator was determined in blastogenesis assays. Results are expressed as mean c.p.m. of triplicate reactions. The SD of the mean was less than 10%. FIG. 1B. Dose-dependent suppression of $CD4^+$ T cell alloreactivity to the specific stimulator in the presence of primed $CD8^+$, $CD8^+$ $CD28^+$, and $CD8^+CD28^-$ T cells. Mean c.p.m. in cultures without $T_s$ was 28,470±1730. FIG. 1C. Flow-cytometry determination of target cell apoptosis. The percent of allogeneic APCs stained by Annexin V was determined after 4 and 24 hours of incubation with or without $CD4^+$ and $CD8^+CD28^-$ T cells. FIG. 1D. Suppression of $CD4^+$ T cell proliferation to specific stimulator by $CD8^+CD28^-$ T cells added to the cultures 0, 4, 8 and 16 hours after the initiation of the assay. Mean c.p.m. in cultures without $T_s$ was 22,630±1860.

FIG. 2A. $CD4^+$ $T_h$ from TCL SS-anti-JL were tested in blastogenesis assay for reactivity against APC from the original stimulator JL and from donors sharing with JL HLA-class I and class II (PO) or only class II (ST). Separate cultures were stimulated with a mixture of APCs from two donors (GC sharing with JL class I and ST sharing class II). $CD8^+CD28^-$ $T_s$ from TCL SS-anti JL were added at the initiation of the blastogenesis assay. Percent suppression was calculated from the ratio of c.p.m. in cultures containing mixtures of $T_h$ and $T_s$ and cultures containing only $T_h$. Mean c.p.m. in cultures without $T_s$ was 33,212±2160, 27,630±1940, 28,430±2070 and 37,400±3450 when APCs from JL, PO, ST or mixtures of GC and ST were used as stimulators respectively. FIG. 2B. $CD4^+$ $T_h$ from TCL SS-anti-JL and naive $CD4^+$ T cells from SS were stimulated with APC from JL. Alloreactive $CD8^+CD28^-$ T cells from SS generated by priming against JL, GC (sharing with JL class I) or ST (sharing with JL class II) were added to these cultures. Percent suppression was calculated as above.

FIGS. 7A and 7B) against APCs from the same pig (pig B) was tested in a 3-day blastogenesis assay. The response of the unfractionated TCLs, purified CD4$^+$ cells, and mixtures of CD4 and CD8$^+$CD28$^-$ cells from both lines to pig APCs is presented as mean counts/min of triplicate reactions. The SD of the mean is indicated.

FIG. 8A, Diffusion chamber experiments. Th cells from TCL CG anti-W were tested for reactivity to APC from the specific stimulator (strain W) on close contact with Ts cells (from the same TCL) or separated from Ts cells by a semipermeable membrane. Percent suppression of Th cells reactivity by Ts cells is indicated. FIG. 8B, Th cells from TCL ES-anti-W were tested for reactivity to APC from the specific stimulator (strain W) in the presence of autologous Ts cells and the indicated mAbs.

FIG. 10A, Pig APCs were incubated for 4 hours with Th cells, Ts cells, or both Th and Ts cells. The percent of early apoptotic (annexin V positive, PI negative) and late apoptotic/necrotic (annexin V positive, PI positive) pig APCs in cultures with and without xenoreactive human T cells was determined by flow cytometry. Camptothecin-treated APCs were used as positive controls for apoptosis. FIG. 10B, CD8$^+$CD28$^+$ and CD8$^+$CD28$^-$ T cells from TCL ES-anti-Q were tested for their ability to kill PHA-stimulated target cells from strain Q in a $^{51}$Cr release assay. Results are expressed as percent lysis. FIG. 10C, Human Th cells were incubated with pig APCs in the presence or absence of Ts cells. The percent of CD4$^+$ human T cells undergoing apoptosis was determined by staining with annexin V and PI. The percent of early apoptotic (annexin V positive, PI negative) and late apoptotic/necrotic (annexin V positive, PI positive) Th cells is shown. CD4$^+$ Th cells treated with camptothecin served as positive controls.

FIGS. 19A-1–19-C-5. Vβ repertoire of CD4+ Th and CD8+CD28− Ts primed to rTT. The relative intensity of TCR Vβ families expressed by CD8+CD28− Ts after five weeks (FIGS. 19A–19E) and six weeks in cultures (FIGS. 19F–19J) and by CD4+ Th (FIGS. 19K–19O) was calculated from the ratio between the peak area of each TCR and the sum of all area peaks.

FIGS. 20A–20L. CD8+CD28− Ts prevent upregulation of CD40, CD80, and CD86 on antigen-loaded APCs. CD4+ Th and CD8+CD28− Ts from a Tat-DR4 peptide specific T cell line were incubated alone or together with autologous APCs and antigen for 24 hours. The expression of CD40, CD80, and CD86 on autologous APCs (CD14+ and CD20+ cells) was analyzed by flow-cytometry. The percent positive APCs and the mean fluorescence intensity (MFI) are indicated.

FIGS. 21A–21D. Ts mediated suppression of Th activation and proliferation requires the presence of APCs. CD4+ Th and CD8+CD28− Ts cells from the same TCL were activated alone or together either by mAb CD3 (FIGS. 21A, 21B) or allogeneic APCs (FIGS. 21C, 21D). Mouse IgG or autologous APCs were used as controls. Proliferation was determined in a three day assay (FIGS. 21A, 21C), and CD40L expression on CD4+ T cells were analyzed after 6 h of culture (FIGS. 21B, 21D). CPM of triplicate reactions are shown. SD to the mean was less than 10%. The results represent one of three independent experiments.

FIGS. 23A1–23E-5. Early recognition of APCs by Ts is required for suppression of the expression of costimulatory molecules on APCs. APCs used for stimulation were cultures alone (FIGS. 23A-1–23A-5) or with allospecific Th for 48 h (FIGS. 23B-1–23B-5). Ts were added at the initiation of the cultures (FIGS. 23C-1–23C-5), after 6 h (FIGS. 23D-1–23D-5) or after 18 h (FIGS. 23E-1–23E-5). Expression of costimulatory molecules on CD14+ and CD20+ cells were analyzed at the end of the incubation period. Percent of positive cells is indicated. The data are the results of one of three repeat experiments.

FIG. 24. Exogenous IL-2 restores Th reactivity in the presence of Ts. CD4+ Th and CD8+CD28− Ts cells from the same TCL were activated alone or together with allogeneic APCs. rIL-2 (% units/ml) was added to parallel cultures at the initiation of the blastogenesis assay. CPM of triplicate reactions are shown. SD to the mean was less than 10%. The resuklts represent one of three repeat experiments.

FIG. 26. HLA A, B and DR values and split equivalence. Various HLA A loci, HLA B loci and HLA DR loci which may be used as antigens for priming T suppressor cells.

FIGS. 27A–27H. DRB Protein Sequences. Amino acid sequences of DRB proteins correspond to hypervariable regions of HLA-DR B1 antigens. These antigens may be used as allopeptides for priming T suppressor cells (SEQ ID NOS:2–198).

FIG. 29. Amino acid sequences of SLA DRA alleles. These amino acid sequences may be used for generating xenospecific human suppressor T cells in the methods described infra (SEQ ID NOS:199–204).

FIG. 30. Amino acid sequences of SLA DRB alleles. These amino acid sequences may be used for generating xenospecific human suppressor T cells in the methods described infra (SEQ ID NOS:205–213).

FIG. 31. Amino acid sequences of SLA DQA alleles. These amino acid sequences may be used for generating xenospecific human suppressor T cells in the methods described infra (SEQ ID NOS:214–219).

FIG. 32. Amino acid sequences of SLA DQB alleles. These amino acid sequences may be used for generating xenospecific human suppressor T cells in the methods described infra (SEQ ID NOS:220–228).

DETAILED DESCRIPTION OF THE INVENTION

Figure 1A:
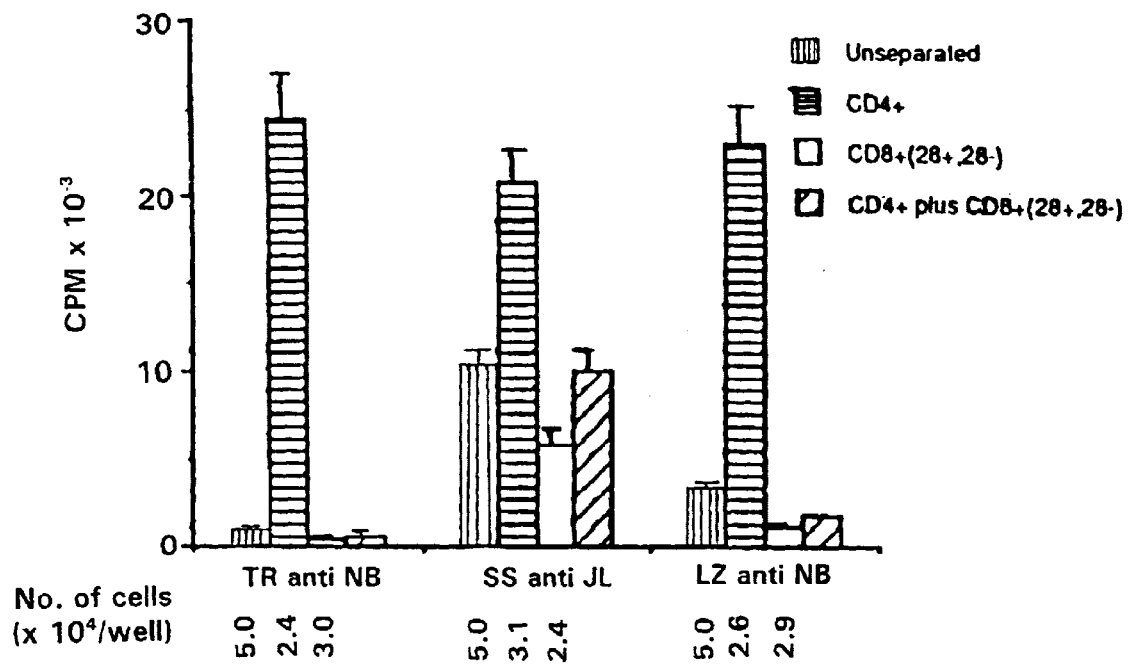
FIGS. 1A–1D. Detection and characterization of $CD8^+$ $CD28^-$ Ts in alloreactive TCLs.

This invention provides a method of generating antigen specific allospecific human suppressor CD8+CD28− T cells which comprises: a) obtaining peripheral blood T cells from a subject; b) stimulating by multiple priming a T cell line from the T cells obtained in step (a) with allogeneic antigen presenting cells (APCs), said APCs expressing an MHC class I antigen recognized by the primed T cell line and an MHC class II antigen recognized by CD4+ T helper cells from said primed T cell line; c) isolating primed CD8+ T cells and CD4+ T helper cells from the T cell line stimulated in step (b); d) isolating primed CD8+CD28− T cells from the isolated primed CD8+ T cells of step (c); e) detecting suppression by the primed CD8+CD28− T cells isolated in step (d) of interaction between the CD4+ T helper cells isolated in step (c) and allogeneic antigen presenting cells (APCs) expressing the same MHC class I antigen and the same MHC class II antigen expressed by the APCs used to stimulate the T cell line of step (b), thereby identifying antigen specific allospecific human suppressor CD8+CD28− T cells; and f) expanding the antigen specific allospecific human suppressor CD8+CD28− T cells identified in step (e), thereby generating the antigen specific allospecific human suppressor CD8+CD28− T cells.

Accordingly, the suppressor cells are obtained by a) isolating first the CD8+ T cells from the antigen-specific T cell lines; and b) isolating next the CD8+CD28− fraction from the CD8+ population above. Since only a small portion of suppressor T cells from step (d) is used for suppression analysis of step (e). Once suppression is detected in step (e) the cells isolated in step (d) may be expanded by techniques known to the skilled artisan, for example by weekly restimulation of the APCs used to stimulate the T cells of step (b) in culture medium containing recombinant human interleukin-2 (IL-2).

In an embodiment of the above-described method of generating antigen specific allospecific human suppressor CD8+CD28− T cells the MHC class I antigen is an HLA-A or HLA-B antigen expressed by the APC used for priming. Antigen specific supressor cells can be generated by T cell priming against any of the existing HLA-A or HLA-B antigens of which there are more than two hundred such antigens. One of skill may select but is not limited to the HLA-A or HLA-B antigens from the group of HLA-A and HLA-B antigens listed in FIG. 26.

In an embodiment of the above-described method of generating antigen specific allospecific human suppressor CD8+CD28− T cells the MHC class II antigen is an HLA antigen selected from the group consisting of HLA-DR, HLA-DQ and HLA-DP. One of skill in the art will recognize that there are hundreds of HLA class II antigens. For example HLA class II antigens may be but are not limited to DRB antigens which may be selected from but are not limited to the group of DRB proteins listed in FIG. 27.

All APCs express two HLA-DR, HLA-DQ and two HLA-DP antigens. It is irrelevant which HLA-class II antigens are expressed by the APCs, in order to generate suppressor T cells. It is important, however, that the response of CD4+ T helper cells to alloegeic APC can be inhibited only by CD8+ T suppressor cells which recognize the MHC class I antigens expressed by the same APC.

This invention provides an antigen specific allospecific human suppressor CD8+CD28+ T cells produced by the method of generating antigen specific allospecific human suppressor CD8+CD28− T cells which comprises: a) obtaining peripheral blood T cells from a subject; b) stimulating by multiple priming a T cell line from the T cells obtained in step (a) with allogeneic antigen presenting cells (APCs), said APCs expressing an MHC class I antigen recognized by the primed T cell line and an MHC class II antigen recognized by CD4+ T helper cells from said primed T cell line; c) isolating primed CD8+ T cells and CD4+ T helper cells from the T cell line stimulated in step (b); d) isolating primed CD8+CD28− T cells from the isolated primed CD8+ T cells of step (c); e) detecting suppression by the primed CD8+ CD28− T cells isolated in step (d) of interaction between the CD4+ T helper cells isolated in step (c) and allogeneic antigen presenting cells (APCs) expressing the same MHC class I antigen and the same MHC class II antigen expressed by the APCs used to stimulate the T cell line of step (b), thereby identifying antigen specific allospecific human suppressor CD8+CD28− T cells; and f) expanding the antigen specific allospecific human suppressor CD8+CD28− T cells identified in step (e), thereby generating the antigen specific allospecific human suppressor CD8+CD28− T cells.

This invention provides a method of generating xenospecific human suppressor CD8+CD28− T cells which comprises: a) obtaining peripheral blood T cells from a human subject; b) stimulating by multiple priming a human T cell line from the T cells obtained in step (a) with xenogeneic mammalian antigen presenting cells (APCs), said APCs expressing a xenogeneic MHC class I antigen and a xenogeneic MHC class II antigen; c) isolating primed human CD8+ T cells and human CD4+ T helper cells from the T cell line stimulated in step (b); d) isolating primed human CD8+CD28− T cells from the isolated primed human CD8+ T cells of step (c); e) detecting suppression by the primed human CD8+CD28− T cells isolated in step (d) of interaction between the human CD4+ T helper cells isolated in step (c) and xenogeneic antigen presenting cells (APCs) expressing the same xenogeneic MHC class I antigen and xenogeneic MHC class II antigen expressed by the xenogeneic APCs used to stimulate the human T cell line of step (b), thereby identifying xenospecific human suppressor CD8+ CD28− T cells; f) expanding the xenospecific human suppressor CD8+CD28− T cells identified in step (e), thereby generating the xenospecific human suppressor CD8+CD28− T cells.

Expansion techniques which may be used to culture cells in step (f) are well known to the ordinary skilled artisan. For example the expansion technique described above for the method of generating antigen specific allospecific human suppressor CD8+CD28− T cells may be used to expand xenospecific human suppressor CD8+CD28− T cells. In an embodiment of the above-described method of generating antigen specific xenospecific human suppressor CD8+ CD28− T cells the xenogeneic antigen presenting cells (APCs) may be mammalian antigen presenting cells (APCs). For example, the APCs may be pig APCs or primate APCs.

In an embodiment of the above-described method of generating xenospecific human suppressor CD8+CD28− T cells, the xenogeneic mammalian antigen presenting cells (APCs) are selected from pig or primate APCs. One of skill in the art will recognize that pig antigens may be selected from numerous SLA antigens class I antigens. The antigens may be selected from but are not limited to the group of SLA DRA, SLA-DRB, SLA-DRQ-A and SLA-DQB listed in FIGS. 29 through 32.

In an embodiment of the above-described method of generating xenospecific human suppressor CD8+CD28− T cells, the xenogeneic MHC class I antigen is selected from the group consisting of swine histocompatibility leukocyte antigen (SLA) class-I and MHC class II antigen is selected from the group consisting of swine histocompatibility leukocyte antigen (SLA) class-II. T cells specific for any SLA class I antigen or class II MHC antigen may be obtained by using said SLA class I or II antigens for priming. The SLA antigens may be expressed by the APCs used for priming. APCs of other mammals including all species of primates may be used according to the above-described method.

This invention provides a xenospecific human suppressor CD8+CD28+ T cells produced by the above-described method of generating xenospecific human suppressor CD8+ CD28− T cells.

This invention provides a method of generating allopeptide antigen specific human suppressor CD8+CD28− T cells which comprises: a) obtaining peripheral blood T cells from a subject; b) stimulating by multiple priming a T cell line from the T cells obtained in step (a) with autologous antigen presenting cells (APCs) pulsed with an allopeptide, said allopeptide comprising an amino acid sequence comprising both MHC class I and MHC class II amino acid sequences wherein the amino acid sequences are binding sequences (motifs) and are recognized by the primed T cell line; c) isolating primed CD8+ T cells and CD4+ T helper cells from the T cell line stimulated in step (b); d) isolating primed CD8+CD28− T cells from the isolated primed CD8+ T cells of step (c); e) detecting suppression by the primed CD8+ CD28− T cells isolated in step (d) of interaction between the CD4+ T helper cells isolated in step (c) and autologous antigen presenting cells (APCs) expressing the same MHC class I and MHC class II binding motifs as expressed by the APCs used to stimulate the T cell line of step (b), thereby identifying allopeptide antigen specific human suppressor CD8+CD28− T cells; and f) expanding the allopeptide antigen specific human suppressor CD8+CD28− T cells identified in step (e), thereby generating the antigen specific human suppressor CD8+CD28− T cells. The identified human suppressor CD8+CD28− T cells are allospecific T suppressor cells. As discussed above any expansion method known to the skilled artisan may be used for expansion in culture of step (f).

In an embodiment of the above-described method of generating the antigen specific human suppressor CD8+ CD28− T cells the allopeptide is a peptide antigen or a whole protein. For example the allopeptide may be selected from an allopeptide corresponding to hypervariable regions of HLA-DR B1 antigens which may be selected from but not limited to the HLA-DR B1 antigens listed in FIG. 27.

This invention provides an antigen specific human suppressor CD8+CD28− T cells produced by the above-described method of generating the antigen specific human suppressor CD8+CD28− T cells.

This invention provides a method of determining whether a level of immunosuppresant therapy given to a subject undergoing the level immunosuppression therapy requires a reduction which comprises: a) obtaining a blood sample from the subject; and b) determining the presence of T suppressor cells present in the sample, the presence of T suppressor cells indicating that the subject requires the reduction of immunosuppresant therapy.

The presence of T suppressor cells in the sample may be determined in step (b) as follows: CD4+ T cells and CD8+ T cells are isolated from the recipient's (the subject undergoing the level immunosuppression therapy) blood. The CD8+CD28− T cell subset is isolated from the CD8+ population of T cells. II. Cultures are set up as follows: I. Recipient CD4+ Th plus donor APCs (depleted of CD2+ cells); Recipient CD8+CD28− T cells plus donor APCs (depleted of CD2+ cells); Recipient CD4+ Th plus CD8+ CD28− T cells plus donor APCs. In control cultures donor APCs are replaced by APCs from a subject with different HLA-class I antigens. III. APCs are stained with mAb specific for CD19 and CD14 (PE, and with mAb specific for CD80 (FITC). IV. Suppression is considered to be present when the level of CD80 expresion on donor APCs is 209% lower in cultures containing CD4+ Th and CD8+CD28− Ts than in cultures without Ts.

The presence of Ts in three consecutive samples of blood obtained at one month intervals indicates that the patient (recipient, i.e. subject undergoing the level immunosuppression therapy) is "accepting" the graft (transplant) and that immunosuppression can be tapered down, i.e. decreased.

In an embodiment of the above-described method of determining whether a level of immunosuppresant therapy given to a subject undergoing the level immunosuppression therapy requires a reduction the T suppressor cells are suppressor CD8+CD28− T cells.

This invention provides a method of reducing the risk of rejection of an allograft in a subject undergoing immunosuppression therapy which comprises: a) obtaining a blood sample from the subject; b) removing T suppressor cells from the blood sample; c) expanding the T suppressor cells of step (b); and d) reintroducing the expanded T suppressor cells of step (b) into the subject. In an embodiment of the above-desribed method of reducing the risk of rejection of an allograft in a subject undergoing immunosuppression therapy, the expansion in step (c) may be to produce an amount of approximately $10^7$ T suppressor cells. One of skill is not limited to expanding the T suppresor cells to this amount of cells. In another embodiment of the above-described method of reducing the risk of rejection of an allograft in a subject undergoing immunosuppression therapy the T suppressor cells are suppressor CD8+CD28− T cells.

This invention provides a method of reducing the level of rejection of an allograft in a subject undergoing immunosuppression therapy which comprises administering to the subject the T suppressor cells produced by the above-described method of generating antigen specific allospecific human suppressor CD8+CD28− T cells, thereby preventing rejection of the tissue or organ transplant in the subject.

This invention provides a method of reducing the level of rejection of an allograft in a subject undergoing immunosuppression therapy which comprises administering to the subject the T suppressor cells produced by the above-described method of generating allopeptide antigen specific human suppressor CD8+CD28− T cells, thereby preventing rejection of the tissue or organ transplant in the subject.

This invention provides a method of preventing rejection of an allograft in a subject which comprises: a) obtaining a blood sample from the subject; b) removing T suppressor cells from the blood sample; c) expanding the T suppressor cells of step (b); and d) reintroducing the expanded T suppressor cells of step (b) into the subject, thereby preventing the rejection of the allograft in the subject.

This invention provides a method of preventing rejection of an allograft in a subject which comprises administering the T suppressor cells produced by the above-described method of generating antigen specific allospecific human suppressor CD8+CD28− T cells to the subject, thereby preventing rejection of the allograft in the subject.

This invention provides a method of preventing rejection of an allograft in a subject which comprises administering the T suppressor cells produced by the above-described method of generating allopeptide antigen specific human suppressor CD8+CD28− T cells to the subject, thereby preventing rejection of the allograft in the subject.

This invention provides a method of preventing rejection of a xenograft in a subject which comprises: a) obtaining a blood sample from the subject; b) removing T suppressor cells from the blood sample; c) expanding the T suppressor cells of step (b); and d) reintroducing the expanded T suppressor cells of step (b) into the subject, thereby preventing the rejection of the xenograft in the subject.

In an embodiment of the above-described method of preventing rejection of a xenograft in a subject the T suppressor cells are suppressor CD8+CD28− T cells. The suppressor CD8+CD28− T cells have to be primed with APCs from the donor, i.e. to specific xeno antigens before step (c), e.g. MHC class I antigens. CD8+CD28− T cells acquire T suppressor function only after priming with APCs expressing the donor's MHC class I antigens.

This invention provides a method of preventing rejection of a xenograft in a subject which comprises administering the T suppressor cells produced by the above-described method of generating xenospecific human suppressor CD8+ CD28− T cells to the subject, thereby preventing rejection of the xenograft in the subject.

This invention provides a method of preventing autoimmune disease in a subject which comprises: a) obtaining a blood sample from the subject; b) removing T suppressor cells from the blood sample; c) expanding the T suppressor cells of step (b); and d) reintroducing the expanded T suppressor cells of step (b) into the subject, thereby preventing autoimmune disease in the subject.

In an embodiment of the above-described method of preventing autoimmune disease in a subject the expansion in step (c) may be to produce an amount of approximately $10^7$ T suppressor cells. One of skill is not limited to expanding the T suppresor cells to this amount of cells. In another embodiment of the above-described method of preventing autoimmune disease in a subject the T suppressor cells are suppressor CD8+CD28− T cells.

This invention provides a method of preventing autoimmune disease in a subject which comprises administering the T suppressor cells produced by the above-described method of generating antigen specific allpspecific human suppressor CD8+CD28− T cells to the subject, thereby preventing autoimmune disease in the subject.

Suppressors CD8+CD28− T cells must be primed to acquire antigen specific function. The possible antigens which may be used for priming includes all peptides known to elicit an autoimmune disease This invention provides a method of preventing autoimmune disease in a subject which comprises administering the T suppressor cells produced by above-described method of generating allopeptide antigen specific human suppressor CD8+CD28− T cells to the subject, thereby preventing autoimmune disease in the subject.

This invention provides a vaccine comprising allospecific T suppressor cells stimulated by APCs expressing an MHC class I antigen and an MHC class II antigen which T suppressor cells suppress an interaction between CD4+ T helper cells and allogeneic antigen presenting cells (APCs) expressing the same MHC class I antigen and the same MHC class II antigen expressed by the APCs used to stimulate the allospecific T suppressor cells.

In an embodiment of the above-described vaccine comprising allospecific T suppressor cells the APCs are allogeneic APCs said APCs expressing an MHC class I antigen recognized by the T suppressor cells and an MHC class II antigen recognized by allogeneic CD4+ T helper cells. In another embodiment of the above-described vaccine the APCs are APCs pulsed with an allopeptide, said allopeptide comprising an amino acid sequence having both MHC class I and MHC class II binding motifs wherein both motifs are recognized by the stimulated T suppressor cells. In an embodiment said allopeptide comprise an amino acid sequence comprising both MHC class I and MHC class II amino acid sequences wherein the amino acid sequences are binding sequences (motifs) and are recognized by the primed T cell line. In an embodiment of the above-described vaccine the T suppressor cells are suppressor CD8+CD28− T cells.

This invention provides a vaccine comprising xenospecific T suppressor cells stimulated by APCs expressing a xenogeneic MHC class I antigen and a xenogeneic MHC class II antigen which xenospecific T suppressor cells suppress an interaction between CD4+ T helper cells and xenogeneic antigen presenting cells (APCs) expressing the same xenogeneic MHC class I antigen and xenogeneic MHC class II antigen expressed by the APCs used to stimulate the xenospecific T suppressor cells.

In an embodiment of the above-decribed vaccine comprising xenospecific T suppressor cells wherein the T suppressor cells are suppressor CD8+CD28− T cells.

This invention will be better understood from the Experimental Details which follow. However, one skilled in the art will readily appreciate that the specific methods and results discussed are merely illustrative of the invention as described more fully in the claims which follow thereafter.

METHODS AND RESULTS

First Series of Experiments

Abbreviations used herein are: CsA—Cyclosporine; TCL—T cell line; Th—T helper cell; $T_s$—T suppressor cells TNF—tumor necrosis factor; PIN—Perforin-induced necrosis; PBMC—perpheral blood moncleare cells; PE—Phycoerythrin; MLR—Mixed lymphocyte reaction; APC—antigen-presenting cell.

METHODS

HLA Typing. Lymphocytes were typed for HLA class I and class II antigens by conventional serology. The class II genotype of the cells was determined by genomic typing of in vitro amplified DNA with sequence-specific oligonucleotide probes for DRB1, DQA1 and DQB1.

Generation of alloreactive T cell lines (TCL). Perpherial Blood mononuclear cells (PBMC) from healthy blood volunteers were separated from buffy coats by Ficoll-Hypaque centrifugation. Responding PBMCs ($1 \times 10^6$/ml) were stimulated in 24-well plates with irradiated (1600 rad) APCs ($0.5 \times 10^6$/ml) obtained from allogeneic PBMC by depletion of $CD2^+$ cells. Cells were co-cultured for 7 days in complete medium (RPMI 1640 supplemented with 10% human serum, 2 mM L-glutamine and 50 g/ml gentamicin) (GIBCO, N.Y.). After 7 days responding cells were collected, washed and rechallenged with the original stimulating cells. Three days later rIL-2 (Boehringer Mannheim, Ind.) was added (10 $\mu$g/ml) and the cultures were expanded for an additional 4 days. Blastogenesis assays were performed on day 14. The HLA phenotypes of the responders and stimulators used for generating the seven different T cell lines used in these experiments are shown in Table 1. The xenoreactive TCL were generated by the same method using irradiated pig PBMC as stimulating cells.

TABLE 1

HLA Phenotypes of the Blood Donors

| Donor ID | A | B | DR | DQA | DQB |
|---|---|---|---|---|---|
| TR | 1, 2 | 7, 37 | 0701, 1501 | 0102, 0201 | 0201, 0602 |
| RV | 31, 33 | 35, 49 | 0701, 1501 | 0102, 0201 | 0201, 0602 |
| NB | 3, 24 | 27 | 0101, 0401 | 0101, 0301 | 0501, 0302 |
| SS | 26 | 35, 52 | 0402, 1502 | 0103, 0103 | 0302, 0601 |
| JL | 3, 29 | 44, 57 | 0701, 0701 | 0201, 0201 | 0201, 0201 |
| GC | 3, 74 | 45, 49 | 0801, 0801 | 0401, 0401 | 0402, 0402 |
| ST | 2, 24 | 13, 38 | 0701, 1301 | 0201, 0103 | 0201, 0603 |
| PO | 29, 31 | 44, 61 | 0701, 1101 | 0201, 0501 | 0201, 0301 |
| LZ | 2, 11 | 39, 67 | 1101, 1201 | 0501, 0501 | 0301, 0301 |

Cell separation and culture. The $CD4^+$ and $CD8^+$ T cell subsets were isolated from PBMC by negative selection using Dynal $CD4^+$ and $CD8^+$ magnetic beads (Dynal, N.Y.). Goat-anti-mouse Dynal beads were coupled with mAb anti-CD28 (Becton Dickinson, Calif.) according to the manufacturer's instructions. To separate $CD28^+$ and $CD28^-$ T cells from $CD8^+$ T cell suspensions, isolated $CD8^+$ T cells ($1 \times 10^7$/ml) were incubated with $4 \times 10^7$ CD28 beads for 20 min at 4° C. The suspension was then placed on a magnetic particle concentrator for 2–3 minutes. The unbound cells ($CD8^+$ $CD28^-$) were transferred to another tube and washed three times in complete medium. The bound $CD8^+CD28^+$ T cell population was detached from the beads by overnight incubation at 37° C. Cells were collected, washed and resuspended in complete culture medium. Cytofluorographic analysis showed that the purity of $CD4^+$, $CD8^+$ and $CD8^+$ $CD28^+$ suspensions was >96%. The $CD8^+CD28^-$ population contained less than 7% $CD28^+$ T cells.

Flow Cytometry. T cell subsets were defined using mAb CD4-PerCP, CD8-FITC, CD28-phycoerythrin from Becton Dickinson Immunocytometry System, Calif. Cell suspensions were phenotyped prior to use in blastogenesis assays using a FACScan flow cytometer instrument (BDIS) equipped with a 15 mm Argon Laser. To study the effect of $T_h$ and $T_s$ on the expression of B7 molecules on allogeneic APC, $CD4^+$ and $CD8^+$ T cells were isolated from alloreactive TCL by positive selection using CD4 and CD8 magnetic beads. The $CD8^+CD28^-$ subset was obtained from the CD8 population by negative selection using beads coupled with anti-CD28 mAB. $T_h$ cells were cultured with APC from the specific stimulator at a 5:1 ratio. $T_s$ were cultured with the APC at a 1:1 ratio. In mixed cultures containing $T_h$, $T_s$, and allogeneic APC the ratio was 5:1:1. APC to which no T cells were added served as a control. After 24 hours of incubation cells were stained with saturating amounts of mAbs recognizing CD3-PerCP, CD80-PE (Becton Dickinson) and CD86-FITC (Pharmingen, Calif.). CD3$^+$ T cells were gated out, and the remaining cells were analysed using CellQuest software on a 650 Apple Macintosh Computer. Five parameter analysis (forward scatter, side scatter and 3 fluorescence channels) were used for list mode data analysis. FL3 channel was used as fluorescence trigger, FL1 and FL2 as analysis parameters. Mouse IgG (γ1 and γ2) reagents were used as isotype controls for non-specific binding of test reagents and as markers for delineating the positive and negative populations. CaliBrite flow cytometer beads (Becton Dickinson) and FACSComp program were used for calibration of the cytometer.

Flow Cytometry Analysis of Apoptosis. The capacity of alloreactive CD8$^+$CD28$^-$ T cells to induce apoptosis of CD2-depleted allogeneic APC was tested by flow cytometry using annexin V as a marker for apoptotic cells. APCs were incubated for 4 hrs or 24 hrs at 370 with $T_h$, $T_s$, and mixtures of $T_h$ and $T_s$. The ratio between T cells and APC was 5:1. Cells were stained with mABs recognizing CD20-PE or CD4-PE (Becton Dickinson). After 15 min. of incubation cells were washed and stained with annexin V-FITC and propidium iodide according to the manufacturer's instructions (R&D Systems, Minneapolis, Minn.). Log FL2 (PE) versus Side scatter parameters were used to gate on CD20$^+$ or CD4$^+$ cells. Log FL1 (FITC) versus FL3 (PI) dot plot of the gated cells were used for cell apoptosis and necrosis analysis.

Proliferation Assays. Unseperated responding T cells were tested for blastogenesis at a concentration of 5×10$^4$/well. T cell subsets sorted from the same cultures (CD4$^+$ T, CD8$^+$ T, CD8$^+$CD28$^+$ T, or CD8$^+$CD28$^-$ T) were tested at a concentration that corresponded to their frequency in the unseperated population as determined by flow cytometry analysis of the TCL and of each population sorted. In experiments which required no comparison between unseperated TCL and T cell subsets, CD4+ and CD8+ T were tested at 2.5×10$^4$ cells/well and CD8$^+$CD28$^-$ T cells were tested at 1.25×10$^4$ cells/well. Cell concentrations were adjusted after establishing the purity of the fraction by flow cytometry. In all blastogenesis assays the concentration of APC used for stimulation was 5×10$^4$/well. After 48 hr of incubation, the cultures were pulsed with [$^3$H] Thymidine and harvested 18 hr later. [$^3$H] Thymidine incorporation was determined by scintillation spectrometry in an LK Betaplate counter. Mean cpm of the triplicate cultures and the standard deviation to the mean were calculated.

The percent suppression was calculated as follows: % suppression=[1−(c.p.m. in mixed cultures of activated CD4$^+$ $T_h$ and CD8$^+$CD28$^-$ $T_s$)/(c.p.m. in cultures with activated CD4$^+$ $T_h$)]×100

The effect of mAb anti-CD28 (clone 37407.11 from R & D Systems, Minneapolis, Minn.) and anti-CTLA4 (clone BN 13 from Coulter, Miami, Fla.) on the suppressor effect was tested by adding the mAb to the cultures (1 μg/ml) at the initiation of the blastogenesis assay.

Statistical Analysis. Statistical analysis of the results was performed using BMDP statistical software. Analysis of variance to assess significance of group differences (ANOVA) followed by Tukey's method for multiple comparison was applied to flow cytometry results. Correlation coefficients were obtained using Linear Regression Analysis.

Results

Suppression of alloreactivity is mediated by CD8$^+$CD28$^-$ T cells and is dose-dependent. TCL were generated by stimulating PBMC from HLA unrelated individuals with irradiated APCs from blood donors mismatched from the responders for both HLA-class I and class II antigen. The HLA phenotypes of the blood donors used in this study are shown in Table 1. Although all TCL showed strong reactivity after primary and secondary stimulation, they displayed low reactivity when challenged for the third time in 3-day blastogenesis assays.

However, strong reactivity of CD4$^+$ T cells to the specific stimulator was restored when CD8$^+$ T cells were depleted from the TCL. CD8$^+$ T cells from the same culture showed little blastogenic response against the stimulator. When the cultures were reconstituted by mixing together the CD4$^+$ and CD8$^+$ subsets of cells, at the original ratio, the response of CD4$^+$ Th to the allogeneic priming cells was inhibited (FIG. 1A). The percent inhibition by CD8$^+$ $T_s$ from different TCL ranged from 50 to >90% (mean 76%+23%). These experiments indicate that the CD8$^+$ fraction of the TCL contains a population of Ts which suppress the proliferative response of CD4$^+$ $T_h$ against the specific stimulator.

Figure 1B:
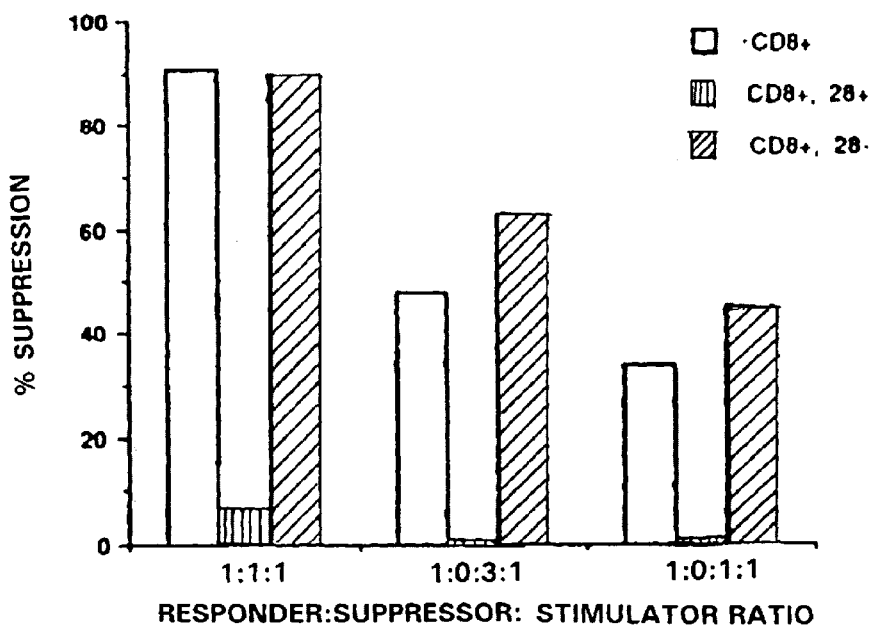

To characterize the population of CD8$^+$ T cells which mediate suppression, the CD8$^+$CD28$^+$ and $^+$CD8 CD28 populations from an alloreactive TCL (TCL-LZ anti-NB) were separated and tested for their capacity to inhibit the proliferative response of CD4$^+$ T cells from the same TCL against the specific stimulator (NB). The CD8$^+$CD28$^-$ T cells exhibited dose-dependent suppression of the CD4$^+$ T cell response to the specific allostimulator, while the CD8$^+$CD28$^+$ T cells had no inhibitory effect (FIG. 1B). Naive CD8$^+$ T cells from the peripheral blood of the same responder had no inhibitory effect on the reactivity of CD4 T cells from this TCL (data not shown).

Since the kinetics of proliferative responses can shift under certain culture conditions the proliferative response of Th cells to allogeneic APC was measured in the presence or absence of $T_s$ cells, by harvesting the cultures after 24, 48, 72, 96, and 120 hours of incubation. The data in Table 2 show that suppression of Th proliferation became detectable after 48 hours. The magnitude of the suppressor effect increased over the next 3 days of incubation. Because the peak of Th blastogenesis occured on day 3 all suppressor assays were harvested after 72 hours of incubation.

To establish whether killing of stimulating cells by alloactivated CD8+ T cells contributes to the suppressive effect, the ability of separated CD8$^+$CD28$^+$ and CD8$^+$CD28$^-$ T cells to lyse PHA-activated target cells from the specific stimulator was tested. $^{51}$Cr release assays showed that the cytotoxic activity resided entirely in the CD8$^+$CD28$^+$ T cell population (data not shown).

Figure 1C:
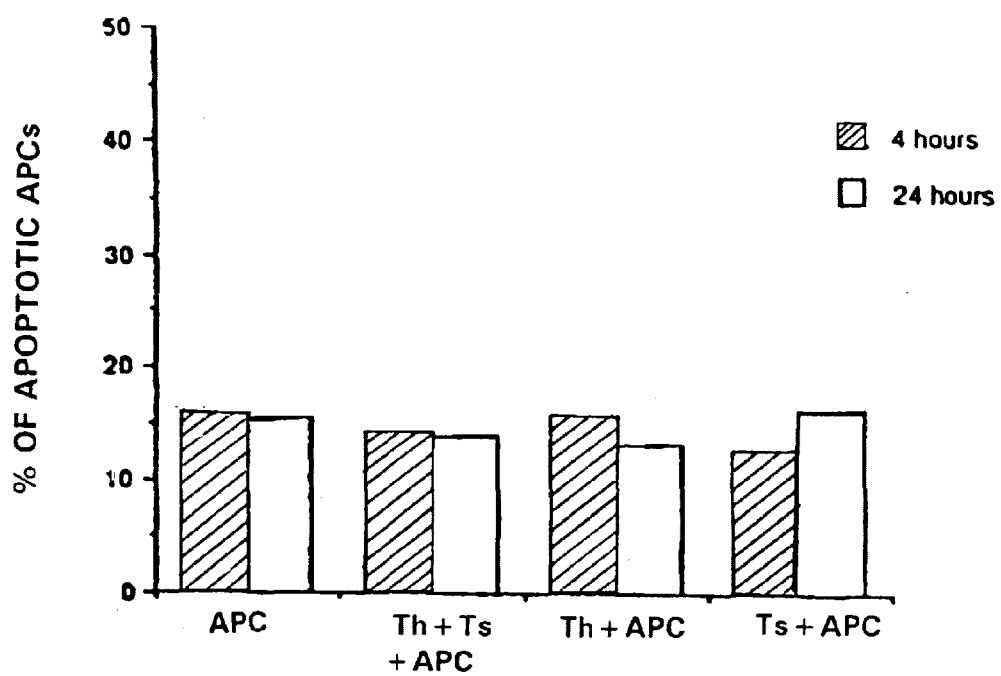

Since lymphocyte-mediated cytotoxicity maybe caused not only by perforin induced necrosis (PIN) of the target but also by PIN/granzyme induced apoptosis (14) the capacity of $T_s$ to cause apoptosis of allogeneic target cells was tested. No evidence of $T_s$-induced apoptosis was found. The percent apoptotic APC was similar in cultures to which Ts cells were added and in cultures containing only APC or $T_h$ and APC (FIG. 1C). Also $T_s$ did not cause apoptosis of $T_h$ as the percentage of annexin V positive $T_h$ was the same in cultures with or without $T_s$ (data not shown). Hence the suppressive activity exhibited by allostimulated CD8$^+$CD28$^-$ T cells on the proliferative response of CD4$^+$ T cells is not caused by killing of the stimulating cell targets or by killing of Th cells.

TABLE 2

Kinetics of the responses of $T_h$ and $T_s$ cells

| | ($^3$H) Thymidine incorporation (mean c.p.m. ± SD) | | | | | |
|---|---|---|---|---|---|---|
| Incubation | $T_h$ | | $T_s$ | | $T_h + T_s$ | |
| time (h) | LZ | NB | LZ | NB | LZ | NB |
| 24 | 14,190 ± 986 | 17,840 ± 1532 | 2315 ± 204 | 3796 ± 284 | 13,806 ± 1067 | 16,396 ± 1353 |
| 48 | 3081 ± 274 | 31,783 ± 2654 | 454 ± 29 | 3529 ± 310 | 4,143 ± 342 | 16,878 ± 1625 |
| 72 | 599 ± 57 | 31,673 ± 2015 | 92 ± 8 | 970 ± 67 | 491 ± 42 | 7606 ± 548 |
| 96 | 1610 ± 135 | 23,372 ± 1763 | 57 ± 4 | 155 ± 14 | 162 ± 12 | 780 ± 67 |
| 120 | 145 ± 14 | 15,940 ± 1032 | 50 ± 3 | 84 ± 7 | 96 ± 7 | 820 ± 75 |

CD4$^+$ $T_h$ cells from TCL (LZ anti-NB) were tested for reactivity to specific target cells in the absence or presence of CD8$^+$CD28$^-$ $T_s$ cells derived from the same TCL. The cultures were harvested at 24, 48, 72, 96, and 120 h after initiation.

Figure 1D:
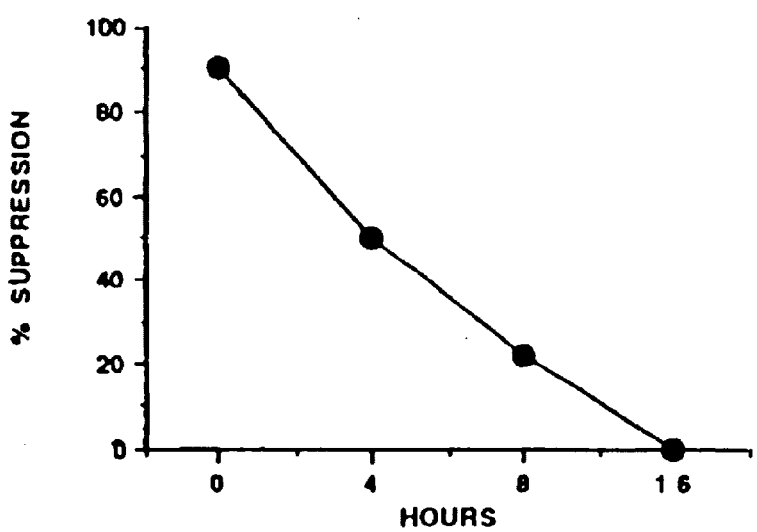

Suppression of CD4$^+$ T cell alloreactivity by allostimulated CD8$^+$CD28$^-$ T cells is an early event. To investigate the kinetics of the suppressive effect, CD8$^+$CD28$^-$ T cells were isolated from an alloreactive TCL (TR anti-NB) and added to CD4$^+$ T cells from the same TCL at the initiation of the blastogenesis assay or after 4, 8 or 16 hours. Results obtained on day 3 showed that suppression was highest (90%) when CD8$^+$CD28$^-$ T cells were added at the initiation of the cultures (FIG. 1D). When $T_s$ were added 4 or 8 hours after exposure of CD4$^+$ T cells to the specific stimulator, the inhibitory activity decreased to 50 and 20 percent, respectively. No inhibitory effect was observed when the addition of Ts was delayed by 16 hours after activation of CD4$^+$ T cells. The correlation between the time when Ts were added and their inhibitory effect was statistically significant (r=0.953, p<0.05). This indicates that suppression of specific reactivity of $T_h$ cells by activated CD8$^+$CD28$^-$ T cells is an early event.

In an attempt to determine which surface molecule(s) and lymphokines may play a role in suppression we performed blocking experiments in which various mAbs were added to the cultures at the initiation of the blastogenesis assay. Antibodies to IL-4, IL-10 and (TNF)-β did not block the suppressive activity of CD8$^+$CD28$^-$ T cells, indicating that these cytokines are not the mediators of the inhibitory effect. The addition of anti-HLA-class I mAb to the cultures, however, reduced the amount of suppression, indicating that allorecognition of HLA class I antigens by Ts is required for suppression to occur (data not shown).

Antigenic specificity of alloactivated CD8$^+$CD28$^-$ $T_s$. To determine the nature of the HLA-antigens recognized by CD8$^+$CD28$^-$ $T_s$, APC sharing with the original priming cells HLA-class II (required for responder CD4$^+$ T cell activation), or both HLA class I and class II antigens were used as stimulators in suppressors assays. One of the six representative experiments is described below.

Figure 2A:
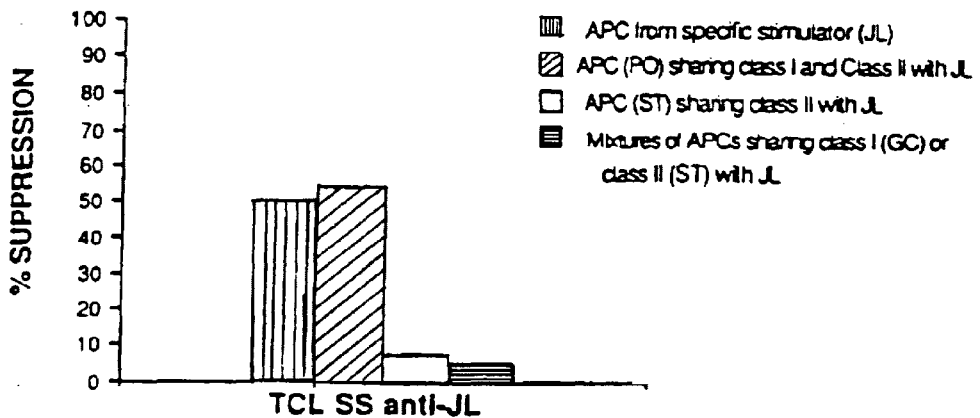
FIGS. 2A–2B. Antigenic specificity of $CD8^+CD28^-$ T suppressor cells.

Ts obtained from TCL SS-anti-JL inhibited by 51% the response of separated CD4$^+$ T cells to the original stimulator (JL). Reactivity against other APC (PO) sharing both HLA-class I and class II antigens was equally suppressed, while the response to APC (ST) sharing only class II antigens with the specific stimulator was not affected (FIG. 2A). Hence, CD8$^+$CD28$^-$ $T_s$ recognize specifically HLA-class I antigens expressed by the APC used for in vitro immunization.

To establish whether APCs must co-express the target antigens recognized by CD4$^+$ Th and CD8$^+$CD28$^-$ Ts for suppression to occur, mixtures of two APC, sharing with the original priming cells either class II (ST) or class I (GC) antigens (but not both) were used for stimulation. There was no inhibition of CD4$^+$ Th reactivity by CD8$^+$CD28$^-$ $T_s$ in these blastogenesis assays, indicating that suppression requires cell-to-cell interaction between CD4$^+$ $T_h$, CD8$^+$ Ts and allogeneic APC expressing the class I and class II antigens against which the T cells were primed (FIG. 2A).

Figure 2B:
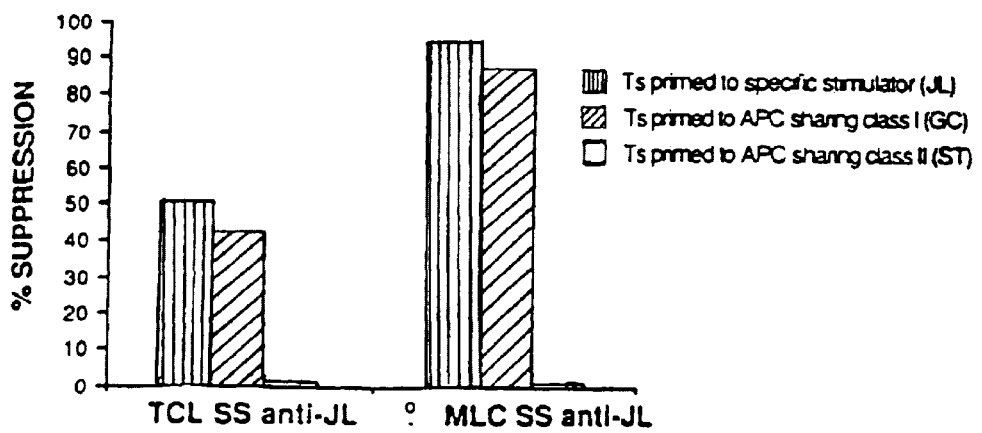

To further substantiate the conclusion that CD8$^+$CD28$^-$ Ts recognize HLA-class I antigens on allogeneic APC, CD4$^+$ T cells from TCL SS-anti-JL were mixed with autologous CD8$^+$CD28$^-$ Ts from other TCLs which had been primed against APC sharing with the original stimulator (JL) either HLA-class I (GC) or class-II (ST) antigens (FIG. 2b). Suppression was induced by CD8$^+$CD28$^-$ T cells (TCL SS-anti-GC) primed against shared HLA-class I antigen(s) (GC). CD8$^+$CD28$^-$ T cells from a TCL (TCL SS anti-ST) primed against shared HLA-DR, but different class I alloantigens (ST), had no suppressive effect. Hence, Ts generated by allostimulation are allorestricted by HLA-class I antigens.

To determine whether CD8$^+$CD28$^-$ $T_s$ can also inhibit the recognition phase of the MLC response and whether such an effect is allo-MHC-class I restricted, alloactivated CD8$^+$CD28$^-$ T cells were added to a primary MLC at the initiation of the cultures. For this MLC, naive CD4$^+$ T cells obtained from peripheral blood (SS) were tested as responders against one stimulator (JL). Ts from the three TCL used in the experiment described above were tested for inhibitory activity. Only Ts which had been activated against the allogeneic stimulator used for the primary MLC (JL) or against APC sharing with JL an HLA-class I antigen (GC) were able to inhibit the primary MLC. CD8$^+$CD28$^-$ T cells from a TCL primed against stimulating cells sharing with JL HLA-class II but not class I antigens (ST) had no suppressor effect (FIG. 2B). These data indicate that alloactivated CD8$^+$CD28$^-$ T cells which recognize HLA-class I antigens specifically suppress the activation of CD4$^+$ T cells via the direct recognition pathway.

Lack of MHC restriction of $T_h$–$T_s$ interaction. The interaction between alloreactive CD4$^+$ $T_h$ and CD8$^+$CD28$^-$ $T_s$ may require T cell recognition of peptide(s) presented by self HLA-class I or class II antigens expressed by the responding or suppressing T cell population. To examine this possibility we generated alloreactive TCLs by priming T cells from three individuals (TR, RV and LZ) against the same allogeneic APC (NB). These three responders shared with each other either class I or class II antigens: RV shared with TR HLA-DR and DQ but not HLA-A, B; LZ shared with TR only HLA-A2. CD4$^+$ T cells from one of these TCLs (TR anti-NB) were next tested in 3 day blastogenesis assays for reactivity against APC from the specific stimulator. The proliferative response of CD4⁺ T cells was inhibited with equal efficiency by autologous and allogeneic CD8+CD28− T cells which had been primed to the same stimulator. Thus, the regulatory effect of CD8⁺CD28⁻ T cells on CD4⁺ responding T cells is not restricted either by the HLA-class I or class II antigens which they express (Table 3).

Figures 1, 19A:
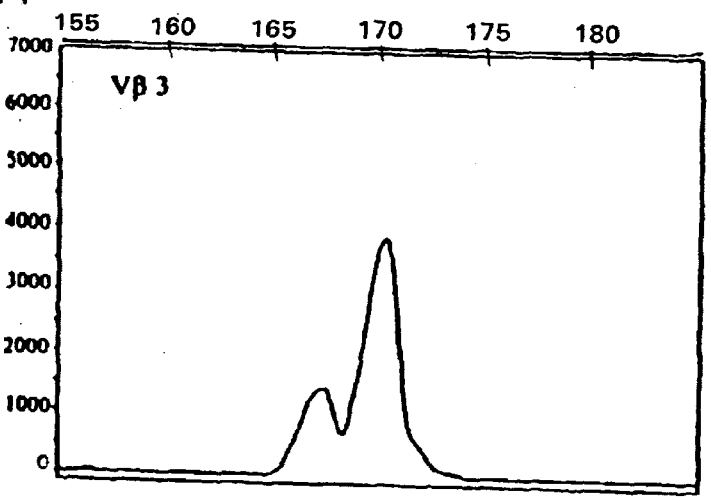
Figures 2, 19A:
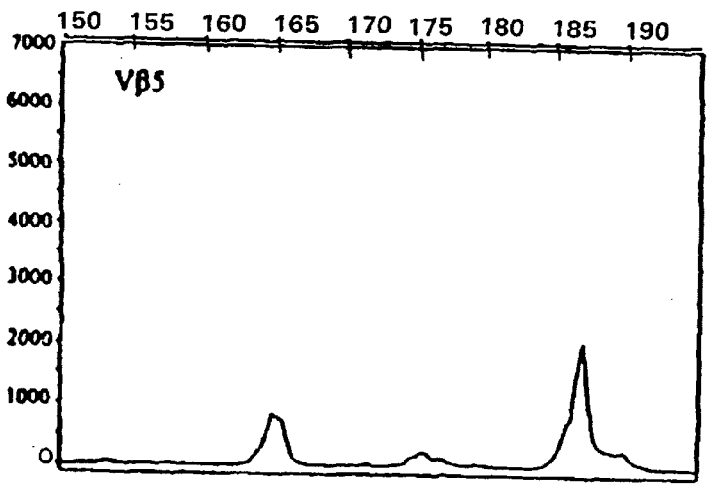
Figures 3, 19A:
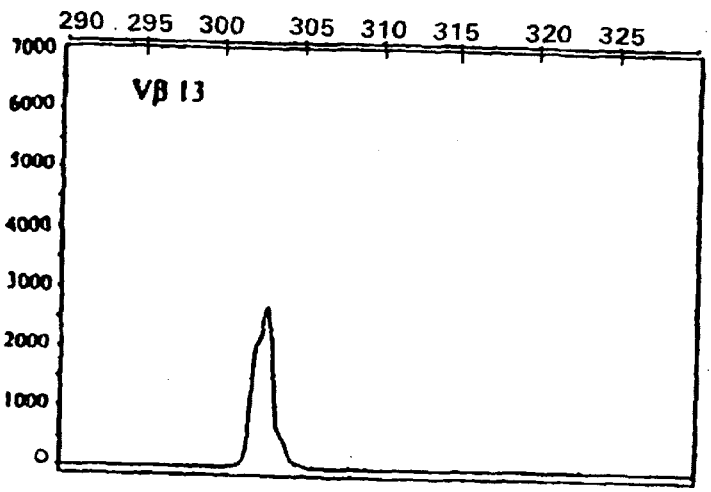

Suppression of xenoreactivity by CD8⁺CD28⁻ T cells. The finding that the direct recognition pathway of alloreactivity can be suppressed specifically by activated CD8⁺ CD28⁻ T cells has important implications for specific inhibition of allograft immunity. To determine whether in vitro educated T cells can also inhibit direct recognition of xenogeneic target cells, we generated xenoreactive TCLs by priming human PBMC with irradiated PBMC from a pig. Responding cells were primed on day 0 and restimulated on day 7 with pig PBMC. IL-2 was added on day 10, and the cultures were tested on day 14 for reactivity against pig PBMC. While the non-fractionated TCL showed low blastogenic responses, the purified CD4⁺ subset showed strong reactivity to pig stimulating cells in 3-day blastogenesis assays. Neither unseparated CD8⁺ T cells or separated CD8⁺CD28⁻ T cells proliferated in response to the priming cells. When added to CD4⁺ responding cells at the beginning of the assay both CD8⁺ and CD8⁺CD28⁻ T cells strongly inhibited the proliferative response (FIG. 3). These results were confirmed in a large series of experiments. Experiments using inbred strains of swine showed that $T_s$ were xenorestricted by MHC-class I antigens (see Third Series of Experiments).

TABLE 3

Lack of MHC Restriction of T Helper-Suppressor Cell Interactions

| CD4⁺ T responding cells | CD + CD28 − $T_s$ | [³H] Thymidine Incorporation (mean cpm) Stimulators | |
|---|---|---|---|
| | | TR | NB |
| TCL TR anti-NB | | 1,159 ± 80 | 24,454 ± 1960 |
| TCL TR anti-NB | TCL TR anti-NB | 689 ± 50 | 611 ± 40 |
| TCL TR anti-NB | TCL RVᵃ anti-NB | 4,199 ± 370 | 1,179 ± 90 |
| TCL TR anti-NB | TCL LZᵇ anti-NB | 4,271 ± 280 | 785 ± 80 |

ᵃSharing with TR HLA-DR, and DQ but not HLA-A and B.
ᴮ*Sharing with TR only HLA-A2.
CD4⁺ T cells from an alloreactive TCL (TR anti-NB) were tested for specific alloreactivity in the presence of CD8⁺ CD28⁻ T cells from the same TCL or from other TCLs which have been generated by priming PBMC from unrelated blood donors against the same allogeneic stimulator.

These data indicate that human CD8⁺CD28⁻ T cells can be educated in vitro to suppress the response of CD4⁺ T cells against xenogeneic target cells.

Figure 4A:
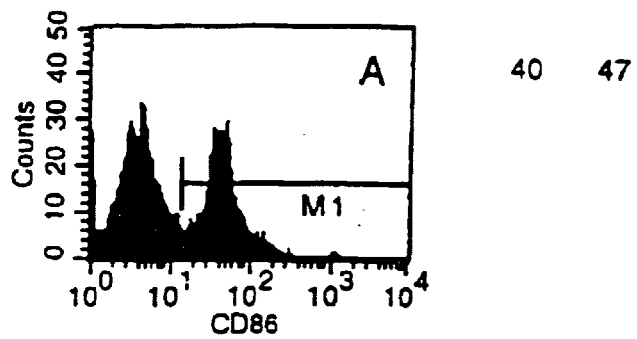
FIGS. 4A–4H. Expression of CD80 and CD86 on allostimulatory APC. CD2$^-$ depleted APCs from JL (the specific stimulator of TCL SS-anti-JL) were cultured for 24 hours without T cells (FIGS. 4A and 4B), with CD4$^+$ T cells from SS-anti-JL (FIGS. 4C and 4D), purified CD8+CD28− T cells from SS anti-JL (FIGS. 4E and 4F) and both CD4$^+$ and CD8$^+$CD28$^-$ T cells (FIGS. 4G and 4H). Three-color flow cytometry was performed using mAbs anti-CD3 (for gating out the T cells), anti-CD80 and anti-CD86. Percent positive (i) and mean fluorescence intensity (MFI) of the positively staining population are indicated.
Figure 4B:
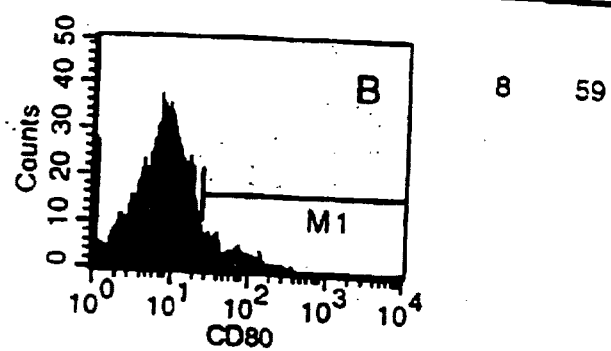
Figure 4C:
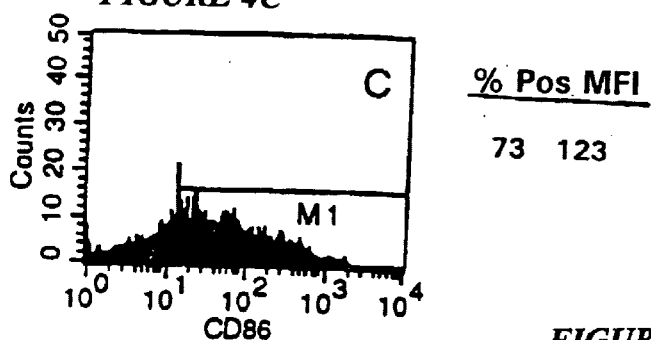
Figure 4D:
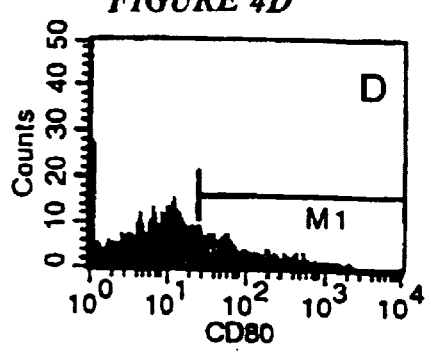
Figure 4E:
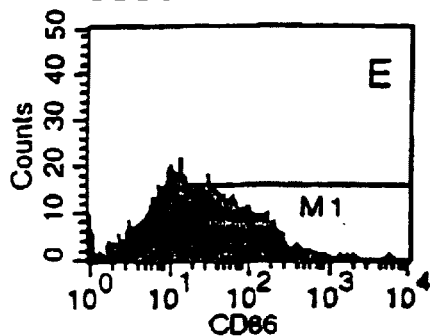
Figure 4F:
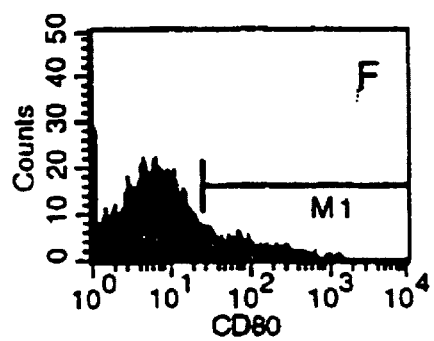
Figure 4G:
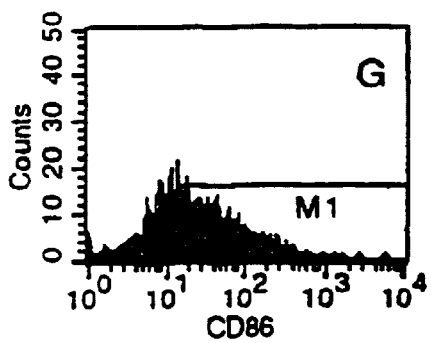
Figure 4H:
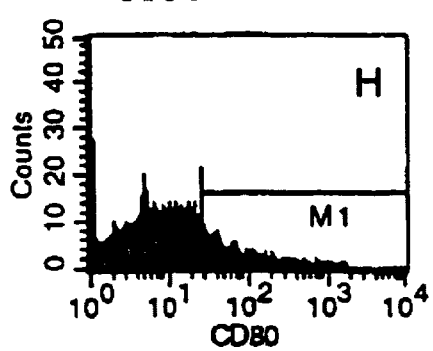
Figures 4, 19A:
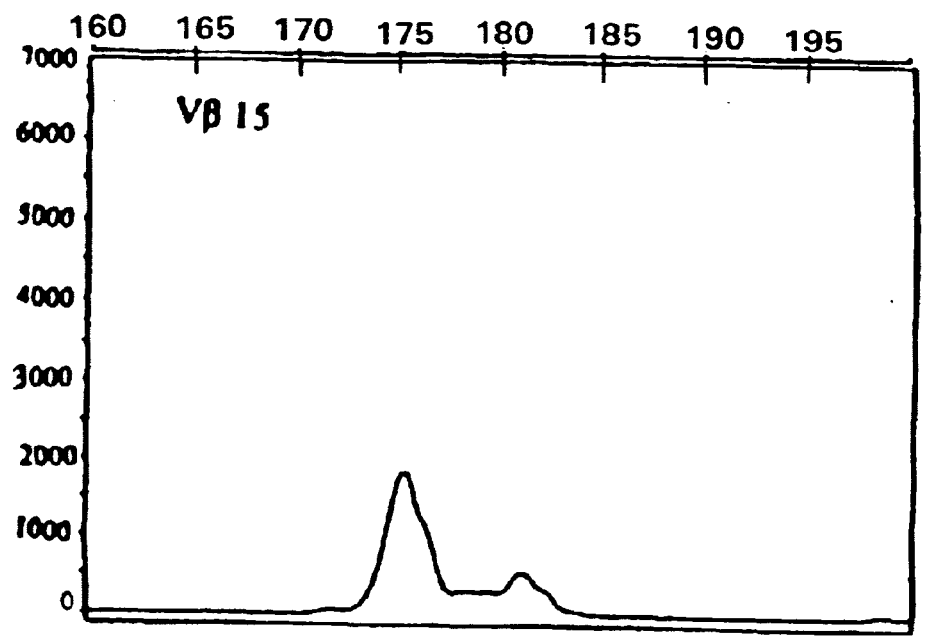
Figures 5, 19A:
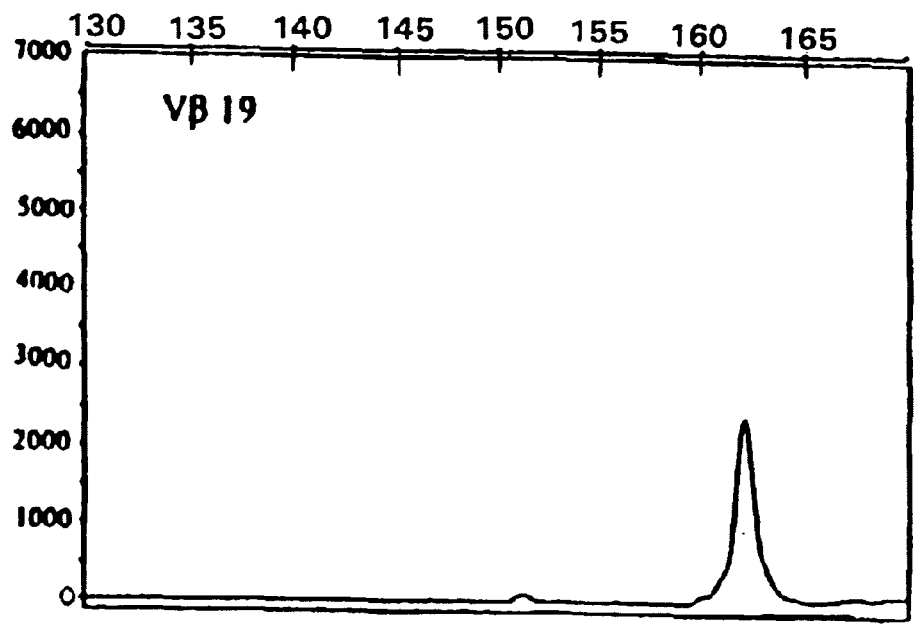
Figures 1, 19B:
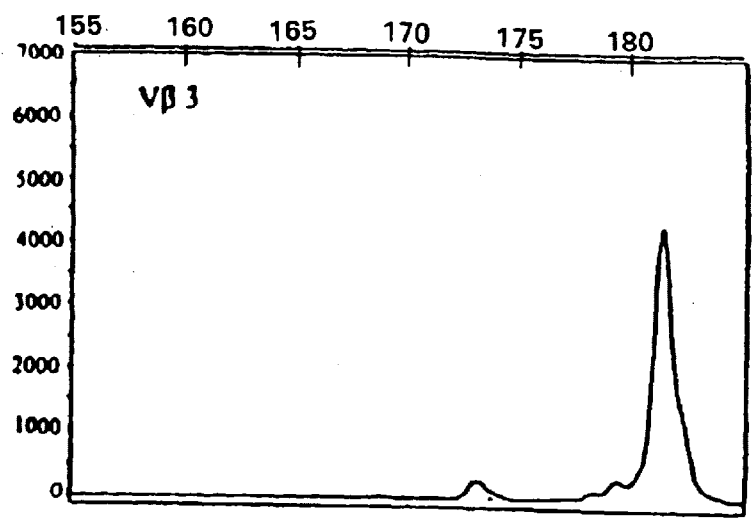
Figures 2, 19B:
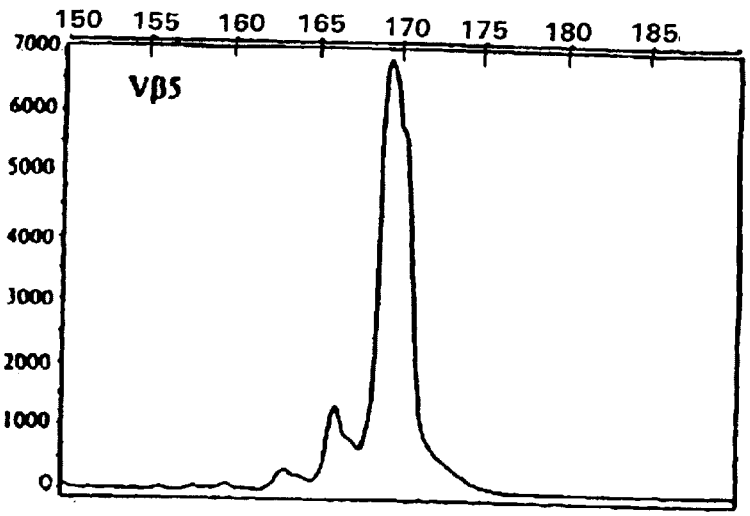
Figures 3, 19B:
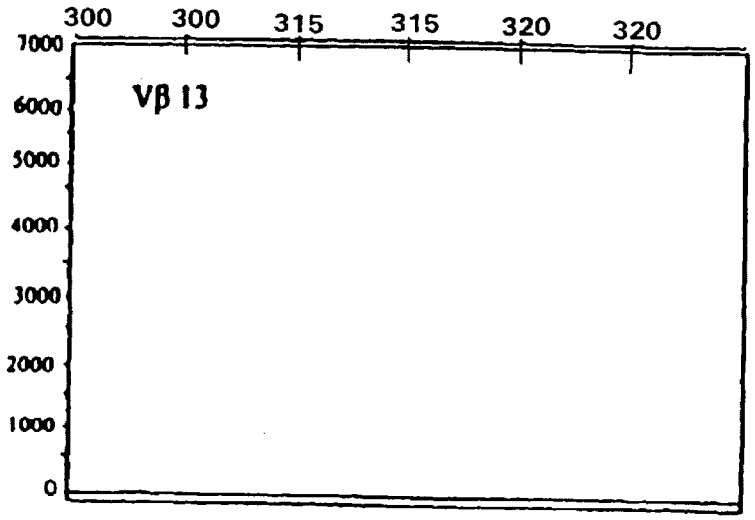
FIG. 3. Suppression of xenoreactivity by $CD8^+CD28^-$ T cells primed to xenogeneic cells. TCL was generated by priming human T cells against pig PBMC. Reactivity of unseparated TCL, separated CD4$^+$, CD8$^+$, CD8$^+$CD28$^-$ T cell subsets and mixtures of CD4$^+$ T cells with CD8$^+$ or CD8$^+$CD28$^-$ population to pig PBMC was determined in 3-day blastogenesis assay.
Figures 4, 19B:
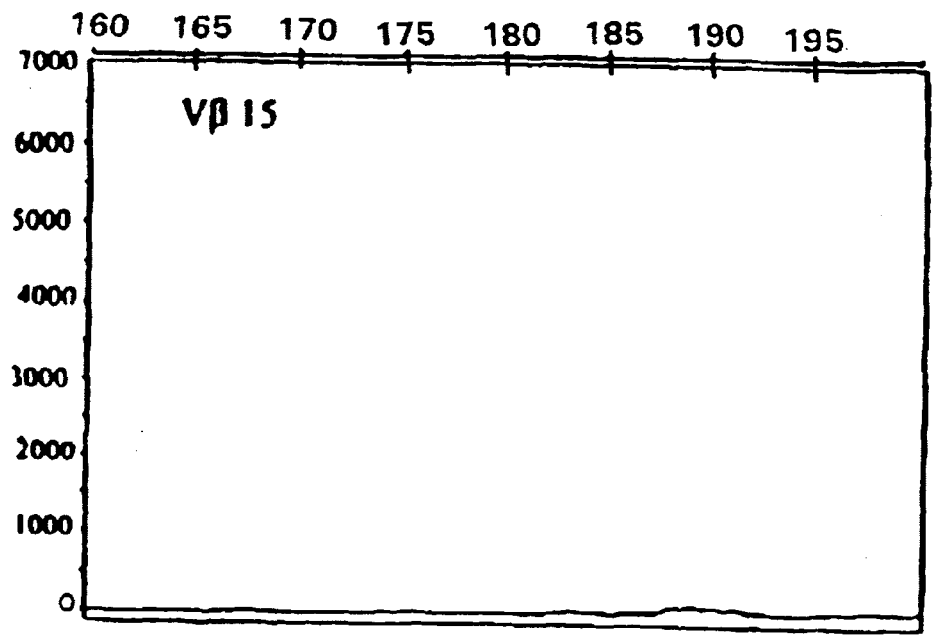
Figures 5, 19B:
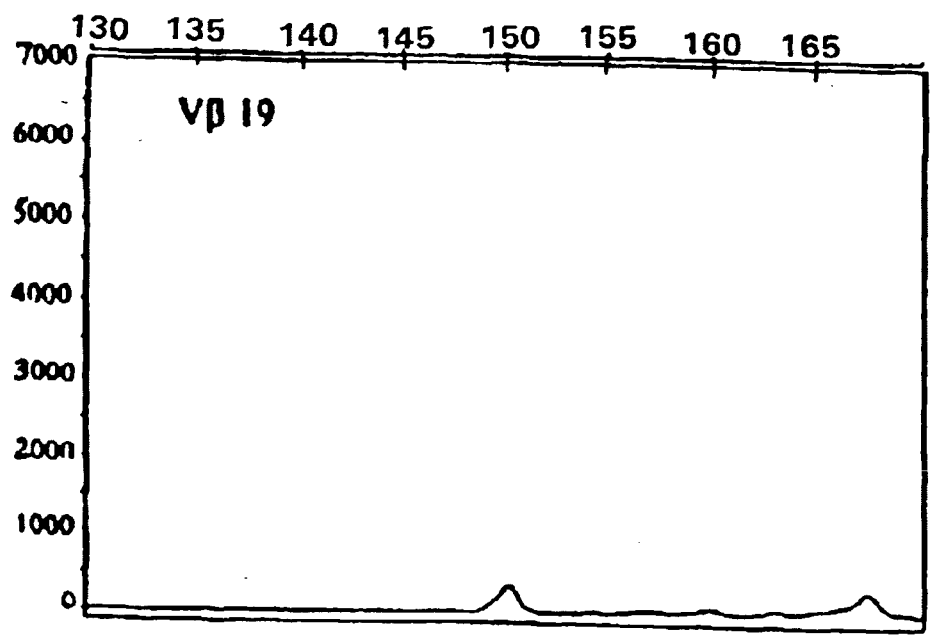
Figures 1, 19C:
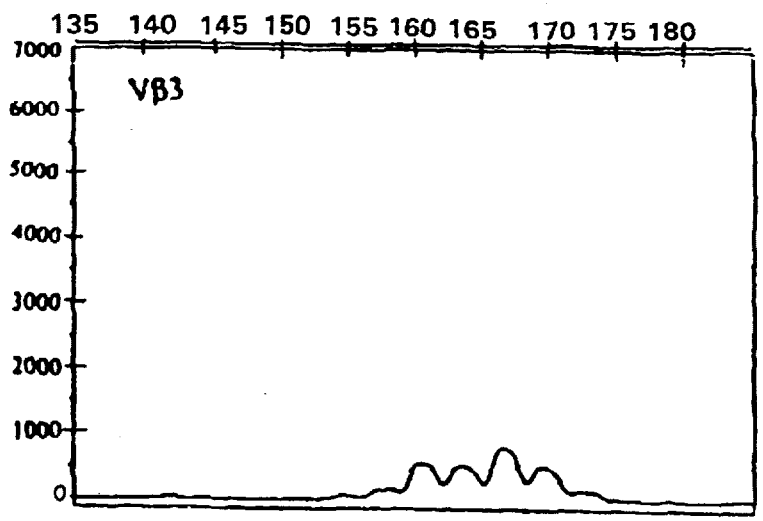
Figures 2, 19C:
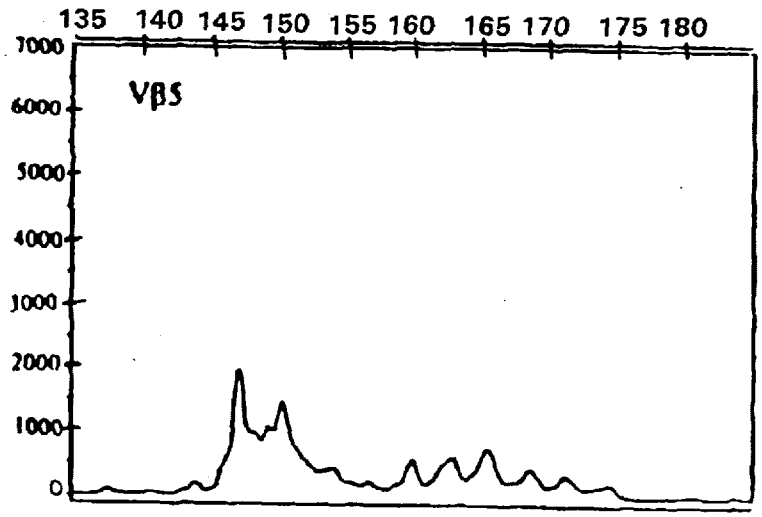
Figures 3, 19C:
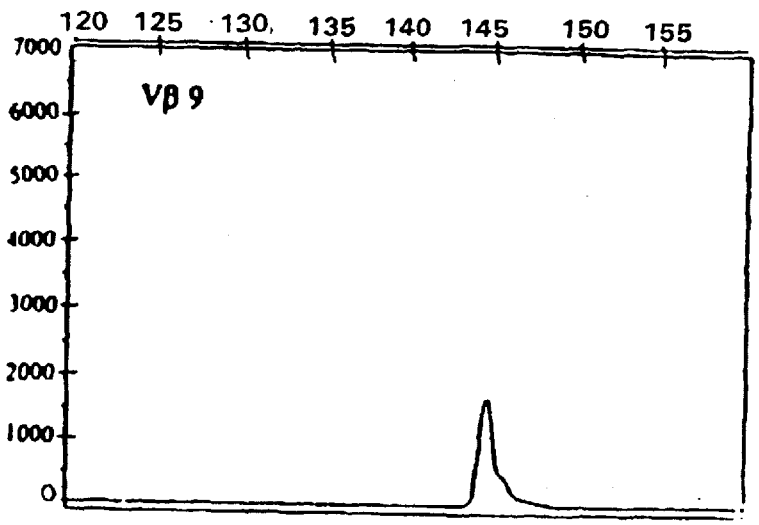
Figures 4, 19C:
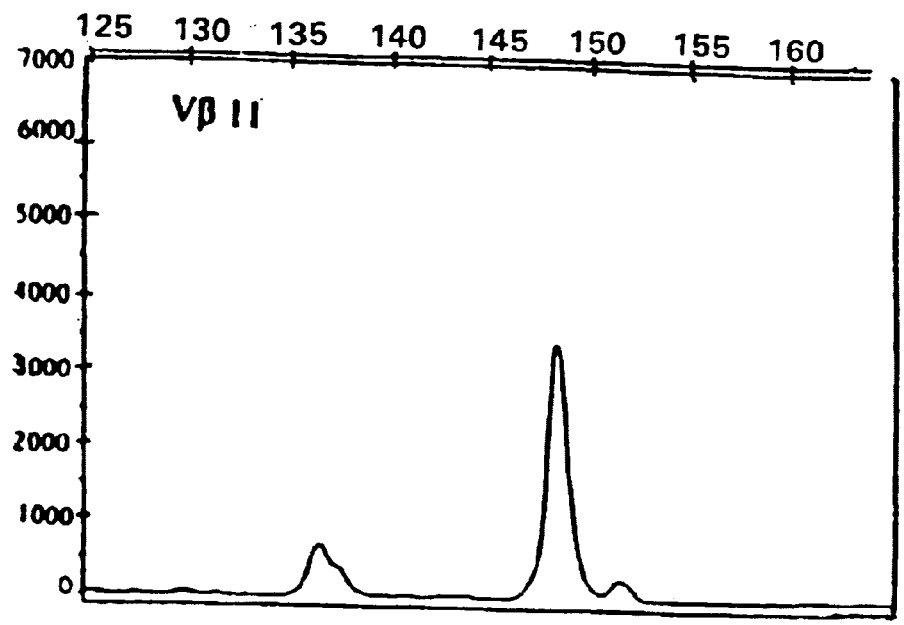
Figures 5, 19C:
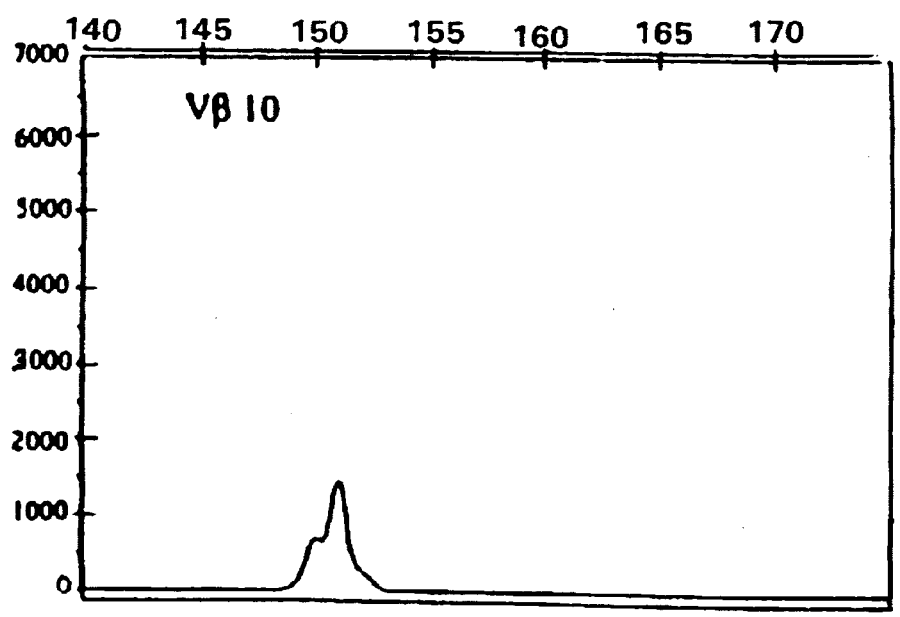
Figure 20A:
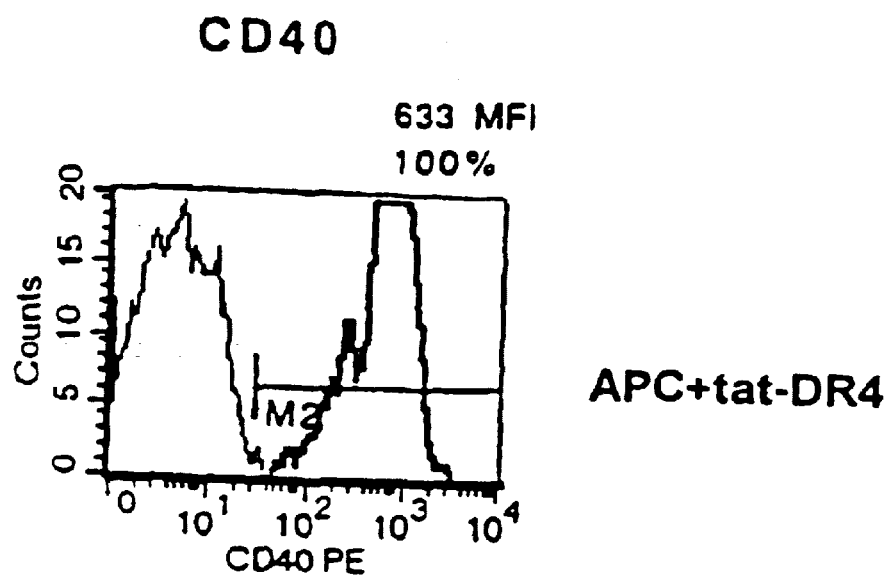
Figure 20B:
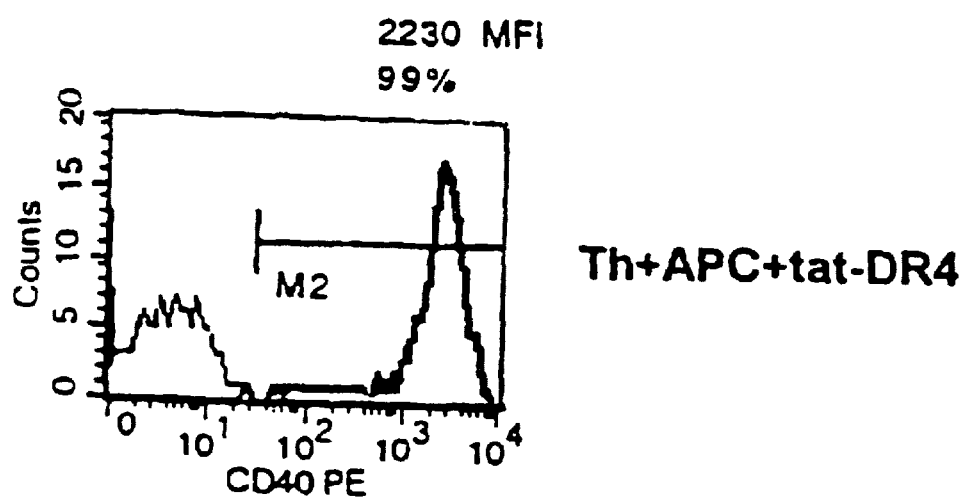
Figure 20E:
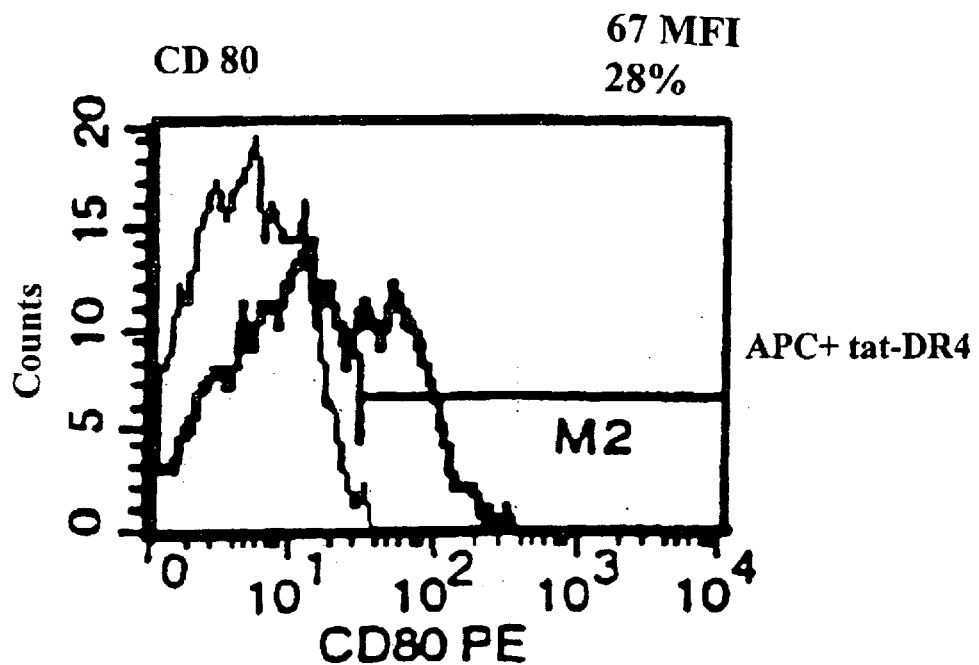
Figure 20F:
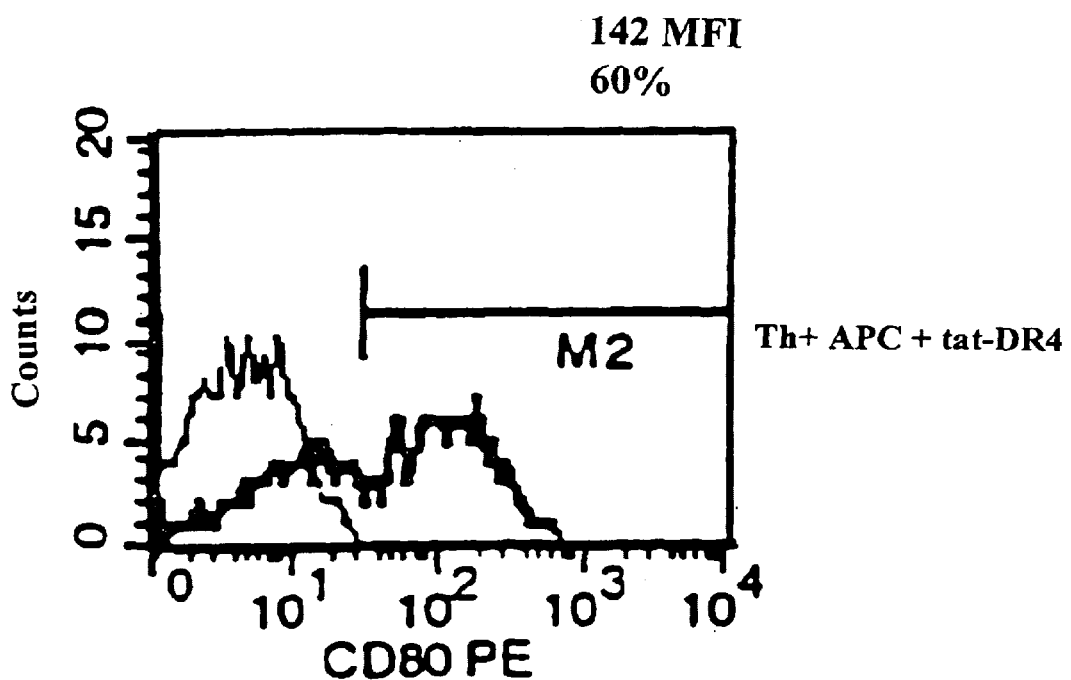
Figure 20G:
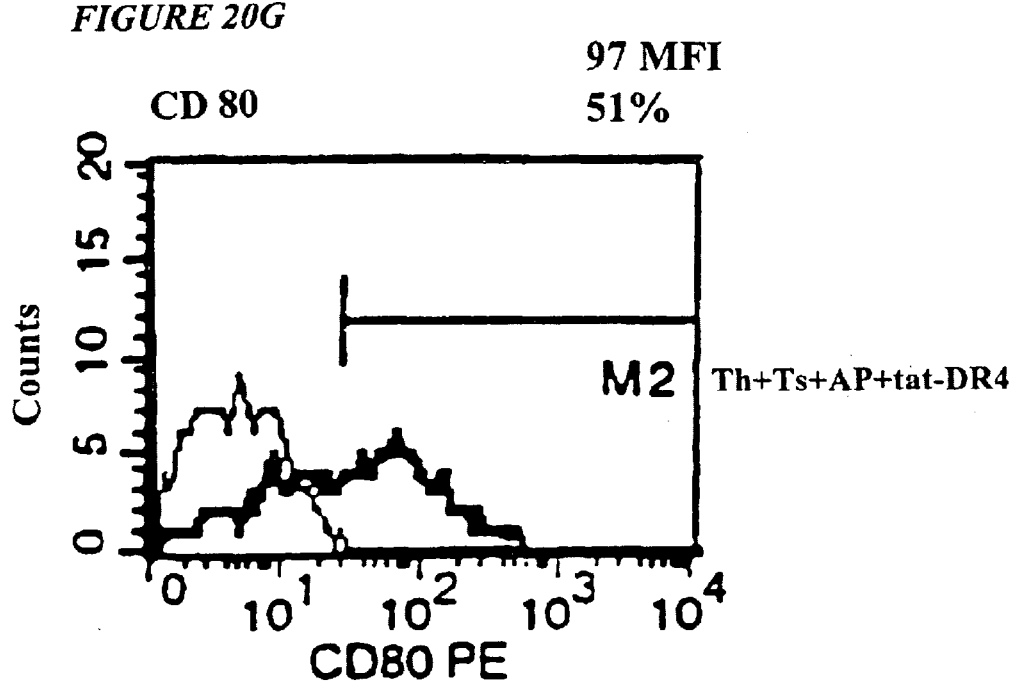
Figure 20H:
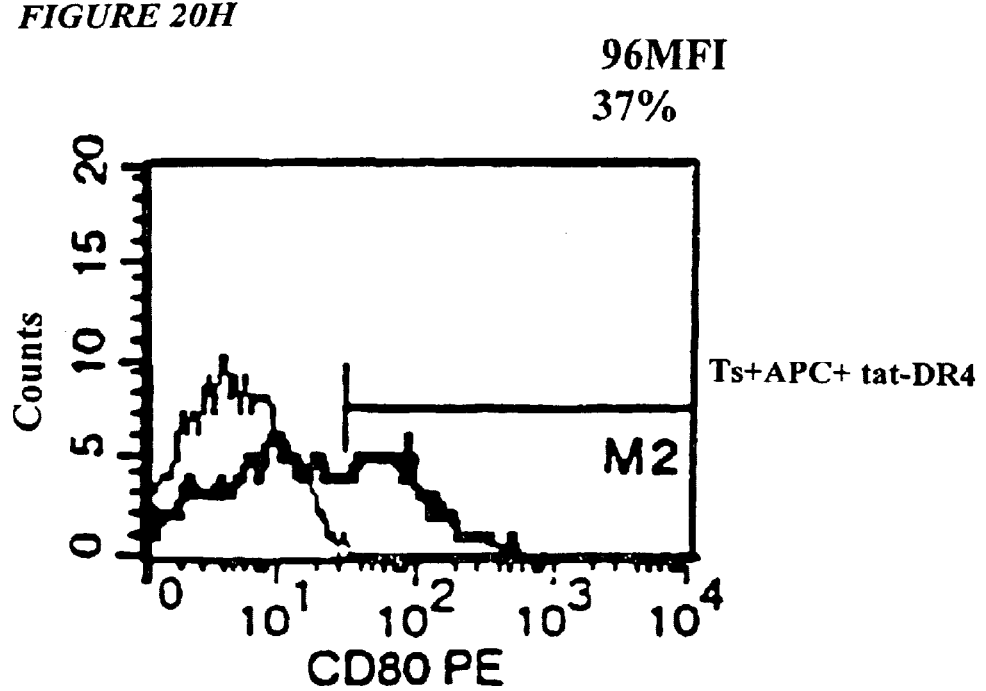
Figure 20I:
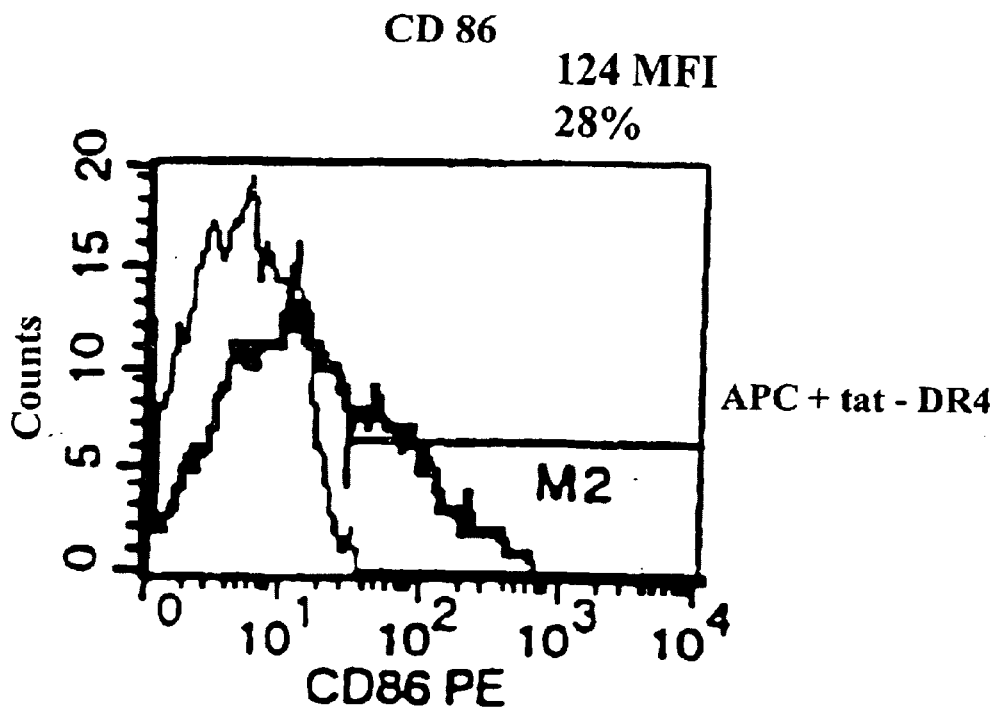
Figure 20J:
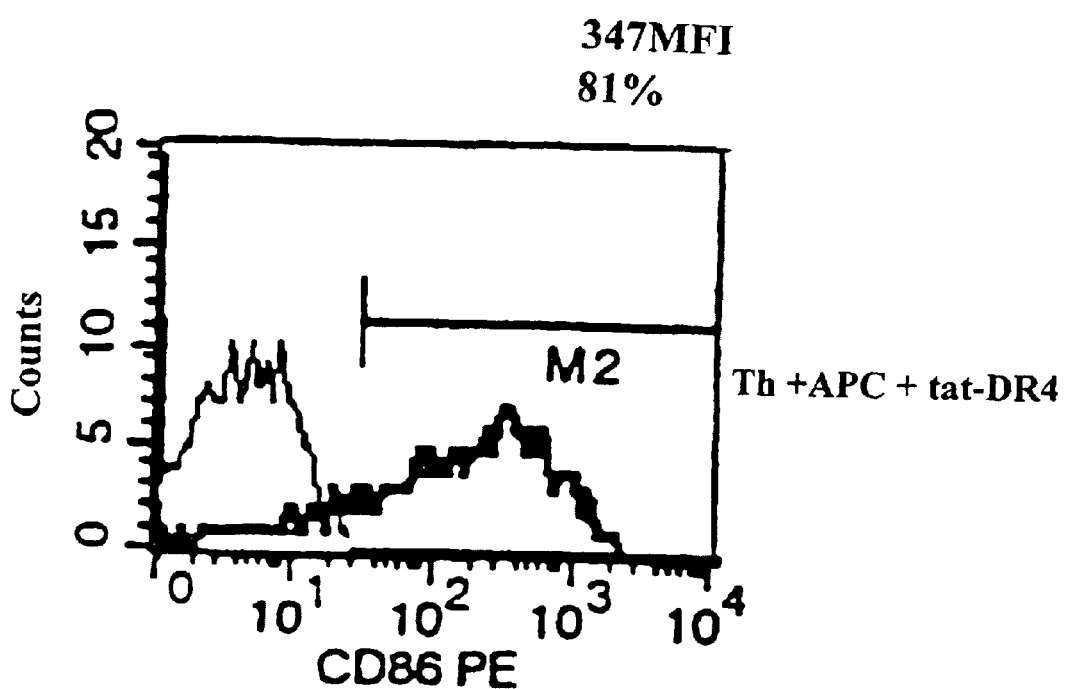
Figure 20K:
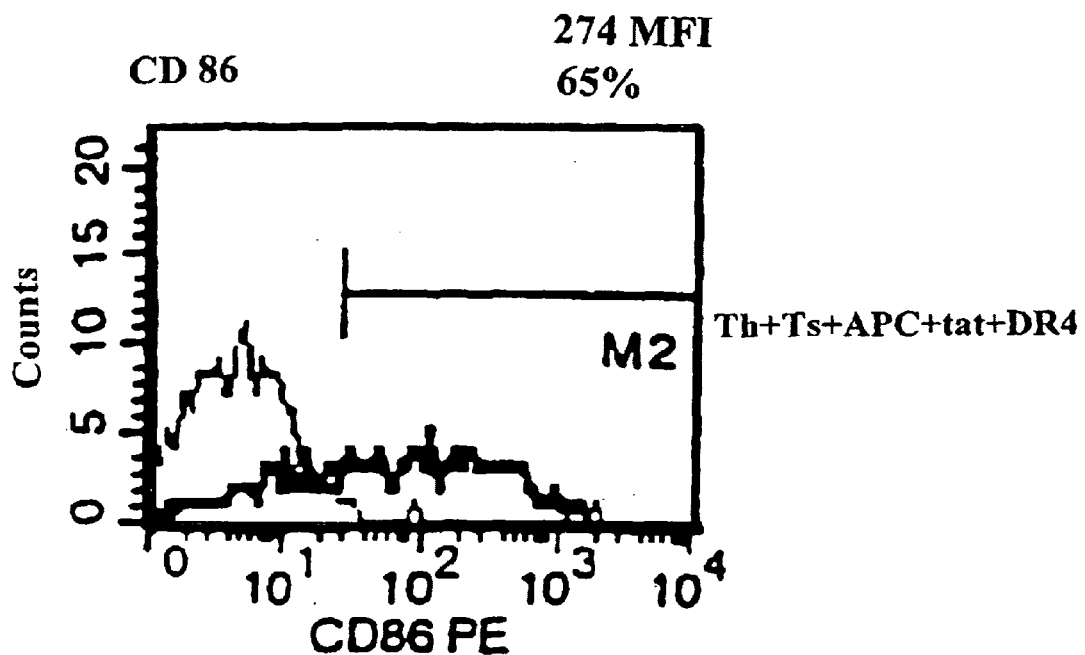
Figure 20L:
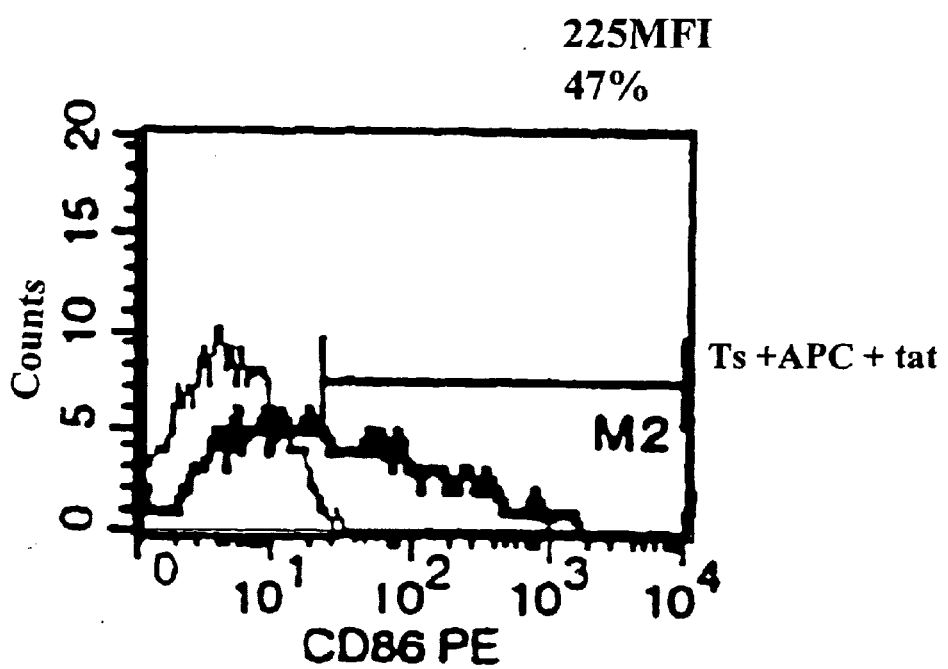

Expression of CD80 and CD86 on stimulatory APC in the presence of $T_s$. Since inhibition of alloreactivity occured only when the stimulating APCs were recognized by both $T_s$ and $T_h$, we examined the possibility that $T_s$ interfere with the expression of costimulatory molecules. Interaction of CD28 on T cells with B7 molecules (CD80 and CD86) on APCs is the most important costimulatory pathway for the response to alloantigens (15,16). CD80 and 86 are absent on resting B and T cells, but are induced after activation. While CD86 is constitutively present on resting monocytes, CD80 is expressed only after stimulation with IFN-γ (17). To determine whether $T_s$ alter the pattern of B7 expression on allogeneic APC, we cultured $T_h$ and/or $T_s$ from five different individuals with CD2-depleted APC from the specific allogeneic stimulator. FIG. 4 illustrates the results of one of these experiments. Analysis of CD80 and CD86 expression on stimulating APC, showed that after 24 hours the level of expression increased significantly in the presence of alloreactive CD4⁺ Th (FIGS. 4C and 4D) compared with the level of expression in the absence of T cells (FIGS. 4A and 4B) or in the presence of CD8⁺CD28⁻ $T_s$ (FIGS. 4E and 4F). APC from parallel cultures containing both $T_h$ and $T_s$ displayed much lower levels of CD80 and CD86 expression (FIGS. 4G and 4H) than APC cultured only with $T_h$. This indicates that allospecific CD8⁺CD28⁻ $T_s$ interfere with the upregulation of CD80 and CD86 expression induced on stimulating APCs by alloreactive CD4⁺ $T_h$.

To analyze the statistical significance of the decreased B7 expression in cultures containing $T_s$, the results obtained in the five different experiments were grouped together. Comparison of the mean percentage of target cells expressing B7 molecules in cultures containing only $T_h$ and in cultures with both $T_h$ and $T_s$ showed that the decrease in the upregulation of B7 expression in the presence of $T_s$ was statistically significant (Table 4).

Figure 5:
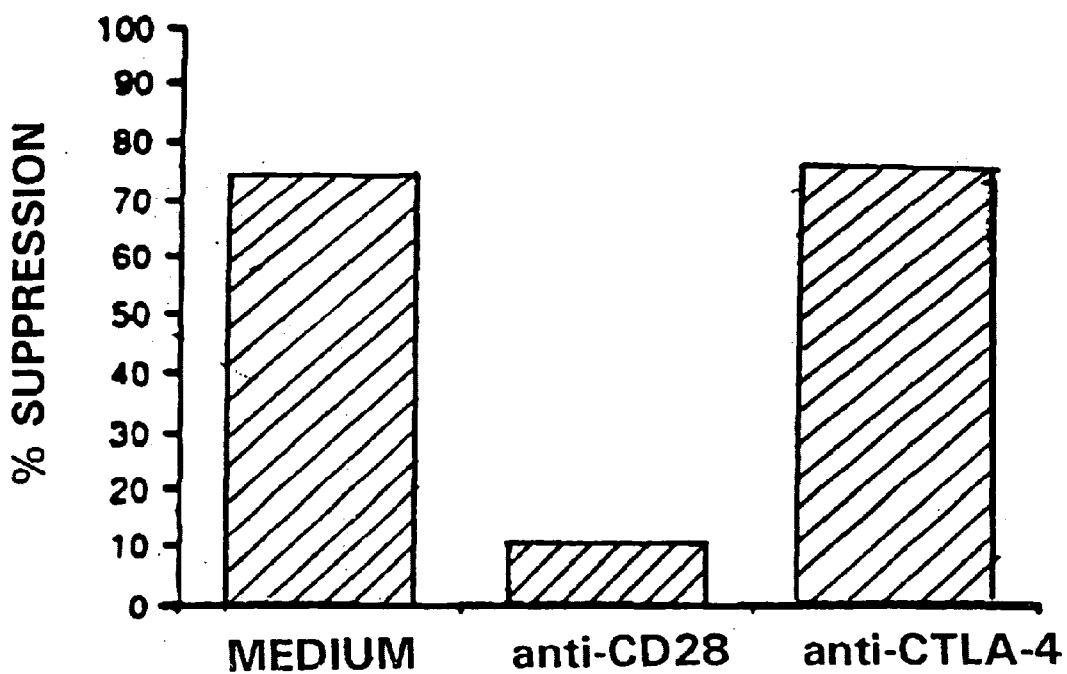
FIG. 5. Prevention of suppression by mAb anti-CD28. CD4$^+$ and CD8 CD28 T cells were separated from TCL SS-anti-JL and tested alone or together for reactivity against APCs from JL in 3 day blastogenesis assays. MAbs anti-CD28 and anti-CTLA-4 (1 μg/ml) were added to parallel cultures at the initiation of the assay. Percent suppression of CD4+ T cell proliferation induced by CD8$^+$CD28$^-$ T cells in the absence and in the presence of either mAb. anti-CD28 or mAb anti-CTLA4 was calculated. Mean c.p.m. in $T_h$ cultures without $T_s$ were 32,510±2720.

The impaired upregulation of CD80 and CD86 on stimulating APC may prevent the efficient costimulation of $T_h$ in the presence of $T_s$. Alternatively, this may be the consequence rather than the cause of $T_h$ inhibition by $T_s$. To explore these possibilities we tested the effects of mAbs anti-CD28 and anti-CTLA-4 on the reactivity of CD4⁺ $T_h$ from a TCL (SS anti-JL) to the specific stimulator (JL) in the presence and absence of CD8⁺CD28⁻ Ts. MAb anti-CTLA-4 did not affect $T_s$-mediated inhibition of the Th proliferative response. In contrast, ligation of CD28 by use of mAb anti-CD28 restored the ability of CD4⁺ $T_h$ to respond to the specific stimulator in the presence of CD8⁺ CD28⁻ $T_s$ (FIG. 5). This result is consistent with the notion that suppression is caused by defective costimulation.

TABLE 4

Effect of $T_s$ cells on Th induced up-regulation of B7 molecules on APC

| | Percentage of B7⁺ target cells | | | | |
|---|---|---|---|---|---|
| | APC | $T_h$ + $T_s$ + APC | $T_h$ + APC | $T_s$ + APC | P valueᵃ |
| CD80 | 12.4 ± 4.6ᵇ | 20.4 ± 4.0ᵇ | 47.2 ± 11.8 | 13.0 ± 3.8ᵇ | 0.0001 |
| CD86 | 18.6 ± 12.4ᵇ | 35.8 ± 15.5ᶜ | 66.4 ± 7.1 | 27.6 ± 19.2ᵇ | 0.0005 |

Results are expressed as mean ± SD of five different experiments.
ᵃP value for differences between all groups was computed by ANOVA.
ᵇThe difference between B7 expression on targets incubated with $T_h$ versus targets incubated with $T_s$, $T_s$ plus $T_h$ or medium was significant (P < 0.01).
ᶜThe difference between CD86 expression on targets incubated with $T_h$ only versus targets cultured with both $T_h$ and $T_s$ was significant (P < 0.05).

DISCUSSION

The present study demonstrates that allospecific and xenospecific human Ts can be generated and expanded in vitro by multiple priming of PBMCs with allogeneic or xenogeneic stimulator cells. Alloreactive Ts derive from the CD8⁺CD28⁻ population of T lymphocytes and recognize specifically the MHC-class I antigens expressed by the allogeneic APC used for in vitro immunization. Suppression of Th alloreactivity occured only when the stimulatory APC co-expressed MHC class II antigens recognized by the Th to be suppressed and MHC-class I antigens recognized by the suppressor T cell population. Thus, CD4⁺ $T_h$ reactivity was not inhibited by CD8⁺CD28⁻ $T_s$ when the cells were stimulated in blastogenesis assay with mixtures of two allogeneic APCs sharing with the original priming cells either MHC class I or class II antigens. Suppression of alloreactive $T_h$, therefore, requires cell-to-cell interaction between CD4+ Th, $CD8^+CD28^-$ $T_s$ and allogeneic APC expressing the class I and class II antigens against which the T cells were primed. Since no suppression occured when mixtures of allogeneic APC were used, it is unlikely that competition between $T_h$ and $T_s$ for the surface of the APC or locally produced IL-2 is the mechanism underlying suppression (18). The role of other lymphokines such as IL-4, IL-10 and TNF-β can also be excluded as antibodies to these lymphokines did not block suppression. Suppression was an early event as it did not occur when the addition of $T_s$ was delayed by more than 8 hours after $T_h$ stimulation.

The need for cell-to-cell interaction between $T_h$, $T_s$, and APC, suggests that $T_s$ may act by inhibiting costimulatory signals delivered by the APCs used for priming. This possibility is strongly supported by our finding that the addition of $T_s$ to the cultures inhibited Th-mediated upregulation of CD80/CD86 expression on stimulating APC. Suppression was first detected after 48 hours of co-culturing Th and Ts consistant with the finding that CD80/CD86 down modulation was seen at 24 hours. Therefore, it appears that $T_s$ induce early changes in target APC, by a yet unknown mechanism, which interfere with the upregulation of B7 molecules required for $T_h$ co-stimulation.

The B7 family has been shown to play a critical role in providing T cell costimulation which is required for the induction of maximal proliferation and cytokine production (15–17). It has been shown that T cells are sensitive to quantitative changes in the molecular interactions that contribute to antigen recognition such as those transmitted through the TCR and CD28 cell surface molecules (19). Allospecific Ts may, therefore, display their effector function by preventing the APC from upregulating the surface density of costimulatory molecules to the threshold required for inducting $T_h$ proliferation. Such a mechanism is consistent with the finding that the capacity of $T_h$ to display proliferative responses in the presence of $T_s$ was restored upon ligation of CD28 by anti-CD28 mAb. Previous studies have shown that blocking the interaction of CD28 with CD80/CD86 either by use of anti-CD28 mAb Fab fragments or CTLA-4-Ig, leads to sustained T cell hyporesponsiveness to the specific alloantigen in MLC (20). Both agents blocked T cell alloreactivity and achieved a similar degree of inhibition on naive and memory T cells. However, T cell responsiveness was not completely abolished suggesting that other CD28– independent costimulatory pathways contributed to $T_h$ alloactivation. Residual $T_h$ proliferation in the presence of suppressor cells was also observed in our experiments, consistent with this possibility.

The fact that the CD8+ subset of lymphocytes contains a CD28+ population with alloantigen-specific cytotoxic activity and a CD28− population with suppressor activity has been previously described (21). However, the suppressive effect of $CD8^+CD28^-$ cells as tested in primary MLC was found to be specific for HLA-DR antigens of the allogeneic target rather than for HLA class I antigens. Since CD8 molecule serves as coreceptor for T cells recognizing MHC-class I molecules, it is difficult to understand how allospecific Ts carrying the $CD8^+CD28^-$ phenotype recognize and react against HLA-DR antigens.

The finding of the present study that allospecific $CD8^+CD28^-$ $T_s$ recognize on target APCs HLA class I antigens, and that they suppress the response of $CD4^+$ $T_h$ to HLA-class II antigens of the same APC, inhibiting upregulation of CD80/CD86 expression, provides a reasonable explanation for the suppressor effect.

Several lines of evidence have demonstrated that molecular mimicry, an extensively discussed phenomenon (22), represents the main mechanism for direct allorecognition (23). Alloreactive T cell clones often display dual recognition ability for a nominal antigen and an alloantigen (24,25). This indicates that allogeneic MHC antigens can mimic immunogenic peptide/self MHC complexes which activate self-restricted T cells. It is, therefore, likely that allo-MHC class I restricted $T_s$ regulate not only T helper/inducer reactivity against allogeneic HLA-DR antigens, but also $T_h$ reactivity against other antigenic peptides bound to self-MHC class II molecules. In this context the molecular characterization of MHC class I bound peptides which activate $T_s$ may have important implications for the treatment of autoimmune and infectious diseases. While suppression of autoimmunity may be accomplished by priming $CD8^+CD28^-$ T cells with suppressor-inducing peptides, ablation of such a population may be required for treatment of certain infectious diseases. The observation that the proportion of $CD8^+CD28^-$ T cells within the CD8+ subset increases in HIV+ individuals as the disease progresses (26), supports the notion that this population of cells has important immunoregulatory function, and that it may depress $T_h$ reactivity.

Very recently it was shown that chronic activation of both human and murine CD4+ T cells in the presence of IL-10 generates antigen specific $T_s$ which produce high level of IL-10 and inhibit T cell responses to allogeneic monocytes. No direct interaction between $T_h$, $T_s$ and APC was required in this system. These CD4+ T regulatory cells were shown to inhibit antigen-specific immune responses through the secretion of IL-10 and TGF-β (27). Hence, regulatory T cells operating by different mechanisms exist within the CD4 and CD8 subset.

The present study demonstrates for the first time that allospecific and xenospecific $T_s$ can be generated from any individual by in vitro education and expansion. Preliminary experiments indicate that large numbers of $T_s$ can be obtained in cultures. Since allospecific and xenospecific $CD8^+CD28^-$ $T_s$ inhibit both the recognition and memory response of CD4+ T cells in primary and secondary MLCs, it is possible that generation of Ts can provide a tool for prevention and suppression of transplant rejection. "Adoptive transfer" of autologous $CD8^+CD28^-$ $T_s$ primed in vitro with donor APC may confer specific immunologic tolerance to human recipients of allogeneic or xenogeneic transplants.

References for First Series of Experiments

1. Nisco, S. J., Hissink, R. T., Vriens, P. W., Hoyt, E. G., Reitz, B. A., and Clayberger, C. (1995) In vivo studies of the maintenance of peripheral transplant tolerance after cyclosporine. Transplantation 59: 1444.
2. Field, E. H., Rouse, T. M., Gao, Q. and Chang, B. (1997) Association between enhanced Th2/Th1 cytokine profile and donor T-cell chimerism following total lymphoid irradiation. Human Immunol. 52: 144.
3. Strober, S. (1984) Natural suppressor (NS) cells, neonatal tolerance and total lymphoid irradiation: exploring obscure relationships. Annu. Rev. Immunol. 2, 219.
4. Maki, T., Simpson, M., and Monaco, A. P. (1982.) Development of suppressor T cells by anti-lymphocyte serum treatment in mice. Transplantation 34: 376.
5. Qin, S., Cobbold, S. P., Pope, H., Elliott, J., Kioussis, D., Davies, J., and Waldmann, H. (1993) 'Infectious' transplantation tolerance. Science 259: 974.
6. de Waal, L. P., and van Twuyver, E. (1991) Blood transfusion and allograft survival: Is mixed chimerism the solution for tolerance induction in clinical transplantation? Immunol. 10: 417.
7. Saitovitch, D., Bushell, A., Mabbs, D. W., Morris, P. J. and Wood, K. J. (1996) Kinetics of induction of transplantation tolerance with a nondepleting anti-CD4 monoclonal antibody and donor-specific transfusion before transplantation. Transplantation 61: 1642.
8. Shoskes, D. A. and Wood, K. J. (1994) Indirect presentation of MHC antigens in transplantation. Immunol. Today 15: 32.
9. Hall, B. M., Pearce, N. W., Gurley, K. E. and Dorsch, S. E. (1990) Specific unresponsiveness in rats with prolonged cardiac allograft survival after treatment with cyclosporine. III. Further characterization of the CD4+ suppressor cell and its mechanisms of action. J. Exp. Med. 171: 141.
10. Roser, B. J. 11989) Cellular mechanisms in neonatal and adult tolerance. Immunol. Rev. 107: 179.
11. Padberg, W. M., Lord, R. H., Kupiec-Weglinski, J. W., Williams, J. M., Di Stefano, R., Thornburg, L. E., Araneda, D., Storm, T. B. and Tilney, N. L. (1987) Two phenotypically distinct populations of T cells have suppressor capabilities simultaneously in the maintenance phase of immunologic enhancement. J. Immunol. 138: 1751.
12. Mosmann, T. R., Cherwinski, H., Bond, M. W., Giedlin, M. A. and Coffman, R. L. (1986) Two types of murine helper T cell clone: I. Definition according to profiles of lymphokine activities and secreted proteins. J. Immunol. 136: 2348.
13. Lorber, M. I., Wall, K. A, Loken, M. R. and Fitch, F. W. (1984) Control of cloned alloreactive T lymphocyte proliferative responses: A possible role for cell-surface-bound alloantigen. Transplantation 38: 361.
14. Talanian, R. V., Yang, X., Turbor, J., Seth, P., Ghayur, T., Casiano, C. A., and Froelich, C. J. (1997) Granule-mediated killing: Pathways for Granzyme B-initiated apoptosis. J. Exp. Med. 186:1323.
15. Linsley, P. S., and Ledbetta, J. A. (1993) The role of the CD28 receptor during T cell responses to antigen. Annu. Rev. Immunol. 11: 191.
16. Sayegh, M. H., Akalin, E., Hancock, W. W., Russell, M. E., Carpenter, C. B., Linsley, P. S. and Turka, L. A. (1997) CD28—B7 blockade after alloantigenic challenge in vivo inhibits Thi cytokines but spares Th2. J. Exp. Med. 185: 393.
17. Lanier, L. L., O'Fallon, S., Somoza, C., Philips, J. H., Linsley, P. S., Okumura, K., Ito, D. and Azuma, M. (1995) CD80 (B7) and CD86 (B70) provide similar costimulatory signals for T cell proliferation, cytokine production, and generation of CTL. J. Immunol. 154: 97.
18. Lombardi, G., Sidhu, S., Batchelor, R., Lechler, R. (1994) Anergic T cells as suppressor cells in vitro. Science 264: 1587.
19. van der Merwe, P. A., Bodian, D. L., Daenke, S., Linsley, P. S., and Davis S. J. (1997) CD80 (B7-1) binds both CD28 and CTLA-4 with a low affinity and very fast kinetics. J. Exp. Med. 185: 393.
20. Tan, P., Anasetti, C., Hansen, J. A., Melrose, J., Brunvand, M., Bradshaw, J., Ledbetter, J. A. and Linsley, P. S. (1993) Induction of alloantigen-specific hyporesponsiveness in human T lymphocytes by blocking interaction of CD28 with its natural ligand B7/BB1. J. Exp. Med. 177: 165.
21. Damle, N. K., Mohagheghpour, N., Hansen, J. A., and Engleman, E. G. (1993) Alloantigen-specific cytotoxic and suppressor T lymphocytes are derived from phenotypically distinct precursors. J. Immunol. 131: 2296.
22. De Berardinis, P., Guardiola, J. and Manca, F. (1997) Epitope context and reshaping of activated T helper cell repertoire. Human Immunol. 54: 189.
23. Benichou, G. and Fedoseyeva, E. V. (1996) The contribution of Peptides to T cell allorecognition and allograft rejection. Intern. Rev. Immunol. 13: 231.
24. Lechler, R. I., Heaton, T., Barber, L., Bal, V., Batchelor, J. R. and Lombardi, G. (1992) Molecular mimicry by major histocompatibility complex molecules and peptides accounts for some alloresponses. Immunol. Lett. 34: 63.
25. Liu, Z., Sun, Y. K., Xi, Y. P., Harris, P. and Suciu-Foca, N. (1992) T cell recognition of self-human histocompatibility leukocyte antigens (HLA)-DR peptides in context of syngeneic HLA-DR molecules. J. Exp. Med. 175: 1663.
26. Lloyd, T. E., Yang, L., Tank, D. N., Bennett, T., Schober, W. and Lewis, D. E. (1997) Regulation of CD28 co-stimulation in human CD8+ T cells. J. Immunol. 158: 1551.
27. Groux, H., O'Garra, A., Bigler, M., Rouleau, M., Antonenko, S., de Vries, J. E. and Roncarolo, M. G. (1997) A CD4+ T-cell subset inhibits antigen-specific T-cell responses and prevents colitis. Nature 389: 737.

Second Series of Experiments

The shortage of organ donors is an ever increasing problem in clinical transplantation. Although the use of pig organs may offer a solution, there are still several immunological barriers that should be overcome before xenotransplantation can be envisioned. The first is the hyperacute rejection caused by the binding of naturally occurring antibodies and complement, present in primates, to pig endothelial cells. Recent progress in the generation of transgenic pigs expressing human complement-regulatory molecules on vascular endothelium may solve this critical problem (1–4). However, T helper cell recognition of xenogeneic MHC antigens via the direct and indirect pathways is likely to result in strong cellular immune responses that may be difficult to suppress using currently available strategies (4, 5). It is therefore apparent that the development of methods for specific suppression of xenograft rejection is an important objective for achieving successful xenotransplantation.

Although immunologic tolerance to allogeneic and xenogeneic tissues has been induced in a variety of experimental models (2,6), attempts to ablate specifically the immune response to HLA-incompatible transplants in human patients have failed thus far. However, two recent reports have described strategies for in vitro education of regulatory T cells that suppress in a specific manner the direct recognition by $CD4^+$ T cells of MHC class II antigens expressed on allogeneic APCs (7, 8). In one of these studies, regulatory T cells with suppressor activity were generated by stimulation of $CD4^+$ T cells with allogeneic monocytes in the presence of IL-10. These regulatory T cells inhibited specifically the reactivity of $CD4^+$ T helper cells through the secretion of IL-10 and TGF-b (7).

In the other study, suppressor T cells were generated by multiple stimulations of human peripheral blood lymphocytes (PBL) with allogeneic APCs and shown to display the $CD8^+CD28^-$ phenotype (8). These CO8CD28 T cells recognized specifically HLA class I antigens expressed by the stimulatory APCs and suppressed the proliferative response of alloreactive $CD4^+$ T cells against APCs used for priming. The suppressive effect was not mediated by lymphokines but instead required cell-to-cell interaction between $CD4^+$ T helper (Th) cells, $CD8^+CD28^-$ T suppressor (Ts) cells, and allogeneic APCs expressing antigens against which the T cells were primed. In this system, Ts cells appeared to act by inhibiting costimulatory signals delivered by the allogeneic APCs, such as those provided by CD80/CD86 molecules (8).

This report demonstrates that xenospecific suppressor T cells can be also generated by multiple in vitro stimulations of human T cells with pig PBMCs. The CD8$^+$CD28$^-$ population from these T cell lines (TCL) recognizes specifically xenogeneic MHC class I antigens and suppresses the proliferative response of Th cells to MHC class II antigens expressed by the xenogeneic APCs. Xenospecific Ts cells interfere with the expression of CD154, the CD40 ligand, on xenoreactive Th cells, further supporting the concept that the suppressor effect results from inhibition of costimulatory interactions between Th cells and APCs.

The abbreviations used herein are as follows: PI=Propidium Iodide; TCL=T Cell Lines; Ts=T Suppressor cells; SLA=Swine Histocompatibility leukocyte antigen; and CD40L=CD40 Ligand.

Materials and Methods

Pig specimens. Blood was obtained from outbred pigs and from Yucatan miniature swine (Sinclair Research Center, Columbia, Mo.) MHC haplotypes were defined by RFLP using swine histocompatibility leukocyte antigen (SLA) class I- and class II-specific probes (9–11). For experiments aimed at the identification of MHC antigens recognized by xenospecific Ts cells, blood was obtained from three SLA homozygous lines named W, Z, and Q. Line Q is homozygous for a crossover haplotype that carries the SLA class I genes of strain W and the SLA class II genes of Z (9–11).

Human specimens. Blood was obtained f rom healthy blood donors typed for HLA class I and class II antigens by conventional serology and by genomic typing of in vitro amplified DNA with sequence-specific oligonucleotide probes.

Generation of xenoreactive and alloreactive T cell lines. Human and pig PBMCs were separated from buffy coats by Ficoll-Hypaque centrifugation. Responding human PBMCs ($1 \times 10^6$/ml) were stimulated in 24-well plates with irradiated (1600r) pig or human PBMCs ($1 \times 10^6$/ml). Cells were cocultured for 7 days in complete medium (RPMI 1640 supplemented with 10% heat-inactivated fetal calf serum (FCS), 2 mM glutamine and 50 mg/ml gentamicin) (Gibco, Baltimore, Md.). Responding cells were restimulated at seven day intervals in medium containing 10 U/ml rIL-2 (Boehringer Mannheim, Indianapolis, Ind.).

Cell separation. NK cells were depleted from the alloreactive or xenoreactive TCLs before testing using goat anti-mouse magnetic beads (Dynal, Lake Success, N.Y.) coupled with mAb anti-CD16 and CD56 (Becton Dickinson, San Jose, Calif.). Suspensions used in blastogenesis assays contained <2% CD16/CD56-positive cells, as indicated by flow cytometry. CD4$^+$ and CD8$^+$ T cells were separated from alloreactive and xenoreactive TCL by negative selection using Dynal CD4 and CD8 magnetic beads. T cell suspensions used as responders in blastogenesis assays were >98% positive for the CD4 and CD45RO markers. CD8$^+$CD28$^-$ T cell suspensions were prepared by depletion of CD28$^+$ T cells from purified CD8$^+$ T cell suspensions. For this procedure, goat anti-mouse Dynal beads were coupled with mAb anti-CD28 (Becton Dickinson, San Jose, Calif.), according to the manufacturer's instructions. The CD28-coupled beads were washed and incubated at $4 \times 10^7$ beads/ml with $1 \times 10^7$ CD8$^+$ T cells for 20 minutes at 4° C., with gentle end-over-end mixing. Rosetted CD8$^+$CD28$^+$ T cells were detached from the beads by overnight incubation at 37° C. and used in cell-mediated lysis experiments. Nonrosetted cells were collected, washed three times and resuspended at $2.5 > 10^5$ cells/ml in complete RPMI 1640 culture medium. The purity of the suspension was monitored by cytofluorographic analysis. The suspension was rerosetted with CD28 beads when necessary, to obtain a population contaminated by <2% CD28$^+$ bright cells.

Proliferation Assays. Blastogenesis assays were performed on day 14 or 21, after two or three stimulations, respectively, of human T cells with allogeneic or xenogeneic PBMCs. TCLs were then tested for reactivity to stimulating APCs either as nonfractionated, NK-depleted suspensions ($5 \times 10^4$ cells/well) or as NK-depleted CD4$^+$ T cell suspensions ($2.5 \times 10^4$ cells/well). Responding cells were stimulated with irradiated allogeneic or xenogeneic PBMCs ($5 \times 10^4$ cells/well). CD8$^+$CD28$^-$ T cells tested for suppressor activity were added to the cultures ($1.25 \times 10^4$ cells/well) at the initiation of the blastogenesis assay. To study the dose-dependent effect of CD8$^+$CD28$^-$ T cells on Th cell proliferation, increasing concentrations of Ts cells were added to parallel cultures as indicated. Cultures were set-up in 96-well trays in a total volume of 0.2 ml. In some experiments, murine mAbs to human IL-10 (at 1 µg/ml) or TGF-b (at 5 µg/ml) from R&D Systems (Minneapolis, Minn.) were added to the cultures at the initiation of the assay. After 48 hours of incubation, the cultures were pulsed with [$^3$H] thymidine ([$^3$H] TdR) and harvested 18 hours later. [$^3$H] TdR incorporation was determined by scintillation spectrometry in an LK Betaplate counter. Results were expressed as mean counts/min of triplicate reactions. Percent suppression was calculated as 1–[(cpm in Th+Ts+APC cultures)/(cpm in Th+APC cultures)].

Diffusion chamber experiments. Xenoreactive CD4$^+$ T cells ($2.5 \times 10^4$ cells/well) and irradiated xenogeneic APCs ($5 \times 10^4$ cells/well) were cocultured in the bottom compartment of a transwell system (Nalge Nunc International, Roskilde, Denmark). Xenospecific CD8$^+$CD28$^-$ T cells ($1.25 \times 10^4$ cells/well) were added either to the bottom compartment or cocultured with specific pig APCs in the top compartment of the transwell system. After 48 hours the semipermeable membranes were removed and the proliferative response of Th cells was measured by [$^3$H] TdR incorporation during the last 18 hours of culture.

Flow cytometry. Human T cell subsets were defined using mAb CD4, CD8, CD28, CD45RO, and CD16/56 (Becton Dickinson). Cell suspensions were phenotyped before testing with a FACScan flow cytometer instrument (Becton Dickinson) equipped with a 15-mm argon laser. CaliBRITE flow cytometer beads and FACSComp program (Becton Dickinson) were used for calibration of the cytometer.

To study the expression of CD154 on responding human Th cells, cells were incubated for 6 or 18 hours in MLC and then stained with saturating amounts of mabs CD3-Per CP (peridinin chlorophyll protein-conjugated anti-CD3 mAb), CD154-PE and CD4-FITC or CD8-FITC (Becton Dickinson).

Cells were analyzed with CellQuest software on a 650 Apple Macintosh computer. Five parameter analysis (forward scatter, side scatter and three fluorescence channels) were used for list mode data analysis. The FL3 channel was used as fluorescence trigger, FL1 and FL2 were used as analysis parameters.

The cytokine profile of xenoreactive Th and Ts cells was determined by flow cytometry. CD4$^+$ Th cells and CD8$^+$ CD28$^-$ Ts cells were isolated from TCLs and activated in 4 hour cultures with 25 ng/ml PMA and 1 µg/ml of ionomycin.

Brefeldin A (Sigma Chemical, St. Louis, Mo.) was added at 10 μg/ml for the last 2 hours of incubation to inhibit intracellular transport. Cells were fixed and stained for detection of intracellular cytokines using mAbs IL-2-FITC, IFN-γ FITC, IL-4 PE (Becton Dickinson), and IL-10 PE (R&D Systems).

Study of Apoptosis. The ability of xenoreactive $CD8^+$ $CD28^-$ human Ts cells to induce apoptosis of pig PBMCs and of xenoreactive human $CD4^+$ Th cells after 4 hours of coincubation at 37° C. was tested by flow cytometry with the use of annexin V as a marker for apoptotic cells. As positive controls, cells treated with camptothecin (Sigma) were used. The ratio of pig PBMC, human Th cells and human Ts cells was 1:0.5:0.25, as also used in blastogenesis assays. After incubation, cells were stained with mAb anti-human CD3–PE or CD4–PE, washed and subsequently stained with annexin V-FITC and propidium iodide (PI) (R&D Systems). To analyze the population of pig PBMCs, log FL2 (CD3–PE) versus side scatter parameters were used to gate out human $CD3^+$ T cells. The percentage of apoptotic pig cells was determined from log FL1 (annexin-FITC) versus FL3 (PI) dot plots. To analyze the population of human $CD4^+$ Th cells undergoing apoptosis, log FL2 (CD4-PE) versus side scatter parameters were used to gate on CD4 positive cells. Log FL1 (annexin V-FITC) versus FL3 (PI) dot plots of the gated population provided the percentage of apoptotic $CD4^+$ Th cells.

Cytotoxicity Assays. $CD8^+CD28^-$ and $CD8^+CD28^+$ were isolated from activated $CD8^+$ cells and tested for cytotoxicity in a $^{51}Cr$ release assay. Target cells were pig PBMCs stimulated with PHA (2 μg/ml) 3 days before the cytotoxicity assay. The cytotoxicity assay was performed with different effector to target cell ratios (E:T).

The percent cytotoxicity was calculated as % Lysis=100× {[Experimental release (cpm)–Spontaneous release (cpm)]/ [Maximum release (cpm)–Spontaneous release (cpm)]}.

TCR Spectratyping

Total RNA was extracted using QIAGEN columns (QIAGEN Inc., Valencia, Calif.) from xenoreactive human $CD8^+CD28^-$ Ts cells. RNA was reverse transcribed into cDNA in a reaction using Moloney murine leukemia virus reverse transcriptase primed with oligo(dT)$_{18}$ (Clontech Laboratories Inc., Palo Alto, Calif.), as recommended by the manufacturer.

Aliquots of the cDNA synthesis reaction were amplified in 50-ml reactions with each of the 24 Vβ oligonucleotides (0.5 μM final concentration) and the Cβ oligonucleotide (0.5 μM final concentration). Vβ and Cβ primers were previously described (12, 13). As an internal control for the amount of cDNA used per reaction, a tube containing sense and antisense primers for the first exon of Cβ region was included. Two microliters of the Vβ–Cβ PCR products were subjected to elongation with a fluorophore-labeled Cβ or Jβ-specific primer (0.5 μM final concentration) (12). The size and fluorescence intensity of labeled runoff products were determined on a 377 DNA sequencer (Perkin Elmer Applied Biosystem Division, Foster City, Calif.) and analyzed by ABI PRISM 377 GENESCAN Analysis Program (Perkin Elmer Applied Biosystem Division) (13).

The relative intensity of each Vβ family or Jβ-Vβ fragment was calculated as the peak area corresponding to each Vβ family or Jβ-Vβ fragment divided by the sum of all area peaks (12).

Statistical Analysis

Statistical analysis of the results was performed using BMDP statistical software. Analysis of variance to assess significance of group differences (ANOVA) followed by Tukey's method for multiple comparison was applied. Correlation coefficients were obtained using Linear Regression Analysis. Student's t test of significance was also used to access the differences between groups.

RESULTS

Specificity of Xenoreactive T Suppressor (Ts) Cells

Figure 6A:
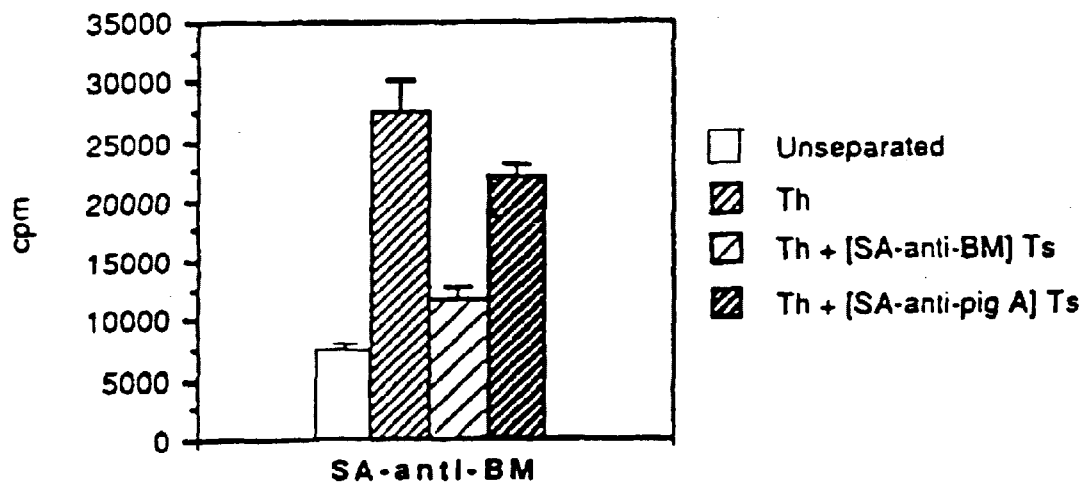
FIGS. 6A–6B. Species specificity of CD8$^+$CD28$^-$ Ts cells. The response of alloreactive (SA-anti-BM) (FIG. 6A) and xenoreactive (SA-anti-pig A) (FIG. 6B) human T cell lines against the specific stimulator was measured in a 3-day proliferation assay. Reactivity of the unseparated TCLs, separated CD4$^+$ Th cells, and mixtures of CD4$^+$ and CD8$^+$CD28$^-$ (Ts) cells from either TCL is illustrated. Results are expressed as mean counts/min of triplicate reactions. The SD of the mean is indicated.
Figure 6B:
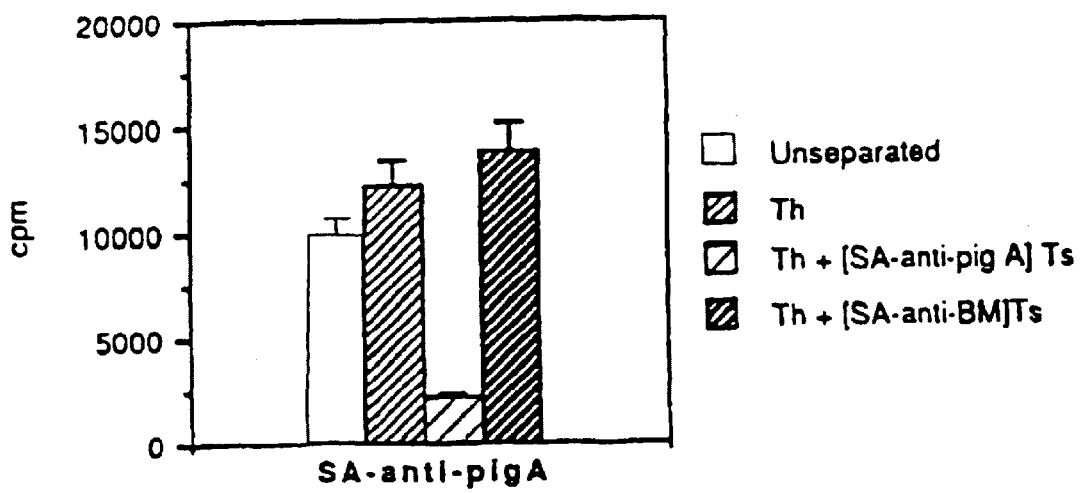

TCLs were generated by priming T cells from a healthy volunteer (SA) with PBMCs from an unrelated blood donor (BM) or with PBMCs from an outbred pig (pig A). The allospecific TCL (SA-anti-BM) as well as the xenospecific TCL (SA-anti-pig A) showed higher reactivity against APCs from the original stimulator after removal of $CD8^+CD28^-$ Ts cells from the suspensions (FIG. 6). Furthermore, when $CD8^+CD28^-$ T cells were added to the cultures at the initiation of the blastogenesis assay, they inhibited significantly ($p<0.05$) the reactivity of $CD4^+$ Th cells against APCs used for priming. The suppressive effect was species-specific since $CD8^+CD28^-$ Ts cells primed to pig APCs did not inhibit the response of $CD4^+$ Th cells primed to human APCs. Similarly, Ts cells primed to human APCs did not inhibit the response of CD4 Th cells primed to pig APCs, indicating that Ts cells recognize species-specific antigens (FIG. 6). Studies of an additional four xenospecific and allospecific TCLs yielded similar results.

To determine whether the suppressive effect correlates with the number of Ts cells present in the cultures, Ts cells from two xenoreactive TCLs, MN-anti-pig B and AP-anti-pig B, were tested at various concentrations for their ability to inhibit proliferation of Th cells from TCLs MN-anti-pig B and AP-anti-pig B, respectively. As illustrated in Table 5, the strength of the suppressive effect increased with the number of Ts cells, indicating that suppression was dose dependent ($r=0.85$, $p<0.008$).

To determine the nature of the SLA antigens recognized by $CD8^+CD28^-$ T cells on pig stimulating cells, xenoreactive TCLs were generated by stimulating PBMCs from a human blood donor (ES) with irradiated APCs from three different strains of inbred swine: Q, W, and Z. Strain Q shares class I antigens with W and class II antigens with Z, being homozygous for a recombinant haplotype which carries the SLA class I antigens of W and the class II antigens of Z.

Table 6 shows the results of independent experiments in which TCL generated on three different occasions, by priming PBMC from individual ES with APCs from strain Q, W, and Z, were used.

TABLE 5

Dose-Dependent Suppression of $CD4^+$ Th Reactivity to Irradiated Pig APCs in the Presence of $CD8^+CD28^-$ Ts.

| Number of cells/well | | | Reactivity (mean cpm) of Th cells from TCL* | |
|---|---|---|---|---|
| APCs | Th | Ts | MN-anti-pig B | AP-anti-pig B |
| $5 \times 10^4$ | 0 | 0 | 278 | 118 |
| $5 \times 10^4$ | $2.5 \times 10^4$ | 0 | 27,031 | 13,306 |
| $5 \times 10^4$ | $2.5 \times 10^4$ | $1.25 \times 10^4$ | 13,808 | 6,394 |

TABLE 5-continued

Dose-Dependent Suppression of CD4+ Th Reactivity
to Irradiated Pig APCs in the Presence of
CD8+CD28− Ts.

| Number of cells/well | | | Reactivity (mean cpm) of Th cells from TCL* | |
|---|---|---|---|---|
| APCs | Th | Ts | MN-anti-pig B | AP-anti-pig B |
| $5 \times 10^4$ | $2.5 \times 10^4$ | $2.5 \times 10^4$ | 8,516 | 2,848 |
| $5 \times 10^4$ | $2.5 \times 10^4$ | $5.0 \times 10^4$ | 6,480 | 2,689 |

*All reactions were performed in triplicate. The SD to the mean was <10%.

TABLE 6

Reactivity of CD4+ Th Cells from TCL ES-anti-swine Q in the Presence of CD8+CD28− T Suppressor Cells

| Ts from | Source of APCs used for priming of Ts | Genotype of APCs | | Reactivity (mean cpm) of CD4+ Th from TCL ES-anit-Q* Source of APCs used in blastogenesis assay | | | |
|---|---|---|---|---|---|---|---|
| | | Class I | Class II | Q | W | Z | W + Z |
| Experiment 1 | | | | | | | |
| No Ts added | — | — | — | 31,079 | 3,719 | 28,269 | 38,040 |
| ES-anti-Q | Q | W | Z | 7,301 | 1,746 | — | 32,280 |
| ES-anti-W | W | W | W | 12,140 | 2,711 | 25,545 | — |
| ES-anti-Z | Z | Z | Z | 25,946 | 2,709 | 17,018 | — |
| Experiment 2 | | | | | | | |
| No Ts added | — | — | — | 33,787 | — | 32,880 | — |
| ES-anti-Q | Q | W | Z | 8,417 | — | 30,510 | — |
| ES-anti-W | W | W | W | 15,240 | — | 33,150 | — |
| ES-anti-Z | Z | Z | Z | 32,790 | — | 15,208 | — |
| Experiment 3 | | | | | | | |
| No Ts added | — | — | — | 22,540 | 1,452 | 20,715 | 19,830 |
| ES-anti-Q | Q | W | Z | 5,215 | 1,310 | 25,487 | 20,156 |
| EA-anti-W | W | W | W | 7,523 | 1,640 | 22,519 | 9,780 |
| ES-anti-Z | Z | Z | Z | 19,834 | 1,415 | 8,328 | 9,530 |

*For each experiment, reactions were set up in triplicate cultures. The SD to the mean of triplicate reactions was <10%.

In these experiments CD4+ Th cells from ES-anti-swine Q were tested for reactivity in cultures without Ts cells or with Ts cells from ES-anti-Q, ES-anti-W and ES-anti-Z.

The reactivity of Th cells primed to APCs of strain Q to the specific stimulator Q was inhibited efficiently by autologous Ts cells primed to Q or to W (which shares MHC class I antigens with Q), but not by Ts cells primed to Z (which is MHC class II identical, yet class I different from the specific stimulator Q) (p<0.05). CD4+ T cell reactivity to strain Z was inhibited only by Ts cells primed to Z, but not by Ts cells primed to strain Q or W which are class I different from Z (p<0.05) (Table 6). This indicates that CD8+CD28− Ts cells are activated by SLA class I antigens on xenogeneic APCs and inhibit the response of CD4+ Th cells against class II antigens expressed by the same stimulating target cells. The MHC class II specificity of Th cell reactivity was confirmed by the fact that human CD4+ T cells primed to APCs from a strain Q swine reacted to APCs from strain Z (class II identical with Q) but not from strain W (class II different from Q).

To establish whether the suppressive activity of CD8+CD28− T cells requires the direct interaction of these cells with the APCs that trigger Th cells reactivity, cell-mixing experiments were performed. In these experiments, mixtures of APCs from strain Z and W were used to stimulate the reactivity of Th cells from TCL ES-anti-Q. The reactivity of Th cells anti-Q was tested in cultures with or without Ts cells primed to Q, W, or Z. In cultures without Ts cells, Th cells primed to Q proliferated vigorously, consistent with the specific recognition of MHC class II antigens shared by strains Q and Z. This response, however, was not inhibited by Ts cells primed to Q or W, indicating that Ts cells do not inhibit Th cell reactivity to SLA class II antigens unless the SLA class I antigens which they recognize are coexpressed by the same APCs. Indeed inhibition of the response to mixtures of APCs from W and Z was observed only in the presence of Ts cells primed to Z (p<0.05), further demonstrating that the interaction of Ts cells and Th cells with the same APCs is required for suppression. This finding is consistent with the hypothesis that Ts cells interfere with the delivery of costimulatory signals by APCs to CD4+ Th cells(8).

Figure 7A:
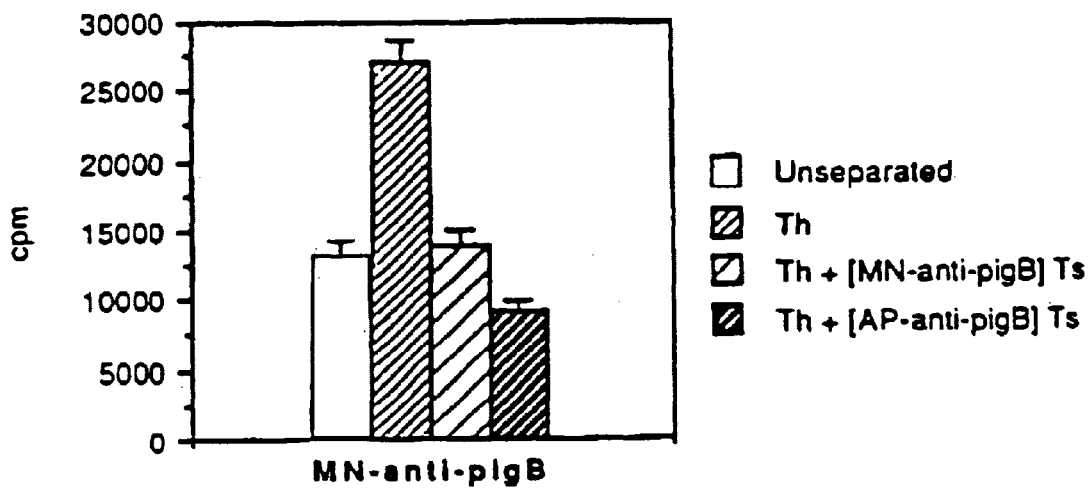
FIGS. 7A–7B. The suppressive effect of xenoreactive CD8$^+$CD28$^-$ T cells does not involve idiotypic or MHC-restricted interactions between Ts cells and Th cells. The reactivity of xenoreactive T cell lines from two human donors (MN and AP.
Figure 7B:
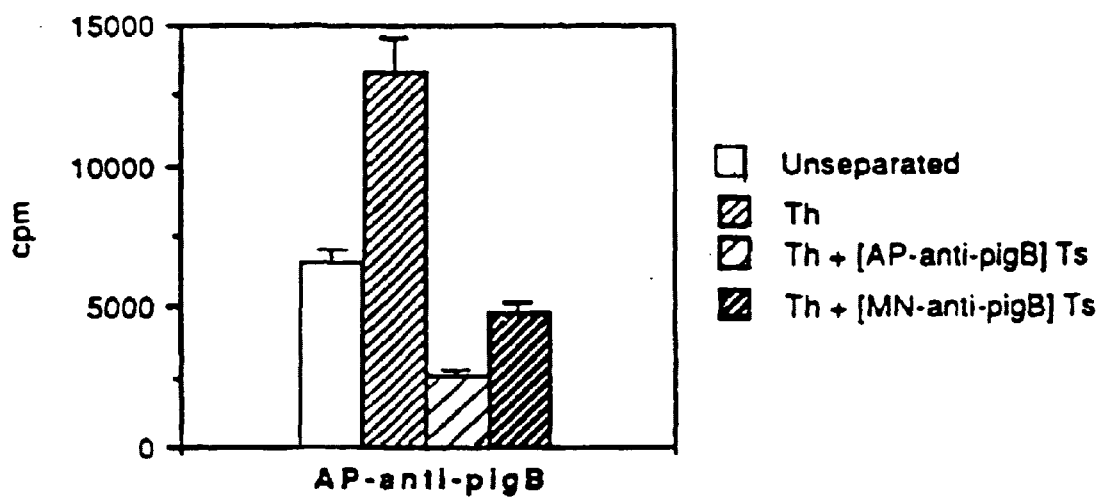

It is possible, however, that in addition to interacting with APCs, Ts cells and Th cells also "communicate" with each other, recognizing TCR determinants or other structures in an MHC-restricted manner (14, 15). To explore this possibility, TCLs were generated by stimulating PBMCs from two HLA-disparate individuals, AP (HLA-A30, B35, DRb1*0701, 1301) and MN (HLA-A1, A32, B8, B44, DRb1*0101, 0301) with APCs from the same outbred pig (pig B). The blastogenic response of both TCLs (MN-anti-pig B and AP-anti-pig B) to pig APCs was significantly stronger (p<0.01) when CD8+CD28− Ts cells were depleted from the cell suspensions, indicating that CD4+ Th cell responses were suppressed by autologous Ts cells (FIG. 7). The reactivity of CD4+ Th cells from both lines to stimulating APCs was inhibited by CD8+CD28− Ts cells from either of these lines (p<0.01). The difference between the suppressor activity of Ts cells from MN-anti-piq B and AP-anti-pig B was not statistically significant. These results were confirmed in two additional experiments for which other TCL were used. Hence, no MHC-restricted interaction between Th cells and Ts cells is required for suppression to occur.

Figure 8A:
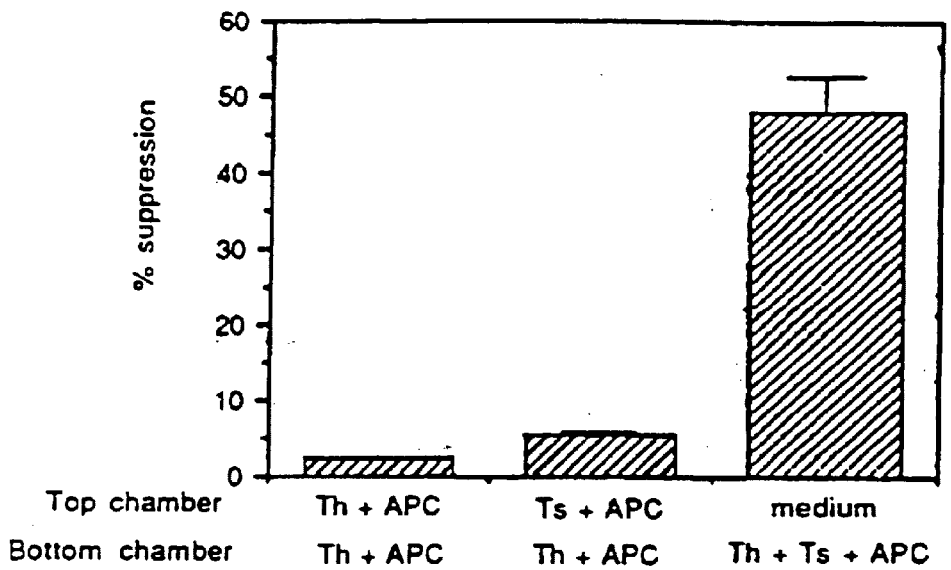
FIGS. 8A–8B.

To determine whether Ts cells secrete inhibitory factors, coculture experiments using semipermeable membranes, for separating Ts cells from Th cells, were performed. Th cells from TCL ES-anti-W were stimulated with irradiated xenogeneic APC from strain W in the bottom compartment, whereas Ts cells were stimulated with the same APCs in the top compartment. Xenoantigen-specific stimulation of Th cells was inhibited significantly only when Ts cells, Th cells, and APCs were in close contact, but not when Ts cells and Th cells were separated by a membrane (p=0.0001), indicating that cell-to-cell interaction is required for the suppressive effect induced by $CD8^+28^-$ Ts cells to occur (FIG. 8A).

Figure 8B:
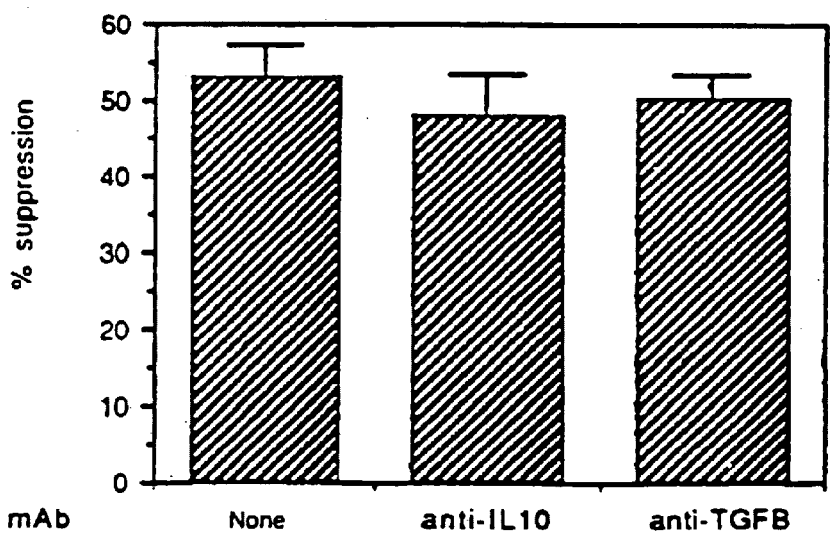
Figure 9A:
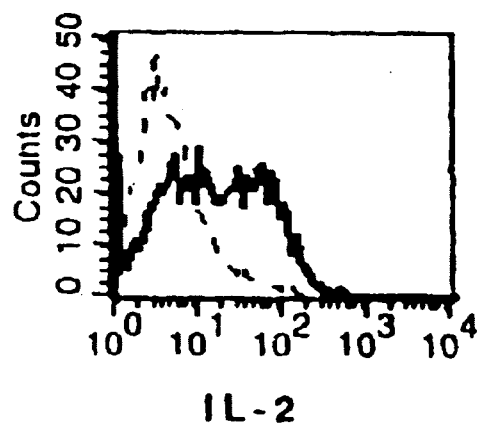
FIGS. 9A–9H. Cytokine profile of xenoreactive Th cells and Ts cells. Th cells and Ts cells from TCL CG-anti-pig Z were activated with PMA and ionomycin. Cells were treated with Brefeldin A, then fixed and stained with monoclonal antibodies specific for IL-2, IFN-γ, IL-4, and IL-10. Histograms obtained for the activated samples (solid line) and resting control samples (dotted lines) are presented. The results are representative of three independent experiments.
Figure 9B:
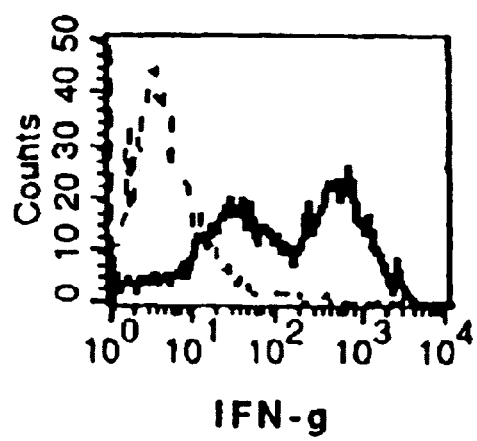
Figure 9C:
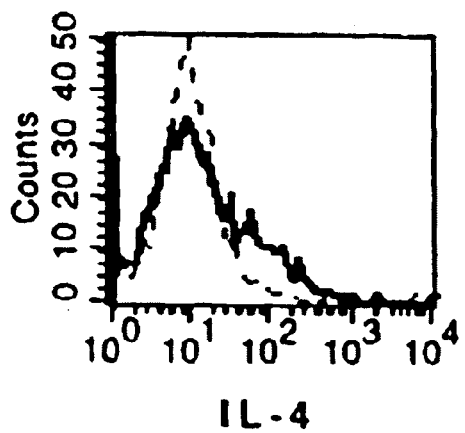
Figure 9D:
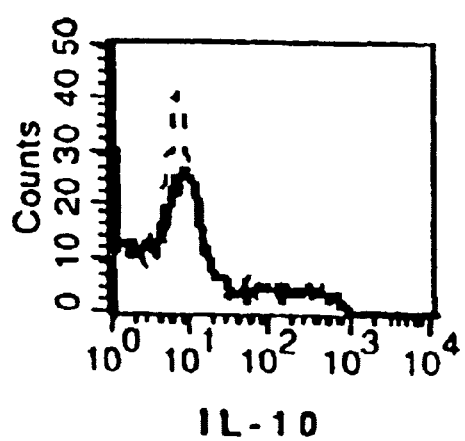
Figure 9E:
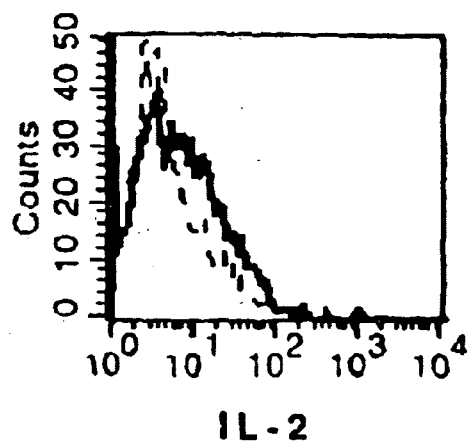
Figure 9F:
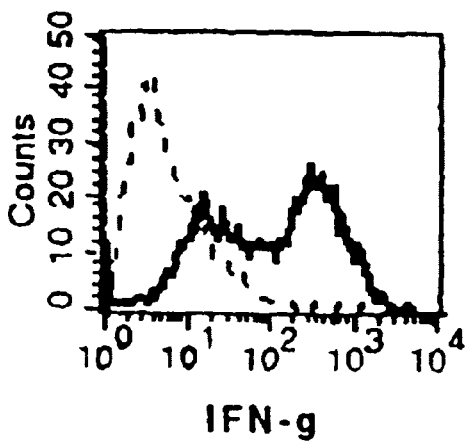
Figure 9G:
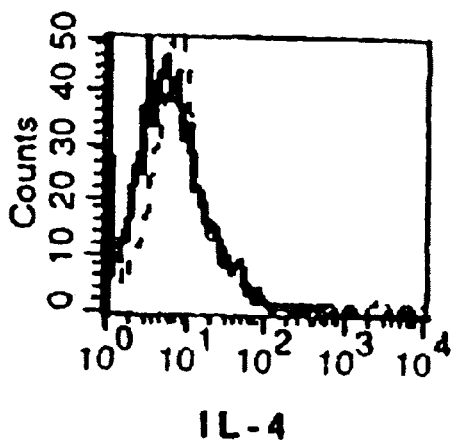
Figure 9H:
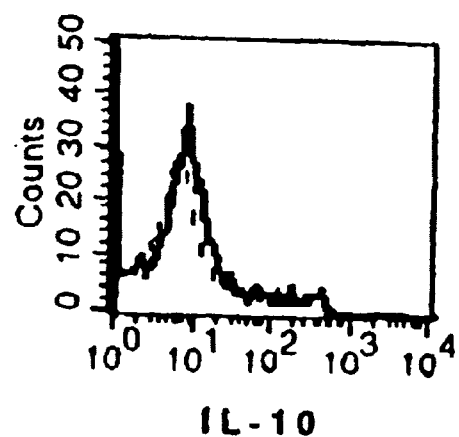

To further explore the possibility that suppression is mediated by inhibitory cytokines, such as IL-10 or TGF-b, experiments were performed in which mAbs to IL-10 and to TGF-b were added to cultures containing only Th cells, or both Th cells, Ts cells, and stimulating APCs. These mAbs had no significant effect on Th cells proliferation in the absence of Ts cells (data not shown) and failed to abrogate or decrease the inhibitory effect induced by Ts cells on Th cell reactivity (FIG. 8B).

Cytofluorographic analysis of Ts cells from three different TCLs (ES-anti-Q, ES-anti-W and ES-anti-Z) showed that they produced high levels of IFN-$\gamma$ and moderate amounts of IL-2, yet no detectable levels of IL-4 and IL-10. Th cells from the same cultures produced high levels of IL-2 and IFN-$\gamma$, moderate amounts of IL-4, and no IL-10 (FIG. 9).

Study of Ts Cell-Induced Apoptosis

Figure 10A:
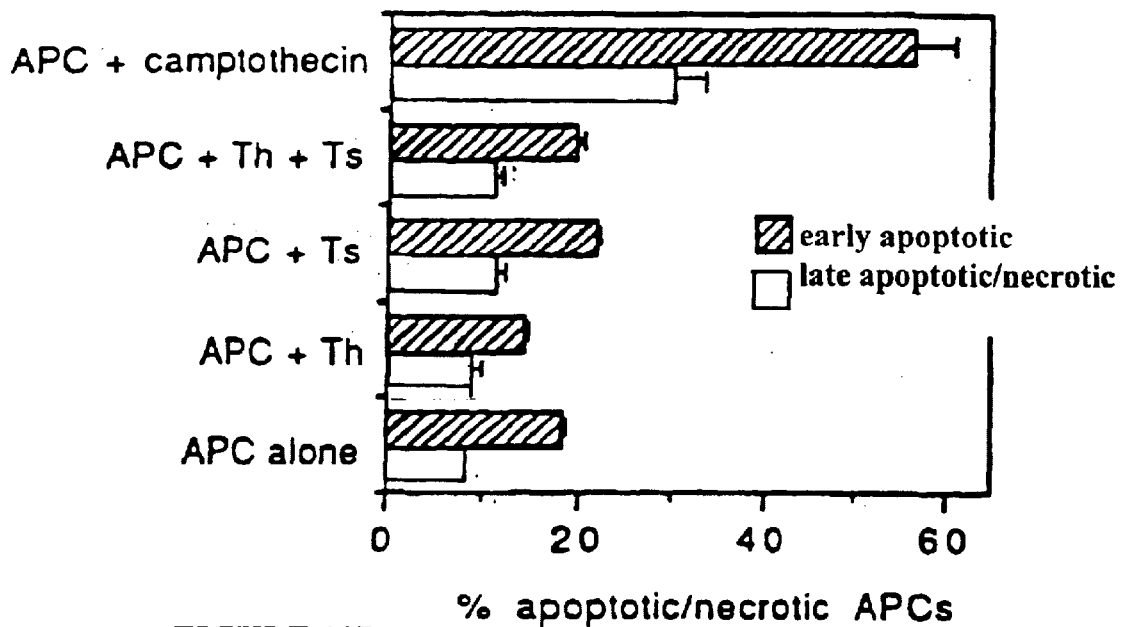
FIGS. 10A–10C. Failure of Ts cells to induce killing of pig APCs or human xenoreactive Th cells.
Figure 10B:
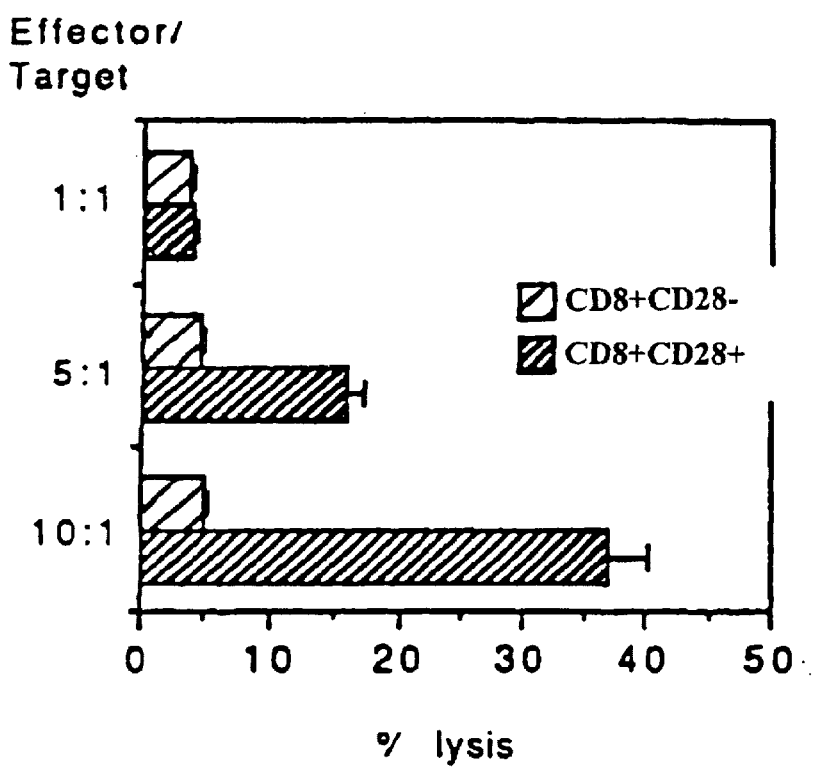

The possibility that the suppressive activity of xenospecific Ts may be due to killing of pig APCs was explored. Ts cells from a human TCL (GC-anti-swine Z), which inhibited by 88% the response of autologous Th cells to the specific stimulator, were tested for their ability to induce apoptosis or lysis of pig APC. Flow cytometry studies of apoptosis were performed by incubating Ts cells for 4 hours with pig APCs in the presence or absence of xenoreactive $CD4^+$ Th cells and then staining the cultures with annexin V. The percentage of annexin V positive APCs was not significantly different in cultures with or without Ts cells, indicating that no apoptosis of pig APCs was induced (FIG. 10A). Also, the percentage of necrotic pig cells stained by PI was not significantly different in cultures with or without human Ts cells. Furthermore, cell mediated lysis experiments in which PHA-activated pig lymphocytes were used as targets showed lysis when $CD8^+CD28^+$ T cells were used as effectors, but not when $CD8^+CD28^-$ T cells from the same line were tested. This demonstrates that Ts cells do not kill xenogeneic APCs used for priming (FIG. 10B).

Figure 10C:
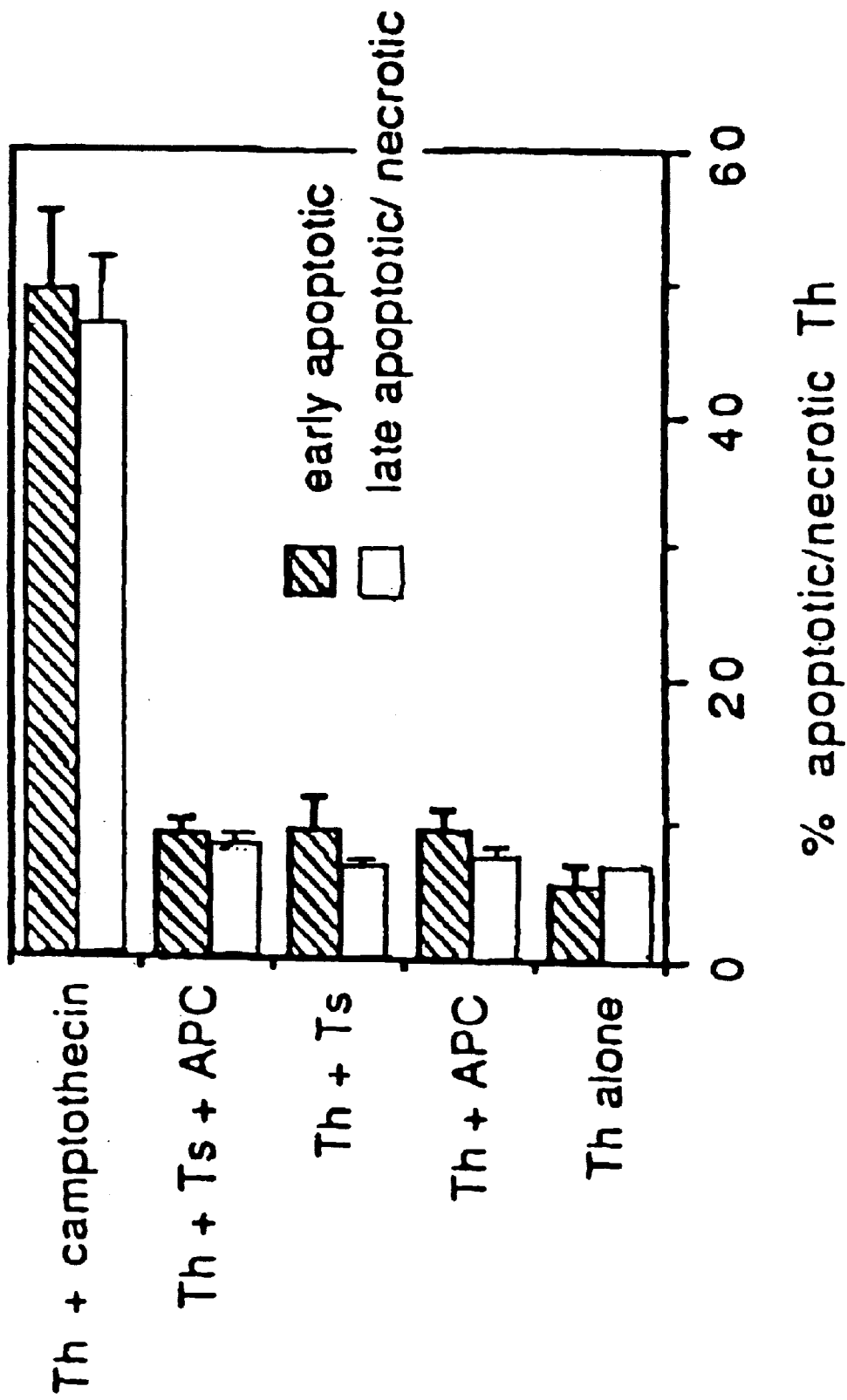

Next investigated was the hypothesis that Ts cells may cause apoptotic death of xenoreactive Th cells. In these experiments, $CD4^+$ Th cells from TCL GC-anti-swine Z were incubated for 4 hours with APCs from swine Z, in the presence or absence of autologous Ts cells. The percentage of annexin V-positive $CD4^+$ Th cells in cultures with Ts cells was not significantly different from the percentage found in cultures without Ts cells, indicating that suppression is not mediated by killing of xenoreactive Th cells (FIG. 10C). Hence, Ts cell suppressive activity is not due to killing of either Th cells or stimulatory APCs.

Expression of CD40 Ligand (CD40L) (CD154) on Xenoreactive Th Cells

Figure 11A:
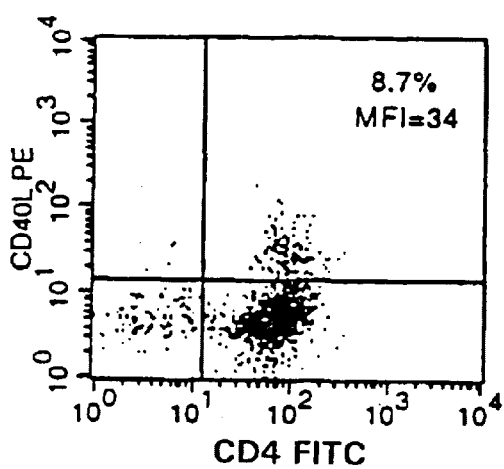
FIGS. 11A–11D. Xenoreactive CD8$^+$CD28$^-$ T suppressor cells prevent up-regulation of CD40L expression on xenoreactive CD4$^+$ T cells. Human CD4$^+$ T cells were incubated for 6 hours without APCs (FIG. 11A), with APCs from the specific xenostimulator (pig W) (FIG. 11B), with APCs and Ts cells (FIG. 11C) or with control APCs from a pig (pig Z) that has different SLA class II antigens (FIG. 11D). CD154 expression on CD3$^+$CD4$^+$ human T cells was analyzed by flow cytometry. The percent CD154 positive T cells and the mean fluorescence intensity (MFI) are indicated. The results obtained with this TCL (CO-anti-pig W) are representative of data obtained from six TCLs.
Figure 11B:
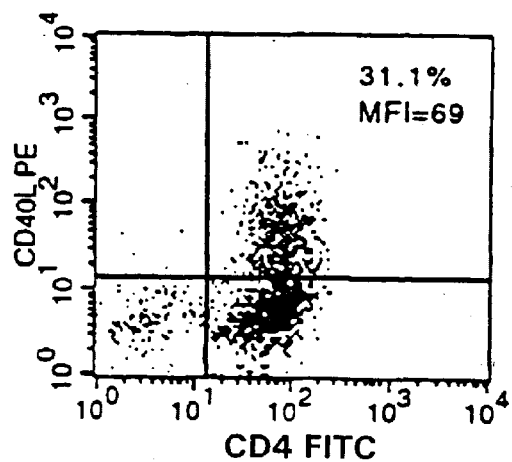
Figure 11C:
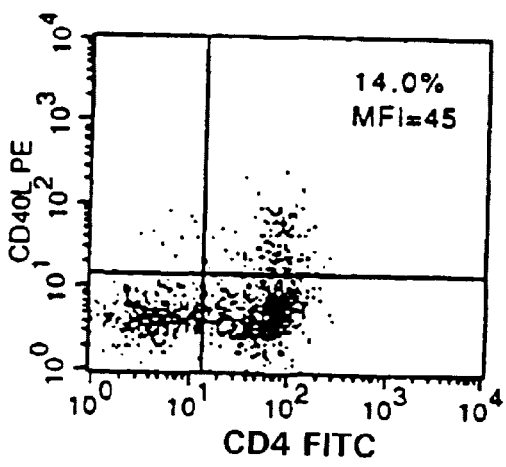
Figure 11D:
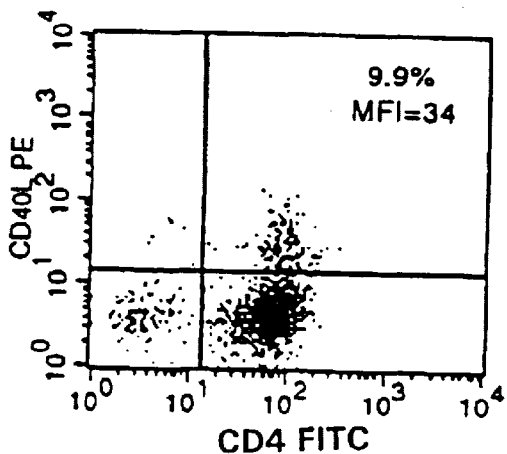

The possibility that Ts cells interfere with the costimulatory interaction between CD154 on Th cells (CD40L, T-BAM, p39, or TRAP) and CD40 on xenogeneic APCs has been explored. For this, the expression of CD154 on xenoreactive $CD4^+$ Th cells which were stimulated with pig APCs in the presence or in the absence of Ts cells was studied. After 6 hours of incubation, cells were stained with mAbs anti-CD3, CD154, and either CD4 or CD8. Analysis of the results obtained in independent experiments, using six different TCLs, showed that the level of CD154 expression on $CD4^+$ Th cells was significantly higher (p<0.01) in cultures containing pig APCs than in cultures without stimulating cells (FIGS. 11A and 11B). However, expression of CD154 on $CD4^+$ Th cells was drastically reduced in the presence of Ts cells (FIG. 11C), indicating that Ts cells prevent antigen-induced up-regulation of CD154 on $CD4^+$ Th cells. There was a statistically significant difference between the level of CD154 expression on Th cell cultures with and without Ts cells (p<0.01) in all six experiments. The up-regulation of CD154 was antigen specific, requiring TCR activation, since it did not occur on $CD4^+$ Th cells challenged with APCs from an SLA class II-different pig (FIG. 11D). The expression of CD154 on xenoreactive $CD4^+$ Th cells was maximal after 6 hours and decreased significantly after 18 hours of incubation with stimulating APCs (data not shown). No expression of CD154 was observed on Ts cells at any time point studied. Hence, Ts cell-induced events that result in Th cell inhibition occur within the first 6 hours of stimulation.

Spectratyping of TCLs Expressed by Ts

Figure 12:
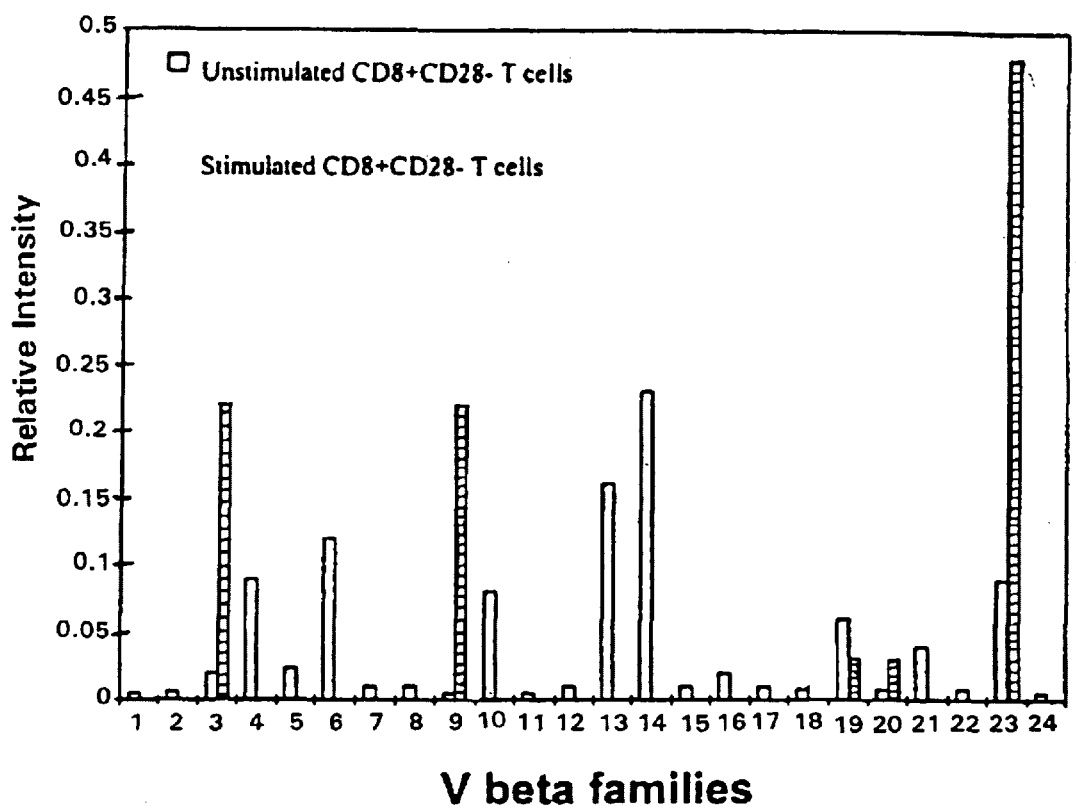
FIG. 12. Vβ repertoire of unstimulated CD8$^+$CD28$^-$ T cells from individual MN and of xenoreactive Ts cells from TCL MN-anti-pig B expressed as relative intensity. To analyze spectratypes, relative intensity was calculated as the peak area corresponding to each Vβ family divided by the sum of all peak areas.
Figure 13A:
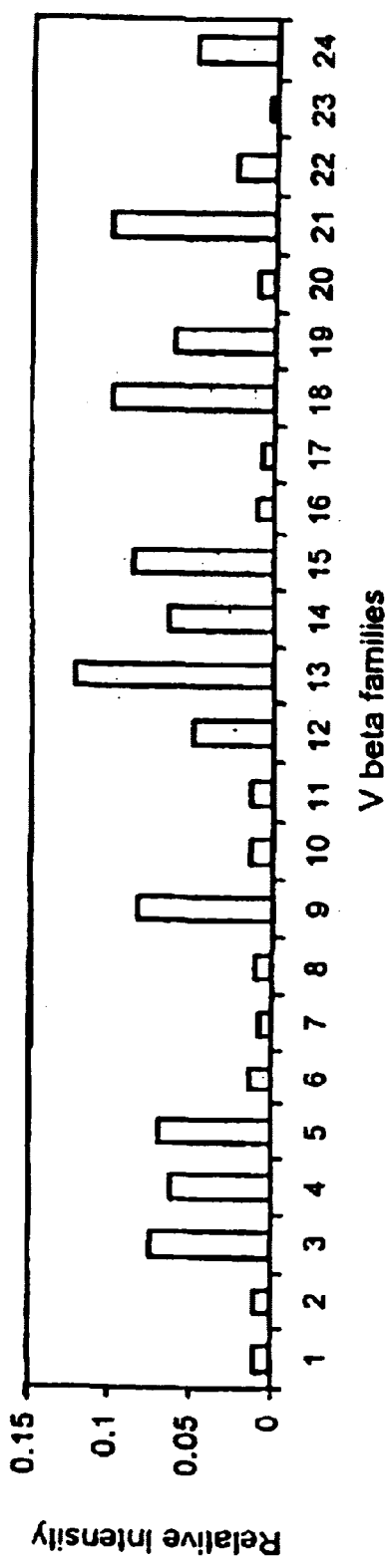
FIGS. 13A–13D. Vβ repertoire of unstimulated CD8$^+$CD28$^-$ T cells from individual ES (FIG. 13A) and of Ts cells from TCL ES-anti-pig Q (FIG. 13B), ES-anti-pig W (FIG. 13C), ES-anti-pig Z (FIG. 13D) expressed as relative intensity (histogram bars).
Figure 13B:
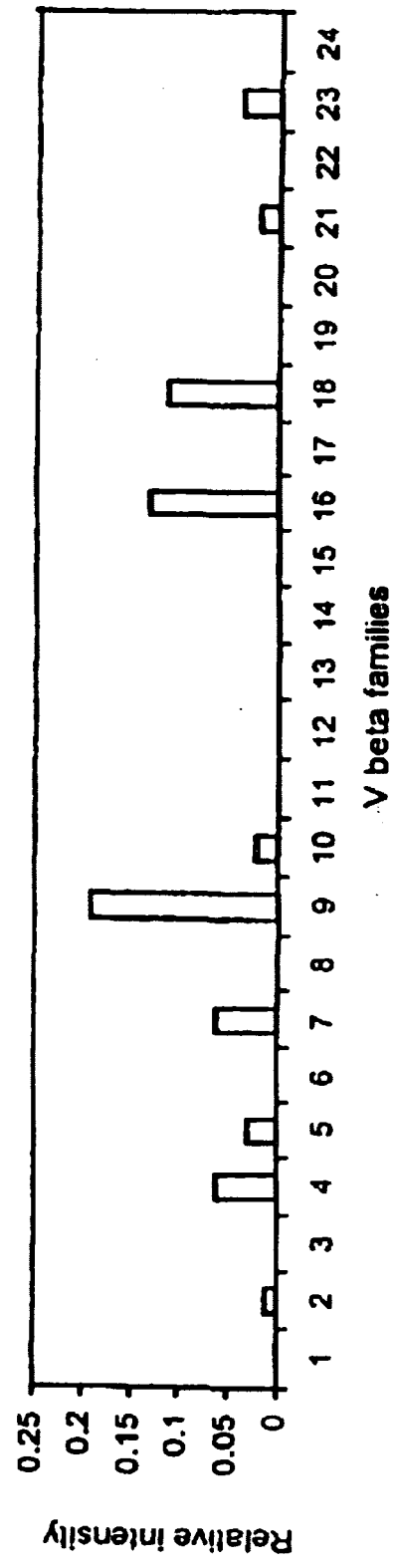
Figure 13C:
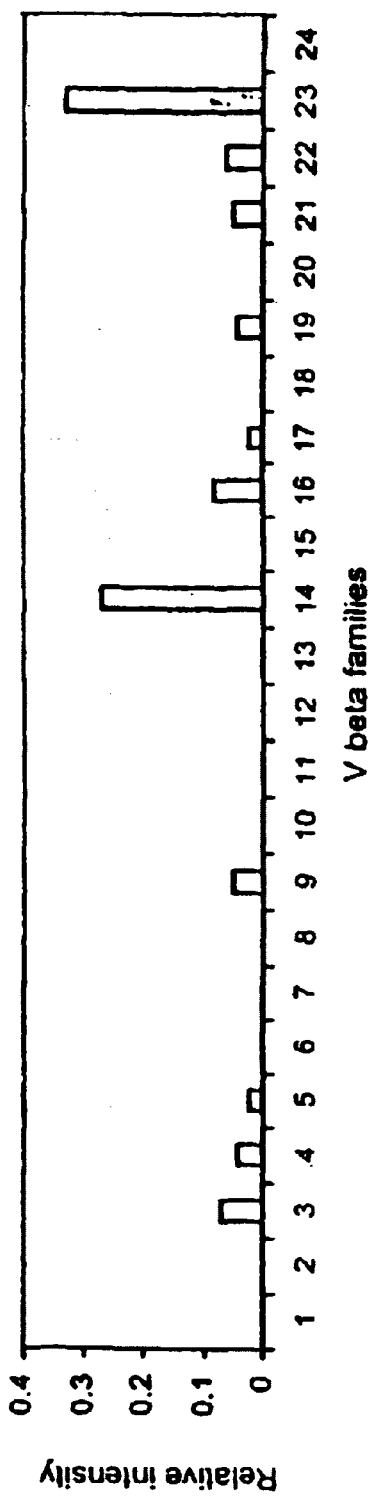
Figure 13D:
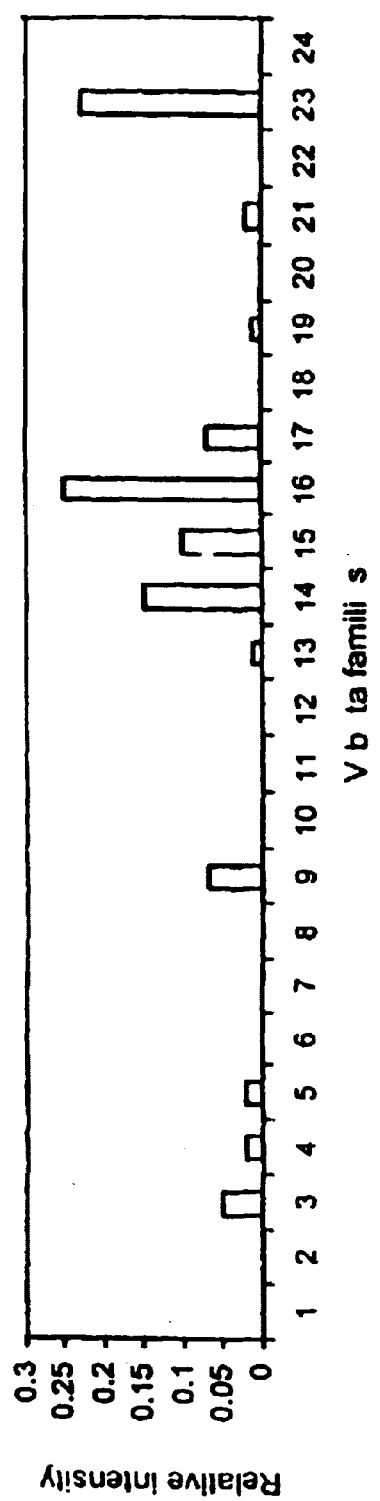
Figure 14A:
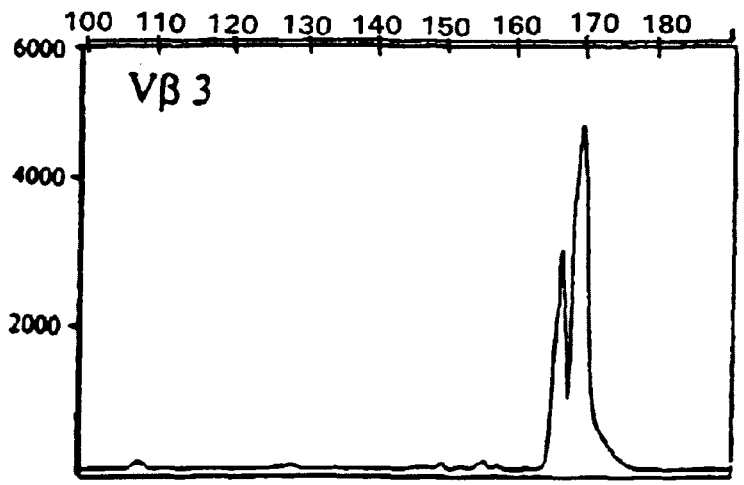
FIGS. 14A–14F. Vβ spectratyping of Ts cells from TCL MN-anti-pig B. Only the families with positive signal are shown x-axis, fragment lengths on base pairs; y-axis, fluorescence amplitude.
Figure 14B:
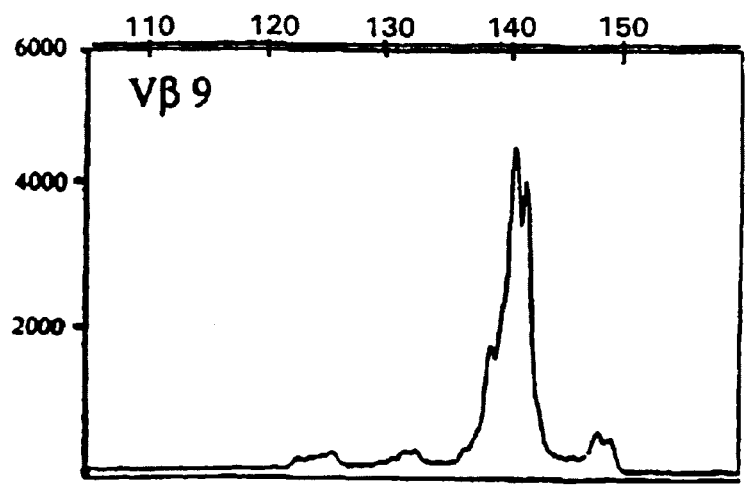
Figure 14C:
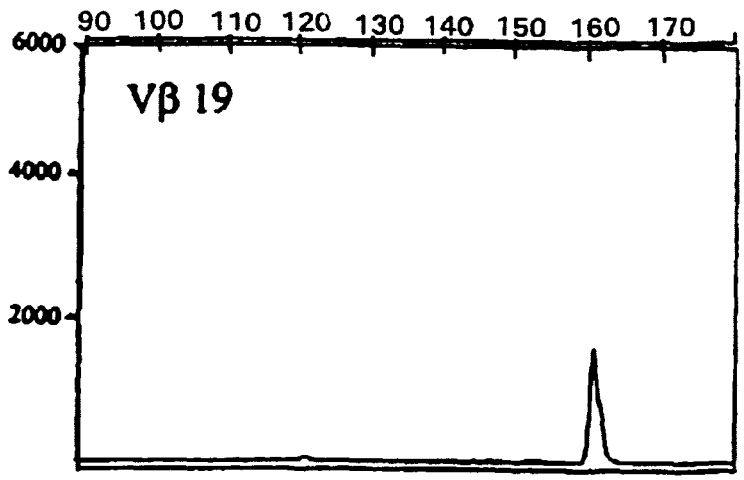
Figure 14D:
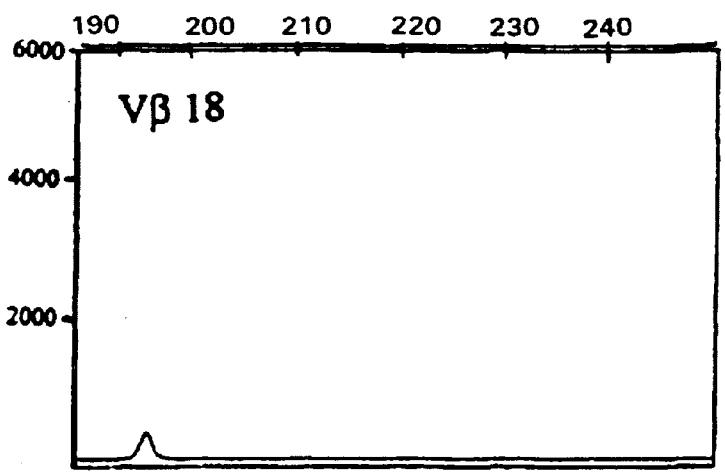
Figure 14E:
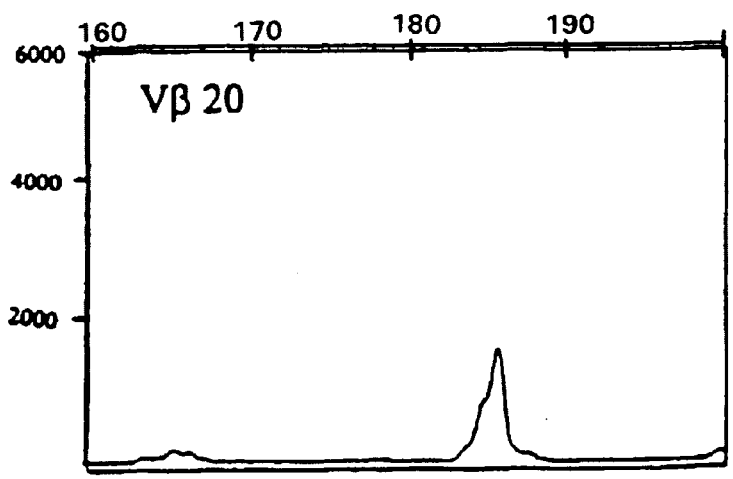
Figure 14F:
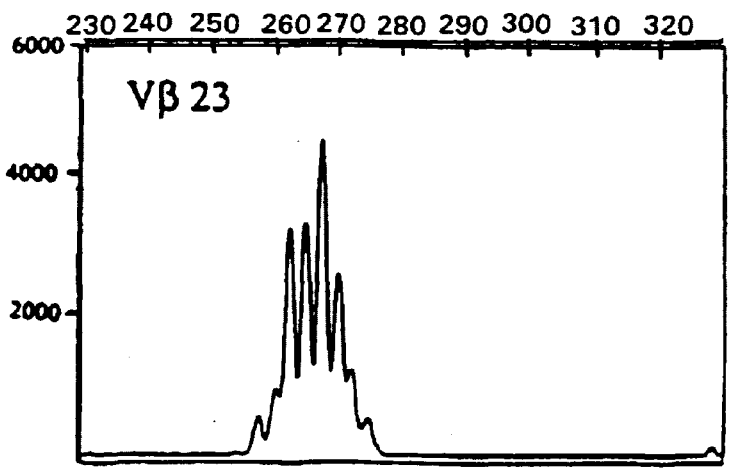

The V$\beta$ gene usage of Ts cells from four human anti-pig TCLs (MN-anti-pig B, ES-anti-Q, ES-anti-W, and ES-anti-Z) was determined by spectratyping (FIGS. 12 and 13). Ts cells from each of these xenoreactive TCL showed a restricted TCR V$\beta$ gene usage. The side-by-side comparison of the Vb repertoire expressed in unstimulated and stimulated $CD8^+CD28^-$ T cells indicates that after two stimulations with xenogeneic APCs, there was oligoclonal expansion of Ts cells, as illustrated in FIG. 12 and 13.

Figure 15A:
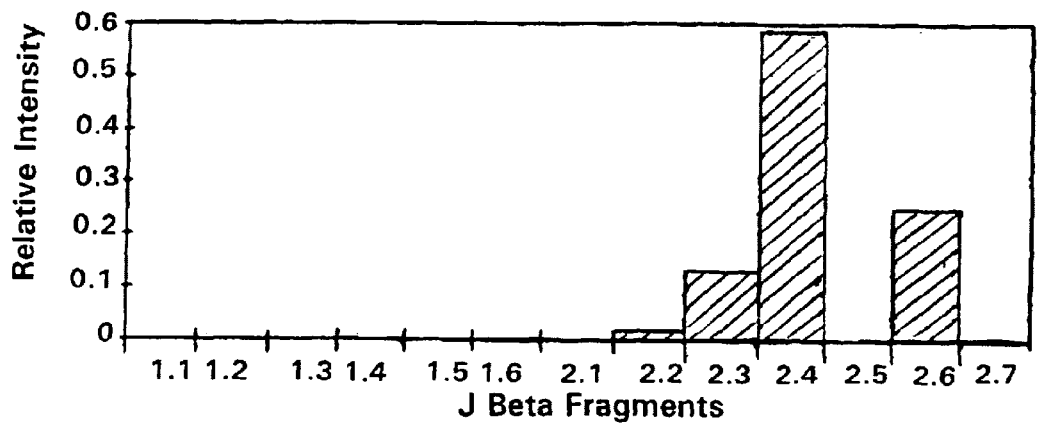
FIGS. 15A–15C. Distribution of Jβ-Vβ combination fragments in the Vβ9 (FIG. 15A), Vβ16 (FIG. 15B) and Vβ23 (FIG. 15C) families found in Ts cells from TCL ES-anti-pig Q. x-axis, fragment lengths on base pairs; y-axis, fluorescence amplitude.
Figure 15B:
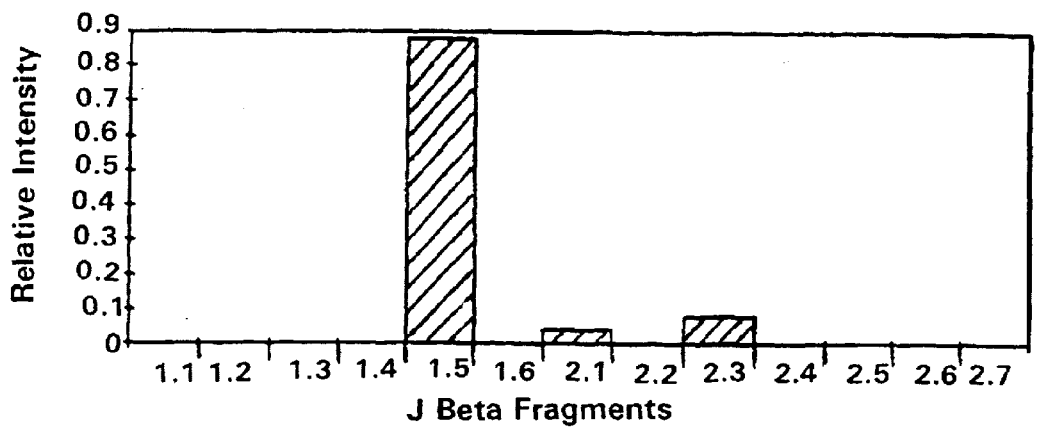
Figure 15C:
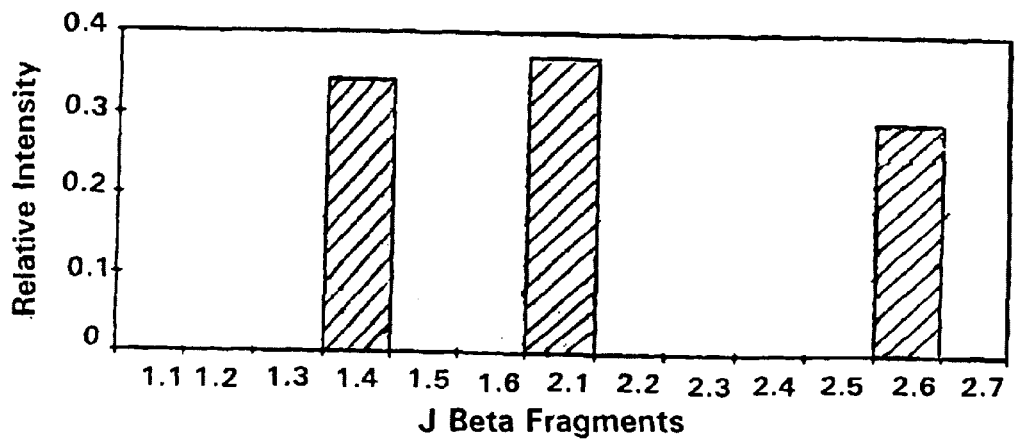

The V$\beta$9 and V$\beta$23 families were expressed by all TCLs yet with different relative intensities (FIGS. 12 and 13). The relative intensities of V$\beta$9 family in TCL MN-anti-pig B, ES-anti-Q, ES-anti-W, ES-anti-Z were 0.22, 0.19, 0.05, and 0.07, respectively, and the relative intensity of V$\beta$23 was 0.48, 0.38, 0.30, 0.23, respectively. V$\beta$16 was highly represented in all TCL generated from individual ES yet was absent in TCL obtained from another human subject (MN). V$\beta$5 was also expressed by Ts cells from all TCL derived from responder ES, but with lower intensity than V$\beta$16. In two of the TCLs from individual ES (ES-anti-pig W and ES-anti-pig Z), V$\beta$14 was represented with high intensity (FIG. 13, B and C). Other V$\beta$ families, such as V$\beta$15 were uniquely represented in one suppressor cell line (ES-anti-pig Z) (FIG. 13C), while absent from the other lines (ES-anti-Q, ES-anti-W and MN-anti-pig B). Analysis of the CDR3 size distribution revealed a unimodal or bimodal distribution for each V$\beta$ family, except V$\beta$23 that showed a multipeak gaussian-like distribution (FIG. 14). The oligoclonality of the V$\beta$ repertoire expressed by xenoreactive Ts cells was also confirmed by analyzing the J$\beta$-V62 fragments of V$\beta$ families (FIG. 15).

DISCUSSION

The phenotypic characteristics of suppressor cells as well as the mechanisms that underlie their function have been the object of numerous studies (16–25) Both $CD4^+$ and $CD8^+$ T cells with suppressive activity have been described, although antigen-specific suppressor cell lines have been difficult to generate.

CD4+ T cells producing TGF-b, IL-4, and IL-10 were shown to play an important role in protecting animals from experimental autoimmune encephalomyelitis (EAE) after oral feeding with antigen (21). IL-10 was recently shown to induce in vitro differentiation of regulatory CD4+ T cells with suppressor activity and inhibit alloantigen-specific reactivity of CD8+ T cells (7, 23). MHC class-II restricted CD8+ Ts cells that release IL-4 and suppress Th1 cell proliferation were described in human leprosy (24, 25). In the mouse model, CD8+ Ts cells were also described, yet these cells were restricted by nonclassical MHC class I antigens (Qa-1) expressed by B cells and inhibited Th2 responses by production of IFN-γ (18). In other studies, suppression was mediated by Qa-1 restricted CD8+ T cells, which recognize TCR determinants on the membrane of CD4+ Th cells (14, 15, 25). The mechanism of antiidiotypic suppression involved Th cell lysis or induction of Th cell apoptosis via ligation of Fas (15, 19).

An alternative mechanism of suppression seems to reside in inhibition of TCR-mediated cytotoxicity by CD8+CD28− and CD4+CD28− T cells which express NK inhibitory receptors (26–28). The inhibitory effect of these killing-inhibitory receptors results from mobilization of protein tyrosine phosphatases on the cytoplasmic tail of killing-inhibitory receptor molecules (28).

In a previous study it was shown that human CD8+CD28− Ts cells, which inhibit alloreactive CD4+ Th cells, recognize HLA class I antigens on the surface of allogeneic APCs used for priming (8). The suppression was mediated by down-regulation of CD80 and CD86 expression on the allogeneic APCs and, thus, by impairment of their ability to deliver the costimulatory signals required for the activation of CD4+ Th cells in response to HLA class II alloantigens.

The present study demonstrates for the first time that the xenospecific response of human CD4+ Th cells to pig MHC class II antigens can be also suppressed by CD8+CD28− T cells immunized in vitro against xenogeneic MHC class I antigens. The suppressive effect was not mediated by idiotypic interactions between xenoreactive Ts cells and Th cells, since Th cells primed to APCs from an individual pig were efficiently suppressed not only by autologous but also by allogeneic human Ts cells immunized against the same SLA class I antigens.

The possibility that suppression of CD4+ Th cells was mediated by lymphokines secreted by CD8+CD28− Ts cells is also unlikely, since the suppressive activity required the interaction between Th cells and Ts cells with the same APCs. Thus, Th cell inhibition occurred only when the immunizing SLA class I and class II antigens were coexpressed on the membrane of stimulating APCs, but not when these antigens were expressed by two distinct populations of APCs. Furthermore, diffusion chamber experiments in which Ts and Th cells were separated by semipermeable membranes showed that Th cell reactivity to xenogeneic APCs was not inhibited, indicating that suppression is not mediated by soluble factors.

Cytofluorographic analysis of CD8+CD28− Ts cells showed that these cells produce IL-2 and IFN-γ, but not IL-4 and IL-10. Moreover, experiments using mabs against inhibitory cytokines, such as IL-10 and TGF-β, excluded their contribution to the suppressor effect. Hence, neither the production or consumption of lymphokines by Ts cells (22, 24, 29) can explain their inhibitory effect on Th cells in this system.

In the allogeneic system, it was demonstrated that Ts cells interfere with Th cell-induced up-regulation of B7 (CD80, CD86) expression on APC (8). The interaction between CD40 on APC and CD40L (CD154), a transiently expressed CD4+ T cell molecule, is essential for the induction of accessory molecules on APCs, in particular CD80, CD86, and 4-1BB ligand, and for the initiation of antigen-specific T cell reactivity (30–35). However, blockade of either CD28/B7 or CD40L/CD40 pathways does not inhibit completely T cell mediated alloimmune responses, indicating that, although interrelated, the CD28 and CD40L pathways serve as independent regulators of T cell responses (36).

The possibility that Ts cells interfere with the expression of CD40L (CD154) on activated CD4+ Th cells has been explored. Cytofluorographic analysis showed that up-regulation of CD154 expression on xenoreactive CD4+ Th cells was induced by pig APCs, indicating that human CD154/pig CD40 interaction contributes to the strong proliferative response occurring on recognition by human TCRs of SLA class II antigens. Hence, in the human-pig system, xenoantigen-specific CD4+ Th cell responses involve not only the CD28/B7 and CD2/LFA1 costimulatory pathways, as previously described (37), but also the CD154/CD40 pathway. However, the expression of CD154 on xenoreactive CD4+ Th cells was significantly reduced in the presence of Ts cells. The molecular mechanism of CD154 down-regulation on xenoreactive CD4+ Th cells by Ts cells is currently under investigation. The possibility that Ts cells prevent up-regulation of CD40L on CD4+ T cells by killing the xenogeneic stimulating cells or by inducing Th cell apoptosis was ruled out since no evidence of Ts cell-induced cell death was found by either flow cytometry of $^{51}$Cr release studies. Proliferation of CD4+ T cells was not restored in the presence of cells expressing constitutively CD40L, suggesting that costimulation of xenogeneic APCs through the CD40–CD40L pathway is not sufficient to circumvent the suppressive effect of Ts cells (A.I. Colovai, manuscript in preparation). Down-modulation of CD154 by Ts cells may lead, however, to disengagement of Th cells from the targets, preventing full activation and proliferation of these cells. T cell reactivity to allogeneic and xenogeneic MHC antigens bears resemblance to TCR activation by nominal antigens and pathogens, as it involves recognition of targets expressing novel MHC/peptide complexes. Since the generation of allo-or xenospecific Ts cells in vitro requires multiple rounds of stimulation, it is possible that the chronic exposure to antigen is also required in vivo for the induction of Ts cells. The oligoclonal expansion of a few TCR Vβ families observed within the population of xenoreactive Ts cells is reminiscent of the skewed TCR repertoire displayed by T lymphocytes with HLA class I-specific NK-inhibitory receptors (27), a phenomenon suggested to result from chronic antigenic stimulation.

MHC class I-restricted Ts cells may play a physiologic role in regulating the immune response of Th cells against self or non-self peptide/MHC class II complexes. The finding that there is cross-talk between the MHC class I and class II pathways of peptide processing supports the notion that the same APCs present both helper- and suppressor-inducing peptides (38). It is possible that recognition by Ts cells of MHC class I-bound peptides helps control local inflammation caused by antigen-specific Th cells. Identification of suppressor-inducing peptides may be useful for induction of unresponsiveness to auto-, allo-, or xenoantigens. Furthermore, understanding of the mechanism of Ts cell-mediated down-regulation of CD154 expression on activated Th cells may contribute to the development of new immunotherapeutic strategies.

This issue becomes particularly important in view of the recent finding that Th cells condition the APCs to directly stimulate T killer cells by CD154-CD40 signaling, rather than by delivering short range acting lymphokines (39–42). The emerging picture from our studies is that Ts cells down-regulate the immune response by interfering with CD154-CD40 signaling, thus preventing the up-regulation of costimulatory (B7) molecules on APCs.

References for the Second Series of Experiments

1. Sachs, D. H. 1994. The pig as a xenograft donor. Path Biol. 42: 217.
2. Cozzi, E. and D. J. G. White. 1995. The generation of transgenic pigs as potential organ donors for humans. *Nature Medicine*. 1:964.
3. Morgan, B. P. 1995. Complement regulatory molecules: application to therapy and transplantation. *Immunol. Today*. 16:257.
4. Platt, J. L. 1996. The immunological barriers to xenotransplantation. *Critical Rev. Immunol.* 16:331.
5. Choo, J. K., J. D. Seebach, V. Nickeleit, A. Shimizu, H. Lei, D. H. Sachs, and J. C. Madsen. 1997. Species differences in the expression of major histocompatibility complex class II antigens on coronary artery endothelium. *Transplantation*. 64:1315.
6. Cobbold, S. P., E. Adams, S. E. Marshall, J. D. Davies, and H. Waldmann. 1996. Mechanisms of peripheral tolerance and suppression induced by monoclonal antibodies to CD4 and CD8. *Immunol. Rev.* 149:6.
7. Groux, H., A. O'Garra, M. Bigler, M. Rouleau, S. Antonenko, J. E. de Vries, and M. G. Roncarolo. 1997. A $CD4^+$ T-cell subset inhibits antigen-specific T-cell responses and prevents colitis. *Nature*. 389:737.
8. Liu, Z., S. Tugulea, R. Cortesini, and N. Suciu-Foca. 1998. Specific suppression of T helper alloreactivity by allo-MHC-class I restricted $CD8^+CD28^-$ T cells. *Int. Immunol.* 10:101.
9. Singer, D. S., R. Ehrlich, L. Satz, W. Frels, J. Bluestone, R. Hodes, and S. Rudikoff. 1987. Structure and expression of class I MHC genes in the miniature swine. *Vet. Immun. and Immunopath.* 17:211.
10. Hirsh, F., S. Germana, K. Gustafsson, K. Pratt, D. H. Sachs, and C. Laguern. 1992. Structure and expression of class II alpha genes in miniature swine. *J. Immunol.* 149:841.
11. Gustafsson, K., S. Germana, F. Hirsch, K. Platt, C. Laguern, and D. H. Sachs. 1990. Structure of miniature swine class II DRB genes: conservation of hypervariable amino acid residues between distantly related mammalian species. *Proc. Natl. Acad. Sci.* 87:9798.
12. Puiseux, I., J. Even, F. Joterau, M. Favrot, and P. Kourilsky. 1994. Oligoclonality of tumor infiltrating lymphocytes from human melanomas. *J. Immunol.* 153:2807.
13. Gardenet, L., D. Nicolas, C. Dovay, N. Chalumeau, V. Shaeffer, M. Ts Zilber, A. Lim, J. Even, N. Mooney, C. Gelin, E. Gluckman, D. Charron, and A. Toubert. 1998. The umbilical blood ab T-cell repertoire: characteristics of a polyclonal and naive but completely formed repertoire. *Blood* 91:340.
14. Ware, R., H. Jiang, N. Braunstein, J. Kent, E. Wiener, B. Pernis, and L. Chess. 1995. Human $CD8^+$ T lymphocyte clones specific for T cell receptor Vb families expressed on autologous $CD4^+$ T cells. *Immunity.* 2:177.
15. Jiang, H., R. Ware, A. Stall, L. Flaherty, L. Chess, and B. Pernis. 1995. Murine $CD8^+$ T cells that specifically delete autologous $CD4^+$ T cells expressing Vβ8 TCR: a role of the Qa-1 molecule. *Immunity.* 2:185.
16. Jenkins, M. K., C. A. Chen, G. Jung, D. L Mueller, and R. H. Schwartz. 1990. Inhibition of antigen-specific proliferation of type 1 murine T cell clones after stimulation with immobilized anti-CD3 monoclonal antibody. *J. Immunol.* 144:16.
17. Schwartz, R.H. 1990. A cell culture model for T lymphocyte clonal anergy. *Science*. 248:1349.
18. Noble, A., Z. S. Zhao, and H. Cantor. 1998. Suppression of immune responses by CD8 cells. II. Qa-1 on activated B cells stimulate CD8 cell suppression of T helper 2 responses. *J. Immunol.* 160:566.
19. Noble, A., G. A. Pestano, and H. Cantor. 1998. Suppression of immune responses by CD8 cells. I. Superantigen-activated CD8 cells induce unidirectional Fas-mediated apoptosis of antigen-activated CD4 cells. *J. Immunol.* 159:559.
20. Barker, T. D., D. Weissman, J. A. Daucher, K. M. Roche, and A. S. Fauci. 1996. Identification of multiple and distinct $CD8^+$ T cell suppressor activities: dichotomy between infected and uninfected individuals, evolution with progression of disease, and sensitivity to gamma irradiation. *J. Immunol.* 156:4476
21. Chen, Y., V. K. Kuchroo, J. I. Inobe, D. A. Hafler, H. L. Weiner. 1994. Regulatory T cell clones induced by oral tolerance: suppression of autoimmune encephalomyelitis. *Science*. 265:1237.
22. Salgame, P., J. S. Abrams, C. Clayberger, H. Goldstein, J. Convit, R. L. Modlin,and B. R. Bloom. 1991. Differing lymphokine profiles of functional subsetsofhuman CD4 and CD8 T cell clones. *Science* 254:279.
23. Groux, H., M. B., Bigler, J. E. de Vries, and M-G Roncarolo. 1998. Inhibitory and stimulatory effects of IL-10 on human $CD8^+$ T cells. *J. Immunol.* 160:3188.
24. Bloom, B. R., R. I. Modlin, P. Salgame. 1992. Stigma variations: observations on suppressor T cells and leprosy. *Annu. Rev. Immunol.* 10:453.
25. Kuchroo, V. K., M. C. Byrne, Y. Astumi, E. Greenfield, J. B. Connolly, M. J. Whitters, R. M. O'Hara, Jr. M. Collins, and M. E. Dorf. 1991. T-cell receptor alpha chain plays a critical role in antigen-specific suppressor cell function. *Proc. Natl. Sci.* 88:8700.
26. Philips, J. H., J. E. Gumperz, P. Parham, and L. L. Lanier. 1995. Superantigen-dependent, cell-mediated cytotoxicity inhibited by MHC class I receptors of T lymphocytes. *Science*. 268:403.
27. Moretta, A., R. Biassoni, C. Bottino, D. Pende, M. Vitale, A. Poggi, M. C. Mingari, and L. Moretta. 1997. Major histocompatibility complex class-I specific receptors on human natural killer and T lymphocytes. *Immunol. Rev.* 155:105.
28. Strominger, J. L. 1997. Human NK cells: their ligand receptors and functions. *Immunol. Rev.* 155:119.
29. Lombardi, G., S. Sidhu, R. Batchelor, and R. Lechler. 1994. Anergic T cells as suppressor cells in vitro. *Science*. 264:1587.
30. Renheim, E. A., T. J. Kipps. 1993. Activated T cells induce expression of B7/BB1 on normal or leukemic B cells through a CD40 dependent signal. *J. Exp. Med.* 177:925.
31. Yang, Y., J. M. Wilson. 1996. CD40 ligand-dependent T cell activation: requirement of B7-CD28 signaling through CD40. *Science*. 273:1862.
32. Lederman, S., M. J. Yellin, A. Krichevsky, J. Belko, J. J. Lee, and L. Chess. 1992. Identification of a novel surface protein on activated $CD4^+$ T cells that induces contact dependent B cell differentiation (help). *J. Exp. Med.* 175:1091.

33. Grewal, I. S., J. Xu, and R. A. Flavell. 1995. Impairment of antigen-specific T cell priming in mice lacking CD40 ligand. *Nature*. 378: 617.
34. Jaiswal, A. I., and M. Croft. 1997. CD40 ligand induction on T cell subsets by peptide-presenting B cells. *J. Immunol*. 159: 2282.
35. DeBendette, M. A., A. Shahinian, T. W. Mak, and T. H. Watts. 1997. Costimulation of CD28⁻ T lymphocytes by 4-1BB ligand. *J. Immunol*. 158:551.
36. Larsen, C. P., E. Ts Elwood, D. Z. Alexander, S. C. Rotchie, R. Hendrix, C. Tucker-Burden, H. R. Cho, A. Aruffo, D. Hollenbaugh, P.S. Linsley, K. J. Winn, and T. C. Pearson. 1996. Long-term acceptance of skin and cardiac allografts after blocking CD40 and CD28 pathways. *Nature* 381:434.
37. Murray, A. G., M. M. Khodadoust, J. S. Pober, and A. L. M. Bothwell. 1994. Porcine aortic endothelial cells activate human T cells: direct presentation of MHC antigens and costimulation by ligands from human CD2 and CD28. *Immunity*. 1:57.
38. Harris, P. E., A. I. Colovai, A. Maffei, Z. Lui, N. Suciu-Foca. 1995. MHC class I presentation of exogenous and endogenous protein-derived peptides by a transfected human monocyte cell line. *Immunol*. 86:606.
39. Lanzavecchia, A. 1998. Licence to kill. *Nature* 393:413.
40. Ridge, J. P., F. Di Rosa, and P. Matzinger. 1998. A conditioned dendritic cell can be a temporal bridge between a CD4⁺ T-helper and a T-killer cell. *Nature* 393:474.
41. Bennett, S. R. M., F. R. Carbone, F. Karamalis, R. A. Flavells, J. F. A. P. Miller, and W. R. Heath. 1998. Help for cytotoxic-T-cell responses is mediated by CD40 signaling. *Nature* 393:478.
42. Schoenberger, S. P., R. E. M. Toes, E. I. H. van der Voort, R. Offringa, and C. J. M. Melief. 1998. T-cell help for cytotoxic T lymphocytes is mediated by CD40–CD40L interactions. *Nature* 393:480.
43. J. K. Lunney and J. E. Butler, Immunogenetics, In *The Genetics of the Pig*, 1998, eds., M. F. Rothschild and A. Ruvinsky, CAB International.

Third Series of Experiments
Induction of MHC-class I Restricted Human Suppressor T Cells by Peptide Priming in Vitro A major goal in the treatment of T-cell mediated autoimmune diseases and allograft rejection is the development of antigen-specific immunosuppression. Induction of antigen-specific T suppressor cells may offer a means of preventing or treating pathogenic responses to self and allogeneic antigens without the complications associated with general immunosuppression.

Although suppressor T cell lines (TCL) are difficult to generate, the existence within the CD4⁺ and CD8⁺ T cell population of a functional subset of T lymphocytes that act to downregulate the immune response is well documented (1–5). Different mechanisms have been implicated, yet the cellular and molecular basis of antigen-specific suppression is still unclear (1–5). Recently, it has been demonstrated that allospecific as well as xenospecific Ts can be generated by in vitro priming of human T cells with APCs from an individual of the same (allogeneic) or different (xenogeneic) (6) species (7). Allospecific and xenospecific(6) Ts derive from the CD8⁺CD28⁻ subset and recognize specifically the MHC-class I antigens expressed by the APCs used for priming (7).

Allospecific Ts prevent the upregulation of B7 molecules on target APCs, interfering with the CD28-B7 interaction required for T helper (Th) activation. Furthermore, these Th show no upregulation of the CD154 (CD40L) molecule when stimulated with the priming APCs in the presence of Ts, indicating that Ts also inhibit the CD154/CD40 costimulatory pathway (6).

Cell mixture experiments showed that suppression of Th alloreactivity (7) and Th xenoreactivity (6) occurred only when the stimulatory APCs co-expressed MHC-class II antigens, recognized by the Th to be suppressed, and MHC-class I antigens, recognized by the suppressor population. Hence the interaction of the APC with both Ts and Th is a necessary requirement for the development of the suppressor effect.

However, T cell reactivity against both allogeneic and xenogeneic MHC antigens in MLC, occurs primarily via the direct recognition pathway, which is not restricted by the responder's self MHC antigens. Ts-induced alterations of the APCs used for priming may, therefore, represent a pecularity of the direct recognition pathway.

The aim of the present study was to determine whether MHC-class I restricted T cells with suppressor function can be also induced by T cell priming in vitro with nominal antigens such as Tetanus Toxoid and synthetic peptides.

Reported in the third series of experiments is the in vitro generation and characterization of self MHC restricted Ts which recognize antigens that have been processed and presented by autologous APCs.

The following abbreviations are used herein: T helper determinants—HD; Mean fluorescence intensity—MFI; Suppressogenic determinants—SD; Recombinant Tetanus Toxoid—rTT; tat-DR4 comprising residues 49–57 of HIV-1 tat and residues 64–88 of DRB1*0401—Tat-DR4 chimeric peptide; T cell lines—TCL; T suppressor lymphocytes—Ts.

Materials and Methods
Peptide Synthesis and Ag Preparations

Recombinant Tetanus Toxoid (rTT) C fragment was obtained from Boehringer Mannheim (Indianapolis, Ind.) and conjugated to carboxylated polystyrene microparticles (Latex beads; Polysciences, Inc., Warrington, Pa.) using the Carbodiimide Kit according to the manufacturer's instructions.

A chimeric peptide tat-DR4, comprising residues 49–57 of HIV-1 tat and residues 64–88 of DRB1*0401 was purchased from Chiron Technologies, Australia. The purity of the peptide was >85% as determined by reverse-phase HPLC. The amino acid sequence of this peptide :is as follows: RKKRRQRRRQKDLLEQKRAAVDTY-CRHNYGVGES (SEQ ID NO:1).
HLA Typing Lymphocytes were typed for HLA class I antigens by conventional serology. The class II genotype of the cells was determined by genomic typing of in vitro amplified DNA with sequence-specific oligonucleotide probes for DRB1, DQA1, and DQB1. The HLA phenotype of the blood donor (PR) used in these studies is: HLA-A29, A32, B40, B44, DRB1*1101, DRB1*0701.
Generation of Antigen Specific T Cell Lines (TCL)

PBMCs from a healthy blood male (PR) were separated from buffy coats by Ficoll-Hypaque centrifugation. Responding PBMCs at $2 \times 10^6$/ml were stimulated in 24-well plates (Nunc, Inc., Ill.) with 10 μg/ml of tat-DR4 peptide or with 50 μl (approximately 1 mg) of rTT-beads in RPMI 1640 medium supplemented with 10% human serum (Sigma Chemical Co., St. Louis, Mo., 2 mM L-glutamine, and 50 μg/ml gentamicin (Gibco, Grand Island, N.Y.). On day five, 20 U/ml of rIL-2 (Boehringer Mannheim, Indianapolis, Ind.) were added. Ten days after priming, T cells ($2 \times 10^6$/ml) were collected, washed and restimulated with antigen in medium containing 20 U/ml of rIL-2 and irradiated (3000 rad) autologous PBMCs ($2\times10^6$/ml). Antigen specific T cell lines were obtained after two or three restimulations. Two cell lines, named PR-anti-rTT and PR-anti-tat-DR4 peptide were used in this study.

Cell Isolation and Culture $CD4^+$ and $CD8^+$ T cells were isolated from TCL PR-anti-rTT by positive selection using Dynal CD4 and CD8 beads according to the manufacturer's instructions. After 30 minutes of incubation at 4° C., the rosetted cells were washed and resuspended in 0.1 ml of medium containing 15 microliters of DETACHaBead CD4/CD8. After 3 hours of incubation at 37° C., non-rosetted cells were collected, washed, and resuspended in medium.

$CD4^+$ and $CD8^+$ T cells from TCL PR-anti-tat-DR4 peptide were separated by negative selection using Dynal CD4 and CD8 beads. $CD8^+CD28^-$ T cell suspensions were obtained from both TCLs by depleting $CD28^+$ T cells from purified $CD8^+$ T cell suspensions. For this procedure goat-anti-mouse Dynal beads were coupled with mAb anti-CD28 (Becton Dickinson, San Jose, Calif.) according to the manufacturer's instructions. The CD28-coupled beads were washed and incubated at $4\times10^7$ beads per ml with $1\times10^7$ CD8 T cells for 20 min at 4° C. with gentle end-over-end mixing. Non-rosetted cells were collected, washed and resuspended in complete RPMI 1640 medium.

The purity of the $CD4^+$ and $CD8^+CD28^-$ suspensions used in blastogenesis assays was greater than 98% as indicated by cytofluorographic analysis.

Proliferation Assay

Antigen-specific $CD4^+$ T cells or $CD8^+CD28^-$ T cells (30,000/well) obtained from TCLs were cultured with irradiated (3000 rad) autologous PBMCs, as APCs (30,000/well) in 96-well round bottom microplates (Nunc, Inc. Narperville, Ill.). T cell stimulation with rTT was accomplished using APCs which were pulsed with rTT (5 $\mu$Ag/ml) for 3 hours, then washed and irradiated, tat-DR4 peptide was used at a concentration of 1 $\mu$M. $CD8^+CD28^-$ T cells were tested for suppressor activity (30,000 cells/well) by addition to cultures containing Th cells (30,000/well) at the initiation of the blastogenesis assay. The cultures were labeled with [$^3$H] TdR (0.5 m $\mu$Ci/well) after 48 hours of incubation and harvested 18 hours later. [$^3$H] TdR incorporation was then measured in a LK Betaplate liquid scintillation counter (Wallac, Inc., Gaithersburg, Md.). Mean cpm of triplicate cultures and standard deviation of the mean were calculated. Standard deviations were less than 10% of the mean.

Antibody Blocking Assay

Monoclonal antibodies against HLA class I molecules were added to the cultures at the initiation of the proliferation assays. The human mAb OK4F9 (anti-HLA-A29), mAb OK3C8 (anti-HLA A32), mAb 13E12 (anti-HLA-B44) and mAb Ha2C10B12 (anti-HLA-B40) were used as cell culture supernatants. All antibodies were dialysed against RPMI 1640 medium before use.

TCR Spectratyping

Total RNA was extracted using QIAGEN columns (Qiagen Inc. Santa Clara, Calif.) from $CD8^+CD28^-$ Ts isolated from TCL PR-anti-rTT. RNA was reverse transcribed into cDNA using MMLV reverse transcriptase and primed with oligo $(dT)_{18}$ (Clontech Laboratories Inc., Palo Alto, Calif.) as recommended by the manufacturer. Aliquots of the cDNA synthesis reaction were amplified individually with 24 human V$\beta$ and the C$\beta$ primers that have been previously described(8,9). As an internal control for the amount of cDNA used for each V$\beta$ PCR reaction, a second reaction tube containing sense and antisense primers for the first exon of C$\beta$ region was included. A run-off reaction of the V$\beta$-C$\beta$ PCR products was performed using a fluorochrome labeled C$\beta$-specific primer. The size and fluorescence intensity of labeled run off products were then determined on a 377 DNA sequencer (Perkin Elmer Applied Biosystem Division, Foster City, Calif.) and analyzed using the ABI PRISM 377 GENESCAN Analysis Program. The relative intensity of each V$\beta$ family was calculated as the peak area corresponding to each V$\beta$ family divided by the sum of all area peaks.

Flow Cytometry

T cell subsets were defined using mAb CD4-PerCP, CD8-FITC, and CD28-PE from Becton Dickinson, Calif. Cell suspensions were phenotypedprior to use in blastogenesis assays using a FACScan flow cytometry instrument (Becton Dickinson, San Jose, Calif.) equipped with a 15 mW Argon Laser. To study the expression of CD80, CD86, and CD40 on CD2 depleted PBMCs, i.e. $CD20^+$ B cells, $CD14^+$ monocytes and dendritic cells, used for antigen presentation, cells were incubated with saturating amounts of mAbs recognizing CD80-PE, CD20-FITC, CD14-FITC, CD86-PE, and CD40-PE (all from Becton Dickinson, San Jose, Calif.). CD20 postive and CD14 positive cells were gated in and analyzed for CD80, CD86, and CD40 expression. Five parameter analysis (forward scatter, side scatter and three fluorescence channels) were used for list mode data analysis. FL1 channel was used as fluorescence trigger, FL2 as analysis parameter. Mouse IgG ($\gamma$1 and $\gamma$2) reagents were used as isotype controls for nonspecific binding of test reagents and as markers for delineating the positive and negative populations. Calibrite flow cytometer beads (Becton Dickinson, San Jose, Calif.) and FACSComp program were used for calibration of the cytometer.

Results

Inhibition of Th Reactivity to Tetanus Toxoid by Ts Cells

In previous studies it was demonstrated that xeno(6) and allospecific Ts recognize MHC-class I antigens on stimulating APCs (7). In order to direct soluble rTT protein to the endogenous antigen processing pathway, which supplies MHC-class I bound peptides, rTT was conjugated to microscopic beads (10).

Figure 16:
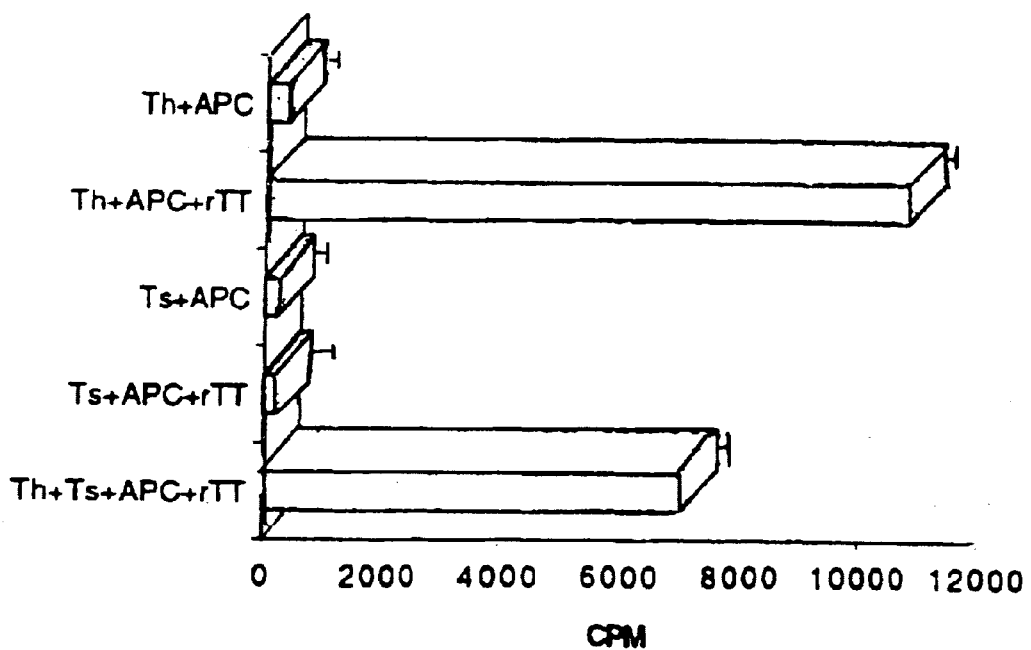
FIG. 16. Suppression of Th reactivity to rTT. CD4$^+$Th cells from a TT-specific TCL were tested in a 3-day blastogenesis assay for reactivity to rTT-pulsed APCs. CD8$^+$CD28$^-$ Ts from the same TCL were added to the cultures at the initiation of the proliferation assay.

To determine whether the Th response to a nominal antigen is suppressed by autologous Ts, PBMCs from a healthy individual (PR) were primed in vitro with rTT conjugated beads. $CD4^+$ Th and $CD8^+CD28^-$ Ts, were isolated from the resulting TCL (TCL PR-anti-rTT) and tested for reactivity to rTT in the presence of irradiated autologous PBMCs. $CD4^+$ Th cells reacted vigorously to autologous APCs pulsed with rTT, while $CD8^+CD28^-$ T cells showed no proliferative response (FIG. 16).

When Th and Ts cells from TCL PR-anti-rTT were mixed together at a 1:1 ratio and primed with rTT, there was significantly less Th proliferation than in control cultures in which no Ts were added. The amount of inhibition seen in four repeat experiments ranged from 34 to 37% (FIG. 16). The inhibitory effect of Ts on Th reactivity to rTT was not due to competition for IL-2, as $CD8^+CD28^-$ Ts obtained from the allopeptide specific TCL (TCL PR anti-tat-DR4) caused no inhibition of Th reactivity to rTT (data not shown). Irradiation (3,000 rad) of $CD8^+CD28^-$ Ts cells prior to co-culture with Th and APCs showed no effect on suppressor activity, indicating that the suppressor cells are not radiation sensitive (data not shown).

Inhibition of Th Reactivity to Tat-DR4 Peptide

Experimental evidence demonstrates that in monocyte/macrophage APCs there is communication between the exogenous and endogenous pathways of antigen processing and that antigens in the extracellular millieu can also be presented in association with MHC class I molecules (11). Recently, it was shown that the entry of exogenous proteins into the MHC class I pathway can be facilitated by conjugating proteins to a short cationic peptide derived from HIV-1 tat (residues 49–57) (12). Based on this knowledge a chimeric peptide consisting of residues 49–57 of tat and residues 64–88 of the DRB1*0401 molecule was synthesized. The latter peptide, which corresponds to the third hypervariable region of the DRB1*0401 antigen, was previously shown to comprise the dominant epitope of the DR 0401 antigen recognized by T cells from individuals carrying the DR*1101 and DR*0701 alleles (13).

To achieve coexpression of Th and Ts epitopes on the same APCs the Tat-DR4 peptide was used for in vitro immunization of T cells from PR (who is DR1101/DR0701 heterozygous).

Figure 17:
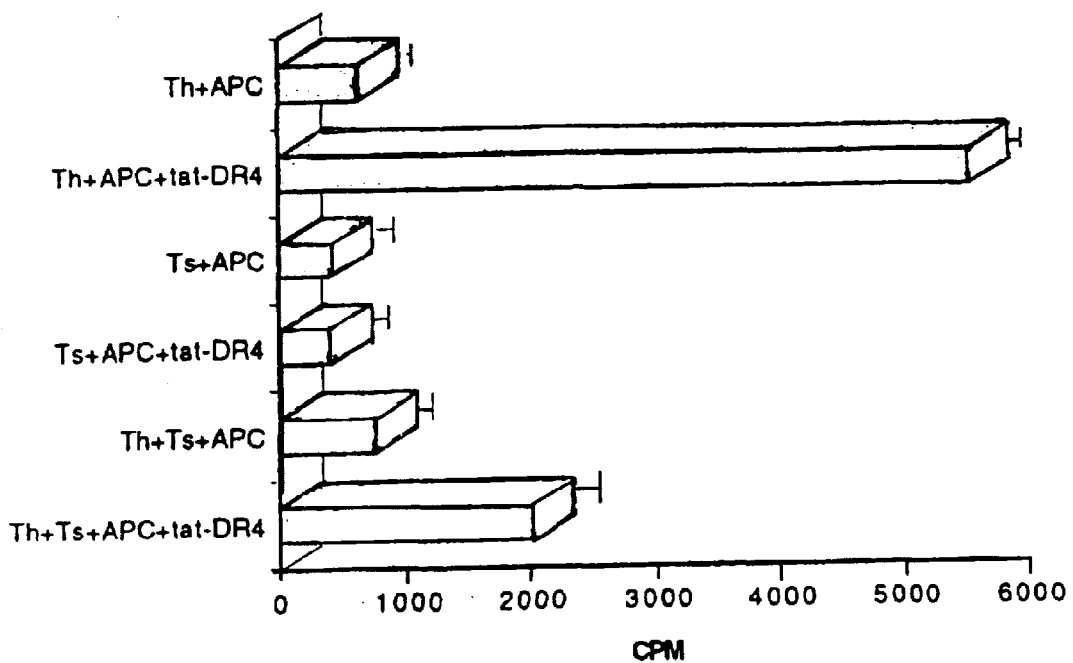
FIG. 17. Suppression of Th reactivity to peptide Tat-DR4. CD4$^+$ Th cells and CD8$^+$CD28− Ts were purified from a Tat-DR4-peptide specific TCL and tested for reactivity to the synthetic peptide in cultures containing irradiated APCs. CD8$^+$CD28$^-$ Ts were added to Th cultures at the initiation of the proliferation assay to measure suppressor activity.

$CD4^+$ and $CD8^+CD28^-$ T cells were isolated from TCL PR-anti-tat DR4 and tested alone or together for reactivity to peptide tat-DR4 presented by autologous APCs. Blastogenesis assays showed that peptide tat-DR4 stimulated the proliferation of $CD4^+$ T cells but not of $CD8^+CD28^-$ T cells. In the presence of $CD8^+CD28^-$ T cells the response of $CD4^+$ Th was suppressed by >70% in four repeat experiments (FIG. 17). $CD8^+CD28^-$ T cells from this line (PR-anti-tat-DR4) did not inhibit the reactivity to rTT of $CD4^+$ T cells from TCL PR-anti-rTT. Similarly, $CD8^+CD28^-$ Ts cells obtained from TCL PR-anti-rTT did not inhibit the reactivity of Th from TCL PR-anti-tat-DR4 to tat-DR4, indicating that the suppressor effect is antigen-specific (data not shown).

Figure 18A:
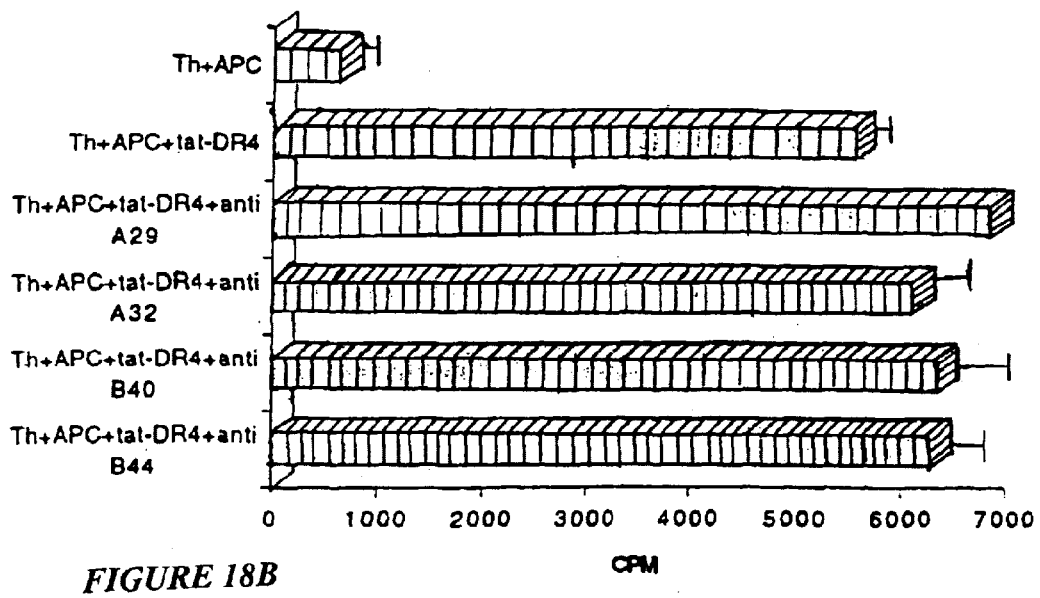
FIGS. 18A–18B. Effect of anti-HLA class I mAbs on T cell reactivity to peptide Tat-DR4. CD4$^+$ Th were tested for reactivity to peptide Tat-DR4 in medium without or with mAbs specific for the HLA-class I antigens expressed by the responder (FIG. 18A). Th and Ts were mixed together and tested for reactivity in the presence of MHC-class I specific mAbs (FIG. 18B).
Figure 18B:
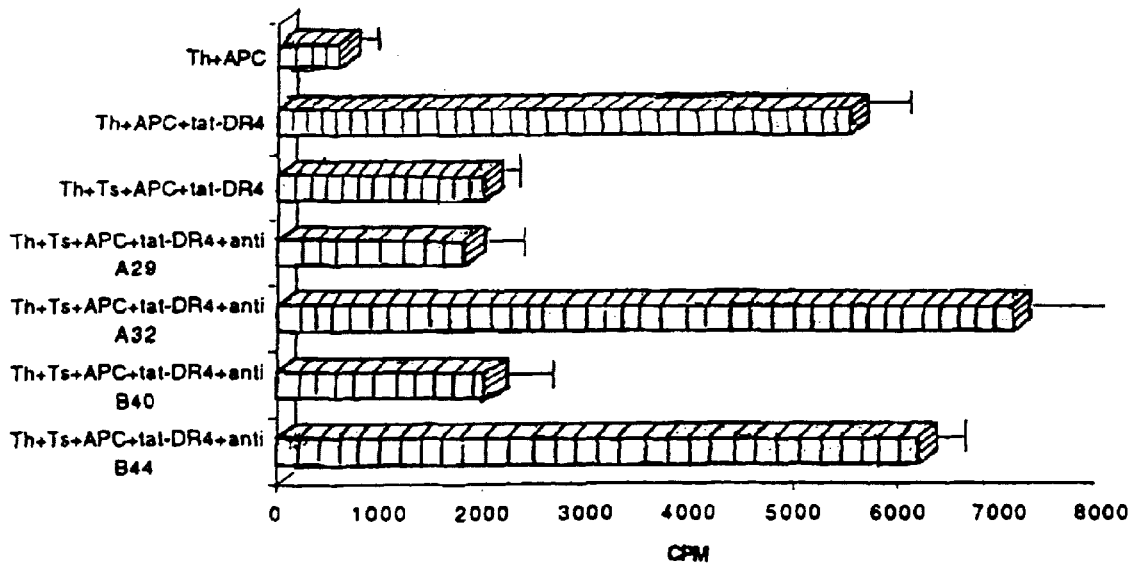

To determine the MHC-restriction element required for peptide recognition by Ts blocking studies were performed using mAbs specific for the HLA-class I antigens expressed by PR (HLA A29, A32, B40 and B44). The blastogenic response of Th cells to peptide tat-DR4 was of the same order of magnitude in cultures with and without anti-HLA class I mAbs (FIG. 18A). Ts cells inhibited the reactivity of Th cells to the peptide in cultures without mAbs or with mabs to HLA-A29 or B40. Hence, blocking of HLA-A29 or B40 by mAbs did not prevent Ts activation, indicating that HLA-A29 and B40 molecules did not present suppressogenic determinants of peptide tat-DR4. The suppressor effect, however, was completely abolished when mAbs specific for HLA-A32 or B44 were added to the assay (FIG. 18B) This indicates that the peptide(s) recognized by Ts are presented by HLA-A32 and B44.

Spectratyping of Vβ Genes Expressed by $CD8^+CD28^-$ Ts from TCR PR-Anti-TT

Study of the TCR-Vβ0 gene repertoire expressed by xenospecific Ts showed an oligoclonal expansion of a few Vβ families. (6) To determine whether the Vβ repertoire used by rTT-specific Ts is also restricted the expression of Vβ families in the population of $CD8^+CD28^-$ Ts derived from TCL PR-anti-rTT was analyzed. $CD8^+CD28^-$ Ts were sorted from the TCL after two stimulations with rTT, and then expanded, by weekly restimulation with rTT-pulsed APCs, in IL-2-containing medium. Blastogenesis assays using Th and Ts showed that the $CD8^+CD28^-$ population maintained suppressor activity throughout five consecutive cycles of antigenic stimulation. T cells obtained at later times showed no suppressor activity when co-cultured with $CD4^+$ Th.

Analysis of the TCRs expressed by suppressor cells propagated for five weeks in culture showed that Vβ3, Vβ5, Vβ13, Vβ15, and Vβ19 were expressed with a relative intensity greater than 10%. The other Vβ families were either completely absent (such as Vβ6, Vβ8, Vβ10, Vβ11, Vβ18, Vβ20, and Vβ21), or expressed with a relative intensity lower than 5%. After an additional week of expansion, the $CD8^+CD28^-$ population lost suppressor activity and expressed only the Vβ3 and Vβ5 families (FIG. 19). The loss of Vβ13, Vβ15 and Vβ19 coincided with the loss of suppressor activity suggesting that they represented the Ts population.

Spectratyping of the TCRs used by $CD4^+$ Th cells from TCL PR-anti-rTT showed expression of Vβ3, Vβ5, Vβ9, Vβ10, and Vβ11. Two of the Vβ families (Vβ3 and Vβ5) represented in the $CD4^+$ T cell population, were also found within the $CD8^+CD28^-$ population (where they apparently had no Ts function). Usage of Vβ9, Vβ10, and Vβ11 was unique to rTT-specific Th cells. This finding suggests that the determinants recognized by Th and Ts on the rTT molecule are distinct.

Effect of Antigen Specific Ts on the Expression of CD80, CD86, and CD40 on APCs.

In previous studies it was shown that allospecific Ts downregulate the expression of CD80 and CD86 on the APCs used for priming, interfering with the delivery of costimulatory signals required for Th activation (7). To establish whether such a mechanism is also involved in Ts-induced-downregulation of Th responses to nominal antigens analysed was the expression of CD80, CD86, and CD40 on antigen-pulsed APCs, cultured for 24 hours in the presence, or absence of Ts.

For these experiments $CD4^+$ Th ($5\times10^6$) were mixed with $CD8^+CD28^-$ Ts ($1.5\times10^6$) and APCs ($5\times10^5$) in medium containing tat-DR4 peptide (1 mM). Control cultures containing only APCs or APCs and Ts were set up in parallel. Within 24 hours the expression of CD40 on APCs increased dramatically in the presence of Th as indicated by the shift of the Mean Fluorescense Intensity (MFI) from 633 to 2230, in cultures without, and with Th respectively. However, when Th were co-cultured with Ts, the level of CD40 expression on APCs was about 50% lower (MFI of 1114) than in the absence of Ts (FIG. 20).

Similarly, the level of CD80 and CD86 expression on APCs was greatly enhanced by Th, while Ts induced only a slight elevation of CD80 and CD86 expression. When Ts were added to Th cultures, the expression of CD80 and CD86 remained at the level seen in the absence of Th (FIG. 20). This indicates that Ts interfere with the Th-induced upregulation of costimulatory molecules (CD40, CD80, and CD86) on APCs.

Discussions

Two general approaches to antigen-specific immunotherapy have been proposed (2). The first is to block the activation of T helper cells using MHC blocking peptides, tolerogenic concentrations of antigen or TCR antagonists (2). The second approach involves the induction of antigen-specific regulatory T cells which downregulate immune responses at inflammatory sites (2). Although T suppressor cells have been induced in a variety of experimental models their role and mechanism of action are not well understood. In both mouse and human systems, suppressor cells have been shown to derive from CD4 as well as CD8 subsets (1–5). It has been suggested that $CD4^+$ T cells act as suppressor inducers, while $CD8^+$ T cells act as suppressor effectors (1). A number of cytokines, including interferons, prostaglandins, tumor necrosis factor, transforming growth factors, and interleukin-10 were shown to exert suppressive activity on the growth, differentiation and effector functions of T lymphocytes(14–16).

Suppression generated by oral tolerance to certain autoantigens is antigen and disease specific. This observation suggests that the secretion and action of cytokines must occur in the microenvironment where the immune response is stimulated (2, 14, 15).

Although suppressogenic determinants (SD) of well-defined antigenic proteins have been shown to be different from immunogenic T helper determinants (HD) it has been suggested that they must be localized on a single processed antigenic fragment (1, 17–19) and/or presented by the same APC in a multi-cell cluster for suppression to occur (20, 21).

The concept that the interaction between Ts and Th cells is regional in nature and requires proximity of suppressogenic and immunogenic determinants, is also supported by previous studies from our laboratory showing that in the allogeneic and xenogeneic system, suppression requires an antigen-mediated tripartite interaction between Ts, Th and APCs. It was demonstrated that suppression is specific for MHC-class I/peptide complexes expressed by the APC used for priming and results in diminished T helper cell reactivity to MHC-class II antigens co-expressed by the same APCs (7). This effect was caused by suboptimal costimulation of alloreactive or xenoreactive $CD4^+$ Th in the presence of CD8 CD28 Ts. Hence Ts induce downregulation or inhibit upregulation of B7 molecules (CD80 and CD86) on priming APCs and of CD154 (CD40L) on activated Th. Cell-mixture experiments in which Ts and Th cells were co-cultured with two different APCs, one expressing the MHC-class I antigens recognized by Ts, and the other, the MHC-class II antigens recognized by Th, showed no suppression indicating that SD and HD must be presented by the same APC to reveal suppression (6,7).

The present study demonstrates that Th recognition of nominal antigens is subjected to the same mechanism of down-regulation by MHC-class I restricted $CD8^+CD28^-$ cells. Study of the TCR-repertoire used by rTT-specific Th and Ts cells showed overlap of only two TCR Vβ families (Vβ3 and Vβ5), neither of which seemed to contribute to the suppressor activity of the $CD8^+CD28^-$ population. This lack of overlap between the Vβ reperoire used by rTT-specific Th and Ts is consistant with the restriction of $CD4^+$ Th cells to MHC class II and $CD8^+$ Ts cells to MHC class I molecules and with the hypothesis that HD and SD determinants are distinct (1).

Additionally, the oligoclonality of the rTT-specific Th and Ts populations suggests that, in spite of its complexity, the TT molecule has a limited number of immunogenic and suppressogenic determinants recognized by T cells in vitro.

To explore the possibility that exogenous antigens can be used for induction of MHC-class I restricted T suppressor cells a chimeric peptide consisting of residues 49–57 of HIV-tat, which facilitates entry into the endogenous antigen processing pathway, and residues 64–88 of the DR 0401 molecule was used. Processing of the chimeric tat-DR4 peptide by APCs resulted in presentation of both Ts and Th determinants. Ts generated in this system inhibited Th proliferation in an antigen-specific manner. Blocking studies using monoclonal anti-HLA-class I antibodies, demonstrated that the determinant(s) recognized by Ts were presented by two of the responder's HLA class I molecules (HLA-A32 or B40). Since the binding motifs of these two HLA class I molecules differs it is likely that the determinants which $CD8^+CD28^-$ T cells recognize on each of them are not the same. Similarly the amino-acid residues of the tat-DR4 peptide which contact the TCR of Th and Ts cells are probably different due to structural differences between MHC-class I and class II molecules. However, it remains to be studied whether differences in peptide presentation by MHC class I and class II antigens explain the differences in the TCR repertoire and in the selection of suppressogenic and immunogenic determinants.

Cytofluorometric analysis of CD40, CD80, and CD86 molecules on APCs co-cultured with Th and Ts showed that the upregulatory effect exhibited by Th on the expression of costimulatory molecules is drastically inhibited in the presence of Ts. Although the mechanism accounting for the effect of Ts on APCs is still under study, these data suggest that inhibition of Th proliferation is secondary to downregulation of the costimulatory potential of APCs. The finding that Ts downregulate the expression of CD40 on APCs during the tripartite interaction with Th is particularly important in light of the recent demonstration that CD40 is also required for the tripartite interaction between Th, cytotoxic T cell lines (Tc), and APC (22–25).

The finding presented here that Ts cells which inhibit Th reactivity to allo and xenogeneic cells as well as Th reactivity to protein antigens can be educated in vitro has significant implications for the development of antigen specific therapy for treatment of allograft rejection and autoimmune diseases. It is conceivable that autologous Ts generated in vitro can be used for "adoptive" transfer of suppression. Alternatively, active immunization with suppressogenic peptides, targeted to the endogenous pathway may offer a viable strategy for inhibition of indirect allorecognition, a major contributor to rejection, and of autoimmune diseases.

References for the Third Series of Experiments

1. Sercarz E E, Krzych U: The distinctive specificity of antigen-specific suppressor T cells. Immunol Today 12:111, 1991.
2. Hafler D A, Weiner H L: Immunologic mechanisms and therapy. Immunol Rev 144:75, 1995.
3. Roser B J: Cellular mechanisms in neonatal and adult tolerance. Immunol Rev 107:179, 1989.
4. Salgame P, Abrams J S, Clayberger C, Goldstein H. Convit J, Modlin R L, Bloom B R: Differing lymphokine profiles of functional subsets of human CD4 and CD8 T cell clones. Science 254:279, 1991.
5. Liblau R, Tisch R, Bercovici N, McDevitt H O: Systemic antigen in the treatment of T-cell-mediated autoimmune diseases. Immunol Today 18:599, 1997.
6. Ciubotariu R., A. I. Colovai, G. Pennesi, Z. Liu, D. Smith, P. Berlocco, R. Cortesini, and N. Suciu-Foca: Specific suppression of human $CD4^+$ T helper cell responses to pig MHC antigens by $CD8^+CD28^-$ regulatory T cells. J. Immunology 161(10):5193–5202., 1998.
7. Liu Z, Tugulea S, Cortesini R, Suciu-Foca N: Specific suppression of T helper alloreactivity by allo-MHC class I-restricted $CD8^+CD28^-$ T cells. Int Immunol 10(6):775–783, 1998.
8. Puisieux I, Even J, Pannetier C, Joterau F, Favrot M, Kourilsky P: Oligoclonality of tumor-infiltrating lymphocytes from human melanomas. J Immunol 153:2807, 1994.
9. Gardevet L, Dulphy N, Dovay N, Chalumeau N, Schaeffer V, Zilber M T, Lim A, Even J, Mooney N, Gelin C, Gluckman E, Charron D, Toubert A: The umbilical cord blood and T-cell repertoire: characteristics of a polyclonal and naive but completely formed repertoire. Blood 91:340, 1998.
10. Harding C V, Song R: Phagocytic processing of exogenous particulate antigens by macrophages for presentation by class I MHC molecules. J Immunol 153:4925, 1994.

11. Harris P E, Colovai A I, Maffei A, Liu Z, Suciu-Foca N: Major histocompatibility complex class I presentation of exogenous and endogenous protein-derived peptides by a transfected human monocyte cell line. Immunol 86:606, 1995.
12. Kim D T, Mitchell D J, Brockstedt D G, Fong L, Nolan G P, Fathman C G, Engleman E G, Rothbard J B: Introduction of soluble proteins into the MHC class I pathway by conjugation to an HIV tat peptide. J Immunol 159:1666, 1997.
13. Liu Z, Harris P, Colovai A I, Reed E F, Maffei A, Suciu-Foca N: Suppression of the indirect pathway of T cell reactivity by high doses of allopeptide. Autoimmunity 21:173, 1995.
14. Miller A, Lider O, Roberts A B, Sporn M B, Weiner H L: Suppressor T cells generated by oral tolerization to myelin basic protein suppress both in vitro and in vivo immune responses by the release of transforming growth factor β after antigen-specific triggering. Proc. Natl Acad Sci 89:421, 1992.
15. Lider O, Santos L M B, Lee C S Y, Higgins P J, Weiner H L: Suppression of experimental autoimmune encephalomyelitis by oral administration of myelin basic protein. J Immunol 142:748, 1989.
16. MacAry P A, Holmes B J, Kemeny D M: Ovalbumin-specific, MHC class I-restricted, αβ-postive, Tc1 and Tc0 $CD8^+$ T cell clones mediate the in vivo inhibition of Rat IgE. J Immunol 160:580, 1998.
17. Shivakumar S, Sercarz E E, Krzych U: The molecular context of determinants within the priming antigen establishes a hierarchy of T cell induction: T cell specificities induced by peptides of β-galactosidase vs. the whole antigen. Eur J Immunol 19:681, 1989.
18. Krzych U, Fowler A V, Sercarz E E: Repertoires of T cell directed against a large protein antigen, β-galactosidase: Only certain T helper or T suppressor cells are relevant in particular regulatory inetractions. J Exp Med 162:311, 1985.
19. Krzych U, Fowler A V, Miller A, Sercarz E E: Repertoires of T cells directed against a large protein antigen, β-galactosidase: Helper cells share a more restricted specificity repertoire than proliferative cells. J Immunol 128:1529, 1982.
20. Asano Y, Hodes R J: T cell regulation of B cell activation: An antigen-mediated tripartite interaction of Ts cells, Th cells, and B cells is required for suppression. J Immunol 133:2864, 1984.
21. Mitchison N A, O'Malley C: Three-cell-type clusters of T cells with antigen-presenting cells best explain the epitope linkage and noncognate requirements of the in vivo cytolytic response. Eur J Immunol 17:1579 1987.
22. Lanzavecchia A: License to kill. Nature 393:413, 1998.
23. Ridge J P, Di Rosa F, Matzinger P: A conditioned dendritic cell can be a temporal bridge between a CD4+ T-helper and T-killer cell. Nature 393:474, 1998.
24. Bennett S R M, Carbone F R, Karamalis F, Flavells R A, Miller J F A P, Heath W R: Help for cytotoxic-T-cell responses is mediated by CD40 signaling. Nature 393:478, 1998.
25. Schoenberger S P, Toes R E M, van der Voort E I H, Offringa R, Melief C J M: T-cell help for cytotoxic T lymphocytes is mediated by CD40–CD40L interactions. Nature 393:480, 1998.

Fourth Series of Experiments
Inhibition of CD40 Signaling Pathway in Antigen Presenting Cells by T Suppressor Cells $CD8^+$ T lymphocytes contain precursors of cytotoxic and suppressor cells [1]. The generation of Tc can occur in "sequential two cell interactions"; first, between $CD4^+$ Th cells and APCs and next, between activated APCs and $CD8^+$ Tc cells [2–4]. Another population of $CD8^+$ T cells, which lack the potential of becoming Tc, is characterized by the ability to display antigen specific T suppressor function [1, 5–7]. It has been previously shown that this population of Ts derives from the oligoclonal $CD8^+$ $CD28^-$ subset [8] and recognizes MHC class I/peptide complexes on the cell surface of APCs [5–7].

Allospecific Th and Ts were generated by multiple priming of human T cells with irradiated APCs from MHC class I and class II disparate blood donors. In this system, $CD4^+$ Th, isolated from the T cell line, recognize specifically MHC-class II antigens expressed by the APCs used for priming. $CD8^+CD28^-$ T cells from the same TCL inhibit, in a dose-dependent manner, the proliferative response of $CD4^+$ Th. Inhibition of Th proliferation is not associated with killing of either APCs or $CD4^+$ Th. $CD8^+CD28^-$ T cells recognize specifically MHC class I antigens expressed by the stimulating APCs and render them unable to upregulate the expression of CD80 and CD86 in the presence of Th. This inhibitory effect requires cell-to-cell interactions between Th, Ts and the APCs used for priming [5].

The aim of the present study was to investigate whether the suppressor effect requires the concomitant interaction between Ts, The and APCs or sequential two cell interactions (first, between Ts and APCs and next, between "suppressed" APCs and The) and whether it is mediated by inhibition of the CD40-signaling pathway.

Materials and Methods

Generation and Isolation of allospecific $CD4^+$ and $CD8^+28^-$ T Cell

Peripheral blood mononuclear cells form healthy blood volunteers were primed in MLC with irradiated (1600 rad) PBMCs from MHC-mismatched blood donors. Stimulating cells from the allogeneic donor were depleted of T cells using CD2 magnetic beads (Dynal, New York, N.Y.). After seven days of incubation in complete medium) RPMI 1640 with 10% human serum 2 mM L-glutamine and 50 μg/ml gentamycin) (Gibco, Grand Island, N.Y.), responding T cells were restimulated with irradiated APCs (CD2-depleated PBMC) from the same blood donor. Three days later $CD4^+$ T cells were isolated by positive selection with Dynal CD4 beads and Detachabeads, according to the manufacturer's instructions. $CD8^+CD28^-$ T cells, from the same culture, were purified first by positive selection of $CD8^+$ T cells with Dynal CD8 beads and Detachabeads, and then by negative selection of $CD28^-$ cells using anti-CD28 mAb coupled to Dynal beads. The separated cells were cultured in complete medium supplemented with 10 μ/ml rIL-2 (Boehringer Mannheim, Indianapolis, Ind.) for four more days. $CD4^+$ Th cells and $CD8^+CD28^-$ Ts cells were further propagated in IL-2 containing medium by weekly stimulations with irradiated APCs from the same blood donor. Prior to testing, $CD4^+$ T cells were purified one more time by negative depletion of CD8 cells using CD8 beads. Similarly, $CD8^+CD28^-$ T cells were repurified by depletion of $CD28^+$ T cells using CD28 beads. The purity of $CD4^+$ Th and $CD8^+CD28^-$ Ts was determined by flow cytometry as previously described [5–7].

Proliferation Assays $CD4^+$ T cells ($5\times10^4$/well) from T cell lines were tested for reactivity to irradiated allogeneic APC ($2.5\times10^4$/well) in the presence or absence of $CD8^+CD28^-$ T cells ($2.5\times10^4$/ well) from the same TCL. When CD3 antibody was used for T cell activation, the plates were coated overnight with CD3 mAb (1 g/ml), then blocked with complete medium and washed. CD4$^+$ and CD8$^+$CD28$^-$ T cells were used at 5×10$^4$/well. Cultures were pulsed with $^3$H thymidine after 48 h of incubation and harvested 18 h later. $^3$H thymidine incorporation was measured in an LK Betaplate counter. Mean cpm of the triplicate cultures and SD to the mean were calculated.

Suppression of CD40L Expression on Activated The Cells

Allospecific Th cells were cultured with allogeneic APCs, in the presence or absence of Ts cells for 6 h. mAb CD40L (1 g/ml) was added to the culture medium to prevent the rapid internalization of CD40L molecules on the surface of CD4$^+$ T cells [9]. The suspension was washed, stained with FITC-conjugated goat-anti-mouse Ig (Becton Dickinson, Mountain View, Calif.), then washed and stained with CD4-PE (Becton Dickinson). Four parameter analyses (forward scatter, side scatter and two fluorescence channels) were used for list mode data analysis. Mouse IgG (γ1 and γ2) was used as isotype control for non-specific binding of test reagents and as markers for delineating the positive and negative populations. CaliBRITE flow cytometry beads (Becton Dickinson) and FACSComp program were used for calibration of the FACScan flow cytometry instrument (Becton Dickinson).

The expression of CD40L on Th activated by use of mAb anti-CD3, in the presence or absence of Ts, was also analyzed after 6 h of incubation by staining the cells with CD40L-PE and CD4-FITC (Becton Dickinson).

Suppression of costimulatory molecules expressed by APC

Crosslinking of CD40 molecules on APCs was accomplished by incubating CD2-depleted PBMCs at 1×10$^6$/ml with an equal number of cells from the CD40L$^+$ D1.1 line [10]. Allospecific CD8$^+$CD28$^-$ Ts (1×10$^6$/ml) primed in vitro to the same APCs were added to parallel cultures. After 24 h of incubation cells were washed, stained and analyzed for expression of costimulatory molecules. The second method for CD40 crosslinking consisted of incubating APCs (2×10$^6$/ml) with FcRII CD32$^+$ L cells (0.5×10$^6$/ml), in medium containing mAb CD40 G28-5 (100 ng/ml) and rIL-4 (10 ng/ml) (Boehringer Mannheim). Cultures were set up in parallel with and without allospecific Ts (2×10$^6$/ml) After 48 h of incubation cultures were washed and processed for cytofluorometric analysis.

Aliquots of the same cultures were stained simultaneously with CD20-FITC, CD14-FITC and PE-conjugated mAb specific for one of the following markers: CD40, CD54, CD58, CD80 and CD86 (Pharmingen, San Diego, Calif.).

To study the kinetics of Ts-mediated suppression of costimulatory molecules induced by the Th, APCs (1×10$^6$/ml) were incubated 48 h with allospecific CD4$^+$ Th cells (2×10$^6$/ml). CD8$^+$CD28$^-$ Ts (1×10$^6$/ml) from the same TCL were added to the culture at the initiation of the assay or 6 and 18 h later. At the end of the incubation time (48 h), cells were washed and stained with CD20-FITC, CD14-FITC, and CD40, CD54, CD58, CD80, or CD86 PE, as described above.

RESULTS AND DISCUSSION

To define the cellular interactions mediating the suppressor activity of CD8$^+$CD28$^-$ Ts, the effects of these cells on the earliest events occurring during the program of CD4$^+$ Th activation were studied. An early and critical step in Th activation is the expression of CD40L (CD154) [11, 12]. This molecule interacts with CD40 on APCs and induces APCs to upregulate surface CD80 and CD86 molecules [10, 13, 14].

Figure 21A:
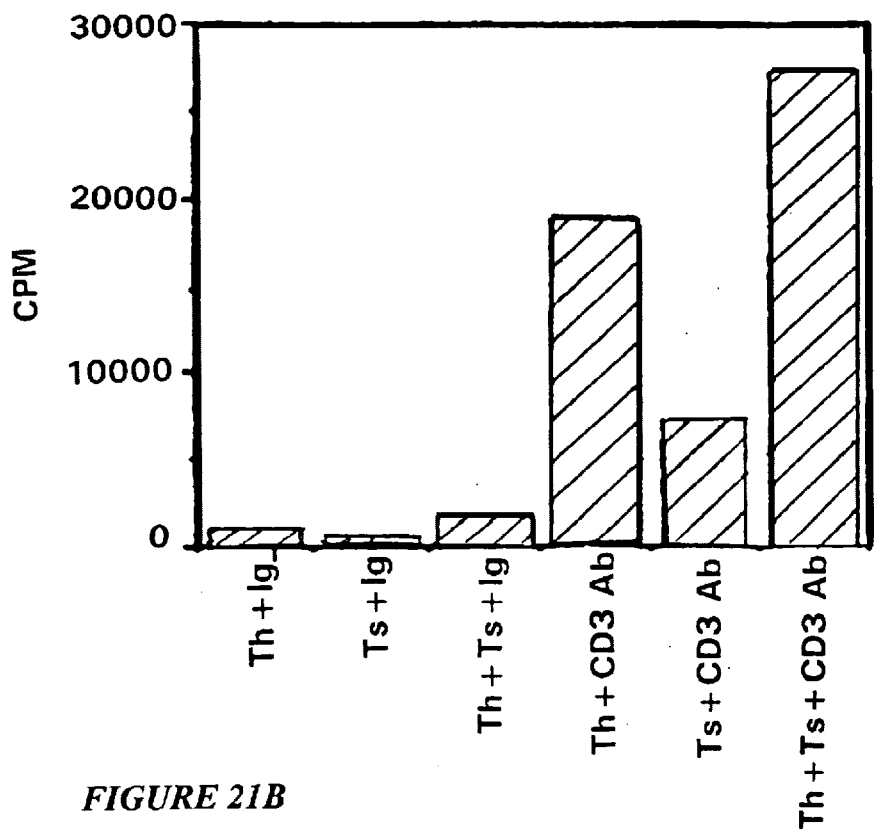
Figure 21B:
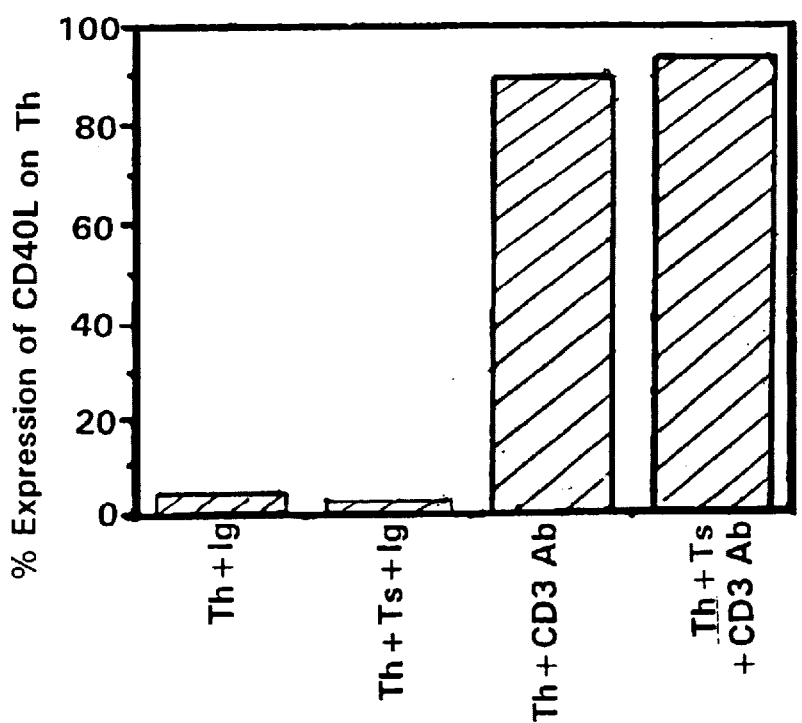
Figure 21C:
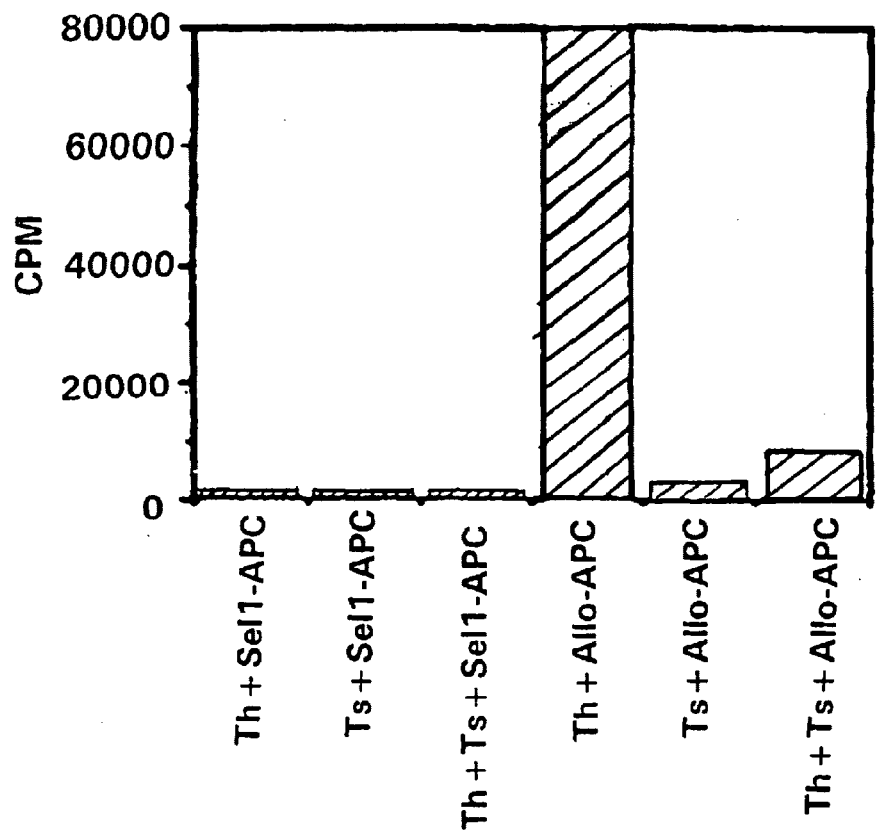
Figure 21C:
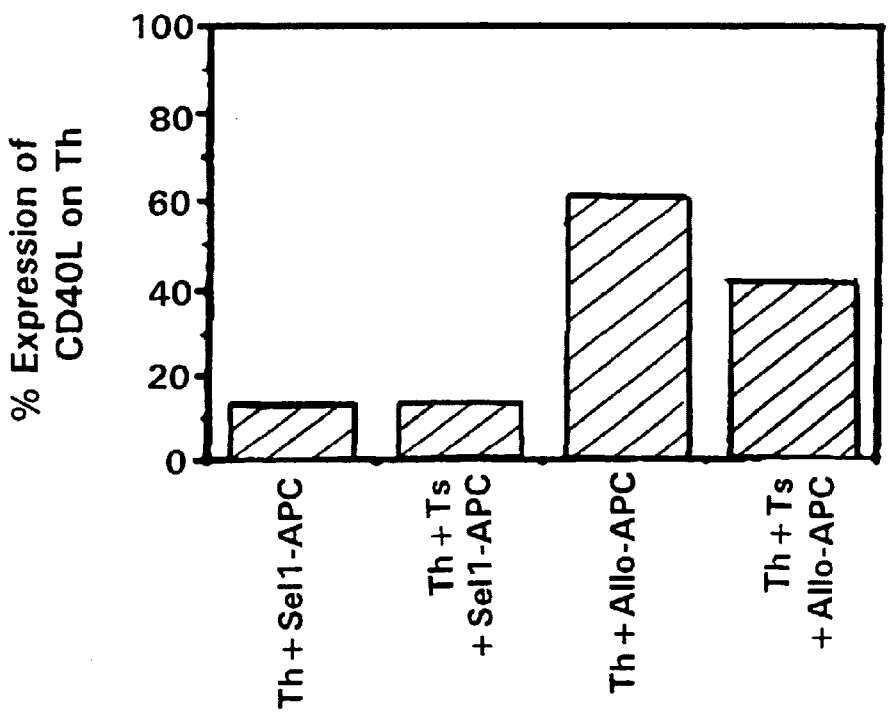

It is possible that Ts act directly on Th, inhibiting the expression of CD40L or, alternatively, they may act on APCs, blocking the CD40 signaling pathway. To discriminate between these two possibilities, first determined was whether Ts can inhibit Th in the absence of APCs. Experiments in which allospecific Th and Ts were co-cultured in the presence of mAb anti-CD3 showed that Ts do not inhibit Th proliferation or CD40L expression (FIGS. 21A, 21B). In contrast, when allospecific Th and Ts are cultured together with the APCs used for priming, both the expression of CD40L and the proliferative capacity of Th are inhibited (FIGS. 21C, 21D). These results indicate that the suppressive activity of Ts on Th prliferation is not determined by the direct interaction between Ts and Th and that it requires the presnece of APCs. This finding is consistent with the previous observation that Ts and Th must recognize the same APC for suppression to occur [5, 6]. It is, therefore, possible that whether APCs can or cannot activate Th depends on their previous encounter with either CD4$^+$ Th or CD8$^+$ CD28$^-$ Ts.

Figure 22:
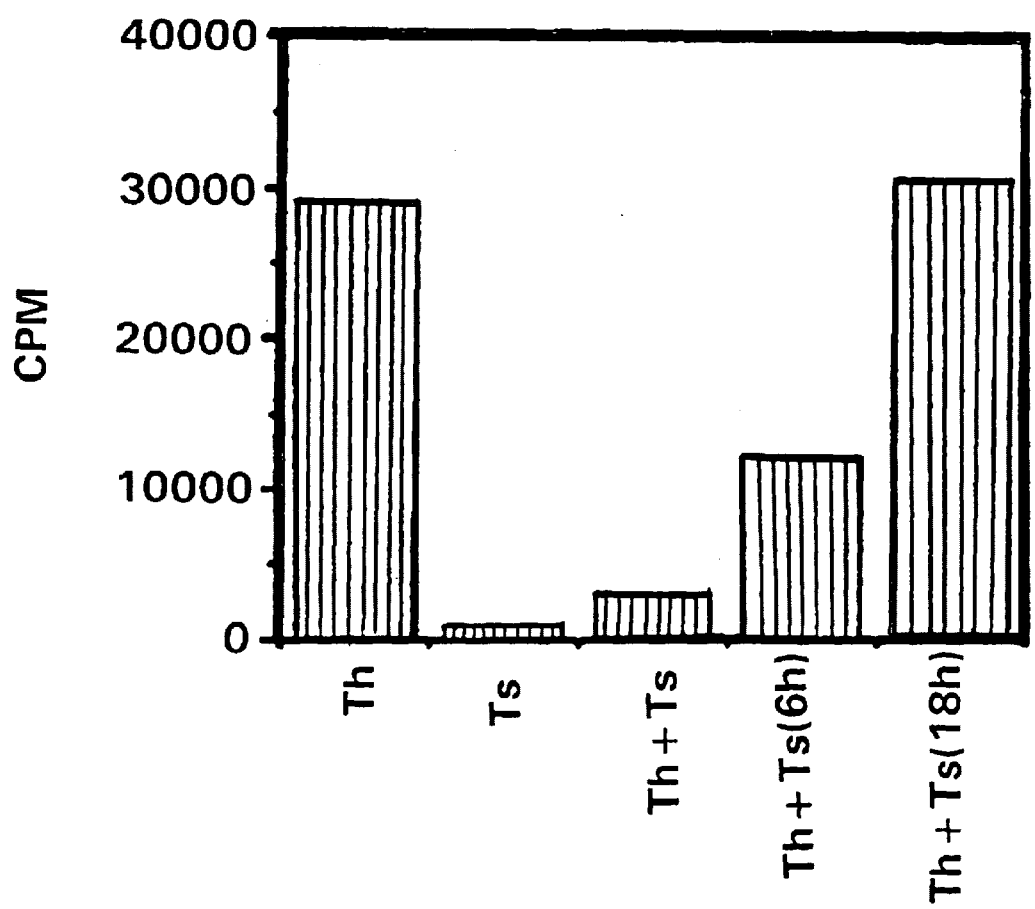
FIG. 22. Early recognition of APCs by Ts is required for suppression of Th proliferation. CD4+ Th cells isolated from a TCL were cultured with APCs used for priming for 3 days. CD8+CD28− Ts cells from the same TCL were added 0, 6, or 18 h after initiation of the culture. Mean CPM of triplicate cultures are shown. SD was less than 10% of the mean. T cell reactivity to self APCs was less than 2,000 cpm. The data are from one of four independent experiments.
Figures 1, 23A:
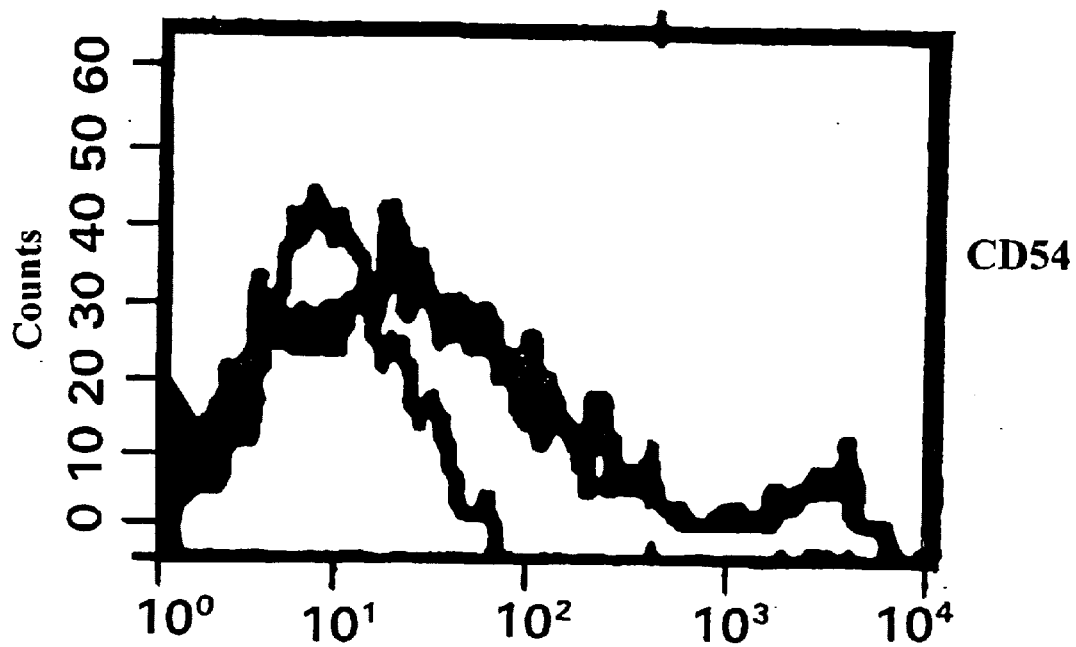
Figures 2, 23A:
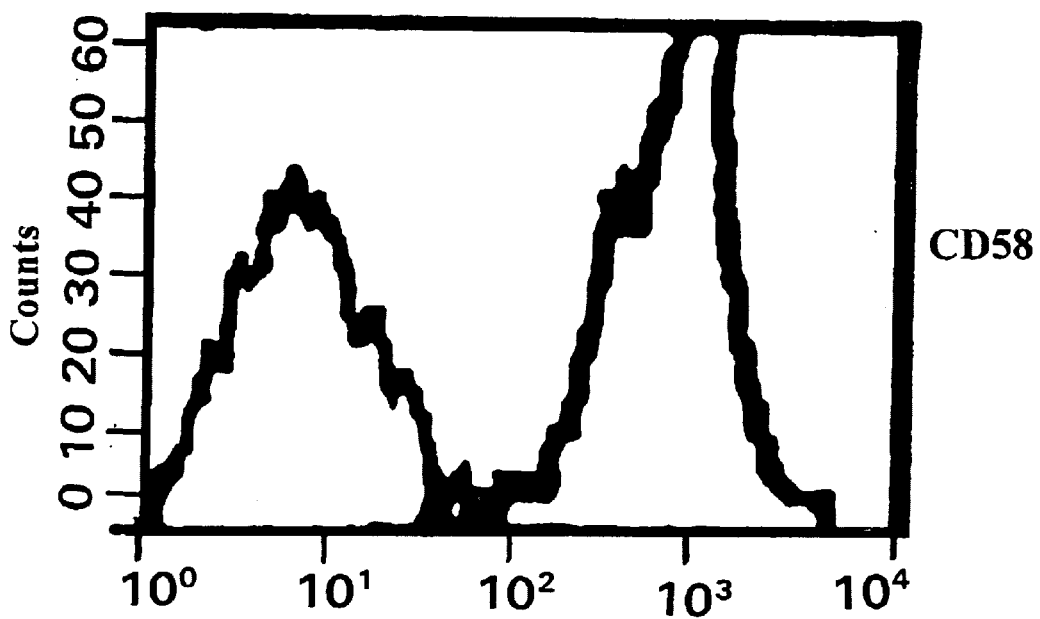
Figures 5, 23A:
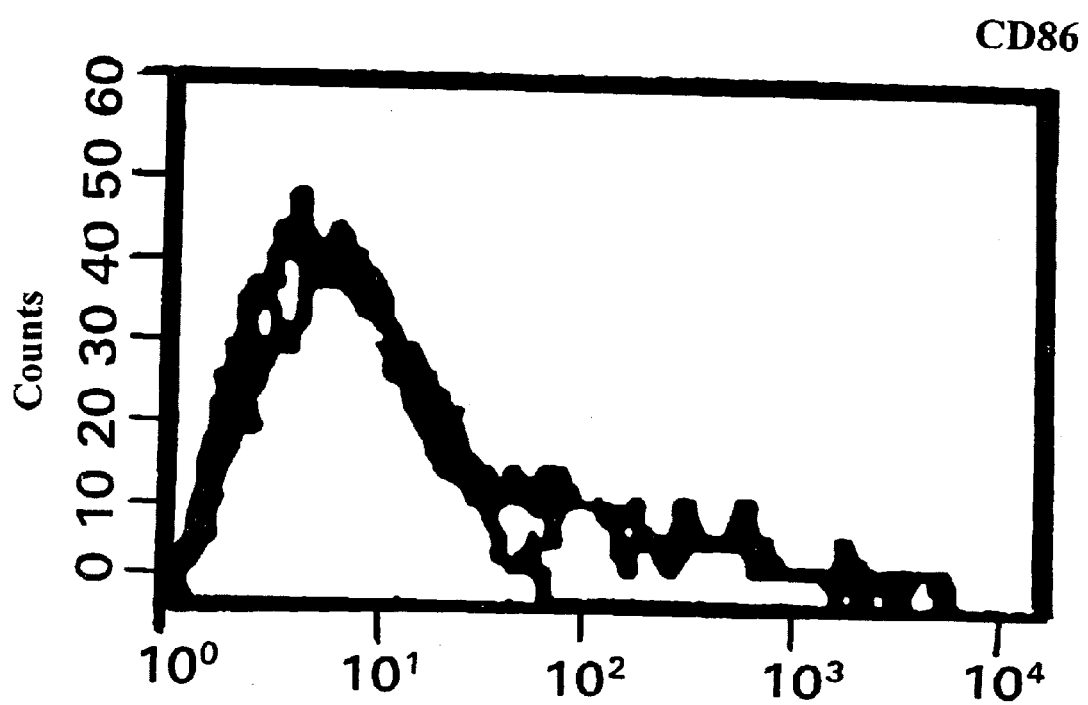
Figures 1, 23B:
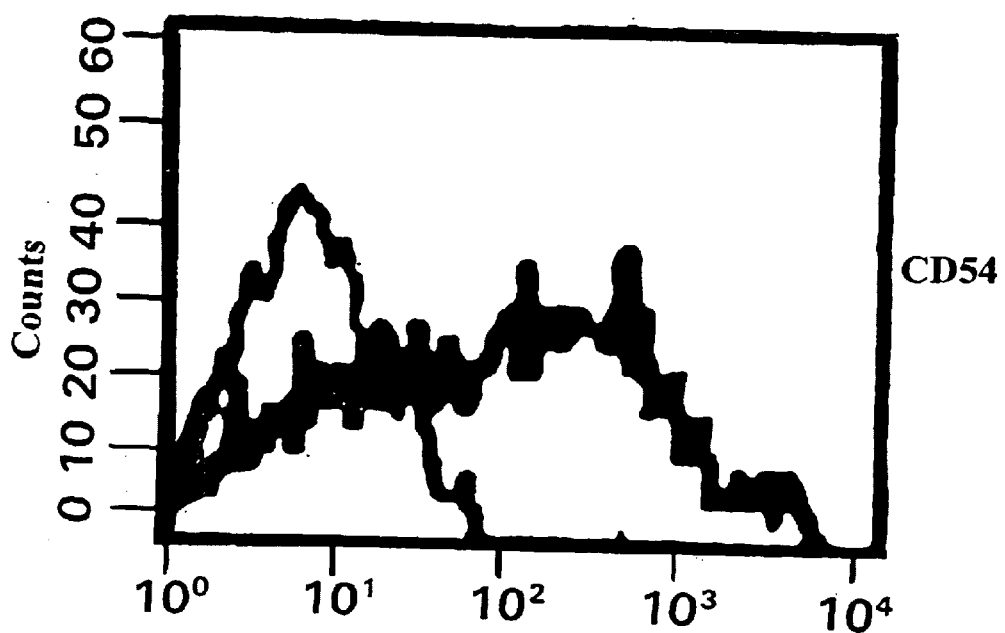
Figures 2, 23B:
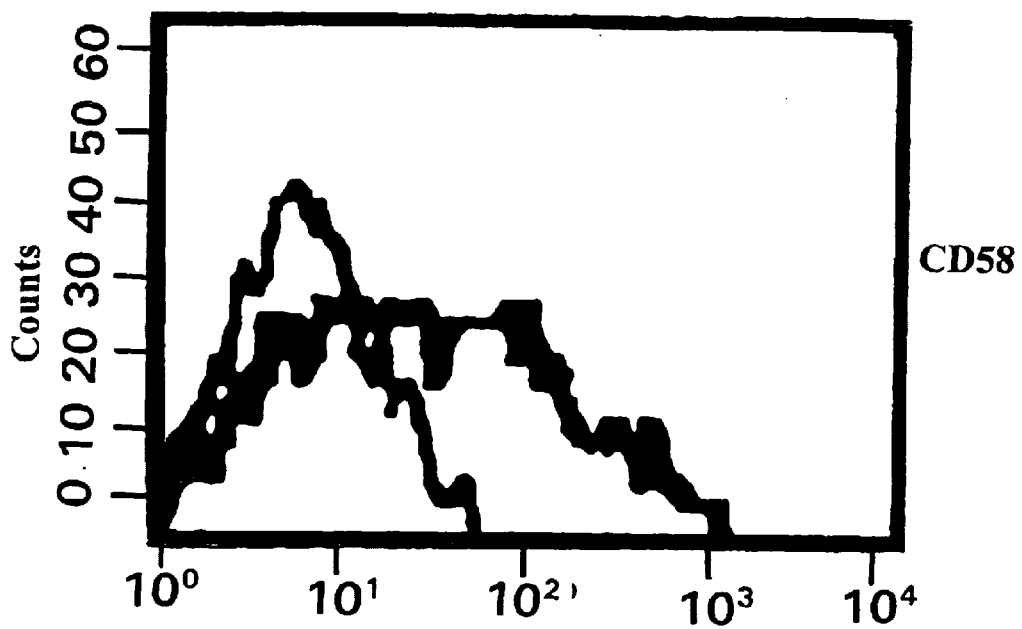
Figures 3, 23B:
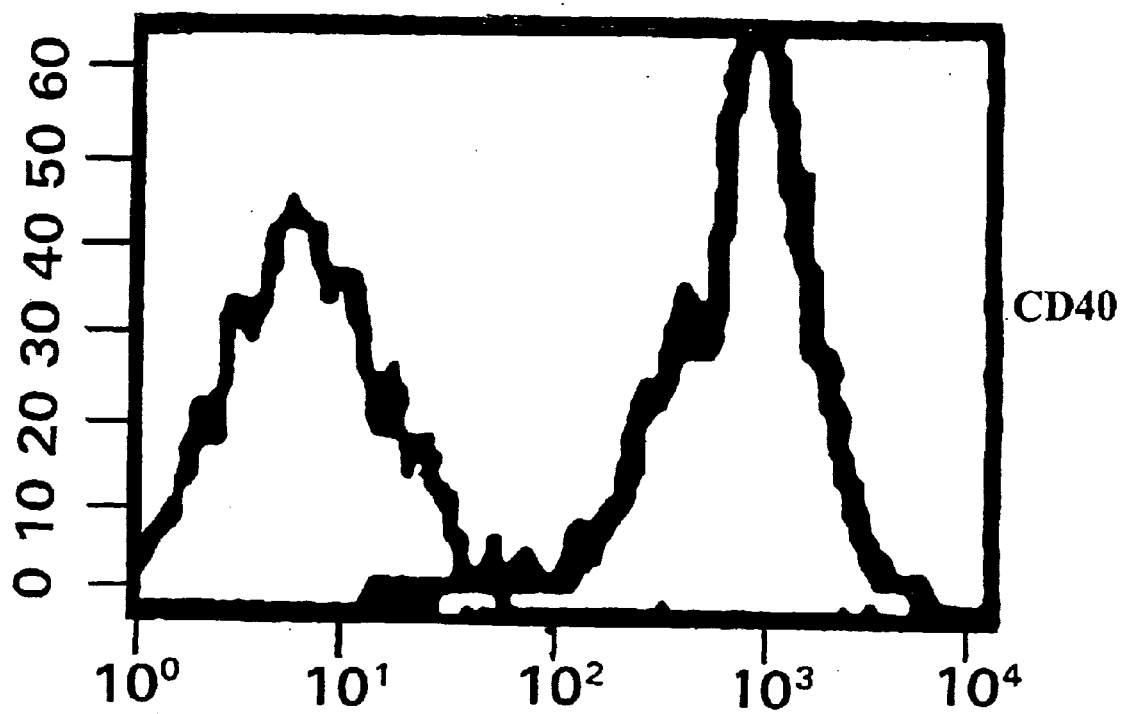
Figures 4, 23B:
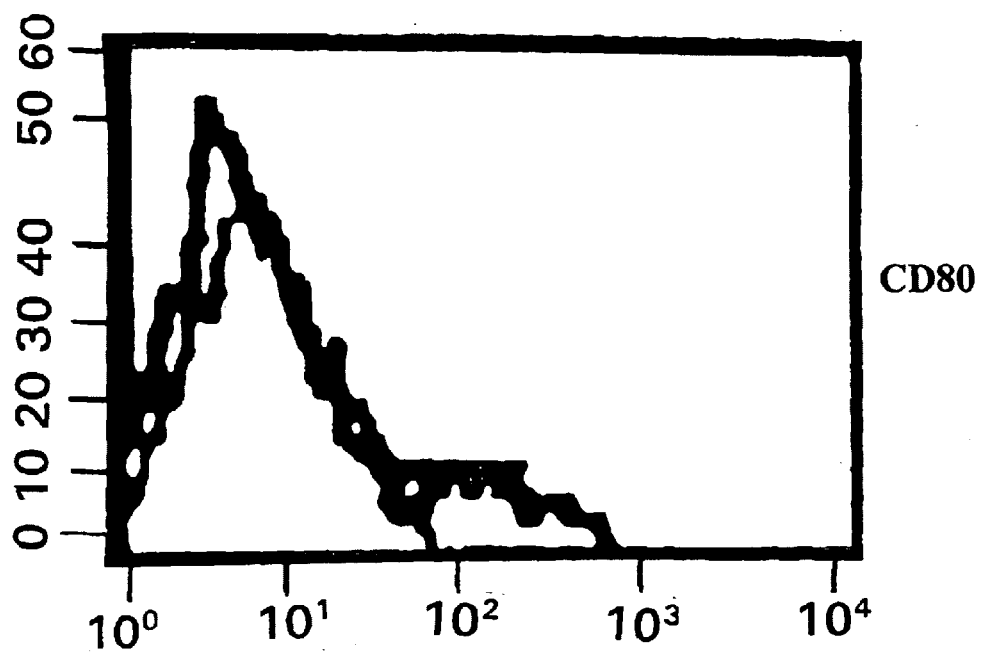
Figures 5, 23B:
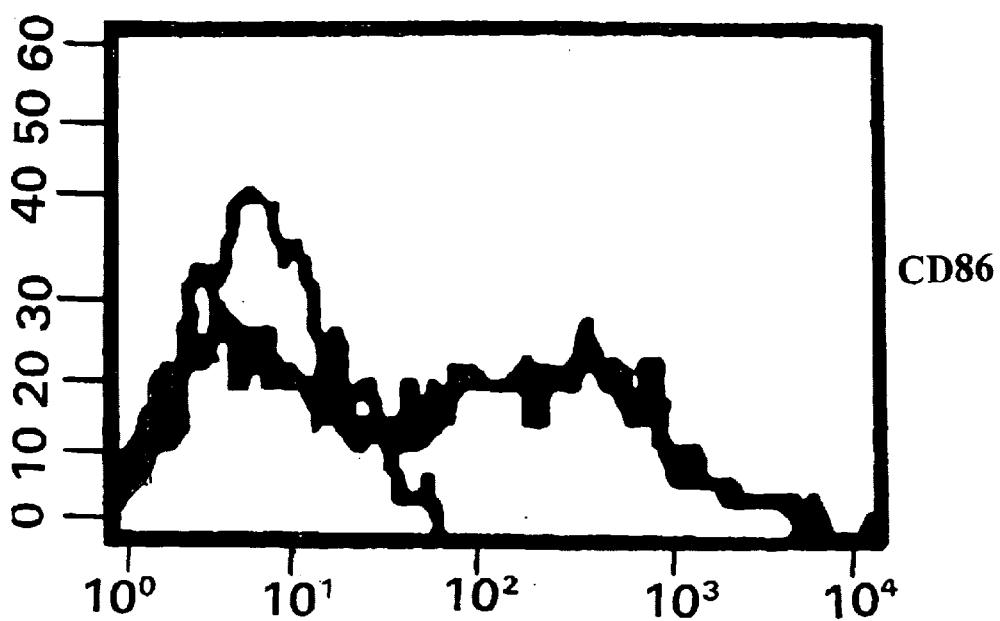
Figures 1, 23C:
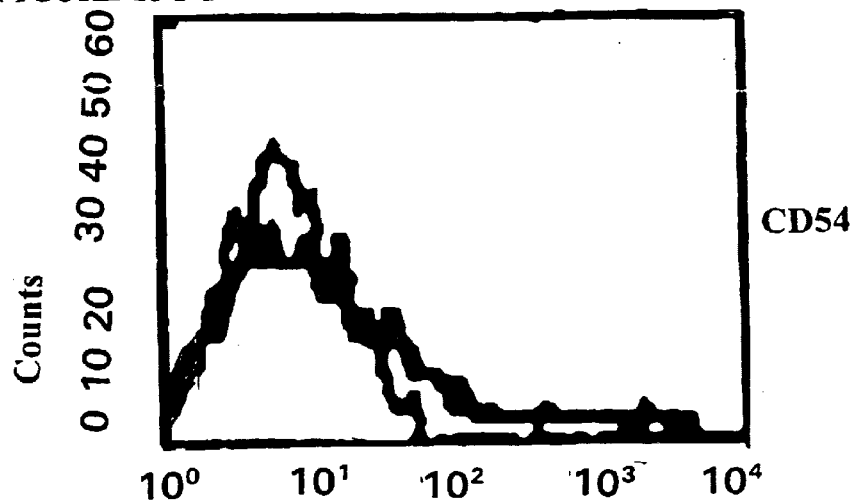
Figures 2, 23C:
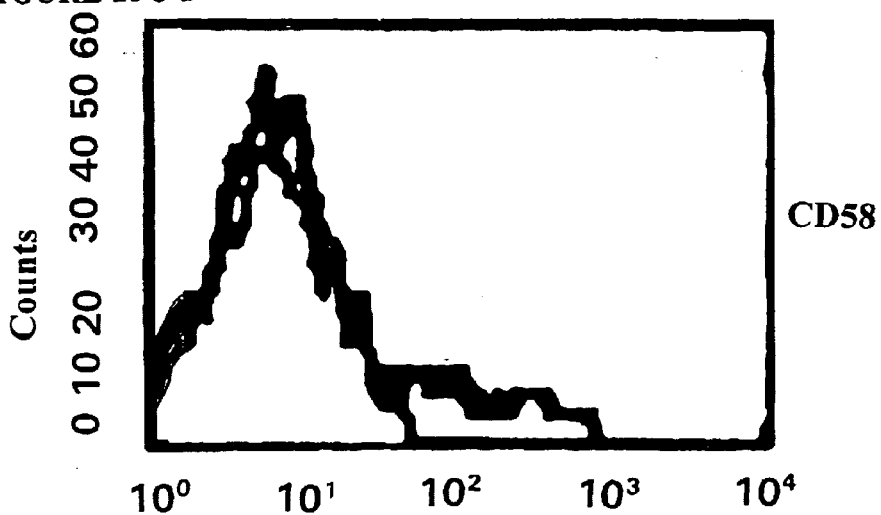
Figures 3, 23C:
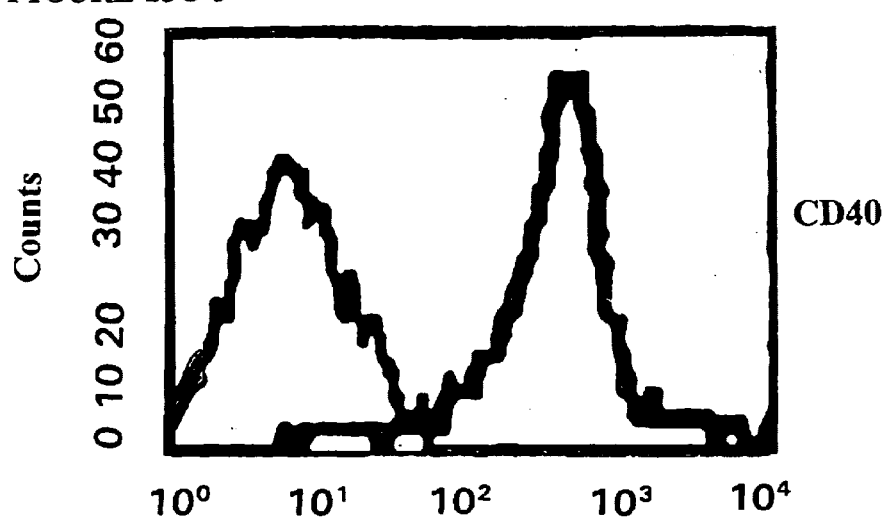
Figures 4, 23C:
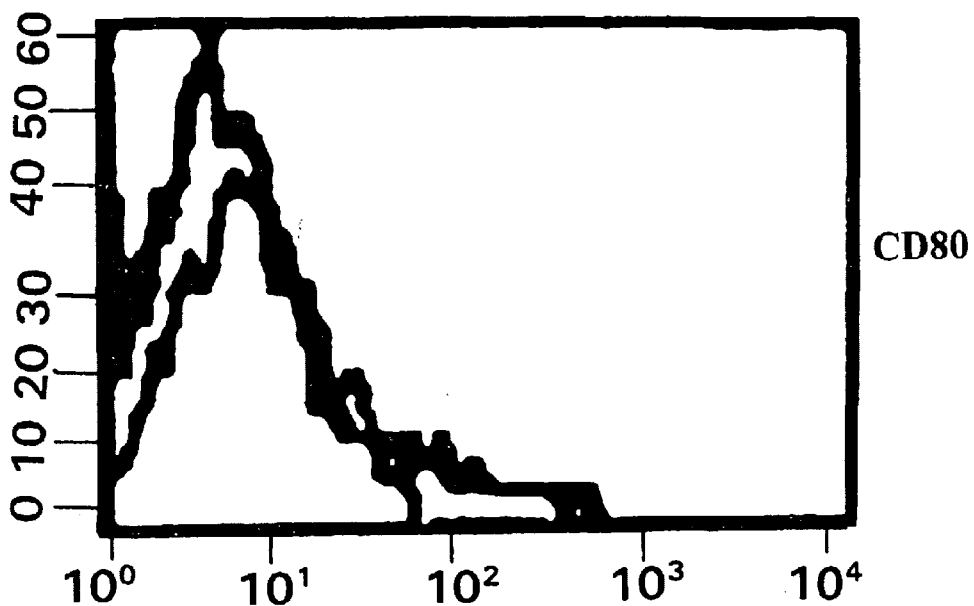
Figures 5, 23C:
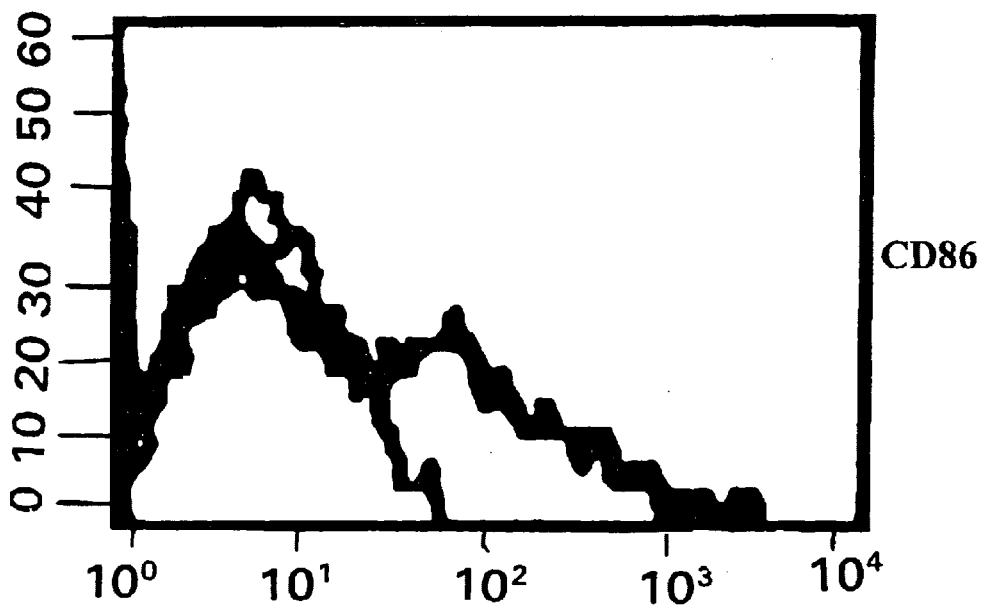
Figures 4, 23D:
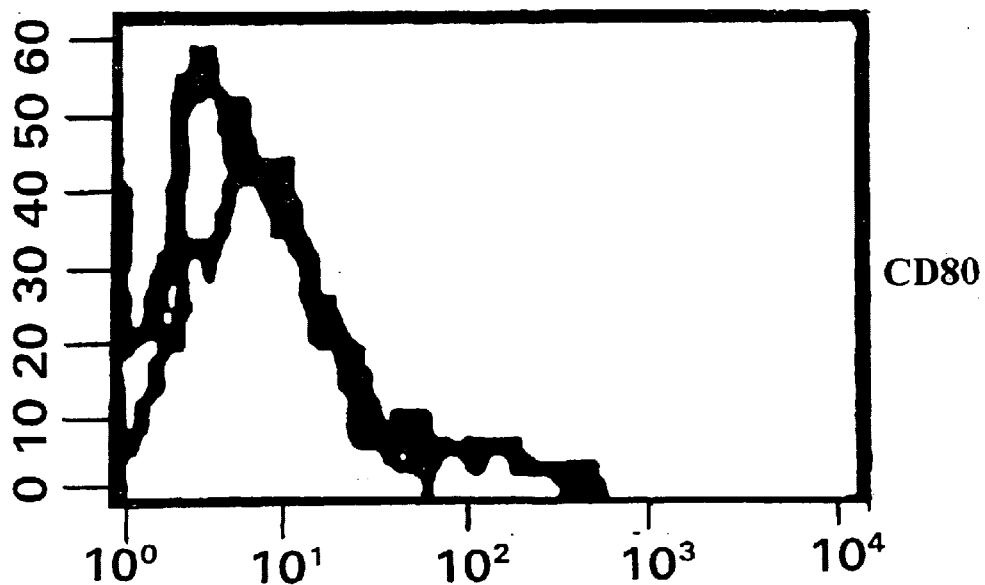
Figures 5, 23D:
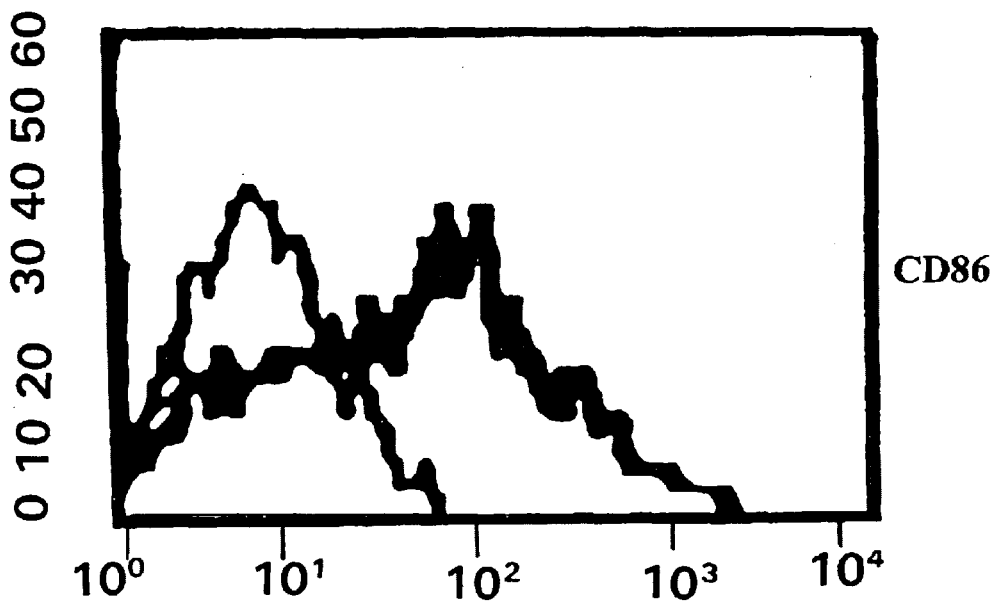
Figures 1, 23E:
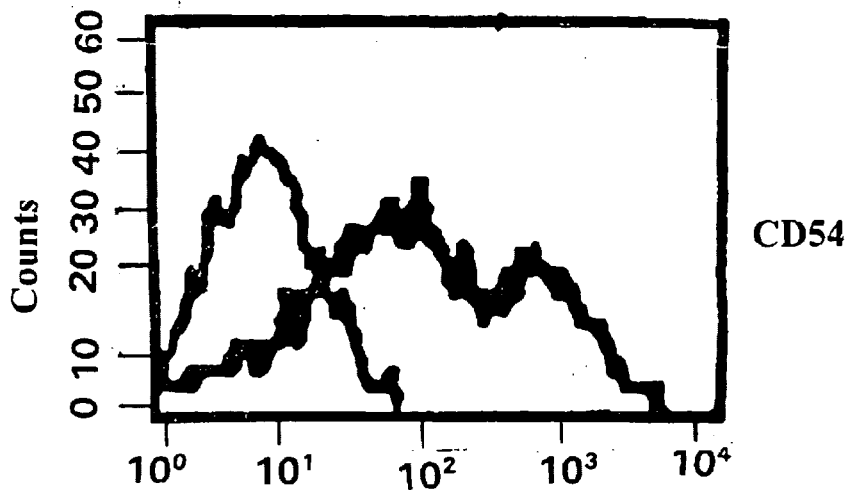
Figures 2, 23E:
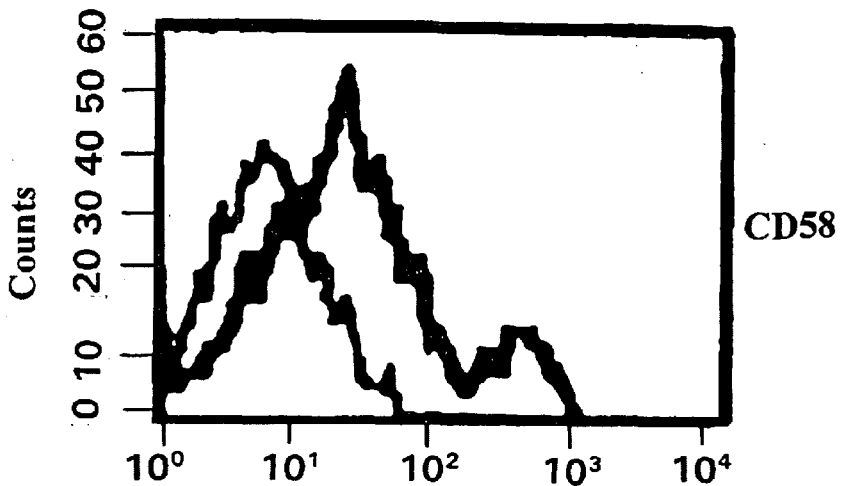
Figures 3, 23E:
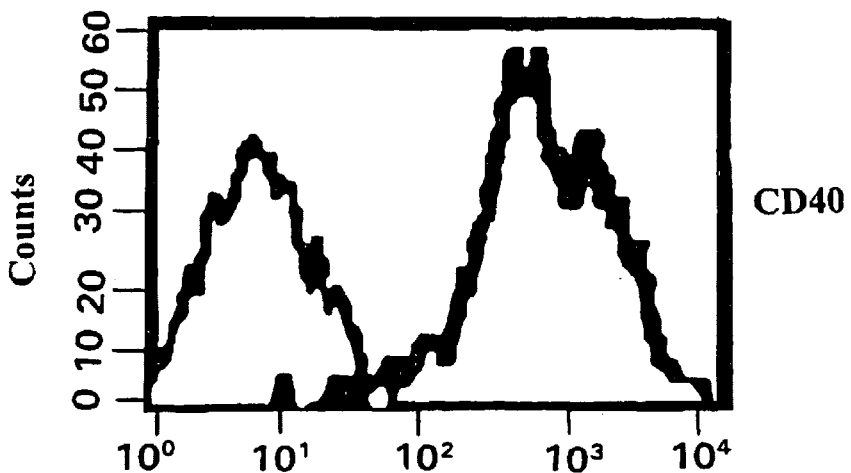
Figures 4, 23E:
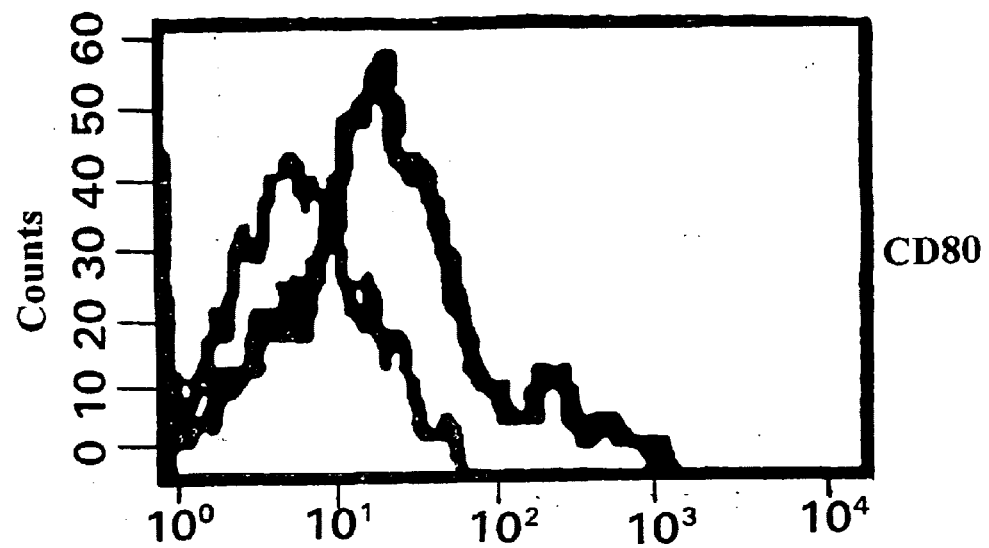
Figures 5, 23E:
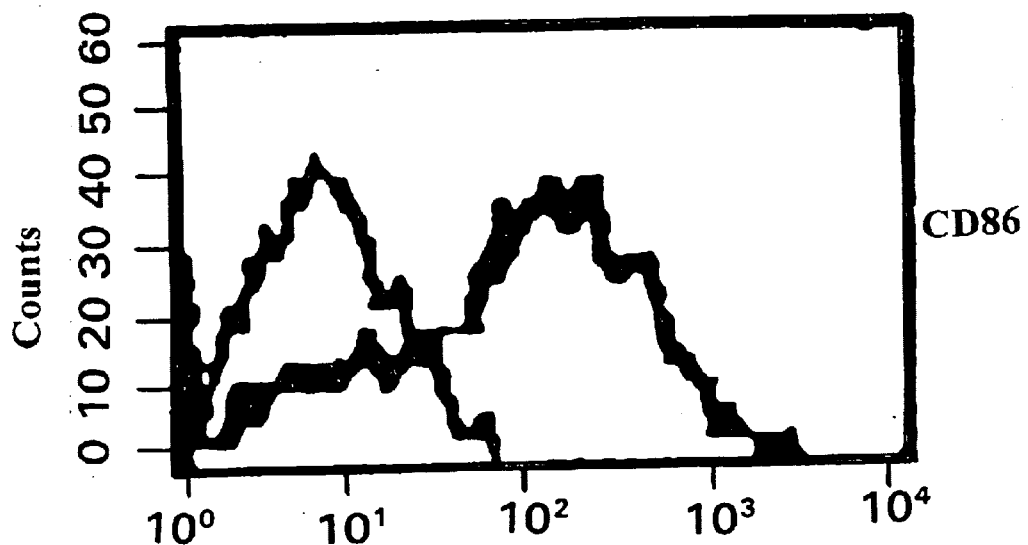

To explore this possibility, Ts were added to cultures containing allospecific Th and the APCs used for priming, 0, 6 and 18 h after the initiation of the assay. The expression of CD40, CD54, CD58, CD80 and CD86 on APCs was analyzed 48 h, and Th proliferation was measured 72 h, after the initiation of the cultures. In the absence of Ts, Th show strong proliferation in response to stimulation with APCs (FIG. 22) and induce the upregulation of CD54, CD58, CD80 and CD86 on APCs (FIG. 23). In contrast, when Ts were added to the cultures at time 0, Th proliferation was strongly inhibited (FIG. 22) and the level of CD54, CD58, CD80 and CD86 expression on APCs was greatly diminished (FIG. 23). The inhibitory effect of Ts decreased when they were added 6 h after initiation of cultures and was virtually absent when added 18 h later (FIG. 22 and FIG. 23). Taken together these data indicate that suppression is an early event which requires the presence of APCs and that APCs may activate CD4$^+$ Th only if they have not first interacted with Ts.

To determine whether Ts render the APCs unable to stimulate Th, allospecific Ts were incubated with the APCs used for priming. After 6 to 24 h of incubation, Ts were removed from the cultures and the APCs were used for stimulating Th derived from the same TCL. While APCs incubated with naive CD8$^+$CD28$^-$ T cells elicit strong proliferatin of Th, APCs that have been incubated with allospecific Ts for 6 to 24 h fail to trigger Th blastogenesis in 3-day assays (Table 7). Propidium iodine and Annexin V staining of the APCs exposed to Ts for 24 h show no loss of viability [5, 6], indicating that Ts do not kill the APCs, yet convert them to a state in which they are no longer capable of sustaining the activation of Th. These data indicate that the costimulatory capacity of APCs is altered by a prior encounter with Ts.

TABLE 7

Ts render APCs unable to stimulate the proliferation of allospecific Th ($^3$H thymidine incorporation)

| Cultures | Self-APC | Medium 6 h | Medium 24 h | Allogeneic APCs preincubated Naive CD8$^+$28$^-$ T cell 6 h | Allogeneic APCs preincubated Naive CD8$^+$28$^-$ T cell 24 h | Allospecific CD$^+$28$^-$ Ts cells 6 h | Allospecific CD$^+$28$^-$ Ts cells 24 h |
|---|---|---|---|---|---|---|---|
| Th | 1.141 ± 67* | 40,283 ± 2,941 | 42,784 ± 3,541 | 41,965 ± 3,762 | 44,283 ± 4,023 | 5,980 ± 548 | 418 ± 36 |
| Ts | 470 ± 45 | 470 ± 45 | 532 ± 49 | 366 ± 41 | 1,324 ± 142 | 456 ± 43 | 64 ± 55 |
| Th + Ts | 936 ± 89 | 7,936 ± 689 | 8,934 ± 815 | 6,009 ± 524 | 7,025 ± 673 | 2,712 ± 231 | 86 ± 11 |

*Mean CPM ± SD.
Th or/and Ts from an allospecific TCL were incubated for 3 days with autologous or allogeneic APCs (CD2$^+$ depleted PBMC). The allogeneic APCs used for stimulation were preincubated for 6 or 24 h with allospecific CD8$^+$28$^-$ cells. The U cells were then depleted from the mixture with CD2 magnetic beads. The cultures were labled and harvested after 72 h. Results are representative of three different experiments.

Since ligation of CD40 molecules on APCs has been shown to upregulate the expression of costimulatory molecules [10, 13], it is possible that Ts can inhibit the CD40 signaling pathway. To explore this hypothesis two well established systems were used. In one of these systems, upregulation of costimulatory molecules on APCs through CD40 signaling is accomplished by ligation of CD40 molecules on APCs using the D1.1 Jurkat T cell line, that constitutively expresses CD40L [10]. In the other system, CD40 antibody bound to the Fc (CD32) receptor of L cells were added to APCs in cultures containing IL-4 [13]. Crosslinking of CD40 molecules on APCs either by incubation for 24 h with the CD40L positive D1.1 line or by incubation for 48 h with anti-CD40 antibody results in upregulation of CD54, CD58, CD80 and CD86 molecules on APCs (Table 8). CD40 triggering also increases the mean fluorescence intensity (MFI) of CD40 on APCs (Table 8). In contrast, in the presence of allospecific Ts, APCs cultured for the same periods of time with D1.1 T cell line or CD40 antibody failed to upregulate any of these molecules (CD40, CD54, CD58, CD80 and CD86). The data indicate that Ts inhibit the costimulatory capacity of APCs, by interfering with CD40 dependent signaling.

TABLE 8

Ts inhibit CD40-induced upregulation of costimulatory molecules on APCs

| Cultures | CD40 | CD54 | CD58 | CD80 | CD86 |
|---|---|---|---|---|---|
| APC | 99(203) | 60(350) | 42(374) | 17(90) | 35(318) |
| APC + D1.1 | 99(312) | 85(358) | 70(380) | 41(141) | 49(327) |
| APC + D1.1 + Ts | 99(172) | 11(147) | 14(209) | 7(78) | 16(178) |
| APC | 99(231) | 65(283) | 40(315) | 16(78) | 30(310) |
| APC + CD 40Ab + IL-4 | 99(430) | 97(443) | 80(458) | 31(109) | 63(464) |
| APC + CD 40Ab + IL-4 + Ts | 93(201) | 56(192) | 22(263) | 10(47) | 33(221) |

% Positive APCs (MFI*)

*Mean channel fluorescence intensity.
APCs (CD2$^+$cell-depleted PBMC) were cultured with either CD40L$^+$ D1.1 cells or mAb CD40 bound to Fcγ receptor of L cells plus IL-4 Ts were added at the initiation of the assay.
Expression of costimulatory molecules on CD14$^+$ and CD 20$^+$. APC was analysed by flow cytometry. Results are representative of three independent experiments.

APCs (CD2$^+$ cell-depleted PBMC) were cultured with either CD40L$^+$ D1.1 cells or mAb CD40 bound to Fcγ receptor of L cells plus IL-4 Ts were added at the initiation of the assay. Expression of costimulatory molecules on CD14$^+$ and CD 20$^+$. APC was analysed by flow cytometry. Results are representative of three independent experiments. (Table 8)

Taken together these data indicate that Ts interacts directly with APCs, inhibiting CD40-mediated CD80 and CD86 upregulation. The "suppressed" APCs are rendered unable to induce and sustain the full program of Th activation. Thus, Th exposed to "suppressed" APCs fail to upregulate completely CD40L expression due to an aborted "crosstalk", that is normally based on CD40-mediated upregulation of CD80 and CD86 [15, 16].

There is ample evidence that in the absence of co-stimulation TCR interaction with MHC/antigen complexes can lead to T cell anergy [17–19]. T cell anergy can be restored by crosslinking the CD28 molecure or by the use of exogenous IL-2 [17–19]. It was found that addition of rIL-2 to cultures containing Th, Ts and APC restores Th proliferation (FIG. 24). This indicates that Th are rendered anergic by Ts-treated APCs consistent with the previous finding that CD28 crosslinking restores Th reactivity in cultures with Ts [5].

Figure 25:
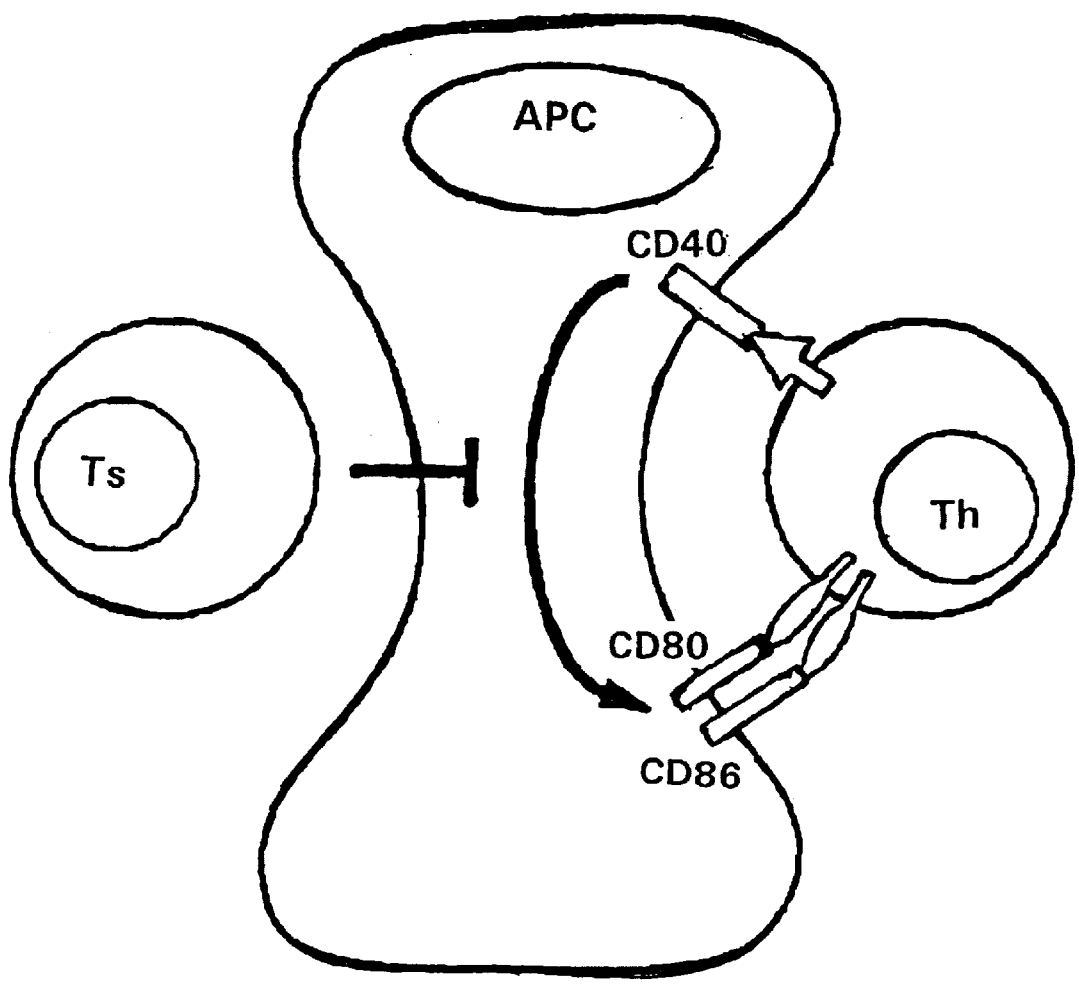
FIG. 25. Ts supress CD40-signaling in APC. The "suppressed" APC do not upregulate the expression of costimulatory molecules (CD80, CD86) and are, therefore, unable to induce and sustain the full program of Th activity.
Figure 28:
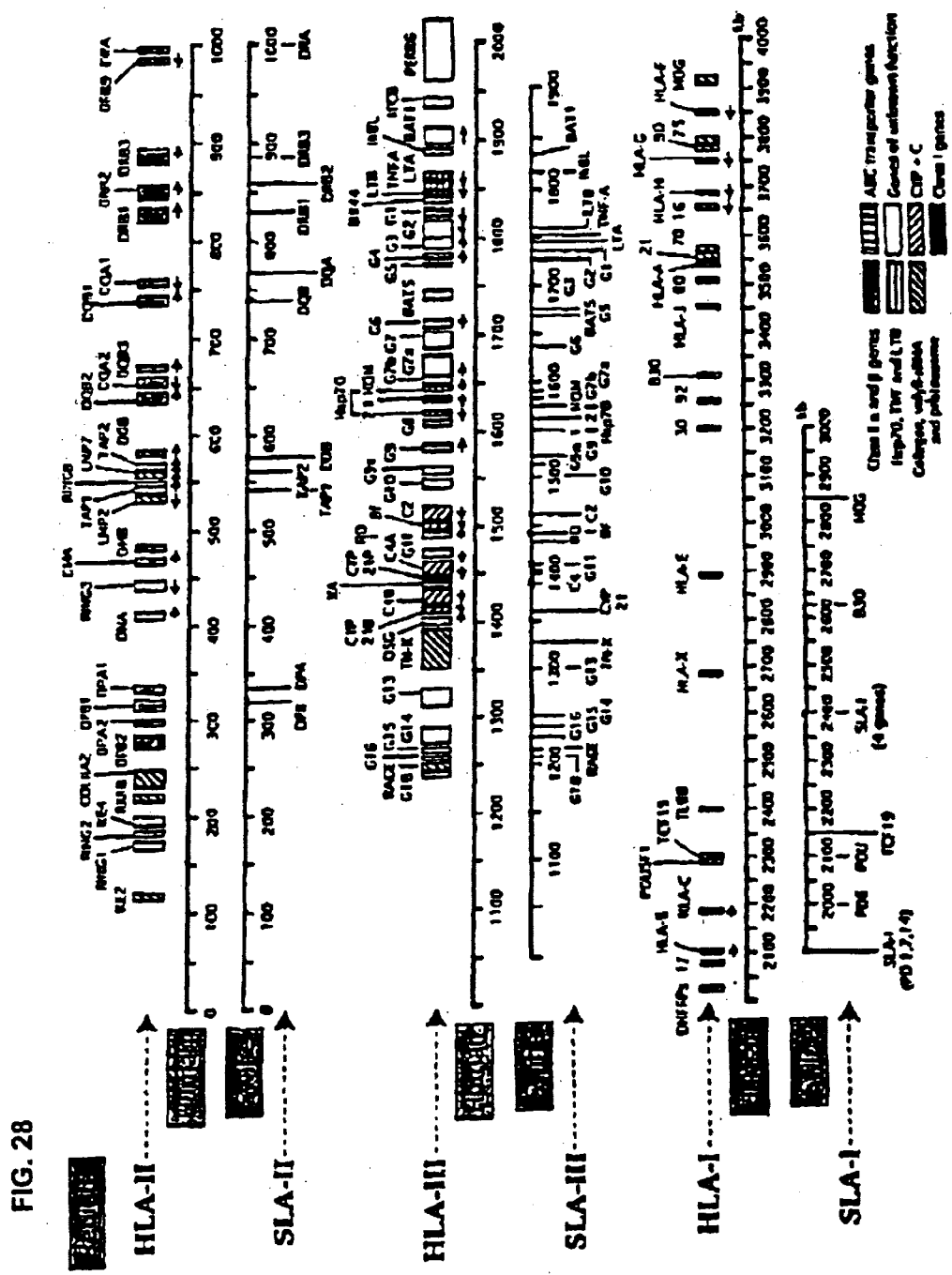
FIG. 28. Detailed map of the swine major histocompatibility or swine leukocyte antigen (SLA) complex as compared to the human leukocyte antigen (HLA) complex. HLA-II and SLA-II, HLA-II and SLA-III and Hla-I and SLA-I. (from J. K. Lunney and J. E. Butler, Immunogenetics, In *The Genetics of the Pig*, 1998, eds., M. F. Rothschild and A. Ruvinsky, CAB International.)

The data herein support a model in which T-cell mediated suppression can result form the sequential interaction between first, TS and APCs and next, "suppressed" APCs and Th (FIG. 25). In this regard the present findings confirm and extend the "temporal bridging" model recently described to account for the complex role that APCs play in Th-mediated generation of CD8$^+$ Tc[2–4]. Furthermore, the present data complement the finding that CD40 signaling is essential for conditioning APCs, by demonstrating that Ts inhibit this pathway. New data show that Ts inhibit The-induced activation of NF-B in APC, thus interfering with the upregulation of B7 costimulatory molecules (Li, J., Liu, Z., Jiang, S., Cortesini, R., Lederman, S., Suciu-Foca, N. submitted).

Further dissection of the molecular interaction between Ts and APCs should allow the development of new strategies for specific suppression of the immune response in transplantation and autoimmune diseases.

References for the Fourth Series of Experiments

1. Damie N K, Mohagheghpour N, Hansen J A, Engleman E G: Alloantigen-specific cytotoxic and suppressor T lymphocytes are derived from phenotypically distinct precursors. J Immunol 131:2296, 1983.
2. Ridge J P, Di Rosa F, Marzinger P: A conditioned dendritic cell can be a temporal bridge between a CD4$^+$ T-helper and a T-killer cell. Nature 393:474, 1998.
3. Bennett S R M, Carbone F R, Karamalis F, Flavells R A, Miller J F A P, Heath W R: Help for cytotoxic-T-Cell responses is mediated by CD40 signaling. Nature 393:478, 1998.
4. Schoenberger S P, Toes R E M, van der Voort E I H, Offringa R, Melief C J M: T-cell help for cytotoxic T lymphocytes is mediated by CD40-CD40L interactions. Nature 393:480, 1998.
5. Liu Z, Tugulea S, Cortesini R, Suciu-Foca N: Specific suppression of T helper alloreactivity by allo-MHC class I-restricted CD8+CD28− T cells. Int Immunol 10:775, 1998.
6. Ciubotariu R, Colovai A I, Pennesi G, Liu Z, Smith D, Berlocco P, Cortesini R, Suciu-Foca N: Specific suppression of human CD4+ Th cell responses to pig MHC antigens by CD8+CD28− regulatory T cells. J Immunol 161:5193, 1998.
7. Jiang S, Tugulea S, Pennesi G, Liu Z, Mulder A, Lederman S, Harris P, Cortesini R, Suciu-Foca N: Induction of MHC-class I restricted human suppressor T cells by peptide priming in vitro. Hum Immunol 59:690, 1998.
8. Monteiro J, Batliwalla F, Ostrer H, Gregersen P K: Shortened telomeres in clonally expanded CD28−CD8+ T cells imply a replicative history that is distinct from their CD28+CD8+ counterparts. J Immunol 156:3587, 1996.
9. Roy M, Aruffo A, Ledbetter J, Linsley P, Kehry M, Noelle R: Studies on the interdependence of gp39 and B7 expression and function during antigen-specific immune responses. Eur J Immunol 25:596, 1995.
10. Yellin M J, Sinning J, Covey L R, Sherman W, Lee J J, Glickman-Nir E, Sippel K C, Rogers J, Cleary A M, Parker M, Chess L, Lederman S: T lymphocyte T cell-B cell-activating molecule/CD40-L molecules induce normal B cells or chronic lymphocytic leukemia B cells to express CD80 (B7/BB-1) and enhance their costimulatory activity. J Immunol 153:666, 1994.
11. Lederman S, Yellin M J, Krichevsky A, Belko J, Lee J J, Chess L: Identification of a novel surface protein on activated CD4+ T cells that induces contact-dependent B cell differentiation (help). J Exp Med 175:1091, 1992.
12. Noelle R J, Roy M, Shepherd D M, Stamenkovic I, Ledbetter J A, Atuffo A: A 39-kDa protein on activated helper T cells binds CD40 and transduces the signal for cognate activation of B cells. Proc Natl Acad Sci 89:6550, 1992.
13. Ranheim E A, Kipps T J: Activated T cells induce expression of B7/BB1 on normal or leukemic B cells through a CD40-dependent signal. J Exp Med 177:925, 1993.
14. Goldstein M D, Debenedette M A, Hollenbaugh D, Watts T H: Induction of costimulatory molecules B7-1 and B7-2 in murine B cells. The CBA/N mouse reveals a role for Bruton's tyrosine kinase in CD40-mediated B7 induction. Mol Imm 33:541, 1996.
15. Clark E A, Ledbetter J A: How B and T cells talk to each other. Nature 367:425, 1994.
16. Banchereau J. Steinman R M: Dendritic cells and the control of immunity. Nature 392:245, 1998.
17. Jenkins M K, Schwartz R H: Antigen presentation by chemically modified splenocytes induces antigen-specific T cell unresponsiveness in vitro and in vivo. J Exp Med 165:302, 1987.
18. Harding F A, McArthur J G, Gross J A, Raulet D H, Allison J P: CD28-mediated signalling co-stimulates murine T cells and prevents induction of energy in T-cell clones. Nature 356:607, 1992.
19. Schwartz R H: Costimulation of T lymphocytes: the role of CD28, CTLA-4, and B7/BB1 in Interleuken-2 production and immunotherapy. Cell 71:1065, 1992.

What is claimed is:

1. A method of generating allopeptide antigen specific human suppressor CD8+CD28− T cells which comprises:
   a) obtaining peripheral blood T cells from a subject;
   b) stimulating by multiple priming a T cell line from the T cells obtained in step (a) with autologous antigen presenting cells (APCs) pulsed with an allopeptide, said allopeptide comprising an amino acid sequence comprising both MHC class I and MHC class II amino acid sequences wherein the amino acid sequences are binding sequences and are recognized by the primed T cell line;
   c) isolating primed populations of CD8+ T cells and of CD4+ T helper cells from the T cell line stimulated in step (b);
   d) isolating primed CD8+CD28− T cells from the isolated primed CD8+ T cells of step (c);
   e) detecting suppression by the primed CD8+CD28− T cells isolated in step (d) of interaction between the CD4+ T helper cells isolated in step (c) and autologous antigen presenting cells (APCs) expressing the same MHC class I and MHC class II binding motifs as expressed by the APCs used to stimulate the T cell line of step (b), thereby identifying allopeptide antigen specific human suppressor CD8+CD28− T cells; and
   f) expanding the allopeptide antigen specific human suppressor CD8+CD28− T cells identified in step (e), thereby generating allopeptide antigen specific human suppressor CD8+CD28− T cells.

2. The method of claim 1 wherein the allopeptide is a peptide antigen or a whole protein antigen.

3. The method of claim 2, wherein the peptide antigen is tat-DR4 (SEQ ID NO:1).

4. The method of claim 2, wherein the peptide antigen is a peptide comprising an amino acid sequence of a hypervariable region of HLA-DR B1.

* * * * *

SEQUENCE LISTING

<160> NUMBER OF SEQ ID NOS: 229

<210> SEQ ID NO 1
<211> LENGTH: 34
<212> TYPE: PRT
<213> ORGANISM: Artificial Sequence
<220> FEATURE:
<223> OTHER INFORMATION: HIV-1 tat - HLA-DRB chimera

<400> SEQUENCE: 1

Arg Lys Lys Arg Arg Gln Arg Arg Gln Lys Asp Leu Leu Glu Gln
1               5                   10                  15

Lys Arg Ala Ala Val Asp Thr Tyr Cys Arg His Asn Tyr Gly Val Gly
            20                  25                  30

Glu Ser

<210> SEQ ID NO 2
<211> LENGTH: 102
<212> TYPE: PRT
<213> ORGANISM: human

<400> SEQUENCE: 2

Gly Asp Thr Arg Pro Arg Phe Leu Trp Gln Leu Lys Phe Glu Cys His
1               5                   10                  15

Phe Phe Asn Gly Thr Glu Arg Val Arg Leu Leu Glu Arg Cys Ile Tyr
            20                  25                  30

Asn Gln Glu Glu Ser Val Arg Phe Asp Ser Asp Val Gly Glu Tyr Arg
        35                  40                  45

```
Ala Val Thr Glu Leu Gly Arg Pro Asp Ala Glu Tyr Trp Asn Ser Gln
    50                  55                  60

Lys Asp Leu Leu Glu Gln Arg Ala Ala Val Asp Thr Tyr Cys Arg
 65                  70                  75                  80

His Asn Tyr Gly Val Gly Glu Ser Phe Thr Val Gln Arg Arg Val Glu
                 85                  90                  95

Pro Lys Val Thr Val Tyr
            100

<210> SEQ ID NO 3
<211> LENGTH: 102
<212> TYPE: PRT
<213> ORGANISM: human

<400> SEQUENCE: 3

Gly Asp Thr Arg Pro Arg Phe Leu Trp Gln Leu Lys Phe Glu Cys His
 1               5                  10                  15

Phe Phe Asn Gly Thr Glu Arg Val Arg Leu Leu Glu Arg Cys Ile Tyr
                20                  25                  30

Asn Gln Glu Glu Ser Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
    50                  55                  60

Lys Asp Leu Leu Glu Gln Arg Ala Ala Val Asp Thr Tyr Cys Arg
 65                  70                  75                  80

His Asn Tyr Gly Ala Val Glu Ser Phe Thr Val Gln Arg Arg Val Glu
                 85                  90                  95

Pro Lys Val Thr Val Tyr
            100

<210> SEQ ID NO 4
<211> LENGTH: 81
<212> TYPE: PRT
<213> ORGANISM: human

<400> SEQUENCE: 4

Arg Phe Leu Trp Gln Leu Lys Phe Glu Cys His Phe Phe Asn Gly Thr
 1               5                  10                  15

Glu Arg Val Arg Leu Leu Glu Arg Cys Ile Tyr Asn Gln Glu Glu Ser
                20                  25                  30

Val Arg Phe Asp Ser Asp Val Gly Glu Tyr Arg Ala Val Thr Glu Leu
            35                  40                  45

Gly Arg Pro Asp Ala Glu Tyr Trp Asn Ser Gln Lys Asp Leu Leu Glu
    50                  55                  60

Gln Arg Ala Ala Val Asp Thr Tyr Cys Arg His Asn Tyr Gly Ala
 65                  70                  75                  80

Val

<210> SEQ ID NO 5
<211> LENGTH: 102
<212> TYPE: PRT
<213> ORGANISM: human

<400> SEQUENCE: 5

Gly Asp Thr Arg Pro Arg Phe Leu Trp Gln Leu Lys Phe Glu Cys His
 1               5                  10                  15

Phe Phe Asn Gly Thr Glu Arg Val Arg Leu Leu Glu Arg Cys Ile Tyr
```

-continued

```
                20                  25                  30

Asn Gln Glu Glu Ser Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Ile Leu Glu Asp Arg Ala Ala Val Asp Thr Tyr Cys Arg
65                  70                  75                  80

His Asn Tyr Gly Val Gly Glu Ser Phe Thr Val Gln Arg Arg Val Glu
                85                  90                  95

Pro Lys Val Thr Val Tyr
            100
```

<210> SEQ ID NO 6
<211> LENGTH: 102
<212> TYPE: PRT
<213> ORGANISM: human

<400> SEQUENCE: 6

```
Gly Asp Thr Arg Pro Arg Phe Leu Trp Gln Leu Lys Phe Glu Cys His
1               5                   10                  15

Phe Phe Asn Gly Thr Glu Arg Val Arg Leu Leu Glu Arg Cys Ile Tyr
                20                  25                  30

Asn Gln Glu Glu Ser Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Leu Leu Glu Gln Arg Ala Ala Val Asp Asn Tyr Cys Arg
65                  70                  75                  80

His Asn Tyr Gly Val Val Glu Ser Phe Thr Val Gln Arg Arg Val Glu
                85                  90                  95

Pro Lys Val Thr Val Tyr
            100
```

<210> SEQ ID NO 7
<211> LENGTH: 102
<212> TYPE: PRT
<213> ORGANISM: human

<400> SEQUENCE: 7

```
Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
                20                  25                  30

Asn Gln Glu Glu Ser Val Arg Phe Asp Ser Asp Val Gly Glu Phe Arg
            35                  40                  45

Ala Val Thr Glu Leu Gly Arg Pro Asp Ala Glu Tyr Trp Asn Ser Gln
        50                  55                  60

Lys Asp Ile Leu Glu Gln Ala Arg Ala Ala Val Asp Thr Tyr Cys Arg
65                  70                  75                  80

His Asn Tyr Gly Val Val Glu Ser Phe Thr Val Gln Arg Arg Val Gln
                85                  90                  95

Pro Lys Val Thr Val Tyr
            100
```

<210> SEQ ID NO 8
<211> LENGTH: 88
<212> TYPE: PRT

<213> ORGANISM: human

<400> SEQUENCE: 8

Arg Phe Leu Trp Gln Pro Lys Arg Glu Cys His Phe Asn Gly Thr
1               5                   10                  15

Glu Arg Val Arg Phe Leu Asp Arg Tyr Phe Tyr Asn Gln Glu Glu Ser
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Ile Leu Glu
    50                  55                  60

Gln Ala Arg Ala Ala Val Asp Thr Tyr Cys Arg His Asn Tyr Gly Val
65                  70                  75                  80

Val Glu Ser Phe Thr Val Gln Arg
                85

<210> SEQ ID NO 9
<211> LENGTH: 102
<212> TYPE: PRT
<213> ORGANISM: human

<400> SEQUENCE: 9

Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Ser Val Arg Phe Asp Ser Asp Val Gly Glu Phe Arg
        35                  40                  45

Ala Val Thr Glu Leu Gly Arg Pro Asp Ala Glu Tyr Trp Asn Ser Gln
    50                  55                  60

Lys Asp Ile Leu Glu Gln Ala Arg Ala Ala Val Asp Thr Tyr Cys Arg
65                  70                  75                  80

His Asn Tyr Gly Val Gly Glu Ser Phe Thr Val Gln Arg Arg Val Gln
                85                  90                  95

Pro Lys Val Thr Val Tyr
            100

<210> SEQ ID NO 10
<211> LENGTH: 73
<212> TYPE: PRT
<213> ORGANISM: human

<400> SEQUENCE: 10

Glu Cys His Phe Phe Asn Gly Thr Glu Arg Val Arg Phe Leu Asp Arg
1               5                   10                  15

Tyr Phe Tyr Asn Gln Glu Glu Ser Val Arg Phe Asp Ser Asp Val Gly
            20                  25                  30

Glu Phe Arg Ala Val Thr Glu Leu Gly Arg Pro Asp Ala Glu Tyr Trp
        35                  40                  45

Asn Ser Gln Lys Asp Ile Leu Glu Gln Ala Arg Ala Ala Val Asp Thr
    50                  55                  60

Tyr Cys Arg His Asn Tyr Gly Val Gly
65                  70

<210> SEQ ID NO 11
<211> LENGTH: 81
<212> TYPE: PRT
<213> ORGANISM: human

<400> SEQUENCE: 11

| Arg | Phe | Leu | Trp | Gln | Pro | Lys | Arg | Glu | Cys | His | Phe | Phe | Asn | Gly | Thr |
|---|---|---|---|---|---|---|---|---|---|---|---|---|---|---|---|
| 1 | | | | 5 | | | | | 10 | | | | | 15 | |

| Glu | Arg | Val | Arg | Phe | Leu | Asp | Arg | Tyr | Phe | Tyr | Asn | Gln | Glu | Glu | Ser |
|---|---|---|---|---|---|---|---|---|---|---|---|---|---|---|---|
| | | | 20 | | | | | 25 | | | | | 30 | | |

| Val | Arg | Phe | Asp | Ser | Asp | Val | Gly | Glu | Phe | Arg | Ala | Val | Thr | Glu | Leu |
|---|---|---|---|---|---|---|---|---|---|---|---|---|---|---|---|
| | | 35 | | | | | 40 | | | | | 45 | | | |

| Gly | Arg | Pro | Asp | Ala | Glu | Tyr | Trp | Asn | Ser | Gln | Lys | Asp | Ile | Leu | Glu |
|---|---|---|---|---|---|---|---|---|---|---|---|---|---|---|---|
| | 50 | | | | | 55 | | | | | 60 | | | | |

| Gln | Ala | Arg | Ala | Ala | Val | Asp | Thr | Tyr | Cys | Arg | His | Asn | Tyr | Gly | Val |
|---|---|---|---|---|---|---|---|---|---|---|---|---|---|---|---|
| 65 | | | | | 70 | | | | | 75 | | | | | 80 |

Gly

<210> SEQ ID NO 12
<211> LENGTH: 98
<212> TYPE: PRT
<213> ORGANISM: human

<400> SEQUENCE: 12

| Gly | Asp | Thr | Arg | Pro | Arg | Phe | Leu | Trp | Gln | Pro | Lys | Arg | Glu | Cys | His |
|---|---|---|---|---|---|---|---|---|---|---|---|---|---|---|---|
| 1 | | | | 5 | | | | | 10 | | | | | 15 | |

| Phe | Phe | Asn | Gly | Thr | Glu | Arg | Val | Arg | Phe | Leu | Asp | Arg | His | Phe | Tyr |
|---|---|---|---|---|---|---|---|---|---|---|---|---|---|---|---|
| | | | 20 | | | | | 25 | | | | | 30 | | |

| Asn | Gln | Glu | Glu | Ser | Val | Arg | Phe | Asp | Ser | Asp | Val | Gly | Glu | Phe | Arg |
|---|---|---|---|---|---|---|---|---|---|---|---|---|---|---|---|
| | | 35 | | | | | 40 | | | | | 45 | | | |

| Ala | Val | Thr | Glu | Leu | Gly | Arg | Pro | Asp | Ala | Glu | Tyr | Trp | Asn | Ser | Gln |
|---|---|---|---|---|---|---|---|---|---|---|---|---|---|---|---|
| | 50 | | | | | 55 | | | | | 60 | | | | |

| Lys | Asp | Ile | Leu | Glu | Gln | Ala | Arg | Ala | Ala | Val | Asp | Thr | Tyr | Cys | Arg |
|---|---|---|---|---|---|---|---|---|---|---|---|---|---|---|---|
| 65 | | | | | 70 | | | | | 75 | | | | | 80 |

| His | Asn | Tyr | Gly | Val | Val | Glu | Ser | Phe | Thr | Val | Gln | Arg | Arg | Val | Gln |
|---|---|---|---|---|---|---|---|---|---|---|---|---|---|---|---|
| | | | | 85 | | | | | 90 | | | | | 95 | |

Pro Lys

<210> SEQ ID NO 13
<211> LENGTH: 85
<212> TYPE: PRT
<213> ORGANISM: human

<400> SEQUENCE: 13

| Phe | Leu | Trp | Gln | Pro | Lys | Arg | Glu | Cys | His | Phe | Phe | Asn | Gly | Thr | Glu |
|---|---|---|---|---|---|---|---|---|---|---|---|---|---|---|---|
| 1 | | | | 5 | | | | | 10 | | | | | 15 | |

| Arg | Val | Arg | Phe | Leu | Asp | Arg | Tyr | Phe | Tyr | Asn | Gln | Glu | Glu | Ser | Val |
|---|---|---|---|---|---|---|---|---|---|---|---|---|---|---|---|
| | | | 20 | | | | | 25 | | | | | 30 | | |

| Arg | Phe | Asp | Ser | Asp | Val | Gly | Glu | Phe | Arg | Ala | Val | Thr | Glu | Leu | Gly |
|---|---|---|---|---|---|---|---|---|---|---|---|---|---|---|---|
| | | 35 | | | | | 40 | | | | | 45 | | | |

| Arg | Pro | Asp | Ala | Glu | Tyr | Trp | Asn | Ser | Gln | Lys | Asp | Phe | Leu | Glu | Gln |
|---|---|---|---|---|---|---|---|---|---|---|---|---|---|---|---|
| | 50 | | | | | 55 | | | | | 60 | | | | |

| Ala | Arg | Ala | Ala | Val | Asp | Thr | Tyr | Cys | Arg | His | Asn | Tyr | Gly | Val | Val |
|---|---|---|---|---|---|---|---|---|---|---|---|---|---|---|---|
| 65 | | | | | 70 | | | | | 75 | | | | | 80 |

| Glu | Ser | Phe | Thr | Val |
|---|---|---|---|---|
| | | | | 85 |

<210> SEQ ID NO 14
<211> LENGTH: 87
<212> TYPE: PRT
<213> ORGANISM: human

<400> SEQUENCE: 14

Phe Leu Trp Gln Pro Lys Arg Glu Cys His Phe Phe Asn Gly Thr Glu
1               5                   10                  15

Arg Val Arg Phe Leu Asp Arg Tyr Phe Tyr Asn Gln Glu Glu Ser Val
            20                  25                  30

Arg Phe Asp Ser Asp Val Gly Glu Phe Arg Ala Val Thr Glu Leu Gly
        35                  40                  45

Arg Pro Asp Ala Glu Tyr Trp Asn Ser Gln Lys Asp Leu Leu Glu Gln
    50                  55                  60

Ala Arg Ala Ala Val Asp Thr Tyr Cys Arg His Asn Tyr Gly Val Val
65                  70                  75                  80

Glu Ser Phe Thr Val Gln Arg
                85

<210> SEQ ID NO 15
<211> LENGTH: 79
<212> TYPE: PRT
<213> ORGANISM: human

<400> SEQUENCE: 15

Trp Gln Pro Lys Arg Glu Cys His Phe Phe Asn Gly Thr Glu Arg Val
1               5                   10                  15

Arg Phe Leu Asp Arg Tyr Phe Tyr Asn Gln Glu Glu Ser Val Arg Phe
            20                  25                  30

Asp Ser Asp Val Gly Glu Phe Arg Ala Ala Thr Glu Leu Gly Arg Pro
        35                  40                  45

Asp Ala Glu Tyr Trp Asn Ser Gln Lys Asp Ile Leu Glu Gln Ala Arg
    50                  55                  60

Ala Ala Val Asp Thr Tyr Cys Arg His Asn Tyr Gly Val Val Glu
65                  70                  75

<210> SEQ ID NO 16
<211> LENGTH: 102
<212> TYPE: PRT
<213> ORGANISM: human

<400> SEQUENCE: 16

Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Ser Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Phe Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val Gln
                85                  90                  95

Pro Lys Val Thr Val Tyr
            100

<210> SEQ ID NO 17
<211> LENGTH: 85
<212> TYPE: PRT
<213> ORGANISM: human

<400> SEQUENCE: 17

Arg Phe Leu Trp Gln Pro Lys Arg Glu Cys His Phe Phe Asn Gly Thr
1               5                   10                  15

Glu Arg Val Arg Phe Leu Asp Arg Tyr Phe Tyr Asn Gln Glu Glu Ser
            20                  25                  30

Val Arg Phe Asp Ser Asp Val Gly Glu Tyr Arg Ala Val Thr Glu Leu
        35                  40                  45

Gly Arg Pro Asp Ala Glu Tyr Trp Asn Ser Gln Lys Asp Phe Leu Glu
50                  55                  60

Asp Arg Arg Ala Ala Val Asp Thr Tyr Cys Arg His Asn Tyr Gly Val
65                  70                  75                  80

Gly Glu Ser Phe Thr
                85

<210> SEQ ID NO 18
<211> LENGTH: 102
<212> TYPE: PRT
<213> ORGANISM: human

<400> SEQUENCE: 18

Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Ser Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val Gln
                85                  90                  95

Pro Lys Val Thr Val Tyr
            100

<210> SEQ ID NO 19
<211> LENGTH: 80
<212> TYPE: PRT
<213> ORGANISM: human

<400> SEQUENCE: 19

Phe Leu Trp Gln Pro Lys Arg Glu Cys His Phe Phe Asn Gly Thr Glu
1               5                   10                  15

Arg Val Arg Phe Leu Asp Arg Tyr Phe Tyr Asn Gln Glu Glu Ser Val
            20                  25                  30

Arg Phe Asp Ser Asp Val Gly Glu Tyr Arg Ala Val Thr Glu Leu Gly
        35                  40                  45

Arg Pro Asp Ala Glu Tyr Trp Asn Ser Gln Lys Asp Leu Leu Glu Asp
    50                  55                  60

Arg Arg Ala Ala Val Asp Thr Tyr Cys Arg His Asn Tyr Gly Val Gly
65                  70                  75                  80

<210> SEQ ID NO 20
<211> LENGTH: 102
<212> TYPE: PRT
<213> ORGANISM: human

<400> SEQUENCE: 20

Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
                20                  25                  30

Asn Gln Glu Glu Ser Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
    50                  55                  60

Lys Asp Phe Leu Glu Asp Arg Ala Ala Val Asp Thr Tyr Cys Arg
65                  70                  75                  80

His Asn Tyr Gly Val Gly Glu Ser Phe Thr Val Gln Arg Arg Val Gln
                85                  90                  95

Pro Lys Val Thr Val Tyr
            100

<210> SEQ ID NO 21
<211> LENGTH: 78
<212> TYPE: PRT
<213> ORGANISM: human

<400> SEQUENCE: 21

Trp Gln Pro Lys Arg Glu Cys His Phe Phe Asn Gly Thr Glu Arg Val
1               5                   10                  15

Arg Phe Leu Asp Arg Tyr Phe Tyr Asn Gln Glu Glu Ser Val Arg Phe
                20                  25                  30

Asp Ser Asp Val Gly Glu Tyr Arg Ala Val Thr Glu Leu Gly Arg Pro
            35                  40                  45

Asp Ala Glu Tyr Trp Asn Ser Gln Lys Asp Phe Leu Glu Asp Arg Arg
    50                  55                  60

Ala Leu Val Asp Thr Tyr Cys Arg His Asn Tyr Gly Val Gly
65                  70                  75

<210> SEQ ID NO 22
<211> LENGTH: 80
<212> TYPE: PRT
<213> ORGANISM: human

<400> SEQUENCE: 22

Leu Trp Gln Pro Lys Arg Glu Cys His Phe Phe Asn Gly Thr Glu Arg
1               5                   10                  15

Val Arg Phe Leu Asp Arg Tyr Phe Tyr Asn Gln Glu Glu Ser Val Arg
                20                  25                  30

Phe Asp Ser Asp Val Gly Glu Tyr Arg Ala Val Thr Glu Leu Gly Arg
            35                  40                  45

Pro Asp Ala Glu Tyr Trp Asn Ser Gln Lys Asp Ile Leu Glu Asp Arg
    50                  55                  60

Arg Ala Ala Val Asp Thr Tyr Cys Arg His Asn Tyr Gly Val Gly Glu
65                  70                  75                  80

<210> SEQ ID NO 23
<211> LENGTH: 86
<212> TYPE: PRT
<213> ORGANISM: human

<400> SEQUENCE: 23

Arg Phe Leu Trp Gln Pro Lys Arg Glu Cys His Phe Phe Asn Gly Thr
1               5                   10                  15

```
Glu Arg Val Arg Phe Pro Asp Arg Tyr Phe Tyr Asn Gln Glu Glu Ser
            20                  25                  30

Val Arg Phe Asp Ser Asp Val Gly Glu Tyr Arg Ala Val Thr Glu Leu
        35                  40                  45

Gly Arg Pro Asp Ala Glu Tyr Trp Asn Ser Gln Lys Asp Ile Leu Glu
    50                  55                  60

Asp Arg Arg Ala Ala Val Asp Thr Tyr Cys Arg His Asn Tyr Gly Val
65                  70                  75                  80

Gly Glu Ser Phe Thr Val
                85
```

<210> SEQ ID NO 24
<211> LENGTH: 89
<212> TYPE: PRT
<213> ORGANISM: human

<400> SEQUENCE: 24

```
Arg Phe Leu Trp Gln Pro Lys Arg Glu Cys His Phe Phe Asn Gly Thr
1               5                   10                  15

Glu Arg Val Arg Phe Leu Asp Arg Tyr Phe Tyr Asn Gln Glu Glu Asn
            20                  25                  30

Val Arg Phe Asp Ser Asp Val Gly Glu Tyr Arg Ala Val Thr Glu Leu
        35                  40                  45

Gly Arg Pro Asp Ala Glu Tyr Trp Asn Ser Gln Lys Asp Phe Leu Glu
    50                  55                  60

Asp Arg Arg Ala Ala Val Asp Thr Tyr Cys Arg His Asn Tyr Gly Val
65                  70                  75                  80

Gly Glu Ser Phe Thr Val Gln Arg Arg
                85
```

<210> SEQ ID NO 25
<211> LENGTH: 102
<212> TYPE: PRT
<213> ORGANISM: human

<400> SEQUENCE: 25

```
Gly Asp Thr Arg Pro Arg Phe Leu Glu Tyr Ser Thr Ser Glu Cys His
1               5                   10                  15

Phe Phe Asn Gly Thr Glu Arg Val Arg Tyr Leu Asp Arg Tyr Phe His
            20                  25                  30

Asn Gln Glu Glu Asn Val Arg Phe Asp Ser Asp Val Gly Glu Phe Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Gly Arg Val Asp Asn Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
            100
```

<210> SEQ ID NO 26
<211> LENGTH: 87
<212> TYPE: PRT
<213> ORGANISM: human

<400> SEQUENCE: 26

```
Arg Phe Leu Glu Tyr Ser Thr Ser Glu Cys His Phe Phe Asn Gly Thr
```

```
1               5                   10                  15
Glu Arg Val Arg Tyr Leu Asp Arg Tyr Phe His Asn Gln Glu Asn
                20                  25              30
Val Arg Phe Asp Ser Asp Val Gly Phe Arg Ala Val Thr Glu Leu
            35              40                  45
Gly Arg Pro Asp Ala Glu Tyr Trp Asn Ser Gln Lys Asp Leu Leu Glu
50                      55                  60
Gln Lys Arg Gly Arg Val Asp Asn Tyr Cys Arg His Asn Tyr Gly Val
65                  70                  75                  80
Val Glu Ser Phe Thr Val Gln
                85

<210> SEQ ID NO 27
<211> LENGTH: 102
<212> TYPE: PRT
<213> ORGANISM: human

<400> SEQUENCE: 27

Gly Asp Thr Arg Pro Arg Phe Leu Glu Tyr Ser Thr Ser Glu Cys His
1               5                   10                  15
Phe Phe Asn Gly Thr Glu Arg Val Arg Phe Leu Glu Arg Tyr Phe His
                20                  25              30
Asn Gln Glu Glu Asn Val Arg Phe Asp Ser Asp Val Gly Glu Tyr Arg
            35                  40                  45
Ala Val Thr Glu Leu Gly Arg Pro Asp Ala Glu Tyr Trp Asn Ser Gln
        50                  55                  60
Lys Asp Leu Leu Glu Gln Lys Arg Gly Arg Val Asp Asn Tyr Cys Arg
65                  70                  75                  80
His Asn Tyr Gly Val Gly Glu Ser Phe Thr Val Gln Arg Arg Val His
                85                  90                  95
Pro Lys Val Thr Val Tyr
            100

<210> SEQ ID NO 28
<211> LENGTH: 100
<212> TYPE: PRT
<213> ORGANISM: human

<400> SEQUENCE: 28

Gly Asp Thr Arg Pro Arg Phe Leu Glu Tyr Ser Thr Ser Glu Cys His
1               5                   10                  15
Phe Phe Asn Gly Thr Glu Arg Val Arg Phe Leu Glu Arg Tyr Phe His
                20                  25              30
Asn Gln Glu Glu Asn Val Arg Phe Asp Ser Asp Val Gly Glu Tyr Arg
            35                  40                  45
Ala Val Thr Glu Leu Gly Arg Pro Asp Ala Glu Tyr Trp Asn Ser Gln
        50                  55                  60
Lys Asp Leu Leu Glu Gln Lys Arg Gly Arg Val Asp Asn Tyr Cys Arg
65                  70                  75                  80
His Asn Tyr Gly Val Gly Glu Ser Phe Thr Val Gln Arg Arg Val His
                85                  90                  95
Pro Lys Val Thr
            100

<210> SEQ ID NO 29
<211> LENGTH: 85
<212> TYPE: PRT
```

```
<213> ORGANISM: human

<400> SEQUENCE: 29

Tyr Ser Thr Ser Glu Cys His Phe Phe Asn Gly Thr Glu Arg Val Arg
1               5                   10                  15

Phe Leu Glu Arg Tyr Phe His Asn Gln Glu Glu Asn Val Arg Phe Asp
                20                  25                  30

Ser Asp Val Gly Glu Tyr Arg Ala Val Thr Glu Leu Gly Arg Pro Asp
            35                  40                  45

Ala Glu Tyr Trp Asn Ser Gln Lys Asp Leu Leu Glu Gln Lys Arg Gly
        50                  55                  60

Arg Val Asp Asn Tyr Cys Arg His Asn Tyr Gly Val Val Glu Ser Phe
65                  70                  75                  80

Thr Val Gln Arg Arg
                85

<210> SEQ ID NO 30
<211> LENGTH: 80
<212> TYPE: PRT
<213> ORGANISM: human

<400> SEQUENCE: 30

Leu Glu Tyr Ser Thr Ser Glu Cys His Phe Phe Asn Gly Thr Glu Arg
1               5                   10                  15

Val Arg Tyr Leu Asp Arg Tyr Phe His Asn Gln Glu Glu Ser Val Arg
                20                  25                  30

Phe Asp Ser Asp Val Gly Glu Phe Arg Ala Val Thr Glu Leu Gly Arg
            35                  40                  45

Pro Asp Ala Glu Tyr Trp Asn Ser Gln Lys Asp Leu Leu Glu Gln Lys
        50                  55                  60

Arg Gly Arg Val Asp Asn Tyr Cys Arg His Asn Tyr Gly Val Val Glu
65                  70                  75                  80

<210> SEQ ID NO 31
<211> LENGTH: 89
<212> TYPE: PRT
<213> ORGANISM: human

<400> SEQUENCE: 31

Arg Phe Leu Glu Tyr Ser Thr Ser Glu Cys His Phe Phe Asn Gly Thr
1               5                   10                  15

Glu Arg Val Arg Tyr Leu Asp Arg Tyr Phe His Asn Gln Glu Glu Asn
                20                  25                  30

Val Arg Phe Asp Ser Asp Val Gly Glu Phe Arg Ala Val Thr Glu Leu
            35                  40                  45

Gly Arg Pro Asp Ala Glu Tyr Trp Asn Ser Gln Lys Asp Leu Leu Glu
        50                  55                  60

Gln Lys Arg Gly Arg Val Asp Asn Tyr Cys Arg His Asn Tyr Gly Val
65                  70                  75                  80

Gly Glu Ser Phe Thr Val Gln Arg Arg
                85

<210> SEQ ID NO 32
<211> LENGTH: 86
<212> TYPE: PRT
<213> ORGANISM: human

<400> SEQUENCE: 32
```

Phe Leu Glu Tyr Ser Thr Ser Glu Cys His Phe Phe Asn Gly Thr Glu
1               5                   10                  15

Arg Val Arg Tyr Leu Asp Arg Tyr Phe His Asn Gln Glu Glu Asn Val
            20                  25                  30

Arg Phe Asp Ser Asp Val Gly Glu Tyr Arg Ala Val Thr Glu Leu Gly
            35                  40                  45

Arg Pro Asp Ala Glu Tyr Trp Asn Ser Gln Lys Asp Leu Leu Glu Gln
        50                  55                  60

Lys Arg Gly Arg Val Asp Asn Tyr Cys Arg His Asn Tyr Gly Val Val
65                  70                  75                  80

Glu Ser Phe Thr Val Gln
                85

<210> SEQ ID NO 33
<211> LENGTH: 102
<212> TYPE: PRT
<213> ORGANISM: human

<400> SEQUENCE: 33

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe His
            20                  25                  30

Asn Gln Glu Glu Asn Val Arg Phe Asp Ser Asp Val Gly Glu Phe Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Gly Arg Val Asp Asn Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
                100

<210> SEQ ID NO 34
<211> LENGTH: 102
<212> TYPE: PRT
<213> ORGANISM: human

<400> SEQUENCE: 34

Gly Asp Thr Arg Pro Arg Phe Leu Glu Tyr Ser Thr Ser Glu Cys His
1               5                   10                  15

Phe Phe Asn Gly Thr Glu Arg Val Arg Tyr Leu Asp Arg Tyr Phe His
            20                  25                  30

Asn Gln Glu Glu Asn Val Arg Phe Asp Ser Asp Val Gly Glu Phe Arg
        35                  40                  45

Ala Val Thr Glu Leu Gly Arg Pro Asp Glu Tyr Trp Asn Ser Gln
    50                  55                  60

Lys Asp Leu Leu Glu Gln Lys Arg Gly Arg Val Asp Asn Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
                100

<210> SEQ ID NO 35
<211> LENGTH: 86

```
<212> TYPE: PRT
<213> ORGANISM: human

<400> SEQUENCE: 35

Leu Glu Tyr Ser Thr Ser Glu Cys His Phe Phe Asn Gly Thr Glu Arg
1               5                   10                  15

Val Arg Tyr Leu Asp Arg Tyr Phe His Asn Arg Glu Glu Asn Val Arg
                20                  25                  30

Phe Asp Ser Asp Val Gly Glu Phe Arg Ala Val Thr Glu Leu Gly Arg
            35                  40                  45

Pro Asp Ala Glu Tyr Trp Asn Ser Gln Lys Asp Leu Leu Glu Gln Lys
        50                  55                  60

Arg Gly Arg Val Asp Asn Tyr Cys Arg His Asn Tyr Gly Val Gly Glu
65                  70                  75                  80

Ser Phe Thr Val Gln Arg
                85

<210> SEQ ID NO 36
<211> LENGTH: 102
<212> TYPE: PRT
<213> ORGANISM: human

<400> SEQUENCE: 36

Gly Asp Thr Arg Pro Arg Phe Leu Glu Tyr Ser Thr Ser Glu Cys His
1               5                   10                  15

Phe Phe Asn Gly Thr Glu Arg Val Arg Tyr Leu Asp Arg Tyr Phe His
                20                  25                  30

Asn Gln Glu Glu Asn Val Arg Phe Asp Ser Asp Val Gly Glu Phe Arg
            35                  40                  45

Ala Val Thr Glu Leu Gly Arg Pro Ala Ala Glu His Trp Asn Ser Gln
        50                  55                  60

Lys Asp Leu Leu Glu Gln Lys Arg Gly Arg Val Asp Asn Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
                100

<210> SEQ ID NO 37
<211> LENGTH: 89
<212> TYPE: PRT
<213> ORGANISM: human

<400> SEQUENCE: 37

Arg Phe Leu Glu Tyr Ser Thr Ser Glu Cys His Phe Phe Asn Gly Thr
1               5                   10                  15

Glu Arg Val Arg Tyr Leu Asp Arg Tyr Phe His Asn Gln Glu Glu Asn
                20                  25                  30

Val Arg Phe Asp Ser Asp Val Gly Glu Phe Arg Ala Val Thr Glu Leu
            35                  40                  45

Gly Arg Pro Asp Ala Glu Tyr Trp Asn Ser Gln Lys Asp Leu Leu Glu
        50                  55                  60

Gln Lys Arg Gly Gln Val Asp Asn Tyr Cys Arg His Asn Tyr Gly Val
65                  70                  75                  80

Val Glu Ser Phe Thr Val Gln Arg Arg
                85
```

-continued

```
<210> SEQ ID NO 38
<211> LENGTH: 102
<212> TYPE: PRT
<213> ORGANISM: human

<400> SEQUENCE: 38

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
                20                  25                  30

His Gln Glu Glu Tyr Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr Val Gln Arg Val
                85                  90                  95

Pro Glu Val Thr Val Tyr
            100

<210> SEQ ID NO 39
<211> LENGTH: 89
<212> TYPE: PRT
<213> ORGANISM: human

<400> SEQUENCE: 39

Arg Phe Leu Glu Gln Val Lys His Glu Cys His Phe Phe Asn Gly Thr
1               5                   10                  15

Glu Arg Val Arg Phe Leu Asp Arg Tyr Phe Tyr His Gln Glu Glu Tyr
                20                  25                  30

Val Arg Phe Asp Ser Asp Val Gly Glu Tyr Arg Ala Val Thr Glu Leu
            35                  40                  45

Gly Arg Pro Asp Ala Glu Tyr Trp Asn Ser Gln Lys Asp Leu Leu Glu
        50                  55                  60

Gln Lys Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 40
<211> LENGTH: 94
<212> TYPE: PRT
<213> ORGANISM: human

<400> SEQUENCE: 40

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
                20                  25                  30

His Gln Glu Glu Tyr Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Ile Leu Glu Asp Glu Arg Ala Ala Val Asp Thr Tyr Cys Arg
65                  70                  75                  80

His Asn Tyr Gly Val Val Glu Ser Phe Thr Val Gln Arg Arg
                85                  90
```

```
<210> SEQ ID NO 41
<211> LENGTH: 102
<212> TYPE: PRT
<213> ORGANISM: human

<400> SEQUENCE: 41

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Arg Arg Ala Glu Val Asp Thr Tyr Cys Arg
65                  70                  75                  80

His Asn Tyr Gly Val Val Glu Ser Phe Thr Val Gln Arg Arg Val Tyr
                85                  90                  95

Pro Glu Val Thr Val Tyr
            100

<210> SEQ ID NO 42
<211> LENGTH: 102
<212> TYPE: PRT
<213> ORGANISM: human

<400> SEQUENCE: 42

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Arg Arg Ala Ala Val Asp Thr Tyr Cys Arg
65                  70                  75                  80

His Asn Tyr Gly Val Val Glu Ser Phe Thr Val Gln Arg Arg Val Tyr
                85                  90                  95

Pro Glu Val Thr Val Tyr
            100

<210> SEQ ID NO 43
<211> LENGTH: 94
<212> TYPE: PRT
<213> ORGANISM: human

<400> SEQUENCE: 43

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Ser Ala Glu Tyr Trp Asn Ser Gln
    50                  55                  60
```

```
Lys Asp Leu Leu Glu Gln Arg Arg Ala Val Asp Thr Tyr Cys Arg
65                  70                  75                  80

His Asn Tyr Gly Val Gly Glu Ser Phe Thr Val Gln Arg Arg
                85                  90
```

<210> SEQ ID NO 44
<211> LENGTH: 88
<212> TYPE: PRT
<213> ORGANISM: human

<400> SEQUENCE: 44

```
Phe Leu Glu Gln Val Lys His Glu Cys His Phe Phe Asn Gly Thr Glu
1               5                   10                  15

Arg Val Arg Phe Leu Asp Arg Tyr Phe Tyr His Gln Glu Glu Tyr Val
                20                  25                  30

Arg Phe Asp Ser Asp Val Gly Glu Tyr Arg Ala Val Thr Glu Leu Gly
            35                  40                  45

Arg Pro Ser Ala Glu Tyr Trp Asn Ser Gln Lys Asp Leu Leu Glu Gln
        50                  55                  60

Arg Arg Ala Ala Val Asp Thr Tyr Cys Arg His Asn Tyr Gly Val Gly
65                  70                  75                  80

Glu Ser Phe Thr Val Gln Arg Arg
                85
```

<210> SEQ ID NO 45
<211> LENGTH: 102
<212> TYPE: PRT
<213> ORGANISM: human

<400> SEQUENCE: 45

```
Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
                20                  25                  30

His Gln Glu Glu Ser Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Leu Leu Glu Gln Arg Arg Ala Glu Val Asp Thr Tyr Cys Arg
65                  70                  75                  80

His Asn Tyr Gly Val Val Glu Ser Phe Thr Val Gln Arg Arg Val Tyr
                85                  90                  95

Pro Glu Val Thr Val Tyr
            100
```

<210> SEQ ID NO 46
<211> LENGTH: 94
<212> TYPE: PRT
<213> ORGANISM: human

<400> SEQUENCE: 46

```
Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
                20                  25                  30

His Gln Glu Glu Tyr Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
```

```
            50                  55                  60
Lys Asp Leu Leu Glu Gln Arg Arg Ala Glu Val Asp Thr Tyr Cys Arg
 65                  70                  75                  80

His Asn Tyr Gly Val Gly Glu Ser Phe Thr Val Gln Arg Arg
                 85                  90
```

<210> SEQ ID NO 47
<211> LENGTH: 88
<212> TYPE: PRT
<213> ORGANISM: human

<400> SEQUENCE: 47

```
Phe Leu Glu Gln Val Lys His Glu Cys His Phe Phe Asn Gly Thr Glu
 1               5                  10                  15

Arg Val Arg Phe Leu Asp Arg Tyr Phe Tyr His Gln Glu Glu Tyr Val
                20                  25                  30

Arg Phe Asp Ser Asp Val Gly Glu Tyr Arg Ala Val Thr Glu Leu Gly
             35                  40                  45

Arg Pro Asp Ala Glu Tyr Trp Asn Ser Gln Lys Asp Leu Leu Glu Gln
         50                  55                  60

Arg Arg Ala Ala Val Asp Thr Tyr Cys Arg His Asn Tyr Gly Val Gly
 65                  70                  75                  80

Glu Ser Phe Thr Val Gln Arg Arg
                 85
```

<210> SEQ ID NO 48
<211> LENGTH: 74
<212> TYPE: PRT
<213> ORGANISM: human

<400> SEQUENCE: 48

```
Glu Cys His Phe Phe Asn Gly Thr Glu Arg Val Arg Phe Leu Asp Arg
 1               5                  10                  15

Tyr Phe Tyr His Gln Glu Glu Tyr Val Arg Phe Asp Ser Asp Val Gly
                20                  25                  30

Glu Tyr Arg Ala Val Thr Glu Leu Gly Arg Pro Ser Ala Glu Tyr Trp
             35                  40                  45

Asn Ser Gln Lys Asp Leu Leu Glu Gln Lys Arg Ala Ala Val Asp Thr
         50                  55                  60

Tyr Cys Arg His Asn Tyr Gly Val Gly Glu
 65                  70
```

<210> SEQ ID NO 49
<211> LENGTH: 84
<212> TYPE: PRT
<213> ORGANISM: human

<400> SEQUENCE: 49

```
Phe Leu Glu Gln Val Lys His Glu Cys His Phe Phe Asn Gly Thr Glu
 1               5                  10                  15

Arg Val Arg Phe Leu Asp Arg Tyr Phe Tyr His Gln Glu Glu Tyr Val
                20                  25                  30

Arg Phe Asp Ser Asp Val Gly Glu Tyr Arg Ala Val Thr Glu Leu Gly
             35                  40                  45

Arg Pro Ser Ala Glu Tyr Trp Asn Ser Gln Lys Asp Leu Leu Glu Gln
         50                  55                  60

Arg Arg Ala Ala Val Asp Thr Tyr Cys Arg His Asn Tyr Gly Val Val
 65                  70                  75                  80
```

Glu Ser Phe Thr

<210> SEQ ID NO 50
<211> LENGTH: 102
<212> TYPE: PRT
<213> ORGANISM: human

<400> SEQUENCE: 50

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Ser Ala Glu Tyr Trp Asn Ser Gln
    50                  55                  60

Lys Asp Leu Leu Glu Gln Arg Arg Ala Glu Val Asp Thr Tyr Cys Arg
65                  70                  75                  80

His Asn Tyr Gly Val Val Glu Ser Phe Thr Val Gln Arg Arg Val Tyr
                85                  90                  95

Pro Glu Val Thr Val Tyr
            100

<210> SEQ ID NO 51
<211> LENGTH: 87
<212> TYPE: PRT
<213> ORGANISM: human

<400> SEQUENCE: 51

Phe Leu Glu Gln Val Lys His Glu Cys His Phe Phe Asn Gly Thr Glu
1               5                   10                  15

Arg Val Arg Phe Leu Asp Arg Tyr Phe Tyr His Gln Glu Glu Tyr Val
            20                  25                  30

Arg Phe Asp Ser Asp Val Gly Tyr Arg Ala Val Thr Glu Leu Gly
        35                  40                  45

Arg Pro Ser Ala Glu Tyr Trp Asn Ser Gln Lys Asp Ile Leu Glu Asp
    50                  55                  60

Arg Arg Ala Leu Val Asp Thr Tyr Cys Arg His Asn Tyr Gly Val Val
65                  70                  75                  80

Glu Ser Phe Thr Val Gln Arg
                85

<210> SEQ ID NO 52
<211> LENGTH: 78
<212> TYPE: PRT
<213> ORGANISM: human

<400> SEQUENCE: 52

His Glu Cys His Phe Phe Asn Gly Thr Glu Arg Val Arg Phe Leu Asp
1               5                   10                  15

Arg Tyr Phe Tyr His Gln Glu Glu Tyr Val Arg Phe Asp Ser Asp Val
            20                  25                  30

Gly Glu Tyr Arg Ala Val Thr Glu Leu Gly Arg Pro Asp Ala Glu Tyr
        35                  40                  45

Trp Asn Ser Gln Lys Asp Leu Leu Glu Gln Lys Arg Ala Ala Val Asp
    50                  55                  60

Thr Tyr Cys Arg His Asn Tyr Gly Val Val Glu Ser Phe Thr 65                     70                    75

<210> SEQ ID NO 53
<211> LENGTH: 74
<212> TYPE: PRT
<213> ORGANISM: human

<400> SEQUENCE: 53

Glu Cys His Phe Phe Asn Gly Thr Glu Arg Val Arg Phe Leu Asp Arg
1               5                   10                  15

Tyr Phe Tyr His Gln Glu Glu Tyr Val Arg Phe Asp Ser Asp Val Gly
            20                  25                  30

Glu Tyr Arg Ala Val Thr Glu Leu Gly Arg Pro Asp Ala Glu Tyr Trp
        35                  40                  45

Asn Ser Gln Lys Asp Ile Leu Glu Asp Glu Arg Ala Ala Val Asp Thr
    50                  55                  60

Tyr Cys Arg His Asn Tyr Gly Val Gly Glu
65                  70

<210> SEQ ID NO 54
<211> LENGTH: 82
<212> TYPE: PRT
<213> ORGANISM: human

<400> SEQUENCE: 54

Arg Phe Leu Glu Gln Val Lys His Glu Cys His Phe Phe Asn Gly Thr
1               5                   10                  15

Glu Arg Val Arg Phe Leu Asp Arg Tyr Phe Tyr His Gln Glu Glu Tyr
            20                  25                  30

Val Arg Phe Asp Ser Asp Val Gly Glu Tyr Arg Ala Val Thr Glu Leu
        35                  40                  45

Gly Arg Pro Asp Glu Glu Tyr Trp Asn Ser Gln Lys Asp Phe Leu Glu
    50                  55                  60

Asp Arg Arg Ala Ala Val Asp Thr Tyr Cys Arg His Asn Tyr Gly Val
65                  70                  75                  80

Val Glu

<210> SEQ ID NO 55
<211> LENGTH: 73
<212> TYPE: PRT
<213> ORGANISM: human

<400> SEQUENCE: 55

Glu Cys His Phe Phe Asn Gly Thr Glu Arg Val Arg Phe Leu Asp Arg
1               5                   10                  15

Tyr Phe Tyr His Gln Glu Glu Tyr Val Arg Phe Asp Ser Asp Val Gly
            20                  25                  30

Glu Tyr Arg Ala Val Thr Glu Leu Gly Arg Pro Asp Ala Gln Tyr Trp
        35                  40                  45

Asn Ser Gln Lys Asp Leu Leu Glu Gln Lys Arg Ala Ala Val Asp Thr
    50                  55                  60

Tyr Cys Arg His Asn Tyr Gly Val Gly
65                  70

<210> SEQ ID NO 56
<211> LENGTH: 73
<212> TYPE: PRT
<213> ORGANISM: human

-continued

```
<400> SEQUENCE: 56

Glu Cys His Phe Phe Asn Gly Thr Glu Arg Val Arg Phe Leu Asp Arg
1               5                   10                  15

Tyr Phe Tyr His Gln Glu Glu Tyr Val Arg Phe Asp Ser Asp Val Gly
            20                  25                  30

Glu Tyr Arg Ala Val Thr Glu Leu Gly Arg Pro Ser Ala Glu Tyr Trp
        35                  40                  45

Asn Ser Gln Lys Asp Leu Leu Glu Gln Arg Arg Ala Glu Val Asp Thr
    50                  55                  60

Tyr Cys Arg His Asn Tyr Gly Val Gly
65                  70

<210> SEQ ID NO 57
<211> LENGTH: 78
<212> TYPE: PRT
<213> ORGANISM: human

<400> SEQUENCE: 57

Glu Cys His Phe Phe Asn Gly Thr Glu Arg Val Arg Phe Leu Asp Arg
1               5                   10                  15

Tyr Phe Tyr His Gln Glu Glu Tyr Val Arg Phe Asp Ser Asp Val Gly
            20                  25                  30

Glu Tyr Arg Ala Val Thr Glu Leu Gly Arg Pro Asp Ala Glu Tyr Trp
        35                  40                  45

Asn Ser Gln Lys Asp Ile Leu Glu Asp Arg Arg Ala Leu Val Asp Thr
    50                  55                  60

Tyr Cys Arg His Asn Tyr Gly Val Val Glu Ser Phe Thr Val
65                  70                  75

<210> SEQ ID NO 58
<211> LENGTH: 79
<212> TYPE: PRT
<213> ORGANISM: human

<400> SEQUENCE: 58

His Glu Cys His Phe Phe Asn Gly Thr Glu Arg Val Arg Phe Leu Asp
1               5                   10                  15

Arg Tyr Phe Tyr His Gln Glu Glu Ser Val Arg Phe Asp Ser Asp Val
            20                  25                  30

Gly Glu Tyr Arg Ala Val Thr Glu Leu Gly Arg Pro Asp Ala Glu Tyr
        35                  40                  45

Trp Asn Ser Gln Lys Asp Leu Leu Glu Gln Arg Arg Ala Ala Val Asp
    50                  55                  60

Thr Tyr Cys Arg His Asn Tyr Gly Val Gly Glu Ser Phe Thr Val
65                  70                  75

<210> SEQ ID NO 59
<211> LENGTH: 73
<212> TYPE: PRT
<213> ORGANISM: human

<400> SEQUENCE: 59

Glu Cys His Phe Phe Asn Gly Thr Glu Arg Val Arg Phe Leu Asp Arg
1               5                   10                  15

Tyr Phe Tyr His Gln Glu Glu Ser Val Arg Phe Asp Ser Asp Val Gly
            20                  25                  30

Glu Tyr Arg Ala Val Thr Glu Leu Gly Arg Pro Asp Ala Glu Tyr Trp
        35                  40                  45
```

-continued

Asn Ser Gln Lys Asp Leu Leu Glu Gln Arg Arg Ala Glu Val Asp Thr
        50                  55                  60

Tyr Cys Arg His Asn Tyr Gly Val Gly
65                  70

<210> SEQ ID NO 60
<211> LENGTH: 83
<212> TYPE: PRT
<213> ORGANISM: human

<400> SEQUENCE: 60

Glu Gln Val Lys His Glu Cys His Phe Phe Asn Gly Thr Glu Arg Val
1               5                   10                  15

Arg Phe Leu Asp Arg Tyr Phe Tyr His Gln Glu Ser Val Arg Phe
            20                  25                  30

Asp Ser Asp Val Gly Glu Tyr Arg Ala Val Thr Glu Leu Gly Arg Pro
            35                  40                  45

Asp Ala Glu Tyr Trp Asn Ser Gln Lys Asp Leu Leu Glu Gln Lys Arg
        50                  55                  60

Ala Ala Val Asp Thr Tyr Cys Arg His Asn Tyr Gly Val Gly Glu Ser
65                  70                  75                  80

Phe Thr Val

<210> SEQ ID NO 61
<211> LENGTH: 82
<212> TYPE: PRT
<213> ORGANISM: human

<400> SEQUENCE: 61

Glu Gln Val Lys His Glu Cys His Phe Phe Asn Gly Thr Glu Arg Val
1               5                   10                  15

Arg Phe Leu Asp Arg Tyr Phe Tyr His Gln Glu Glu Tyr Val Arg Phe
            20                  25                  30

Asp Ser Asp Val Gly Glu Tyr Arg Ala Val Thr Glu Leu Gly Arg Pro
            35                  40                  45

Asp Ala Glu Tyr Trp Asn Ser Gln Lys Asp Leu Leu Glu Gln Lys Arg
        50                  55                  60

Gly Arg Val Asp Asn Tyr Cys Arg His Asn Tyr Gly Val Val Glu Ser
65                  70                  75                  80

Phe Thr

<210> SEQ ID NO 62
<211> LENGTH: 89
<212> TYPE: PRT
<213> ORGANISM: human

<400> SEQUENCE: 62

Arg Phe Leu Glu Gln Val Lys His Glu Cys His Phe Phe Asn Gly Thr
1               5                   10                  15

Glu Arg Val Arg Phe Leu Asp Arg Tyr Phe Tyr His Gln Glu Glu Tyr
            20                  25                  30

Val Arg Phe Asp Ser Asp Val Gly Glu Tyr Arg Ala Val Thr Glu Leu
            35                  40                  45

Gly Arg Pro Asp Ala Glu Tyr Trp Asn Ser Gln Lys Asp Leu Leu Glu
        50                  55                  60

Gln Arg Arg Ala Ala Val Asp Thr Tyr Cys Arg His Asn Tyr Gly Val
65                  70                  75                  80

-continued

Val Glu Arg Phe Thr Val Gln Arg Arg
                85

<210> SEQ ID NO 63
<211> LENGTH: 89
<212> TYPE: PRT
<213> ORGANISM: human

<400> SEQUENCE: 63

Arg Phe Leu Glu Gln Val Lys His Glu Cys His Phe Phe Asn Gly Thr
1               5                   10                  15

Glu Arg Val Arg Phe Leu Asp Arg Tyr Phe Tyr His Gln Glu Glu Tyr
            20                  25                  30

Val Arg Phe Asp Ser Asp Val Gly Glu Tyr Arg Ala Val Thr Glu Leu
        35                  40                  45

Gly Arg Pro Ser Ala Glu Tyr Trp Asn Ser Gln Lys Asp Leu Leu Glu
    50                  55                  60

Arg Arg Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 64
<211> LENGTH: 80
<212> TYPE: PRT
<213> ORGANISM: human

<400> SEQUENCE: 64

Leu Glu Gln Val Lys His Glu Cys His Phe Phe Asn Gly Thr Glu Arg
1               5                   10                  15

Val Arg Phe Leu Asp Arg Tyr Phe Tyr His Gln Glu Glu Tyr Val Arg
            20                  25                  30

Phe Asp Ser Asp Val Gly Glu Tyr Arg Ala Val Thr Glu Leu Gly Arg
        35                  40                  45

Pro Asp Ala Glu Tyr Trp Asn Ser Gln Lys Asp Phe Leu Glu Asp Arg
    50                  55                  60

Arg Ala Leu Val Asp Thr Tyr Cys Arg His Asn Tyr Gly Val Val Glu
65                  70                  75                  80

<210> SEQ ID NO 65
<211> LENGTH: 81
<212> TYPE: PRT
<213> ORGANISM: human

<400> SEQUENCE: 65

Arg Phe Leu Glu Gln Val Lys His Glu Cys His Phe Phe Asn Gly Thr
1               5                   10                  15

Glu Arg Val Arg Phe Leu Asp Arg Tyr Phe Tyr His Gln Glu Glu Tyr
            20                  25                  30

Val Arg Phe Asp Ser Asp Val Gly Glu Tyr Arg Ala Val Thr Glu Leu
        35                  40                  45

Gly Arg Pro Asp Thr Glu Tyr Trp Asn Ser Gln Lys Asp Leu Leu Glu
    50                  55                  60

Gln Lys Arg Ala Ala Val Asp Thr Tyr Cys Arg His Asn Tyr Gly Val
65                  70                  75                  80

Gly

```
<210> SEQ ID NO 66
<211> LENGTH: 86
<212> TYPE: PRT
<213> ORGANISM: human

<400> SEQUENCE: 66

Arg Phe Leu Glu Gln Val Lys His Glu Cys His Phe Asn Gly Thr
1               5                   10                  15

Glu Arg Val Arg Phe Leu Asp Arg Tyr Phe Tyr His Gln Glu Glu Tyr
            20                  25                  30

Val Arg Phe Asp Ser Asp Val Gly Glu Tyr Arg Ala Val Thr Glu Leu
        35                  40                  45

Gly Arg Pro Asp Ala Glu Tyr Trp Asn Ser Gln Lys Asp Leu Leu Glu
    50                  55                  60

Gln Arg Arg Ala Glu Val Asp Thr Tyr Cys Arg His Asn Tyr Gly Ala
65                  70                  75                  80

Val Glu Ser Phe Thr Val
                85

<210> SEQ ID NO 67
<211> LENGTH: 102
<212> TYPE: PRT
<213> ORGANISM: human

<400> SEQUENCE: 67

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Asp Glu Glu Tyr Trp Asn Ser Gln
    50                  55                  60

Lys Asp Phe Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val His
                85                  90                  95

Pro Lys Val Thr Val Tyr
            100

<210> SEQ ID NO 68
<211> LENGTH: 101
<212> TYPE: PRT
<213> ORGANISM: human

<400> SEQUENCE: 68

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Asp Glu Glu Tyr Trp Asn Ser Gln
    50                  55                  60

Lys Asp Phe Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val His
                85                  90                  95
```

```
Pro Lys Val Thr Val
            100

<210> SEQ ID NO 69
<211> LENGTH: 89
<212> TYPE: PRT
<213> ORGANISM: human

<400> SEQUENCE: 69

Arg Phe Leu Glu Tyr Ser Thr Ser Glu Cys His Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Phe Arg Ala Val Thr Glu Leu
        35                  40                  45

Gly Arg Pro Asp Glu Glu Tyr Trp Asn Ser Gln Lys Asp Phe Leu Glu
50                  55                  60

Asp Arg Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 70
<211> LENGTH: 102
<212> TYPE: PRT
<213> ORGANISM: human

<400> SEQUENCE: 70

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Asp Glu Glu Tyr Trp Asn Ser Gln
    50                  55                  60

Lys Asp Ile Leu Glu Asp Glu Arg Ala Ala Val Asp Thr Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
            100

<210> SEQ ID NO 71
<211> LENGTH: 102
<212> TYPE: PRT
<213> ORGANISM: human

<400> SEQUENCE: 71

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Asp Glu Glu Tyr Trp Asn Ser Gln
    50                  55                  60
```

Lys Asp Phe Leu Glu Asp Glu Arg Ala Ala Val Asp Thr Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
            100

<210> SEQ ID NO 72
<211> LENGTH: 94
<212> TYPE: PRT
<213> ORGANISM: human

<400> SEQUENCE: 72

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
                20                  25                  30

Asn Gln Glu Glu Tyr Val Arg Phe Asp Ser Asp Val Gly Glu Phe Arg
            35                  40                  45

Ala Val Thr Glu Leu Gly Arg Pro Asp Glu Glu Tyr Trp Asn Ser Gln
        50                  55                  60

Lys Asp Phe Leu Glu Asp Arg Arg Ala Ala Val Asp Thr Tyr Cys Arg
65                  70                  75                  80

His Asn Tyr Gly Val Val Glu Ser Phe Thr Val Gln Arg Arg
                85                  90

<210> SEQ ID NO 73
<211> LENGTH: 102
<212> TYPE: PRT
<213> ORGANISM: human

<400> SEQUENCE: 73

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
                20                  25                  30

Asn Gln Glu Glu Tyr Val Arg Phe Asp Ser Asp Val Gly Glu Phe Arg
            35                  40                  45

Ala Val Thr Glu Leu Gly Arg Pro Asp Glu Glu Tyr Trp Asn Ser Gln
        50                  55                  60

Lys Asp Phe Leu Glu Asp Arg Arg Ala Ala Val Asp Thr Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
            100

<210> SEQ ID NO 74
<211> LENGTH: 90
<212> TYPE: PRT
<213> ORGANISM: human

<400> SEQUENCE: 74

Pro Arg Phe Leu Glu Tyr Ser Thr Gly Glu Cys His Phe Phe Asn Gly
1               5                   10                  15

Thr Glu Arg Val Arg Phe Leu Asp Arg Tyr Phe Tyr Asn Gln Glu Glu
                20                  25                  30

Tyr Val Arg Phe Asp Ser Asp Val Gly Glu Phe Arg Ala Val Thr Glu

-continued

```
                35                  40                  45
Leu Gly Arg Pro Asp Glu Glu Tyr Trp Asn Ser Gln Lys Asp Phe Leu
            50                  55                  60
Glu Asp Arg Arg Ala Ala Val Asp Thr Tyr Cys Arg His Asn Tyr Gly
 65                  70                  75                  80
Val Gly Glu Ser Phe Thr Val Gln Arg Arg
                 85                  90

<210> SEQ ID NO 75
<211> LENGTH: 85
<212> TYPE: PRT
<213> ORGANISM: human

<400> SEQUENCE: 75

Arg Phe Leu Glu Tyr Ser Thr Ser Glu Cys His Phe Phe Asn Gly Thr
 1               5                  10                  15
Glu Arg Val Arg Phe Leu Asp Arg Tyr Phe Tyr Asn Gln Glu Glu Tyr
                20                  25                  30
Val Arg Phe Asp Ser Asp Val Gly Glu Phe Arg Ala Val Thr Glu Leu
            35                  40                  45
Gly Arg Pro Asp Glu Glu Tyr Trp Asn Ser Gln Lys Asp Phe Leu Glu
        50                  55                  60
Asp Arg Arg Ala Ala Val Asp Thr Tyr Cys Arg His Asn Tyr Gly Ala
 65                  70                  75                  80
Val Glu Ser Phe Thr
                 85

<210> SEQ ID NO 76
<211> LENGTH: 87
<212> TYPE: PRT
<213> ORGANISM: human

<400> SEQUENCE: 76

Leu Glu Tyr Ser Thr Ser Glu Cys His Phe Phe Asn Gly Thr Glu Arg
 1               5                  10                  15
Val Arg Phe Leu Asp Arg Tyr Phe Tyr Asn Gln Glu Glu Tyr Val Arg
                20                  25                  30
Phe Asp Ser Asp Val Gly Glu Phe Arg Ala Val Thr Glu Leu Gly Arg
            35                  40                  45
Pro Asp Glu Glu Tyr Trp Asn Ser Gln Lys Asp Leu Leu Glu Gln Lys
        50                  55                  60
Arg Gly Arg Val Asp Asn Tyr Cys Arg His Asn Tyr Gly Val Val Glu
 65                  70                  75                  80
Ser Phe Thr Val Gln Arg Arg
                 85

<210> SEQ ID NO 77
<211> LENGTH: 79
<212> TYPE: PRT
<213> ORGANISM: human

<400> SEQUENCE: 77

Ser Glu Cys His Phe Phe Asn Gly Thr Glu Arg Val Arg Phe Leu Asp
 1               5                  10                  15
Arg Tyr Phe Tyr Asn Gln Glu Glu Tyr Val Arg Phe Asp Ser Asp Val
                20                  25                  30
Gly Glu Phe Arg Ala Val Thr Glu Leu Gly Arg Pro Asp Glu Glu Tyr
            35                  40                  45
```

```
Trp Asn Ser Gln Lys Asp Leu Leu Glu Asp Arg Arg Ala Ala Val Asp
    50                  55                  60

Thr Tyr Cys Arg His Asn Tyr Gly Val Gly Glu Ser Phe Thr Val
65                  70                  75
```

<210> SEQ ID NO 78
<211> LENGTH: 79
<212> TYPE: PRT
<213> ORGANISM: human

<400> SEQUENCE: 78

```
Ser Glu Cys His Phe Phe Asn Gly Thr Glu Arg Val Arg Phe Leu Asp
1               5                   10                  15

Arg Tyr Phe Tyr Asn Gln Glu Glu Tyr Val Arg Phe Asp Ser Asp Val
                20                  25                  30

Gly Glu Phe Arg Ala Val Thr Glu Leu Gly Arg Pro Asp Glu Glu Tyr
            35                  40                  45

Trp Asn Ser Gln Lys Asp Leu Leu Glu Asp Arg Arg Ala Ala Val Asp
    50                  55                  60

Thr Tyr Cys Arg His Asn Tyr Gly Val Gly Glu Ser Phe Thr Val
65                  70                  75
```

<210> SEQ ID NO 79
<211> LENGTH: 77
<212> TYPE: PRT
<213> ORGANISM: human

<400> SEQUENCE: 79

```
His Phe Phe Asn Gly Thr Glu Arg Val Arg Phe Leu Asp Arg Tyr Phe
1               5                   10                  15

His Asn Gln Glu Glu Asn Val Arg Phe Asp Ser Asp Val Gly Glu Phe
                20                  25                  30

Arg Ala Val Thr Glu Leu Gly Arg Pro Asp Glu Glu Tyr Trp Asn Ser
            35                  40                  45

Gln Lys Asp Phe Leu Glu Asp Arg Arg Ala Ala Val Asp Thr Tyr Cys
    50                  55                  60

Arg His Asn Tyr Gly Val Gly Glu Ser Phe Thr Val Gln
65                  70                  75
```

<210> SEQ ID NO 80
<211> LENGTH: 73
<212> TYPE: PRT
<213> ORGANISM: human

<400> SEQUENCE: 80

```
Glu Cys His Phe Phe Asn Gly Thr Glu Arg Val Arg Phe Leu Asp Arg
1               5                   10                  15

Tyr Phe His Asn Gln Glu Glu Phe Val Arg Phe Asp Ser Asp Val Gly
                20                  25                  30

Glu Phe Arg Ala Val Thr Glu Leu Gly Arg Pro Asp Glu Glu Tyr Trp
            35                  40                  45

Asn Ser Gln Lys Asp Phe Leu Glu Asp Arg Arg Ala Ala Val Asp Thr
    50                  55                  60

Tyr Cys Arg His Asn Tyr Gly Val Gly
65                  70
```

<210> SEQ ID NO 81
<211> LENGTH: 79

```
<212> TYPE: PRT
<213> ORGANISM: human

<400> SEQUENCE: 81

Ser Glu Cys His Phe Phe Asn Gly Thr Glu Arg Val Arg Phe Leu Asp
 1               5                  10                  15

Arg Tyr Phe Tyr Asn Gln Glu Glu Tyr Val Arg Phe Asp Ser Asp Val
            20                  25                  30

Gly Glu Phe Arg Ala Val Thr Glu Leu Gly Arg Pro Asp Glu Glu Tyr
        35                  40                  45

Trp Asn Ser Gln Lys Asp Phe Leu Glu Asp Glu Arg Ala Ala Val Asp
    50                  55                  60

Thr Tyr Cys Arg His Asn Tyr Gly Val Gly Glu Ser Phe Thr Val
65                  70                  75

<210> SEQ ID NO 82
<211> LENGTH: 73
<212> TYPE: PRT
<213> ORGANISM: human

<400> SEQUENCE: 82

Glu Cys His Phe Phe Asn Gly Thr Glu Arg Val Arg Phe Leu Asp Arg
 1               5                  10                  15

Tyr Phe Tyr Asn Gln Glu Glu Phe Val Arg Phe Asp Ser Asp Val Gly
            20                  25                  30

Glu Phe Arg Ala Val Thr Glu Leu Gly Arg Pro Asp Glu Glu Tyr Trp
        35                  40                  45

Asn Ser Gln Lys Asp Phe Leu Glu Asp Arg Arg Ala Ala Val Asp Thr
    50                  55                  60

Tyr Cys Arg His Asn Tyr Gly Val Gly
65                  70

<210> SEQ ID NO 83
<211> LENGTH: 94
<212> TYPE: PRT
<213> ORGANISM: human

<400> SEQUENCE: 83

Gly Asp Thr Arg Pro Arg Phe Leu Glu Tyr Ser Thr Ser Glu Cys His
 1               5                  10                  15

Phe Phe Asn Gly Thr Glu Arg Val Arg Phe Leu Asp Arg Tyr Phe His
            20                  25                  30

Asn Gln Glu Glu Phe Val Arg Phe Asp Ser Asp Val Gly Glu Phe Arg
        35                  40                  45

Ala Val Thr Glu Leu Gly Arg Pro Asp Glu Glu Tyr Trp Asn Ser Gln
    50                  55                  60

Lys Asp Leu Leu Glu Arg Arg Arg Ala Ala Val Asp Thr Tyr Cys Arg
65                  70                  75                  80

His Asn Tyr Gly Val Val Glu Ser Phe Thr Val Gln Arg Arg
                85                  90

<210> SEQ ID NO 84
<211> LENGTH: 93
<212> TYPE: PRT
<213> ORGANISM: human

<400> SEQUENCE: 84

Gly Asp Thr Arg Pro Arg Phe Leu Glu Tyr Ser Thr Ser Glu Cys His
 1               5                  10                  15
```

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
            35                  40                  45

Ala Val Thr Glu Leu Gly Arg Pro Asp Glu Glu Tyr Trp Asn Ser Gln
        50                  55                  60

Lys Asp Ile Leu Glu Asp Arg Ala Ala Val Asp Thr Tyr Cys Arg
65                  70                  75                  80

His Asn Tyr Gly Val Gly Glu Ser Phe Thr Val Gln Arg
                85                  90

<210> SEQ ID NO 85
<211> LENGTH: 102
<212> TYPE: PRT
<213> ORGANISM: human

<400> SEQUENCE: 85

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Asp Leu Arg Phe Asp Ser Asp Val Gly Glu Phe Arg
            35                  40                  45

Ala Val Thr Glu Leu Gly Arg Pro Asp Glu Glu Tyr Trp Asn Ser Gln
        50                  55                  60

Lys Asp Phe Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val His
                85                  90                  95

Pro Lys Val Thr Val Tyr
            100

<210> SEQ ID NO 86
<211> LENGTH: 89
<212> TYPE: PRT
<213> ORGANISM: human

<400> SEQUENCE: 86

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp Ser Asp Val Gly Glu Phe Arg Ala Val Thr Glu Leu
            35                  40                  45

Gly Arg Pro Asp Glu Glu Tyr Trp Asn Ser Gln Lys Asp Ile Leu Glu
        50                  55                  60

Asp Glu Arg Ala Ala Val Asp Thr Tyr Cys Arg His Asn Tyr Gly Val
65                  70                  75                  80

Val Glu Ser Phe Thr Val Gln Arg Arg
                85

<210> SEQ ID NO 87
<211> LENGTH: 102
<212> TYPE: PRT
<213> ORGANISM: human

<400> SEQUENCE: 87

```
Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe His
            20                  25                  30

Asn Gln Glu Glu Phe Val Arg Phe Asp Ser Asp Val Gly Glu Tyr Arg
        35                  40                  45

Ala Val Thr Glu Leu Gly Arg Pro Asp Glu Glu Tyr Trp Asn Ser Gln
50                  55                  60

Lys Asp Leu Leu Glu Arg Arg Ala Glu Val Asp Thr Tyr Cys Arg
65                  70                  75                  80

His Asn Tyr Gly Val Val Glu Ser Phe Thr Val Gln Arg Arg Val His
            85                  90                  95

Pro Lys Val Thr Val Tyr
            100
```

<210> SEQ ID NO 88
<211> LENGTH: 88
<212> TYPE: PRT
<213> ORGANISM: human

<400> SEQUENCE: 88

```
Phe Leu Glu Tyr Ser Thr Ser Glu Cys His Phe Phe Asn Gly Thr Glu
1               5                   10                  15

Arg Val Arg Phe Leu Asp Arg Tyr Phe Tyr Asn Gln Glu Glu Tyr Val
            20                  25                  30

Arg Phe Asp Ser Asp Val Gly Glu Phe Arg Ala Val Thr Glu Leu Gly
        35                  40                  45

Arg Pro Asp Glu Glu Tyr Trp Asn Ser Gln Lys Asp Ile Leu Glu Asp
    50                  55                  60

Arg Arg Ala Ala Val Asp Thr Tyr Cys Arg His Asn Tyr Gly Val Val
65                  70                  75                  80

Glu Ser Phe Thr Val Gln Arg Arg
                85
```

<210> SEQ ID NO 89
<211> LENGTH: 88
<212> TYPE: PRT
<213> ORGANISM: human

<400> SEQUENCE: 89

```
Phe Leu Glu Tyr Ser Thr Ser Glu Cys His Phe Phe Asn Gly Thr Glu
1               5                   10                  15

Arg Val Arg Phe Leu Asp Arg Tyr Phe Tyr Asn Gln Glu Glu Tyr Val
            20                  25                  30

Arg Phe Asp Ser Asp Val Gly Glu Phe Arg Ala Val Thr Glu Leu Gly
        35                  40                  45

Arg Pro Asp Glu Glu Tyr Trp Asn Ser Gln Lys Asp Ile Leu Glu Asp
    50                  55                  60

Arg Arg Ala Ala Val Asp Thr Tyr Cys Arg His Asn Tyr Gly Val Gly
65                  70                  75                  80

Glu Ser Phe Thr Val Gln Arg Arg
                85
```

<210> SEQ ID NO 90
<211> LENGTH: 85
<212> TYPE: PRT
<213> ORGANISM: human

<400> SEQUENCE: 90

Leu Glu Tyr Ser Thr Ser Glu Cys His Phe Phe Asn Gly Thr Glu Arg
1               5                   10                  15

Val Arg Phe Leu Asp Arg Tyr Phe His Asn Gln Glu Glu Asn Val Arg
                20                  25                  30

Phe Asp Ser Asp Val Gly Glu Phe Arg Ala Val Thr Glu Leu Gly Arg
            35                  40                  45

Pro Asp Glu Glu Tyr Trp Asn Ser Gln Lys Asp Ile Leu Glu Asp Glu
        50                  55                  60

Arg Ala Ala Val Asp Thr Tyr Cys Arg His Asn Tyr Gly Val Gly Glu
65                  70                  75                  80

Ser Phe Thr Val Gln
                85

<210> SEQ ID NO 91
<211> LENGTH: 80
<212> TYPE: PRT
<213> ORGANISM: human

<400> SEQUENCE: 91

Leu Glu Tyr Ser Thr Ser Glu Cys His Phe Phe Asn Gly Thr Glu Arg
1               5                   10                  15

Val Arg Phe Leu Asp Arg Tyr Phe Tyr Asn Gln Glu Tyr Ser Val Arg
                20                  25                  30

Phe Asp Ser Asp Val Gly Glu Phe Arg Ala Val Thr Glu Leu Gly Arg
            35                  40                  45

Pro Asp Glu Glu Tyr Trp Asn Ser Gln Lys Asp Ile Leu Glu Asp Glu
        50                  55                  60

Arg Ala Ala Val Asp Thr Tyr Cys Arg His Asn Tyr Gly Ala Val Glu
65                  70                  75                  80

<210> SEQ ID NO 92
<211> LENGTH: 82
<212> TYPE: PRT
<213> ORGANISM: human

<400> SEQUENCE: 92

Arg Phe Leu Glu Gln Val Lys His Glu Cys His Phe Phe Asn Gly Thr
1               5                   10                  15

Glu Arg Val Arg Phe Leu Asp Arg Tyr Phe Tyr Asn Gln Glu Glu Tyr
                20                  25                  30

Val Arg Phe Asp Ser Asp Val Gly Glu Phe Arg Ala Val Thr Glu Leu
            35                  40                  45

Gly Arg Pro Asp Glu Glu Tyr Trp Asn Ser Gln Lys Asp Phe Leu Glu
        50                  55                  60

Asp Arg Arg Ala Ala Val Asp Thr Tyr Cys Arg His Asn Tyr Gly Val
65                  70                  75                  80

Gly Glu

<210> SEQ ID NO 93
<211> LENGTH: 82
<212> TYPE: PRT
<213> ORGANISM: human

<400> SEQUENCE: 93

Pro Arg Phe Leu Glu Tyr Ser Thr Ser Glu Cys His Phe Phe Asn Gly
1               5                   10                  15

Thr Glu Arg Val Arg Phe Leu Asp Arg Tyr Phe Tyr Asn Gln Glu Glu
                20                  25                  30

Tyr Val Arg Phe Asp Ser Asp Val Gly Glu Phe Arg Ala Val Thr Glu
                35                  40                  45

Leu Gly Arg Pro Asp Glu Glu Tyr Trp Asn Ser Gln Lys Asp Phe Leu
        50                  55                  60

Glu Asp Arg Arg Ala Leu Val Asp Thr Tyr Cys Arg His Asn Tyr Gly
65                  70                  75                  80

Val Gly

<210> SEQ ID NO 94
<211> LENGTH: 83
<212> TYPE: PRT
<213> ORGANISM: human

<400> SEQUENCE: 94

Phe Leu Glu Tyr Ser Thr Ser Glu Cys His Phe Phe Asn Gly Thr Glu
1               5                   10                  15

Arg Val Arg Phe Leu Asp Arg Tyr Phe Tyr Asn Gln Glu Glu Asp Val
                20                  25                  30

Arg Phe Asp Ser Asp Val Gly Glu Phe Arg Ala Val Thr Glu Leu Gly
                35                  40                  45

Arg Pro Asp Glu Glu Tyr Trp Asn Ser Gln Lys Asp Phe Leu Glu Asp
        50                  55                  60

Arg Arg Ala Ala Val Asp Thr Tyr Cys Arg His Asn Tyr Gly Val Gly
65                  70                  75                  80

Glu Ser Phe

<210> SEQ ID NO 95
<211> LENGTH: 89
<212> TYPE: PRT
<213> ORGANISM: human

<400> SEQUENCE: 95

Arg Phe Leu Glu Tyr Ser Thr Ser Glu Cys His Phe Phe Asn Gly Thr
1               5                   10                  15

Glu Arg Val Arg Phe Leu Asp Arg Tyr Phe Tyr Asn Gln Glu Glu Tyr
                20                  25                  30

Val Arg Phe Asp Ser Asp Val Gly Glu Phe Arg Ala Val Thr Glu Leu
                35                  40                  45

Gly Arg Pro Asp Glu Glu Tyr Trp Asn Ser Gln Lys Asp Phe Leu Glu
        50                  55                  60

Asp Arg Arg Ala Leu Val Asp Thr Tyr Cys Arg His Asn Tyr Gly Val
65                  70                  75                  80

Val Glu Ser Phe Thr Val Gln Arg Arg
                85

<210> SEQ ID NO 96
<211> LENGTH: 80
<212> TYPE: PRT
<213> ORGANISM: human

<400> SEQUENCE: 96

Leu Glu Tyr Ser Thr Ser Glu Cys His Phe Phe Asn Gly Thr Glu Arg
1               5                   10                  15

Val Arg Phe Leu Asp Arg Tyr Phe Tyr Asn Gln Glu Glu Tyr Val Arg
                20                  25                  30

-continued

```
Phe Asp Ser Asp Val Gly Glu Phe Arg Ala Val Thr Glu Leu Gly Arg
         35                  40                  45
Pro Asp Glu Glu Tyr Trp Asn Ser Gln Lys Asp Leu Leu Glu Gln Arg
 50                  55                  60
Arg Ala Ala Val Asp Thr Tyr Cys Arg His Asn Tyr Gly Val Gly Glu
 65                  70                  75                  80

<210> SEQ ID NO 97
<211> LENGTH: 81
<212> TYPE: PRT
<213> ORGANISM: human

<400> SEQUENCE: 97

Phe Leu Glu Tyr Ser Thr Ser Glu Cys His Phe Phe Asn Gly Thr Glu
 1               5                  10                  15
Arg Val Arg Phe Leu Asp Arg Tyr Phe Tyr Asn Gln Glu Glu Tyr Val
                 20                  25                  30
Arg Phe Asp Ser Asp Val Gly Glu Phe Arg Ala Val Thr Glu Leu Gly
         35                  40                  45
Arg Pro Asp Glu Glu Tyr Trp Asn Ser Gln Lys Asp Phe Leu Glu Asp
 50                  55                  60
Arg Arg Ala Ala Val Asp Asn Tyr Cys Arg His Asn Tyr Gly Val Gly
 65                  70                  75                  80
Glu

<210> SEQ ID NO 98
<211> LENGTH: 83
<212> TYPE: PRT
<213> ORGANISM: human

<400> SEQUENCE: 98

Arg Phe Leu Glu Tyr Ser Thr Ser Glu Cys His Phe Phe Asn Gly Thr
 1               5                  10                  15
Glu Arg Val Arg Phe Leu Asp Arg Tyr Phe Tyr Asn Gln Glu Glu Asn
                 20                  25                  30
Val Arg Phe Asp Ser Asp Val Gly Glu Phe Arg Ala Val Thr Glu Leu
         35                  40                  45
Gly Arg Pro Asp Glu Glu Tyr Trp Asn Ser Gln Lys Asp Phe Leu Glu
 50                  55                  60
Asp Arg Arg Ala Ala Val Asp Thr Tyr Cys Arg His Asn Tyr Gly Val
 65                  70                  75                  80
Gln Arg Arg

<210> SEQ ID NO 99
<211> LENGTH: 81
<212> TYPE: PRT
<213> ORGANISM: human

<400> SEQUENCE: 99

Arg Phe Leu Glu Tyr Ser Thr Ser Glu Cys His Phe Phe Asn Gly Thr
 1               5                  10                  15
Glu Arg Val Arg Phe Leu Asp Arg Tyr Phe Tyr Asn Gln Glu Glu Ser
                 20                  25                  30
Val Arg Phe Asp Ser Asp Val Gly Glu Phe Arg Ala Val Thr Glu Leu
         35                  40                  45
Gly Arg Pro Asp Glu Glu Tyr Trp Asn Ser Gln Lys Asp Phe Leu Glu
 50                  55                  60
```

```
Asp Arg Arg Ala Ala Val Asp Thr Tyr Cys Arg His Asn Tyr Gly Val
 65                  70                  75                  80

Gly

<210> SEQ ID NO 100
<211> LENGTH: 89
<212> TYPE: PRT
<213> ORGANISM: human

<400> SEQUENCE: 100

Arg Phe Leu Glu Leu Leu Lys Ser Glu Cys His Phe Phe Asn Gly Thr
  1               5                  10                  15

Glu Arg Val Arg Phe Leu Asp Arg Tyr Phe Tyr Asn Gln Glu Glu Tyr
                 20                  25                  30

Val Arg Phe Asp Ser Asp Val Gly Glu Phe Arg Ala Val Thr Glu Leu
             35                  40                  45

Gly Arg Pro Asp Glu Glu Tyr Trp Asn Ser Gln Lys Asp Phe Leu Glu
 50                  55                  60

Asp Arg Arg Ala Ala Val Asp Thr Tyr Cys Arg His Asn Tyr Gly Val
 65                  70                  75                  80

Gly Glu Ser Phe Thr Val Gln Arg Arg
                 85

<210> SEQ ID NO 101
<211> LENGTH: 102
<212> TYPE: PRT
<213> ORGANISM: human

<400> SEQUENCE: 101

Gly Asp Thr Arg Pro Arg Phe Leu Glu Tyr Ser Thr Ser Glu Cys His
  1               5                  10                  15

Phe Phe Asn Gly Thr Glu Arg Val Arg Phe Leu Asp Arg Tyr Phe Tyr
                 20                  25                  30

Asn Gln Glu Glu Tyr Val Arg Phe Asp Ser Asp Val Gly Glu Phe Arg
             35                  40                  45

Ala Val Thr Glu Leu Gly Arg Pro Asp Glu Glu His Trp Asn Ser Gln
 50                  55                  60

Lys Asp Ile Leu Glu Asp Arg Arg Ala Val Asp Thr Tyr Cys Arg
 65                  70                  75                  80

His Asn Tyr Gly Val Gly Glu Ser Phe Thr Val Gln Arg Arg Val His
                 85                  90                  95

Pro Lys Val Thr Val Tyr
                100

<210> SEQ ID NO 102
<211> LENGTH: 102
<212> TYPE: PRT
<213> ORGANISM: human

<400> SEQUENCE: 102

Gly Asp Thr Arg Pro Arg Phe Leu Glu Tyr Ser Thr Gly Glu Cys Tyr
  1               5                  10                  15

Phe Phe Asn Gly Thr Glu Arg Val Arg Leu Leu Glu Arg His Phe His
                 20                  25                  30

Asn Gln Glu Glu Leu Leu Arg Phe Asp Ser Asp Val Gly Glu Phe Arg
             35                  40                  45

Ala Val Thr Glu Leu Gly Arg Pro Val Ala Glu Ser Trp Asn Ser Gln
 50                  55                  60
```

```
Lys Asp Ile Leu Glu Asp Arg Arg Ala Ala Val Asp Thr Tyr Cys Arg
 65                  70                  75                  80

His Asn Tyr Gly Ala Val Glu Ser Phe Thr Val Gln Arg Arg Val His
                 85                  90                  95

Pro Lys Val Thr Val Tyr
            100
```

<210> SEQ ID NO 103
<211> LENGTH: 81
<212> TYPE: PRT
<213> ORGANISM: human

<400> SEQUENCE: 103

```
Arg Phe Leu Glu Tyr Ser Thr Gly Glu Cys Tyr Phe Phe Asn Gly Thr
  1               5                  10                  15

Glu Arg Val Arg Leu Leu Glu Arg His Phe His Asn Gln Glu Glu Leu
                 20                  25                  30

Leu Arg Phe Asp Ser Asp Val Gly Glu Phe Arg Ala Val Thr Glu Leu
                 35                  40                  45

Gly Arg Pro Val Ala Glu Ser Trp Asn Ser Gln Lys Asp Phe Leu Glu
             50                  55                  60

Asp Arg Arg Ala Ala Val Asp Thr Tyr Cys Arg His Asn Tyr Gly Ala
 65                  70                  75                  80

Val
```

<210> SEQ ID NO 104
<211> LENGTH: 81
<212> TYPE: PRT
<213> ORGANISM: human

<400> SEQUENCE: 104

```
Phe Leu Glu Tyr Ser Thr Gly Glu Cys Tyr Phe Phe Asn Gly Thr Glu
  1               5                  10                  15

Arg Val Arg Leu Leu Glu Arg His Phe His Asn Gln Glu Glu Leu Leu
                 20                  25                  30

Arg Phe Asp Ser Asp Val Gly Glu Phe Arg Ala Val Thr Glu Leu Gly
                 35                  40                  45

Arg Pro Val Ala Glu Ser Trp Asn Ser Gln Lys Asp Phe Leu Glu Asp
             50                  55                  60

Arg Arg Ala Ala Val Asp Thr Tyr Cys Arg His Asn Tyr Gly Ala Val
 65                  70                  75                  80

Glu
```

<210> SEQ ID NO 105
<211> LENGTH: 88
<212> TYPE: PRT
<213> ORGANISM: human

<400> SEQUENCE: 105

```
Arg Phe Leu Glu Tyr Ser Thr Gly Glu Cys Tyr Phe Phe Asn Gly Thr
  1               5                  10                  15

Glu Arg Val Arg Leu Leu Glu Arg His Phe His Asn Gln Glu Glu Leu
                 20                  25                  30

Leu Arg Phe Asp Ser Asp Val Gly Glu Phe Arg Ala Val Thr Glu Leu
                 35                  40                  45

Gly Arg Pro Val Ala Glu Ser Trp Asn Ser Gln Lys Asp Ile Leu Glu
             50                  55                  60
```

-continued

Asp Arg Arg Ala Ala Val Asp Thr Tyr Cys Arg His Asn Tyr Gly Val
65                  70                  75                  80

Val Glu Ser Phe Thr Val Gln Arg
                85

<210> SEQ ID NO 106
<211> LENGTH: 78
<212> TYPE: PRT
<213> ORGANISM: human

<400> SEQUENCE: 106

Glu Tyr Ser Thr Gly Glu Cys Tyr Phe Phe Asn Gly Thr Glu Arg Val
1               5                   10                  15

Arg Leu Leu Glu Arg His Phe His Asn Gln Glu Leu Leu Arg Phe
            20                  25                  30

Asp Ser Asp Val Gly Glu Phe Arg Ala Val Thr Glu Leu Gly Arg Pro
            35                  40                  45

Val Glu Glu Tyr Trp Asn Ser Gln Lys Asp Ile Leu Glu Asp Arg Arg
        50                  55                  60

Ala Ala Val Asp Thr Tyr Cys Arg His Asn Tyr Gly Ala Val
65                  70                  75

<210> SEQ ID NO 107
<211> LENGTH: 89
<212> TYPE: PRT
<213> ORGANISM: human

<400> SEQUENCE: 107

Arg Phe Leu Glu Tyr Ser Thr Gly Glu Cys Tyr Phe Phe Asn Gly Thr
1               5                   10                  15

Glu Arg Val Arg Leu Leu Glu Arg His Phe His Asn Gln Glu Glu Phe
            20                  25                  30

Leu Arg Phe Asp Ser Asp Val Gly Glu Phe Arg Ala Val Thr Glu Leu
            35                  40                  45

Gly Arg Pro Val Ala Glu Ser Trp Asn Ser Gln Lys Asp Ile Leu Glu
        50                  55                  60

Asp Arg Arg Ala Ala Val Asp Thr Tyr Cys Arg His Asn Tyr Gly Ala
65                  70                  75                  80

Val Glu Ser Phe Thr Val Gln Arg Arg
                85

<210> SEQ ID NO 108
<211> LENGTH: 102
<212> TYPE: PRT
<213> ORGANISM: human

<400> SEQUENCE: 108

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe His
            20                  25                  30

Asn Gln Glu Glu Asn Val Arg Phe Asp Ser Asp Val Gly Glu Phe Arg
            35                  40                  45

Ala Val Thr Glu Leu Gly Arg Pro Asp Ala Glu Tyr Trp Asn Ser Gln
        50                  55                  60

Lys Asp Ile Leu Glu Asp Glu Arg Ala Val Asp Thr Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
            100

<210> SEQ ID NO 109
<211> LENGTH: 102
<212> TYPE: PRT
<213> ORGANISM: human

<400> SEQUENCE: 109

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe His
            20                  25                  30

Asn Gln Glu Glu Asn Val Arg Phe Asp Ser Asp Val Gly Glu Phe Arg
        35                  40                  45

Ala Val Thr Glu Leu Gly Arg Pro Asp Ala Glu Tyr Trp Asn Ser Gln
    50                  55                  60

Lys Asp Ile Leu Glu Asp Glu Arg Ala Ala Val Asp Thr Tyr Cys Arg
65                  70                  75                  80

His Asn Tyr Gly Val Gly Glu Ser Phe Thr Val Gln Arg Arg Val His
                85                  90                  95

Pro Lys Val Thr Val Tyr
            100

<210> SEQ ID NO 110
<211> LENGTH: 101
<212> TYPE: PRT
<213> ORGANISM: human

<400> SEQUENCE: 110

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Tyr Arg
        35                  40                  45

Ala Val Thr Glu Leu Gly Arg Pro Ser Ala Glu Tyr Trp Asn Ser Gln
    50                  55                  60

Lys Asp Ile Leu Glu Asp Lys Arg Ala Ala Val Asp Thr Tyr Cys Arg
65                  70                  75                  80

His Asn Tyr Gly Val Gly Glu Ser Phe Thr Val Gln Arg Arg Val His
                85                  90                  95

Pro Lys Val Thr Val
            100

<210> SEQ ID NO 111
<211> LENGTH: 87
<212> TYPE: PRT
<213> ORGANISM: human

<400> SEQUENCE: 111

Leu Glu Tyr Ser Thr Ser Glu Cys His Phe Phe Asn Gly Thr Glu Arg
1               5                   10                  15

Val Arg Phe Leu Asp Arg Tyr Phe Tyr Asn Gln Glu Glu Tyr Val Arg
            20                  25                  30

Phe Asp Ser Asp Val Gly Glu Tyr Arg Ala Val Thr Glu Leu Gly Arg

```
                 35                  40                  45
Pro Ser Ala Glu Tyr Trp Asn Ser Gln Lys Asp Ile Leu Glu Asp Lys
            50                  55                  60
Arg Ala Val Asp Thr Tyr Cys Arg His Asn Tyr Gly Val Gly Glu
 65                  70                  75                  80
Ser Phe Thr Val Gln Arg Arg
                85

<210> SEQ ID NO 112
<211> LENGTH: 101
<212> TYPE: PRT
<213> ORGANISM: human

<400> SEQUENCE: 112

Gly Asp Thr Arg Pro Arg Phe Leu Glu Tyr Ser Thr Ser Glu Cys His
 1               5                  10                  15
Phe Phe Asn Gly Thr Glu Arg Val Arg Phe Leu Asp Arg Tyr Phe Tyr
                20                  25                  30
Asn Gln Glu Glu Tyr Val Arg Phe Asp Ser Asp Val Gly Glu Phe Arg
            35                  40                  45
Ala Val Thr Glu Leu Gly Arg Pro Ser Ala Glu Tyr Trp Asn Ser Gln
        50                  55                  60
Lys Asp Ile Leu Glu Asp Arg Ala Ala Val Asp Thr Tyr Cys Arg
 65                  70                  75                  80
His Asn Tyr Gly Val Val Glu Ser Phe Thr Val Gln Arg Arg Val His
                85                  90                  95
Pro Lys Val Thr Val
                100

<210> SEQ ID NO 113
<211> LENGTH: 89
<212> TYPE: PRT
<213> ORGANISM: human

<400> SEQUENCE: 113

Arg Phe Leu Glu Tyr Ser Thr Ser Glu Cys His Phe Phe Asn Gly Thr
 1               5                  10                  15
Glu Arg Val Arg Phe Leu Asp Arg Tyr Phe His Asn Gln Glu Glu Asn
                20                  25                  30
Val Arg Phe Asp Ser Asp Val Gly Glu Phe Arg Ala Val Thr Glu Leu
            35                  40                  45
Gly Arg Pro Asp Ala Glu Tyr Trp Asn Ser Gln Lys Asp Phe Leu Glu
        50                  55                  60
Asp Arg Arg Ala Ala Val Asp Thr Tyr Cys Arg His Asn Tyr Gly Val
 65                  70                  75                  80
Gly Glu Ser Phe Thr Val Gln Arg Arg
                85

<210> SEQ ID NO 114
<211> LENGTH: 76
<212> TYPE: PRT
<213> ORGANISM: human

<400> SEQUENCE: 114

Cys His Phe Phe Asn Gly Thr Glu Arg Val Arg Phe Leu Asp Arg Tyr
 1               5                  10                  15
Phe His Asn Gln Glu Glu Asn Val Arg Phe Asp Ser Asp Val Gly Glu
                20                  25                  30
```

```
Phe Arg Ala Val Thr Glu Leu Gly Arg Pro Asp Ala Glu Tyr Trp Asn
            35                  40                  45
Ser Gln Lys Asp Ile Leu Glu Asp Arg Arg Ala Ala Val Asp Thr Tyr
 50                  55                  60
Cys Arg His Asn Tyr Gly Val Val Glu Ser Phe Thr
 65                  70                  75

<210> SEQ ID NO 115
<211> LENGTH: 84
<212> TYPE: PRT
<213> ORGANISM: human

<400> SEQUENCE: 115

Phe Leu Glu Tyr Ser Thr Ser Glu Cys His Phe Phe Asn Gly Thr Glu
 1               5                  10                  15
Arg Val Arg Phe Leu Asp Arg Tyr Phe Tyr Asn Gln Glu Glu Tyr Val
             20                  25                  30
Arg Phe Asp Ser Asp Val Gly Glu Tyr Arg Ala Val Thr Glu Leu Gly
         35                  40                  45
Arg Pro Asp Ala Glu Tyr Trp Asn Ser Gln Lys Asp Phe Leu Glu Asp
     50                  55                  60
Arg Arg Ala Ala Val Asp Thr Tyr Cys Arg His Asn Tyr Gly Val Gly
 65                  70                  75                  80
Glu Ser Phe Thr

<210> SEQ ID NO 116
<211> LENGTH: 85
<212> TYPE: PRT
<213> ORGANISM: human

<400> SEQUENCE: 116

Phe Leu Glu Tyr Ser Thr Ser Glu Cys His Phe Phe Asn Gly Thr Glu
 1               5                  10                  15
Arg Val Arg Phe Leu Asp Arg Tyr Phe His Asn Gln Glu Glu Phe Val
             20                  25                  30
Arg Phe Asp Ser Asp Val Gly Glu Tyr Arg Ala Val Thr Glu Leu Gly
         35                  40                  45
Arg Pro Asp Ala Glu Tyr Trp Asn Ser Gln Lys Asp Ile Leu Glu Asp
     50                  55                  60
Glu Arg Ala Ala Val Asp Thr Tyr Cys Arg His Asn Tyr Gly Val Val
 65                  70                  75                  80
Glu Ser Phe Thr Val
             85

<210> SEQ ID NO 117
<211> LENGTH: 85
<212> TYPE: PRT
<213> ORGANISM: human

<400> SEQUENCE: 117

Phe Leu Glu Tyr Ser Thr Ser Glu Cys His Phe Phe Asn Gly Thr Glu
 1               5                  10                  15
Arg Val Arg Phe Leu Asp Arg Tyr Phe His Asn Gln Glu Glu Asn Val
             20                  25                  30
Arg Phe Asp Ser Asp Val Gly Glu Phe Arg Ala Val Thr Glu Leu Gly
         35                  40                  45
Arg Pro Asp Ala Glu Tyr Trp Asn Ser Gln Lys Asp Ile Leu Glu Gln
```

-continued

```
            50                  55                  60
Ala Arg Ala Ala Val Asp Thr Tyr Cys Arg His Asn Tyr Gly Val Val
 65                  70                  75                  80

Glu Ser Phe Thr Val
                 85

<210> SEQ ID NO 118
<211> LENGTH: 80
<212> TYPE: PRT
<213> ORGANISM: human

<400> SEQUENCE: 118

Leu Glu Tyr Ser Thr Ser Glu Cys His Phe Phe Asn Gly Thr Glu Arg
  1               5                  10                  15

Val Arg Phe Leu Asp Arg Tyr Phe His Asn Gln Glu Glu Asn Val Arg
                 20                  25                  30

Phe Asp Ser Asp Val Gly Glu Phe Arg Ala Val Thr Glu Leu Gly Arg
             35                  40                  45

Pro Asp Ala Glu Tyr Trp Asn Ser Gln Lys Asp Ile Leu Glu Asp Lys
         50                  55                  60

Arg Ala Ala Val Asp Thr Tyr Cys Arg His Asn Tyr Gly Val Val Glu
 65                  70                  75                  80

<210> SEQ ID NO 119
<211> LENGTH: 86
<212> TYPE: PRT
<213> ORGANISM: human

<400> SEQUENCE: 119

Leu Glu Tyr Ser Thr Ser Glu Cys His Phe Phe Asn Gly Thr Glu Arg
  1               5                  10                  15

Val Arg Phe Leu Asp Arg Tyr Phe Tyr Asn Gln Glu Glu Tyr Val Arg
                 20                  25                  30

Phe Asp Ser Asp Val Gly Glu Phe Arg Ala Val Thr Glu Leu Gly Arg
             35                  40                  45

Pro Asp Ala Glu Tyr Trp Asn Ser Gln Lys Asp Phe Leu Glu Asp Arg
         50                  55                  60

Arg Ala Ala Val Asp Thr Tyr Cys Arg His Asn Tyr Gly Val Val Glu
 65                  70                  75                  80

Ser Phe Thr Val Gln Arg
                 85

<210> SEQ ID NO 120
<211> LENGTH: 89
<212> TYPE: PRT
<213> ORGANISM: human

<400> SEQUENCE: 120

Arg Phe Leu Glu Tyr Ser Thr Ser Glu Cys His Phe Phe Asn Gly Thr
  1               5                  10                  15

Glu Arg Val Arg Phe Leu Asp Arg Tyr Phe Tyr Asn Gln Glu Glu Tyr
                 20                  25                  30

Val Arg Phe Asp Ser Asp Val Gly Glu Tyr Arg Ala Val Thr Glu Leu
             35                  40                  45

Gly Arg Pro Ser Ala Glu Tyr Trp Asn Ser Gln Lys Asp Ile Leu Glu
         50                  55                  60

Asp Arg Arg Ala Ala Val Asp Thr Tyr Cys Arg His Asn Tyr Gly Val
 65                  70                  75                  80
```

-continued

Gly Glu Ser Phe Thr Val Gln Arg Arg
                85

<210> SEQ ID NO 121
<211> LENGTH: 86
<212> TYPE: PRT
<213> ORGANISM: human

<400> SEQUENCE: 121

Arg Phe Leu Glu Tyr Ser Thr Ser Glu Cys His Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
        35                  40                  45

Gly Arg Pro Ser Ala Glu Tyr Trp Asn Ser Gln Lys Asp Ile Leu Glu
    50                  55                  60

Asp Arg Arg Ala Leu Val Asp Thr Tyr Cys Arg His Asn Tyr Gly Val
65                  70                  75                  80

Gly Glu Ser Phe Thr Val
                85

<210> SEQ ID NO 122
<211> LENGTH: 75
<212> TYPE: PRT
<213> ORGANISM: human

<400> SEQUENCE: 122

Thr Ser Glu Cys His Phe Phe Asn Gly Thr Glu Arg Val Arg Phe Leu
1               5                   10                  15

Asp Arg Tyr Phe Tyr Asn Gln Glu Glu Tyr Val Arg Phe Asp Ser Asp
            20                  25                  30

Val Gly Glu Phe Arg Ala Val Thr Glu Leu Gly Arg Pro Asp Ala Glu
        35                  40                  45

Tyr Trp Asn Ser Gln Lys Asp Phe Leu Glu Asp Arg Arg Ala Ala Val
    50                  55                  60

Asp Thr Tyr Cys Arg His Asn Tyr Gly Val Gly
65                  70                  75

<210> SEQ ID NO 123
<211> LENGTH: 84
<212> TYPE: PRT
<213> ORGANISM: human

<400> SEQUENCE: 123

Phe Leu Glu Tyr Ser Thr Ser Glu Cys His Phe Phe Asn Gly Thr Glu
1               5                   10                  15

Arg Val Arg Phe Leu Glu Arg Tyr Phe His Asn Gln Glu Glu Asn Val
            20                  25                  30

Arg Phe Asp Ser Asp Val Gly Glu Phe Arg Ala Val Thr Glu Leu Gly
        35                  40                  45

Arg Pro Asp Ala Glu Tyr Trp Asn Ser Gln Lys Asp Ile Leu Glu Asp
    50                  55                  60

Glu Arg Ala Ala Val Asp Thr Tyr Cys Arg His Asn Tyr Gly Val Val
65                  70                  75                  80

Glu Ser Phe Thr

```
<210> SEQ ID NO 124
<211> LENGTH: 82
<212> TYPE: PRT
<213> ORGANISM: human

<400> SEQUENCE: 124

Glu Tyr Ser Thr Ser Glu Cys His Phe Phe Asn Gly Thr Glu Arg Val
1               5                   10                  15

Arg Phe Leu Asp Arg Tyr Phe His Asn Gln Glu Glu Asn Val Arg Phe
            20                  25                  30

Asp Ser Asp Val Gly Glu Phe Arg Ala Val Thr Glu Leu Gly Arg Pro
        35                  40                  45

Asp Ala Glu Tyr Trp Asn Ser Gln Lys Asp Ile Leu Glu Asp Glu Arg
    50                  55                  60

Ala Ala Val Asp Thr Tyr Cys Arg His Asn Tyr Gly Val Asp Glu Ser
65                  70                  75                  80

Phe Thr

<210> SEQ ID NO 125
<211> LENGTH: 102
<212> TYPE: PRT
<213> ORGANISM: human

<400> SEQUENCE: 125

Gly Asp Thr Arg Pro Arg Phe Leu Glu Tyr Ser Thr Gly Glu Cys Tyr
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Asp Ala Glu Tyr Trp Asn Ser Gln
    50                  55                  60

Lys Asp Ile Leu Glu Asp Glu Arg Ala Ala Val Asp Thr Tyr Cys Arg
65                  70                  75                  80

His Asn Tyr Gly Val Val Glu Ser Phe Thr Val Gln Arg Arg Val His
            85                  90                  95

Pro Lys Val Thr Val Tyr
            100

<210> SEQ ID NO 126
<211> LENGTH: 89
<212> TYPE: PRT
<213> ORGANISM: human

<400> SEQUENCE: 126

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Phe Leu Glu
    50                  55                  60

Asp Arg Arg Ala Leu Val Asp Thr Tyr Cys Arg His Asn Tyr Gly Val
65                  70                  75                  80

Val Glu Ser Phe Thr Val Gln Arg Arg
            85
```

-continued

```
<210> SEQ ID NO 127
<211> LENGTH: 102
<212> TYPE: PRT
<213> ORGANISM: human

<400> SEQUENCE: 127

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Glu Arg Tyr Phe His
            20                  25                  30

Asn Gln Glu Glu Phe Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Ile Leu Glu Asp Glu Arg Ala Ala Val Asp Thr Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr
            100

<210> SEQ ID NO 128
<211> LENGTH: 88
<212> TYPE: PRT
<213> ORGANISM: human

<400> SEQUENCE: 128

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Leu Leu Glu
    50                  55                  60

Asp Glu Arg Ala Ala Val Asp Thr Tyr Cys Arg His Asn Tyr Gly Val
65                  70                  75                  80

Val Glu Ser Phe Thr Val Gln Arg
                85

<210> SEQ ID NO 129
<211> LENGTH: 102
<212> TYPE: PRT
<213> ORGANISM: human

<400> SEQUENCE: 129

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Ser Ala Glu Tyr Trp Asn Ser Gln
    50                  55                  60

Lys Asp Phe Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val His
```

-continued

```
                    85                  90                  95
Pro Lys Val Thr Val Tyr
                100

<210> SEQ ID NO 130
<211> LENGTH: 90
<212> TYPE: PRT
<213> ORGANISM: human

<400> SEQUENCE: 130

Pro Arg Phe Leu Glu Tyr Ser Thr Ser Glu Cys His Phe Phe Asn Gly
1               5                   10                  15

Thr Glu Arg Val Arg Phe Leu Asp Arg Tyr Phe Tyr Asn Gln Glu Glu
            20                  25                  30

Tyr Val Arg Phe Asp Ser Asp Val Gly Glu Phe Arg Ala Val Thr Glu
        35                  40                  45

Leu Gly Arg Pro Asp Ala Glu Tyr Trp Asn Ser Gln Lys Asp Ile Leu
    50                  55                  60

Glu Asp Glu Arg Ala Ala Val Asp Thr Tyr Cys Arg His Asn Tyr Gly
65                  70                  75                  80

Val Val Glu Ser Phe Thr Val Gln Arg Arg
                85                  90

<210> SEQ ID NO 131
<211> LENGTH: 88
<212> TYPE: PRT
<213> ORGANISM: human

<400> SEQUENCE: 131

Arg Phe Leu Glu Tyr Ser Thr Ser Glu Cys His Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Ile Leu Glu
    50                  55                  60

Asp Glu Arg Ala Ala Val Asp Thr Tyr Cys Arg His Asn Tyr Gly Val
65                  70                  75                  80

Gly Glu Ser Phe Thr Val Gln Arg
                85

<210> SEQ ID NO 132
<211> LENGTH: 88
<212> TYPE: PRT
<213> ORGANISM: human

<400> SEQUENCE: 132

Arg Phe Leu Glu Tyr Ser Thr Ser Glu Cys His Phe Phe Asn Gly Thr
1               5                   10                  15

Glu Arg Val Arg Phe Leu Asp Arg Tyr Phe Phe Asn Gln Glu Glu Tyr
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Phe Leu Glu
    50                  55                  60

Asp Glu Arg Ala Ala Val Asp Thr Tyr Cys Arg His Asn Tyr Gly Val
65                  70                  75                  80
```

```
Val Glu Ser Phe Thr Val Gln Arg
                85

<210> SEQ ID NO 133
<211> LENGTH: 82
<212> TYPE: PRT
<213> ORGANISM: human

<400> SEQUENCE: 133

Arg Phe Leu Glu Tyr Ser Thr Ser Glu Cys His Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Leu Leu Glu
    50                  55                  60

Asp Arg Arg Ala Ala Val Asp Thr Tyr Cys Arg His Asn Tyr Gly Val
65                  70                  75                  80

Gly Glu

<210> SEQ ID NO 134
<211> LENGTH: 89
<212> TYPE: PRT
<213> ORGANISM: human

<400> SEQUENCE: 134

Arg Phe Leu Glu Tyr Ser Thr Ser Glu Cys His Phe Phe Asn Gly Thr
1               5                   10                  15

Glu Arg Val Arg Phe Leu Glu Arg Tyr Phe His Asn Gln Glu Glu Asn
            20                  25                  30

Val Arg Phe Asp Ser Asp Val Gly Glu Tyr Arg Ala Val Thr Glu Leu
        35                  40                  45

Gly Arg Pro Asp Ala Glu Tyr Trp Asn Ser Gln Lys Asp Phe Leu Glu
    50                  55                  60

Asp Arg Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 135
<211> LENGTH: 89
<212> TYPE: PRT
<213> ORGANISM: human

<400> SEQUENCE: 135

Arg Phe Leu Glu Tyr Ser Thr Ser Glu Cys His Phe Phe Asn Gly Thr
1               5                   10                  15

Glu Arg Val Arg Tyr Leu Asp Arg Tyr Phe His Asn Gln Glu Glu Asn
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Ile Leu Glu
    50                  55                  60

Asp Glu Arg Ala Ala Val Asp Thr Tyr Cys Arg His Asn Tyr Gly Val
65                  70                  75                  80

Val Glu Ser Phe Thr Val Gln Arg Arg
```

-continued

```
                85

<210> SEQ ID NO 136
<211> LENGTH: 82
<212> TYPE: PRT
<213> ORGANISM: human

<400> SEQUENCE: 136

Leu Glu Tyr Ser Thr Ser Glu Cys His Phe Phe Asn Gly Thr Glu Arg
1               5                   10                  15

Val Arg Phe Leu Asp Arg Tyr Phe His Asn Gln Glu Glu Asn Val Arg
            20                  25                  30

Phe Asp Ser Asp Val Gly Glu Phe Arg Ala Val Thr Glu Leu Gly Arg
        35                  40                  45

Pro Asp Ala Glu Tyr Trp Asn Ser Gln Lys Asp Ile Leu Glu Asp Glu
    50                  55                  60

Arg Ala Ala Val Asp Thr Tyr Cys Arg His Asn Tyr Arg Val Val Glu
65                  70                  75                  80

Ser Phe

<210> SEQ ID NO 137
<211> LENGTH: 89
<212> TYPE: PRT
<213> ORGANISM: human

<400> SEQUENCE: 137

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Leu Leu Glu
    50                  55                  60

Asp Glu Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 138
<211> LENGTH: 84
<212> TYPE: PRT
<213> ORGANISM: human

<400> SEQUENCE: 138

Phe Leu Glu Tyr Ser Thr Ser Glu Cys His Phe Phe Asn Gly Thr Glu
1               5                   10                  15

Arg Val Arg Phe Leu Asp Arg Tyr Phe Tyr Asn Gln Glu Glu Tyr Val
            20                  25                  30

Arg Phe Asp Ser Asp Val Gly Glu Phe Arg Ala Val Thr Glu Leu Gly
        35                  40                  45

Arg Pro Ser Ala Glu Tyr Trp Asn Ser Gln Lys Asp Ile Leu Glu Asp
    50                  55                  60

Arg Arg Ala Ala Val Asp Thr Tyr Cys Arg His Asn Tyr Gly Val Gly
65                  70                  75                  80

Glu Ser Phe Thr
```

```
<210> SEQ ID NO 139
<211> LENGTH: 89
<212> TYPE: PRT
<213> ORGANISM: human

<400> SEQUENCE: 139

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp Ser Asp Val Gly Glu Phe Arg Ala Val Thr Glu Leu
        35                  40                  45

Gly Arg Pro Val Ala Glu Tyr Trp Asn Ser Gln Lys Asp Ile Leu Glu
    50                  55                  60

Asp Glu Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 140
<211> LENGTH: 89
<212> TYPE: PRT
<213> ORGANISM: human

<400> SEQUENCE: 140

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp Ser Asp Val Gly Glu Tyr Arg Ala Val Thr Glu Leu
        35                  40                  45

Gly Arg Pro Ser Ala Glu Tyr Trp Asn Ser Gln Lys Asp Ile Leu Glu
    50                  55                  60

Asp Glu Arg Ala Ala Val Asp Thr Tyr Cys Arg His Asn Tyr Gly Val
65                  70                  75                  80

Val Glu Ser Phe Thr Val Gln Arg Arg
                85

<210> SEQ ID NO 141
<211> LENGTH: 81
<212> TYPE: PRT
<213> ORGANISM: human

<400> SEQUENCE: 141

Arg Phe Leu Glu Tyr Ser Thr Ser Glu Cys His Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
        35                  40                  45

Gly Arg Pro Ser Ala Glu Tyr Trp Asn Ser Gln Lys Asp Ile Leu Glu
    50                  55                  60

Asp Lys Arg Ala Ala Val Asp Asn Tyr Cys Arg His Asn Tyr Gly Val
65                  70                  75                  80

Gly

<210> SEQ ID NO 142
<211> LENGTH: 94
```

<212> TYPE: PRT
<213> ORGANISM: human

<400> SEQUENCE: 142

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe His
            20                  25                  30

Asn Gln Glu Glu Phe Val Arg Phe Asp Ser Asp Val Gly Glu Tyr Arg
        35                  40                  45

Ala Val Thr Glu Leu Gly Arg Pro Ala Ala Glu His Trp Asn Ser Gln
    50                  55                  60

Lys Asp Leu Leu Glu Arg Arg Ala Glu Val Asp Thr Tyr Cys Arg
65                  70                  75                  80

His Asn Tyr Gly Val Val Glu Ser Phe Thr Val Gln Arg Arg
                85                  90

<210> SEQ ID NO 143
<211> LENGTH: 94
<212> TYPE: PRT
<213> ORGANISM: human

<400> SEQUENCE: 143

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Glu Arg Tyr Phe His
            20                  25                  30

Asn Gln Glu Glu Asn Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Arg Arg Ala Ala Val Asp Thr Tyr Cys Arg
65                  70                  75                  80

His Asn Tyr Gly Val Gly Glu Ser Phe Thr Val Gln Arg Arg
                85                  90

<210> SEQ ID NO 144
<211> LENGTH: 94
<212> TYPE: PRT
<213> ORGANISM: human

<400> SEQUENCE: 144

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Glu Arg Tyr Phe His
            20                  25                  30

Asn Gln Glu Glu Asn Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Asp Arg Arg Ala Leu Val Asp Thr Tyr Cys Arg
65                  70                  75                  80

His Asn Tyr Gly Val Gly Glu Ser Phe Thr Val Gln Arg Arg
                85                  90

<210> SEQ ID NO 145
<211> LENGTH: 89
<212> TYPE: PRT

<213> ORGANISM: human

<400> SEQUENCE: 145

```
Arg Phe Leu Glu Tyr Ser Thr Gly Glu Cys Tyr Phe Asn Gly Thr
1               5                   10                  15
Glu Arg Val Arg Phe Leu Asp Arg Tyr Phe His Asn Gln Glu Glu Phe
            20                  25                  30
Val Arg Phe Asp Ser Asp Val Gly Glu Tyr Arg Ala Val Thr Glu Leu
            35                  40                  45
Gly Arg Pro Ala Ala Glu His Trp Asn Ser Gln Lys Asp Leu Leu Glu
50                  55                  60
Arg Arg Arg Ala Glu Val Asp Thr Tyr Cys Arg His Asn Tyr Gly Val
65                  70                  75                  80
Val Glu Ser Phe Thr Val Gln Arg Arg
                85
```

<210> SEQ ID NO 146
<211> LENGTH: 88
<212> TYPE: PRT
<213> ORGANISM: human

<400> SEQUENCE: 146

```
Phe Leu Glu Tyr Ser Thr Ser Glu Cys Gln Phe Phe Asn Gly Thr Glu
1               5                   10                  15
Arg Val Arg Phe Leu Asp Arg Tyr Phe His Asn Gln Glu Glu Phe Val
            20                  25                  30
Arg Phe Asp Ser Asp Val Gly Glu Tyr Arg Ala Val Thr Glu Leu Gly
            35                  40                  45
Arg Pro Asp Ala Glu Tyr Trp Asn Ser Gln Lys Asp Leu Leu Glu Arg
50                  55                  60
Arg Arg Ala Glu Val Asp Thr Tyr Cys Arg His Asn Tyr Gly Val Val
65                  70                  75                  80
Glu Ser Phe Thr Val Gln Arg Arg
                85
```

<210> SEQ ID NO 147
<211> LENGTH: 88
<212> TYPE: PRT
<213> ORGANISM: human

<400> SEQUENCE: 147

```
Phe Leu Glu Tyr Ser Thr Ser Glu Cys His Phe Phe Asn Gly Thr Glu
1               5                   10                  15
Arg Val Arg Phe Leu Glu Arg Tyr Phe His Asn Gln Glu Glu Asn Val
            20                  25                  30
Arg Phe Asp Ser Asp Val Gly Glu Tyr Arg Ala Val Thr Glu Leu Gly
            35                  40                  45
Arg Pro Asp Ala Glu Tyr Trp Asn Ser Gln Lys Asp Leu Leu Glu Gln
50                  55                  60
Arg Arg Ala Ala Val Asp Thr Tyr Cys Arg His Asn Tyr Gly Val Val
65                  70                  75                  80
Glu Ser Phe Thr Val Gln Arg Arg
                85
```

<210> SEQ ID NO 148
<211> LENGTH: 78
<212> TYPE: PRT
<213> ORGANISM: human

<400> SEQUENCE: 148

Glu Tyr Ser Thr Ser Glu Cys His Phe Phe Asn Gly Thr Glu Arg Val
1               5                   10                  15

Arg Phe Leu Asp Arg Tyr Phe His Asn Gln Glu Glu Phe Val Arg Phe
            20                  25                  30

Asp Ser Asp Val Gly Glu Tyr Arg Ala Val Thr Glu Leu Gly Arg Pro
        35                  40                  45

Ala Ala Glu His Trp Asn Ser Gln Lys Asp Leu Leu Glu Arg Arg Arg
    50                  55                  60

Ala Glu Val Asp Thr Tyr Cys Arg His Asn Tyr Gly Val Gly
65                  70                  75

<210> SEQ ID NO 149
<211> LENGTH: 87
<212> TYPE: PRT
<213> ORGANISM: human

<400> SEQUENCE: 149

Phe Leu Glu Tyr Ser Thr Ser Glu Cys His Phe Phe Asn Gly Thr Glu
1               5                   10                  15

Arg Val Arg Phe Leu Asp Arg Tyr Phe His Asn Gln Glu Glu Phe Val
            20                  25                  30

Arg Phe Asp Ser Asp Val Gly Glu Tyr Arg Ala Val Thr Glu Leu Gly
        35                  40                  45

Arg Pro Asp Ala Glu His Trp Asn Ser Gln Lys Asp Leu Leu Glu Arg
    50                  55                  60

Arg Arg Ala Glu Val Asp Thr Tyr Cys Arg His Asn Tyr Gly Val Val
65                  70                  75                  80

Glu Ser Phe Thr Val Gln Arg
                85

<210> SEQ ID NO 150
<211> LENGTH: 87
<212> TYPE: PRT
<213> ORGANISM: human

<400> SEQUENCE: 150

Phe Leu Glu Tyr Ser Thr Ser Glu Cys His Phe Phe Asn Gly Thr Glu
1               5                   10                  15

Arg Val Arg Phe Leu Asp Arg Tyr Phe His Asn Gln Glu Glu Asn Val
            20                  25                  30

Arg Phe Asp Ser Asp Val Gly Glu Tyr Arg Ala Val Thr Glu Leu Gly
        35                  40                  45

Arg Pro Asp Ala Glu Tyr Trp Asn Ser Gln Lys Asp Leu Leu Glu Gln
    50                  55                  60

Arg Arg Ala Ala Val Asp Thr Tyr Cys Arg His Asn Tyr Gly Val Gly
65                  70                  75                  80

Glu Ser Phe Thr Val Gln Arg
                85

<210> SEQ ID NO 151
<211> LENGTH: 87
<212> TYPE: PRT
<213> ORGANISM: human

<400> SEQUENCE: 151

Phe Leu Glu Gln Val Lys His Glu Cys His Phe Phe Asn Gly Thr Glu

```
                1               5                  10                      15
Arg Val Arg Phe Leu Asp Arg Tyr Phe His Asn Gln Glu Glu Phe Val
                        20                  25                  30
Arg Phe Asp Ser Asp Val Gly Glu Tyr Arg Ala Val Thr Glu Leu Gly
                        35                  40                  45
Arg Pro Ala Ala Glu His Trp Asn Ser Gln Lys Asp Leu Leu Glu Arg
                50                  55                  60
Arg Arg Ala Glu Val Asp Thr Tyr Cys Arg His Asn Tyr Gly Val Val
65                      70                  75                      80
Glu Ser Phe Thr Val Gln Arg
                        85
```

<210> SEQ ID NO 152
<211> LENGTH: 78
<212> TYPE: PRT
<213> ORGANISM: human

<400> SEQUENCE: 152

```
Glu Tyr Ser Thr Gly Glu Cys Tyr Phe Phe Asn Gly Thr Glu Arg Val
1               5                   10                      15
Arg Phe Leu Asp Arg Tyr Phe His Asn Gln Glu Glu Phe Val Arg Phe
                        20                  25                  30
Asp Ser Asp Val Gly Glu Tyr Arg Ala Val Thr Glu Leu Gly Arg Pro
                35                  40                  45
Asp Glu Glu Tyr Trp Asn Ser Gln Lys Asp Leu Leu Glu Arg Arg Arg
                50                  55                  60
Ala Glu Val Asp Thr Tyr Cys Arg His Asn Tyr Gly Val Val
65                      70                  75
```

<210> SEQ ID NO 153
<211> LENGTH: 74
<212> TYPE: PRT
<213> ORGANISM: human

<400> SEQUENCE: 153

```
Ser Glu Cys His Phe Phe Asn Gly Thr Glu Arg Val Arg Phe Leu Glu
1               5                   10                      15
Arg Tyr Phe His Asn Gln Glu Glu Asn Val Arg Phe Asp Ser Asp Val
                        20                  25                  30
Gly Glu Tyr Arg Ala Val Thr Glu Leu Gly Arg Pro Asp Ala Glu Tyr
                35                  40                  45
Trp Asn Ser Gln Lys Asp Leu Leu Glu Asp Arg Arg Ala Leu Val Asp
                50                  55                  60
Thr Tyr Cys Arg His Asn Tyr Gly Val Val
65                      70
```

<210> SEQ ID NO 154
<211> LENGTH: 78
<212> TYPE: PRT
<213> ORGANISM: human

<400> SEQUENCE: 154

```
Glu Tyr Ser Thr Ser Glu Cys His Phe Phe Asn Gly Thr Glu Arg Val
1               5                   10                      15
Arg Phe Leu Glu Arg Tyr Phe His Asn Gln Glu Glu Asn Val Arg Phe
                        20                  25                  30
Asp Ser Asp Val Gly Glu Tyr Arg Ala Val Thr Glu Leu Gly Arg Pro
                35                  40                  45
```

```
Ser Ala Glu Tyr Trp Asn Ser Gln Lys Asp Leu Leu Glu Gln Arg Arg
    50                  55                  60

Ala Ala Val Asp Thr Tyr Cys Arg His Asn Tyr Gly Val Gly
65                  70                  75
```

<210> SEQ ID NO 155
<211> LENGTH: 85
<212> TYPE: PRT
<213> ORGANISM: human

<400> SEQUENCE: 155

```
Phe Leu Glu Tyr Ser Thr Ser Glu Cys His Phe Phe Asn Gly Thr Glu
1               5                   10                  15

Arg Val Arg Phe Leu Asp Arg Tyr Phe His Asn Gln Glu Glu Phe Val
                20                  25                  30

Arg Phe Asp Ser Asp Val Gly Glu Tyr Arg Ala Val Thr Glu Leu Gly
            35                  40                  45

Arg Pro Asp Ala Glu Tyr Trp Asn Ser Gln Lys Asp Leu Leu Glu Arg
        50                  55                  60

Arg Arg Ala Glu Val Asp Thr Tyr Cys Arg His Asn Tyr Gly Val Gly
65                  70                  75                  80

Glu Ser Phe Thr Val
                85
```

<210> SEQ ID NO 156
<211> LENGTH: 82
<212> TYPE: PRT
<213> ORGANISM: human

<400> SEQUENCE: 156

```
Ser Thr Gly Glu Cys Tyr Phe Phe Asn Gly Thr Glu Arg Val Arg Phe
1               5                   10                  15

Leu Asp Arg Tyr Phe His Asn Gln Glu Glu Phe Val Arg Phe Asp Ser
                20                  25                  30

Asp Val Gly Glu Tyr Arg Ala Val Thr Glu Leu Gly Arg Pro Asp Ala
            35                  40                  45

Glu Tyr Trp Asn Ser Gln Lys Asp Phe Leu Glu Asp Arg Arg Ala Leu
        50                  55                  60

Val Asp Thr Tyr Cys Arg His Asn Tyr Gly Val Val Glu Ser Phe Thr
65                  70                  75                  80

Val Gln
```

<210> SEQ ID NO 157
<211> LENGTH: 80
<212> TYPE: PRT
<213> ORGANISM: human

<400> SEQUENCE: 157

```
Leu Glu Tyr Ser Thr Ser Glu Cys His Phe Phe Asn Gly Thr Glu Arg
1               5                   10                  15

Val Arg Phe Leu Asp Arg Tyr Phe His Asn Gln Glu Glu Phe Val Arg
                20                  25                  30

Phe Asp Ser Asp Val Gly Glu Tyr Arg Ala Val Thr Glu Leu Gly Arg
            35                  40                  45

Pro Ala Ala Glu His Trp Asn Ser Gln Lys Asp Ile Leu Glu Asp Glu
        50                  55                  60

Arg Ala Ala Val Asp Thr Tyr Cys Arg His Asn Tyr Gly Val Val Glu
```

| 65 | 70 | 75 | 80 |

<210> SEQ ID NO 158
<211> LENGTH: 88
<212> TYPE: PRT
<213> ORGANISM: human

<400> SEQUENCE: 158

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp Ser Asp Val Gly Glu Phe Arg Ala Val Thr Glu Leu
        35                  40                  45

Gly Arg Pro Asp Ala Glu Tyr Trp Asn Ser Gln Lys Asp Leu Leu Glu
    50                  55                  60

Gln Arg Arg Ala Ala Val Asp Thr Tyr Cys Arg His Asn Tyr Gly Val
65                  70                  75                  80

Val Glu Ser Phe Thr Val Gln Arg
                85

<210> SEQ ID NO 159
<211> LENGTH: 86
<212> TYPE: PRT
<213> ORGANISM: human

<400> SEQUENCE: 159

Glu Tyr Ser Thr Ser Glu Cys His Phe Phe Asn Gly Thr Glu Arg Val
1               5                   10                  15

Arg Phe Leu Glu Arg Tyr Phe His Asn Gln Glu Glu Asn Val Arg Phe
            20                  25                  30

Asp Ser Asp Val Gly Glu Tyr Arg Ala Val Thr Glu Leu Gly Arg Pro
        35                  40                  45

Asp Ala Glu Tyr Trp Asn Ser Gln Lys Asp Leu Leu Glu Arg Arg Arg
    50                  55                  60

Ala Glu Val Asp Thr Tyr Cys Arg His Asn Tyr Gly Val Val Glu Ser
65                  70                  75                  80

Phe Thr Val Gln Arg Arg
                85

<210> SEQ ID NO 160
<211> LENGTH: 90
<212> TYPE: PRT
<213> ORGANISM: human

<400> SEQUENCE: 160

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Glu Arg Tyr Phe His
            20                  25                  30

Asn Gln Glu Glu Asn Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr
                85                  90

<210> SEQ ID NO 161
<211> LENGTH: 80
<212> TYPE: PRT
<213> ORGANISM: human

<400> SEQUENCE: 161

Leu Glu Tyr Ser Thr Ser Glu Cys His Phe Phe Asn Gly Thr Glu Arg
1               5                   10                  15

Val Arg Phe Leu Glu Arg Tyr Phe His Asn Gln Glu Glu Phe Val Arg
            20                  25                  30

Phe Asp Ser Asp Val Gly Glu Tyr Arg Ala Val Thr Glu Leu Gly Arg
        35                  40                  45

Pro Asp Ala Glu Tyr Trp Asn Ser Gln Lys Asp Leu Leu Glu Gln Arg
    50                  55                  60

Arg Ala Ala Val Asp Thr Tyr Cys Arg His Asn Tyr Gly Val Val Glu
65                  70                  75                  80

<210> SEQ ID NO 162
<211> LENGTH: 80
<212> TYPE: PRT
<213> ORGANISM: human

<400> SEQUENCE: 162

Leu Glu Tyr Ser Thr Ser Glu Cys His Phe Phe Asn Gly Thr Glu Arg
1               5                   10                  15

Val Arg Phe Leu Asp Arg Tyr Phe His Asn Gln Glu Glu Asn Val Arg
            20                  25                  30

Phe Asp Ser Asp Val Gly Glu Phe Arg Ala Val Thr Glu Leu Gly Arg
        35                  40                  45

Pro Asp Ala Glu Tyr Trp Asn Ser Gln Lys Asp Leu Leu Glu Gln Lys
    50                  55                  60

Arg Ala Ala Val Asp Thr Tyr Cys Arg His Asn Tyr Gly Val Val Glu
65                  70                  75                  80

<210> SEQ ID NO 163
<211> LENGTH: 89
<212> TYPE: PRT
<213> ORGANISM: human

<400> SEQUENCE: 163

Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Phe
            20                  25                  30

Val Arg Phe Asp Ser Asp Val Gly Glu Tyr Arg Ala Val Thr Glu Leu
        35                  40                  45

Gly Arg Pro Ala Ala Glu His Trp Asn Ser Gln Lys Asp Phe Leu Glu
    50                  55                  60

Asp Arg Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 164
<211> LENGTH: 89
<212> TYPE: PRT
<213> ORGANISM: human

<400> SEQUENCE: 164

Arg Phe Leu Glu Tyr Ser Thr Ser Glu Cys His Phe Asn Gly Thr
1               5                   10                  15

Glu Arg Val Arg Phe Leu Asp Arg Tyr Phe His Asn Gln Glu Glu Phe
            20                  25                  30

Val Arg Phe Asp Ser Asp Val Gly Glu Tyr Arg Ala Val Thr Glu Leu
        35                  40                  45

Gly Arg Pro Asp Ala Glu Tyr Trp Asn Ser Gln Lys Asp Leu Leu Glu
    50                  55                  60

Arg Arg Arg Ala Glu Val Asp Thr Tyr Cys Arg His Asn Tyr Gly Val
65                  70                  75                  80

Val Glu Ser Phe Thr Val Gln Arg Arg
                85

<210> SEQ ID NO 165
<211> LENGTH: 96
<212> TYPE: PRT
<213> ORGANISM: human

<400> SEQUENCE: 165

Phe Leu Glu Tyr Ser Thr Ser Glu Cys His Phe Phe Asn Gly Thr Glu
1               5                   10                  15

Arg Val Arg Phe Leu Glu Arg Tyr Phe His Asn Gln Glu Glu Asn Val
            20                  25                  30

Arg Phe Asp Ser Asp Val Gly Glu Tyr Arg Ala Val Thr Glu Leu Gly
        35                  40                  45

Arg Pro Asp Ala Glu Tyr Trp Asn Ser Gln Lys Asp Ile Leu Glu Gln
    50                  55                  60

Ala Arg Ala Ala Val Asp Thr Tyr Cys Arg His Asn Tyr Gly Val Gly
65                  70                  75                  80

Glu Ser Phe Thr Val Gln Arg Arg Val His Pro Lys Val Thr Val Tyr
                85                  90                  95

<210> SEQ ID NO 166
<211> LENGTH: 78
<212> TYPE: PRT
<213> ORGANISM: human

<400> SEQUENCE: 166

Glu Tyr Ser Thr Ser Glu Cys His Phe Phe Asn Gly Thr Glu Arg Val
1               5                   10                  15

Arg Phe Leu Asp Arg Tyr Phe Tyr Asn Gln Glu Glu Tyr Val Arg Phe
            20                  25                  30

Asp Ser Asp Val Gly Glu Tyr Arg Ala Val Thr Glu Leu Gly Arg Pro
        35                  40                  45

Ala Ala Glu His Trp Asn Ser Gln Lys Asp Phe Leu Glu Asp Arg Arg
    50                  55                  60

Ala Ala Val Asp Thr Tyr Cys Arg His Asn Tyr Gly Val Gly
65                  70                  75

<210> SEQ ID NO 167
<211> LENGTH: 89
<212> TYPE: PRT
<213> ORGANISM: human

<400> SEQUENCE: 167

Arg Phe Leu Glu Tyr Ser Thr Ser Glu Cys His Phe Phe Asn Gly Thr
1               5                   10                  15

```
Glu Arg Val Gln Phe Leu Asp Arg Tyr Phe His Asn Gln Glu Glu Phe
            20                  25                  30

Val Arg Phe Asp Ser Asp Val Gly Glu Tyr Arg Ala Val Thr Glu Leu
        35                  40                  45

Gly Arg Pro Ala Ala Glu His Trp Asn Ser Gln Lys Asp Leu Leu Glu
        50                  55                  60

Arg Arg Arg Ala Glu Val Asp Thr Tyr Cys Arg His Asn Tyr Gly Val
65                  70                  75                  80

Val Glu Ser Phe Thr Val Gln Arg Arg
                85

<210> SEQ ID NO 168
<211> LENGTH: 89
<212> TYPE: PRT
<213> ORGANISM: human

<400> SEQUENCE: 168

Arg Phe Leu Glu Tyr Ser Thr Ser Glu Cys His Phe Phe Asn Gly Thr
1               5                   10                  15

Glu Arg Val Arg Phe Leu Glu Arg Tyr Phe His Asn Gln Glu Glu Asn
            20                  25                  30

Val Arg Phe Asp Ser Asp Val Gly Glu Tyr Arg Ala Val Thr Glu Leu
        35                  40                  45

Gly Arg Pro Asp Ala Glu Tyr Trp Asn Ser Gln Lys Asp Phe Leu Glu
        50                  55                  60

Asp Arg Arg Ala Leu Val Asp Thr Tyr Cys Arg His Asn Tyr Gly Val
65                  70                  75                  80

Gly Glu Ser Phe Thr Val Gln Arg Arg
                85

<210> SEQ ID NO 169
<211> LENGTH: 81
<212> TYPE: PRT
<213> ORGANISM: human

<400> SEQUENCE: 169

Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe His Asn Gln Glu Glu Phe
            20                  25                  30

Val Arg Phe Asp Ser Asp Val Gly Glu Tyr Arg Ala Val Thr Glu Leu
        35                  40                  45

Gly Arg Pro Ala Ala Glu His Trp Asn Ser Gln Lys Asp Leu Leu Glu
        50                  55                  60

Arg Arg Arg Ala Glu Val Asp Thr Tyr Cys Arg His Asn Tyr Gly Ala
65                  70                  75                  80

Val

<210> SEQ ID NO 170
<211> LENGTH: 89
<212> TYPE: PRT
<213> ORGANISM: human

<400> SEQUENCE: 170

Arg Phe Leu Glu Tyr Ser Thr Ser Glu Cys His Phe Phe Asn Gly Thr
1               5                   10                  15

Glu Arg Val Arg Phe Leu Glu Arg Tyr Phe His Asn Gln Glu Glu Asn
```

-continued

```
                  20                  25                  30

Val Arg Phe Asp Ser Asp Val Gly Glu Tyr Arg Ala Val Thr Glu Leu
             35                  40                  45

Gly Arg Pro Asp Ala Glu Tyr Trp Asn Ser Gln Lys Asp Leu Leu Glu
 50                  55                  60

Gln Arg Arg Ala Ala Val Asp Thr Tyr Cys Arg His Asn Tyr Gly Ala
 65                  70                  75                  80

Val Glu Ser Phe Thr Val Gln Arg Arg
                 85
```

<210> SEQ ID NO 171
<211> LENGTH: 84
<212> TYPE: PRT
<213> ORGANISM: human

<400> SEQUENCE: 171

```
Phe Leu Glu Tyr Ser Thr Ser Glu Cys His Phe Phe Asn Gly Thr Glu
 1               5                  10                  15

Arg Val Arg Phe Leu Asp Arg Tyr Phe His Asn Gln Glu Glu Asn Val
                 20                  25                  30

Arg Phe Asp Ser Asp Val Gly Glu Phe Arg Ala Val Thr Glu Leu Gly
             35                  40                  45

Arg Pro Asp Ala Glu Tyr Trp Asn Ser Gln Lys Asp Leu Leu Glu Gln
 50                  55                  60

Arg Arg Ala Ala Val Asp Thr Tyr Cys Arg His Asn Tyr Gly Val Gly
 65                  70                  75                  80

Glu Ser Phe Thr
```

<210> SEQ ID NO 172
<211> LENGTH: 84
<212> TYPE: PRT
<213> ORGANISM: human

<400> SEQUENCE: 172

```
Phe Leu Glu Tyr Ser Thr Gly Glu Cys Tyr Phe Phe Asn Gly Thr Glu
 1               5                  10                  15

Arg Val Arg Phe Leu Asp Arg Tyr Phe His Asn Gln Glu Glu Phe Val
                 20                  25                  30

Arg Phe Asp Ser Asp Val Gly Glu Tyr Arg Ala Val Thr Glu Leu Gly
             35                  40                  45

Arg Pro Ala Ala Glu His Trp Asn Ser Gln Lys Asp Leu Leu Glu Arg
 50                  55                  60

Arg Arg Ala Ala Val Asp Thr Tyr Cys Arg His Asn Tyr Gly Val Val
 65                  70                  75                  80

Glu Ser Phe Thr
```

<210> SEQ ID NO 173
<211> LENGTH: 102
<212> TYPE: PRT
<213> ORGANISM: human

<400> SEQUENCE: 173

```
Gly Asp Thr Gln Pro Arg Phe Leu Trp Gln Gly Lys Tyr Lys Cys His
 1               5                  10                  15

Phe Phe Asn Gly Thr Glu Arg Val Gln Phe Leu Glu Arg Leu Phe Tyr
                 20                  25                  30

Asn Gln Glu Glu Phe Val Arg Phe Asp Ser Asp Val Gly Glu Tyr Arg
```

```
            35                  40                  45
Ala Val Thr Glu Leu Gly Arg Pro Val Ala Glu Ser Trp Asn Ser Gln
 50                  55                  60

Lys Asp Ile Leu Glu Asp Arg Arg Gly Gln Val Asp Thr Val Cys Arg
 65                  70                  75                  80

His Asn Tyr Gly Val Gly Glu Ser Phe Thr Val Gln Arg Arg Val His
                 85                  90                  95

Pro Glu Val Thr Val Tyr
            100

<210> SEQ ID NO 174
<211> LENGTH: 81
<212> TYPE: PRT
<213> ORGANISM: human

<400> SEQUENCE: 174

Arg Phe Leu Trp Gln Gly Lys Tyr Lys Cys His Phe Phe Asn Gly Thr
  1               5                  10                  15

Glu Arg Val Gln Phe Leu Glu Ser Leu Phe Tyr Asn Gln Glu Glu Phe
                 20                  25                  30

Val Arg Phe Asp Ser Asp Val Gly Glu Tyr Arg Ala Val Thr Glu Leu
             35                  40                  45

Gly Arg Pro Val Ala Glu Ser Trp Asn Ser Gln Lys Asp Ile Leu Glu
 50                  55                  60

Asp Arg Arg Gly Gln Val Asp Thr Val Cys Arg His Asn Tyr Gly Val
 65                  70                  75                  80

Gly

<210> SEQ ID NO 175
<211> LENGTH: 94
<212> TYPE: PRT
<213> ORGANISM: human

<400> SEQUENCE: 175

Gly Asp Thr Arg Pro Arg Phe Leu Glu Tyr Ser Thr Gly Glu Cys Tyr
  1               5                  10                  15

Phe Phe Asn Gly Thr Glu Arg Val Arg Phe Leu Asp Arg Tyr Phe Tyr
                 20                  25                  30

Asn Gln Glu Glu Tyr Val Arg Phe Asp Ser Asp Val Gly Glu Tyr Arg
                 35                  40                  45

Ala Val Thr Glu Leu Gly Arg Pro Ser Ala Glu Tyr Trp Asn Ser Gln
 50                  55                  60

Lys Asp Phe Leu Glu Asp Arg Arg Ala Leu Val Asp Thr Tyr Cys Arg
 65                  70                  75                  80

His Asn Tyr Gly Val Gly Glu Ser Phe Thr Val Gln Arg Arg
                 85                  90

<210> SEQ ID NO 176
<211> LENGTH: 102
<212> TYPE: PRT
<213> ORGANISM: human

<400> SEQUENCE: 176

Gly Asp Thr Arg Pro Arg Phe Leu Glu Tyr Ser Thr Gly Glu Cys Tyr
  1               5                  10                  15

Phe Phe Asn Gly Thr Glu Arg Val Arg Phe Leu Asp Arg Tyr Phe Tyr
                 20                  25                  30
```

```
Asn Gln Glu Glu Tyr Val Arg Phe Asp Ser Asp Val Gly Glu Tyr Arg
            35                  40                  45
Ala Val Thr Glu Leu Gly Arg Pro Asp Ala Glu Tyr Trp Asn Ser Gln
        50                  55                  60
Lys Asp Phe Leu Glu Asp Arg Arg Ala Leu Val Asp Thr Tyr Cys Arg
 65                 70                  75                  80
His Asn Tyr Gly Val Gly Glu Ser Phe Thr Val Gln Arg Arg Val His
                85                  90                  95
Pro Lys Val Thr Val Tyr
            100

<210> SEQ ID NO 177
<211> LENGTH: 97
<212> TYPE: PRT
<213> ORGANISM: human

<400> SEQUENCE: 177

Arg Phe Leu Glu Tyr Ser Thr Gly Glu Cys Tyr Phe Phe Asn Gly Thr
 1               5                  10                  15
Glu Arg Val Arg Phe Leu Asp Arg Tyr Phe Tyr Asn Gln Glu Glu Tyr
            20                  25                  30
Val Arg Phe Asp Ser Asp Val Gly Glu Tyr Arg Ala Val Thr Glu Leu
        35                  40                  45
Gly Arg Pro Asp Ala Glu Tyr Trp Asn Ser Gln Lys Asp Phe Leu Glu
    50                  55                  60
Asp Arg Arg Ala Leu Val Asp Thr Tyr Cys Arg His Asn Tyr Gly Val
 65                 70                  75                  80
Gly Glu Ser Phe Thr Val Gln Arg Arg Val His Pro Lys Val Thr Val
                85                  90                  95
Tyr

<210> SEQ ID NO 178
<211> LENGTH: 102
<212> TYPE: PRT
<213> ORGANISM: human

<400> SEQUENCE: 178

Gly Asp Thr Arg Pro Arg Phe Leu Glu Tyr Ser Thr Gly Glu Cys Tyr
 1               5                  10                  15
Phe Phe Asn Gly Thr Glu Arg Val Arg Phe Leu Asp Arg Tyr Phe Tyr
            20                  25                  30
Asn Gln Glu Glu Tyr Val Arg Phe Asp Ser Asp Val Gly Glu Tyr Arg
            35                  40                  45
Ala Val Thr Glu Leu Gly Arg Pro Ser Ala Glu Tyr Trp Asn Ser Gln
        50                  55                  60
Lys Asp Ile Leu Glu Asp Arg Arg Ala Leu Val Asp Thr Tyr Cys Arg
 65                 70                  75                  80
His Asn Tyr Gly Val Gly Glu Ser Phe Thr Val Gln Arg Arg Val His
                85                  90                  95
Pro Lys Val Thr Val Tyr
            100

<210> SEQ ID NO 179
<211> LENGTH: 101
<212> TYPE: PRT
<213> ORGANISM: human

<400> SEQUENCE: 179
```

```
Gly Asp Thr Arg Pro Arg Phe Leu Glu Tyr Ser Thr Gly Glu Cys Tyr
 1               5                  10                  15

Phe Phe Asn Gly Thr Glu Arg Val Arg Phe Leu Asp Arg Tyr Phe Tyr
             20                  25                  30

Asn Gln Glu Glu Tyr Val Arg Phe Asp Ser Asp Val Gly Glu Tyr Arg
         35                  40                  45

Ala Val Thr Glu Leu Gly Arg Pro Asp Ala Glu Tyr Trp Asn Ser Gln
 50                  55                  60

Lys Asp Phe Leu Glu Asp Arg Arg Ala Leu Val Asp Thr Tyr Cys Arg
 65                  70                  75                  80

His Asn Tyr Gly Val Val Glu Ser Phe Thr Val Gln Arg Arg Val His
                 85                  90                  95

Pro Lys Val Thr Val
                100

<210> SEQ ID NO 180
<211> LENGTH: 76
<212> TYPE: PRT
<213> ORGANISM: human

<400> SEQUENCE: 180

Phe Asn Gly Thr Glu Arg Val Arg Phe Leu Asp Arg Tyr Phe Tyr Asn
 1               5                  10                  15

Gln Glu Glu Tyr Val Arg Phe Asp Ser Asp Val Gly Glu Tyr Arg Ala
             20                  25                  30

Val Thr Glu Leu Gly Arg Pro Asp Ala Glu Tyr Trp Asn Ser Gln Lys
         35                  40                  45

Asp Phe Leu Glu Asp Arg Arg Ala Leu Val Asp Thr Tyr Cys Arg His
 50                  55                  60

Asn Tyr Gly Val Val Glu Ser Phe Thr Val Gln Arg
 65                  70                  75

<210> SEQ ID NO 181
<211> LENGTH: 89
<212> TYPE: PRT
<213> ORGANISM: human

<400> SEQUENCE: 181

Arg Phe Leu Glu Tyr Ser Thr Gly Glu Cys Tyr Phe Phe Asn Gly Thr
 1               5                  10                  15

Glu Arg Val Arg Phe Leu Asp Arg Tyr Phe Tyr Asn Gln Glu Glu Tyr
             20                  25                  30

Val Arg Phe Asp Ser Asp Val Gly Glu Tyr Arg Ala Val Thr Glu Leu
         35                  40                  45

Gly Arg Pro Asp Ala Glu Tyr Trp Asn Ser Gln Lys Asp Phe Leu Glu
 50                  55                  60

Asp Arg Arg Ala Leu Val Asp Thr Tyr Cys Arg His Asn Tyr Gly Val
 65                  70                  75                  80

Val Glu Ser Phe Thr Val Gln Arg Arg
                 85

<210> SEQ ID NO 182
<211> LENGTH: 81
<212> TYPE: PRT
<213> ORGANISM: human

<400> SEQUENCE: 182
```

-continued

Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
            35                  40                  45

Gly Arg Pro Ser Ala Glu Tyr Trp Asn Ser Gln Lys Asp Phe Leu Glu
50                  55                  60

Asp Arg Arg Ala Ala Val Asp Thr Tyr Cys Arg His Asn Tyr Gly Val
65                  70                  75                  80

Gly

<210> SEQ ID NO 183
<211> LENGTH: 90
<212> TYPE: PRT
<213> ORGANISM: human

<400> SEQUENCE: 183

Pro Arg Phe Leu Glu Tyr Ser Thr Gly Glu Cys Tyr Phe Phe Asn Gly
1               5                   10                  15

Thr Glu Arg Val Arg Phe Leu Asp Arg Tyr Phe Tyr Asn Gln Glu Glu
            20                  25                  30

Tyr Val Arg Phe Asp Ser Asp Val Gly Glu Tyr Arg Ala Val Thr Glu
            35                  40                  45

Leu Gly Arg Pro Ser Ala Glu Tyr Trp Asn Ser Gln Lys Asp Phe Leu
50                  55                  60

Glu Asp Arg Arg Ala Leu Val Asp Thr Tyr Cys Arg His Asn Tyr Gly
65                  70                  75                  80

Val Val Glu Ser Phe Thr Val Gln Arg Arg
                85                  90

<210> SEQ ID NO 184
<211> LENGTH: 86
<212> TYPE: PRT
<213> ORGANISM: human

<400> SEQUENCE: 184

Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
            35                  40                  45

Gly Arg Pro Val Ala Glu Tyr Trp Asn Ser Gln Lys Asp Phe Leu Glu
50                  55                  60

Asp Arg Arg Ala Leu Val Asp Thr Tyr Cys Arg His Asn Tyr Gly Val
65                  70                  75                  80

Gly Glu Ser Phe Thr Val
                85

<210> SEQ ID NO 185
<211> LENGTH: 80
<212> TYPE: PRT
<213> ORGANISM: human

<400> SEQUENCE: 185

Leu Glu Tyr Ser Thr Gly Glu Cys Tyr Phe Phe Asn Gly Thr Glu Arg
1               5                   10                  15

```
Val Arg Phe Leu Asp Arg Tyr Phe Tyr Asn Gln Glu Tyr Val Arg
            20                  25                  30

Phe Asp Ser Asp Val Gly Glu Tyr Arg Ala Val Thr Glu Leu Gly Arg
            35                  40                  45

Pro Ala Glu His Trp Asn Ser Gln Lys Asp Phe Leu Glu Asp Arg
        50                  55                  60

Arg Ala Leu Val Asp Thr Tyr Cys Arg His Asn Tyr Gly Val Gly Glu
65                  70                  75                  80

<210> SEQ ID NO 186
<211> LENGTH: 73
<212> TYPE: PRT
<213> ORGANISM: human

<400> SEQUENCE: 186

Glu Cys Tyr Phe Phe Asn Gly Thr Glu Arg Val Arg Phe Leu Asp Arg
1               5                   10                  15

Tyr Phe His Asn Gln Glu Glu Phe Val Arg Phe Asp Ser Asp Val Gly
            20                  25                  30

Glu Tyr Arg Ala Val Thr Glu Leu Gly Arg Pro Asp Ala Glu Tyr Trp
            35                  40                  45

Asn Ser Gln Lys Asp Phe Leu Glu Asp Arg Arg Ala Leu Val Asp Thr
        50                  55                  60

Tyr Cys Arg His Asn Tyr Gly Val Gly
65                  70

<210> SEQ ID NO 187
<211> LENGTH: 89
<212> TYPE: PRT
<213> ORGANISM: human

<400> SEQUENCE: 187

Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
            35                  40                  45

Gly Arg Pro Ser Ala Glu Tyr Trp Asn Ser Gln Lys Asp Ile Leu Glu
        50                  55                  60

Asp Arg Arg Ala Leu Val Asp Thr Tyr Cys Arg His Asn Tyr Gly Val
65                  70                  75                  80

Val Glu Ser Phe Thr Val Gln Arg Arg
                85

<210> SEQ ID NO 188
<211> LENGTH: 86
<212> TYPE: PRT
<213> ORGANISM: human

<400> SEQUENCE: 188

Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
            35                  40                  45
```

```
Gly Arg Pro Ala Ala Glu Tyr Trp Asn Ser Gln Lys Asp Phe Leu Glu
    50                  55                  60

Asp Arg Arg Ala Leu Val Asp Thr Tyr Cys Arg His Asn Tyr Gly Val
65                  70                  75                  80

Gly Glu Ser Phe Thr Val
                85

<210> SEQ ID NO 189
<211> LENGTH: 89
<212> TYPE: PRT
<213> ORGANISM: human

<400> SEQUENCE: 189

Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
        35                  40                  45

Gly Arg Pro Ser Ala Glu Tyr Trp Asn Ser Gln Lys Asp Ile Leu Glu
    50                  55                  60

Asp Arg Arg Ala Leu Val Asp Thr Tyr Cys Arg His Asn Tyr Gly Ala
65                  70                  75                  80

Val Glu Ser Phe Thr Val Gln Arg Arg
                85

<210> SEQ ID NO 190
<211> LENGTH: 80
<212> TYPE: PRT
<213> ORGANISM: human

<400> SEQUENCE: 190

Leu Glu Tyr Ser Thr Gly Glu Cys Tyr Phe Phe Asn Gly Thr Glu Arg
1               5                   10                  15

Val Arg Phe Leu Asp Arg Tyr Phe Tyr Asn Gln Glu Glu Tyr Val Arg
            20                  25                  30

Phe Asp Ser Asp Val Gly Glu Tyr Arg Ala Val Thr Glu Leu Gly Arg
        35                  40                  45

Pro Asp Ala Glu Tyr Trp Asn Ser Gln Lys Asp Leu Leu Glu Asp Arg
    50                  55                  60

Arg Ala Leu Val Asp Thr Tyr Cys Arg His Asn Tyr Gly Val Gly Glu
65                  70                  75                  80

<210> SEQ ID NO 191
<211> LENGTH: 86
<212> TYPE: PRT
<213> ORGANISM: human

<400> SEQUENCE: 191

Arg Phe Leu Glu Tyr Ser Arg Gly Glu Cys Tyr Phe Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
        35                  40                  45

Gly Arg Pro Ser Ala Glu Tyr Trp Asn Ser Gln Lys Asp Ile Leu Glu
    50                  55                  60

Asp Arg Arg Ala Leu Val Asp Thr Tyr Cys Arg His Asn Tyr Gly Val
```

```
65                  70                  75                  80

Gly Glu Ser Phe Thr Val
                85
```

<210> SEQ ID NO 192
<211> LENGTH: 84
<212> TYPE: PRT
<213> ORGANISM: human

<400> SEQUENCE: 192

```
Phe Leu Glu Tyr Ser Thr Gly Glu Cys Tyr Phe Phe Asn Gly Thr Glu
1               5                   10                  15

Arg Val Arg Phe Leu Asp Arg Tyr Phe Tyr Asn Gln Glu Glu Tyr Val
                20                  25                  30

Arg Phe Asp Ser Asp Val Gly Glu Tyr Arg Ala Val Thr Glu Leu Gly
            35                  40                  45

Arg Pro Asp Ala Glu His Trp Asn Ser Gln Lys Asp Ile Leu Glu Asp
        50                  55                  60

Arg Arg Ala Leu Val Asp Thr Tyr Cys Arg His Asn Tyr Gly Val Gly
65                  70                  75                  80

Glu Ser Phe Thr
```

<210> SEQ ID NO 193
<211> LENGTH: 81
<212> TYPE: PRT
<213> ORGANISM: human

<400> SEQUENCE: 193

```
Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe Tyr Asn Gln Glu Glu Asp
                20                  25                  30

Val Arg Phe Asp Ser Asp Val Gly Glu Tyr Arg Ala Val Thr Glu Leu
            35                  40                  45

Gly Arg Pro Ser Ala Glu Tyr Trp Asn Ser Gln Lys Asp Phe Leu Glu
        50                  55                  60

Asp Arg Arg Ala Leu Val Asp Thr Tyr Cys Arg His Asn Tyr Gly Val
65                  70                  75                  80

Gly
```

<210> SEQ ID NO 194
<211> LENGTH: 81
<212> TYPE: PRT
<213> ORGANISM: human

<400> SEQUENCE: 194

```
Arg Phe Leu Glu Tyr Ser Thr Gly Glu Cys Tyr Phe Phe Asn Gly Thr
1               5                   10                  15

Glu Arg Val Arg Phe Leu Asp Arg Tyr Phe Tyr Asn Gln Glu Glu Tyr
                20                  25                  30

Val Arg Phe Asp Ser Asp Val Gly Glu Phe Arg Ala Val Thr Glu Leu
            35                  40                  45

Gly Arg Pro Ser Ala Glu Tyr Trp Asn Ser Gln Lys Asp Phe Leu Glu
        50                  55                  60

Asp Arg Arg Ala Leu Val Asp Thr Tyr Cys Arg His Asn Tyr Gly Val
65                  70                  75                  80

Gly
```

<210> SEQ ID NO 195
<211> LENGTH: 89
<212> TYPE: PRT
<213> ORGANISM: human

<400> SEQUENCE: 195

Arg Phe Leu Glu Tyr Ser Thr Gly Glu Cys Tyr Phe Asn Gly Thr
1               5                   10                  15

Glu Arg Val Arg Phe Leu Asp Arg Tyr Phe Tyr Asn Gln Glu Glu Tyr
            20                  25                  30

Val Arg Phe Asp Ser Asp Val Gly Glu Tyr Arg Ala Val Thr Glu Leu
            35                  40                  45

Gly Arg Pro Ser Ala Glu Tyr Trp Asn Ser Gln Lys Asp Ile Leu Glu
50                  55                  60

Asp Arg Arg Ala Ala Val Asp Thr Tyr Cys Arg His Asn Tyr Gly Val
65                  70                  75                  80

Gly Glu Ser Phe Thr Val Gln Arg Arg
                85

<210> SEQ ID NO 196
<211> LENGTH: 85
<212> TYPE: PRT
<213> ORGANISM: human

<400> SEQUENCE: 196

Phe Leu Glu Tyr Ser Thr Gly Glu Cys Tyr Phe Asn Gly Thr Glu
1               5                   10                  15

Arg Val Arg Phe Leu Asp Arg Tyr Phe Tyr Asn Gln Glu Glu Tyr Val
            20                  25                  30

Arg Phe Asp Ser Asp Val Gly Glu Tyr Arg Ala Val Thr Glu Leu Gly
            35                  40                  45

Arg Pro Ile Ala Glu Tyr Trp Asn Ser Gln Lys Asp Ile Leu Glu Asp
50                  55                  60

Arg Arg Ala Leu Val Asp Thr Tyr Cys Arg His Asn Tyr Gly Val Gly
65                  70                  75                  80

Glu Ser Phe Thr Val
                85

<210> SEQ ID NO 197
<211> LENGTH: 102
<212> TYPE: PRT
<213> ORGANISM: human

<400> SEQUENCE: 197

Gly Asp Thr Gln Pro Arg Phe Leu Lys Gln Asp Lys Phe Glu Cys His
1               5                   10                  15

Phe Phe Asn Gly Thr Glu Arg Val Arg Tyr Leu His Arg Gly Ile Tyr
            20                  25                  30

Asn Gln Glu Glu Asn Val Arg Phe Asp Ser Asp Val Gly Glu Tyr Arg
            35                  40                  45

Ala Val Thr Glu Leu Gly Arg Pro Val Ala Glu Ser Trp Asn Ser Gln
50                  55                  60

Lys Asp Phe Leu Glu Arg Arg Ala Glu Val Asp Thr Val Cys Arg
65                  70                  75                  80

His Asn Tyr Gly Val Gly Glu Ser Phe Thr Val Gln Arg Arg Val His
                85                  90                  95

```
Pro Glu Val Thr Val Tyr
            100

<210> SEQ ID NO 198
<211> LENGTH: 102
<212> TYPE: PRT
<213> ORGANISM: human

<400> SEQUENCE: 198

Gly Asp Thr Arg Pro Arg Phe Leu Glu Val Lys Phe Glu Cys His
1               5                   10                  15

Phe Phe Asn Gly Thr Glu Arg Val Arg Leu Glu Arg Arg Val His
            20                  25                  30

Asn Gln Glu Glu Tyr Ala Arg Tyr Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Leu Leu Glu Arg Arg Ala Ala Val Asp Thr Tyr Cys Arg
65                  70                  75                  80

His Asn Tyr Gly Val Gly Glu Ser Phe Thr Val Gln Arg Arg Val Gln
                85                  90                  95

Pro Lys Val Thr Val Tyr
            100

<210> SEQ ID NO 199
<211> LENGTH: 228
<212> TYPE: PRT
<213> ORGANISM: swine

<400> SEQUENCE: 199

Val Glu Asn His Val Ile Ile Gln Ala Glu Phe Tyr Leu Ser Pro Asp
1               5                   10                  15

Lys Ser Gly Glu Phe Met Phe Asp Phe Asp Gly Asp Glu Ile Phe His
            20                  25                  30

Val Asp Met Glu Lys Arg Glu Thr Val Trp Arg Leu Glu Glu Phe Gly
        35                  40                  45

His Phe Ala Ser Phe Glu Ala Gln Gly Ala Leu Ala Asn Ile Ala Val
    50                  55                  60

Asp Lys Ala Asn Leu Glu Ile Leu Ile Lys Arg Ser Asn Asn Thr Pro
65                  70                  75                  80

Asn Thr Asn Val Pro Pro Glu Val Thr Val Leu Ser Asp Lys Pro Val
                85                  90                  95

Glu Leu Gly Glu Pro Asn Ile Leu Ile Cys Phe Ile Asp Lys Phe Ser
            100                 105                 110

Pro Pro Val Val Asn Val Thr Trp Leu Arg Asn Gly Ser Pro Val Thr
        115                 120                 125

Arg Gly Val Ser Glu Thr Val Phe Leu Pro Arg Glu Asp His Leu Phe
    130                 135                 140

Arg Lys Phe His Tyr Leu Pro Phe Met Pro Ser Thr Glu Asp Val Tyr
145                 150                 155                 160

Asp Cys Gln Val Glu His Trp Gly Leu Asp Lys Pro Leu Leu Lys His
                165                 170                 175

Trp Glu Phe Glu Ala Arg Thr Pro Leu Pro Glu Thr Thr Glu Asn Thr
            180                 185                 190

Val Cys Ala Leu Gly Leu Ile Val Ala Leu Val Gly Ile Ile Val Gly
        195                 200                 205
```

```
Thr Val Leu Ile Ile Lys Gly Val Arg Lys Gly Asn Ala Thr Glu Arg
    210                 215                 220

Arg Gly Pro Leu
225

<210> SEQ ID NO 200
<211> LENGTH: 228
<212> TYPE: PRT
<213> ORGANISM: swine

<400> SEQUENCE: 200

Val Glu Asn His Val Ile Ile Gln Ala Glu Phe Tyr Leu Ser Pro Asp
1               5                   10                  15

Lys Ser Gly Glu Phe Met Phe Asp Phe Asp Gly Asp Glu Ile Phe His
            20                  25                  30

Val Asp Met Glu Lys Arg Glu Thr Val Trp Arg Leu Glu Glu Phe Gly
        35                  40                  45

His Phe Ala Ser Phe Glu Ala Gln Gly Ala Leu Ala Asn Ile Ala Val
    50                  55                  60

Asp Lys Ala Asn Leu Glu Ile Met Ile Lys Arg Ser Asn Asn Thr Pro
65                  70                  75                  80

Asn Thr Asn Val Pro Pro Glu Val Thr Val Leu Ser Asp Lys Pro Val
                85                  90                  95

Glu Leu Gly Glu Pro Asn Ile Leu Ile Cys Phe Ile Asp Lys Phe Ser
            100                 105                 110

Pro Pro Val Val Asn Val Thr Trp Leu Arg Asn Gly Ser Pro Val Thr
        115                 120                 125

Arg Gly Val Ser Glu Thr Val Phe Leu Pro Arg Glu Asp His Leu Phe
    130                 135                 140

Arg Lys Phe His Tyr Leu Pro Phe Met Pro Ser Thr Glu Asp Val Tyr
145                 150                 155                 160

Asp Cys Gln Val Glu His Trp Gly Leu Asp Lys Pro Leu Leu Lys His
                165                 170                 175

Trp Glu Phe Glu Ala Gln Thr Pro Leu Pro Glu Thr Thr Glu Asn Thr
            180                 185                 190

Val Cys Ala Leu Gly Leu Ile Val Ala Leu Val Gly Ile Ile Val Gly
        195                 200                 205

Thr Val Leu Ile Ile Lys Gly Val Arg Lys Gly Asn Ala Thr Glu His
    210                 215                 220

Arg Gly Pro Leu
225

<210> SEQ ID NO 201
<211> LENGTH: 228
<212> TYPE: PRT
<213> ORGANISM: swine

<400> SEQUENCE: 201

Val Glu Asn His Val Ile Ile Gln Ala Glu Phe Tyr Leu Ser Pro Asp
1               5                   10                  15

Lys Ser Gly Glu Phe Met Phe Asp Phe Asp Gly Asp Glu Ile Phe His
            20                  25                  30

Val Asp Met Glu Lys Arg Glu Thr Val Trp Arg Leu Glu Glu Phe Gly
        35                  40                  45

His Phe Ala Ser Phe Glu Ala Gln Gly Ala Leu Ala Asn Ile Ala Val
    50                  55                  60
```

-continued

```
Asp Lys Ala Asn Leu Glu Ile Leu Ile Lys Arg Ser Asn Asn Thr Pro
 65                  70                  75                  80

Asn Thr Asn Val Pro Pro Glu Val Thr Val Leu Ser Asp Lys Pro Val
                 85                  90                  95

Glu Leu Gly Glu Pro Asn Ile Leu Ile Cys Phe Ile Asp Lys Phe Ser
            100                 105                 110

Pro Pro Val Val Asn Val Thr Trp Leu Arg Asn Gly Ser Pro Val Thr
        115                 120                 125

Arg Gly Val Ser Glu Thr Val Phe Leu Pro Arg Glu Asp His Leu Phe
    130                 135                 140

Arg Lys Phe His Tyr Leu Pro Phe Met Pro Ser Thr Glu Asp Val Tyr
145                 150                 155                 160

Asp Cys Gln Val Glu His Trp Gly Leu Asp Lys Pro Leu Leu Lys His
                165                 170                 175

Trp Glu Phe Glu Ala Gln Thr Pro Leu Pro Glu Thr Thr Glu Asn Thr
            180                 185                 190

Val Cys Ala Leu Gly Leu Ile Val Ala Leu Val Gly Ile Ile Val Gly
        195                 200                 205

Thr Val Leu Ile Ile Lys Gly Val Arg Lys Gly Asn Ala Thr Glu His
    210                 215                 220

Arg Gly Pro Leu
225

<210> SEQ ID NO 202
<211> LENGTH: 228
<212> TYPE: PRT
<213> ORGANISM: swine

<400> SEQUENCE: 202

Val Glu Asn His Val Ile Ile Gln Ala Glu Phe Tyr Leu Ser Pro Asp
 1               5                  10                  15

Lys Ser Gly Glu Phe Met Phe Asp Phe Asp Gly Asp Glu Ile Phe His
                20                  25                  30

Val Asp Met Glu Lys Arg Glu Thr Val Trp Arg Leu Glu Glu Phe Gly
            35                  40                  45

His Phe Ala Ser Phe Glu Ala Gln Gly Ala Leu Ala Asn Ile Ala Val
        50                  55                  60

Asp Lys Ala Asn Leu Glu Ile Leu Ile Lys Arg Ser Asn Asn Thr Pro
 65                  70                  75                  80

Asn Thr Asn Val Pro Pro Glu Val Thr Val Leu Ser Asp Lys Pro Val
                 85                  90                  95

Glu Leu Gly Glu Pro Asn Ile Leu Ile Cys Phe Ile Asp Lys Phe Ser
            100                 105                 110

Pro Pro Val Val Asn Val Thr Trp Leu Arg Asn Gly Ser Pro Val Thr
        115                 120                 125

Arg Gly Val Ser Glu Thr Val Phe Leu Pro Arg Glu Asp His Leu Phe
    130                 135                 140

Arg Lys Phe His Tyr Leu Pro Phe Met Pro Ser Thr Glu Asp Val Tyr
145                 150                 155                 160

Asp Cys Gln Val Glu His Trp Gly Leu Asp Lys Pro Leu Leu Lys His
                165                 170                 175

Trp Glu Phe Glu Ala Gln Thr Pro Leu Pro Glu Thr Thr Glu Asn Thr
            180                 185                 190

Val Cys Ala Leu Gly Leu Ile Val Ala Leu Val Gly Ile Ile Val Gly
        195                 200                 205
```

```
Thr Val Leu Ile Ile Lys Gly Val Arg Lys Gly Asn Ala Thr Glu Arg
    210                 215                 220

Arg Gly Pro Leu
225

<210> SEQ ID NO 203
<211> LENGTH: 228
<212> TYPE: PRT
<213> ORGANISM: swine

<400> SEQUENCE: 203

Val Glu Asn His Val Ile Ile Gln Ala Glu Phe Tyr Leu Ser Pro Asp
1               5                   10                  15

Lys Ser Gly Glu Phe Met Phe Asp Phe Asp Gly Asp Glu Ile Phe His
                20                  25                  30

Val Asp Met Glu Lys Arg Glu Thr Val Trp Arg Leu Glu Glu Phe Gly
            35                  40                  45

His Phe Ala Ser Phe Glu Ala Gln Gly Ala Leu Ala Asn Ile Ala Val
        50                  55                  60

Asp Lys Ala Asn Leu Glu Ile Met Ile Lys Arg Ser Asn Asn Thr Pro
65                  70                  75                  80

Asn Thr Asn Val Pro Pro Glu Val Thr Val Leu Ser Asp Lys Pro Val
                85                  90                  95

Glu Leu Gly Glu Pro Asn Ile Leu Ile Cys Phe Ile Asp Lys Phe Ser
            100                 105                 110

Pro Pro Val Val Asn Val Thr Trp Leu Arg Asn Gly Ser Pro Val Thr
        115                 120                 125

Arg Gly Val Ser Glu Thr Val Phe Leu Pro Arg Glu Asp His Leu Phe
    130                 135                 140

Arg Lys Phe His Tyr Leu Pro Phe Met Pro Ser Thr Glu Asp Val Tyr
145                 150                 155                 160

Asp Cys Gln Val Glu His Trp Gly Leu Asp Lys Pro Leu Leu Lys His
                165                 170                 175

Trp Glu Phe Glu Ala Gln Thr Pro Leu Pro Glu Thr Thr Glu Asn Thr
            180                 185                 190

Val Cys Ala Leu Gly Leu Ile Val Ala Leu Val Gly Ile Ile Val Gly
        195                 200                 205

Thr Val Leu Ile Ile Lys Gly Val Arg Lys Gly Asn Ala Thr Glu Arg
    210                 215                 220

Arg Gly Pro Leu
225

<210> SEQ ID NO 204
<211> LENGTH: 228
<212> TYPE: PRT
<213> ORGANISM: swine

<400> SEQUENCE: 204

Val Glu Asn His Val Ile Ile Gln Ala Glu Phe Tyr Leu Ser Pro Asp
1               5                   10                  15

Lys Ser Gly Glu Phe Met Phe Asp Phe Asp Gly Asp Glu Ile Phe His
                20                  25                  30

Val Asp Met Glu Lys Arg Glu Thr Val Trp Arg Leu Glu Glu Phe Gly
            35                  40                  45

His Phe Ala Ser Phe Glu Ala Gln Gly Ala Leu Ala Asn Ile Ala Val
        50                  55                  60
```

-continued

```
Asp Lys Ala Asn Leu Glu Ile Met Ile Lys Arg Ser Asn Asn Thr Pro
 65                  70                  75                  80

Asn Thr Asn Val Pro Pro Glu Val Thr Val Leu Ser Asp Lys Pro Val
                 85                  90                  95

Glu Leu Gly Glu Pro Asn Ile Leu Ile Cys Phe Ile Asp Lys Phe Ser
            100                 105                 110

Pro Pro Val Val Asn Val Thr Trp Leu Arg Asn Gly Ser Pro Val Thr
        115                 120                 125

Arg Gly Val Ser Glu Thr Val Phe Leu Pro Arg Glu Asp His Leu Phe
    130                 135                 140

Arg Lys Phe His Tyr Leu Pro Phe Met Pro Ser Thr Glu Asp Val Tyr
145                 150                 155                 160

Asp Cys Gln Val Glu His Trp Gly Leu Asp Lys Pro Leu Leu Lys His
                165                 170                 175

Trp Glu Phe Glu Ala Gln Thr Pro Leu Pro Glu Thr Thr Glu Asn Thr
            180                 185                 190

Val Cys Ala Leu Gly Leu Ile Val Ala Leu Val Gly Ile Ile Val Gly
        195                 200                 205

Thr Val Leu Ile Ile Lys Gly Val Arg Lys Gly Asn Ala Thr Glu Arg
    210                 215                 220

Arg Gly Pro Leu
225

<210> SEQ ID NO 205
<211> LENGTH: 237
<212> TYPE: PRT
<213> ORGANISM: swine

<400> SEQUENCE: 205

Arg Asp Ile Ala Gln His Phe Phe Met Gly Lys Ser Glu Cys His
 1               5                  10                  15

Phe Phe Asn Gly Thr Glu Arg Val Arg Tyr Leu Gln Lys Tyr Leu Tyr
                 20                  25                  30

Asn Gly Glu Glu Phe Val Arg Phe Asp Ser Asp Leu Gly Glu Phe Arg
             35                  40                  45

Ala Val Thr Glu Leu Gly Arg Pro Asp Ala Lys Tyr Trp Asn Ser Gln
         50                  55                  60

Lys Asp Leu Met Glu Gln Lys Arg Ala Val Asp Thr Tyr Cys Arg
 65                  70                  75                  80

His Asn Tyr Arg Ile Leu Asp Thr Phe Leu Val Pro Arg Arg Ala Glu
                 85                  90                  95

Pro Thr Val Thr Val Tyr Pro Ala Lys Thr Gln Pro Leu Gln His His
            100                 105                 110

Asn Leu Leu Val Cys Ser Val Thr Gly Phe Tyr Pro Gly His Val Glu
        115                 120                 125

Val Arg Trp Phe Arg Asn Gly Gln Glu Glu Ala Ala Gly Val Val Ser
    130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
                165                 170                 175

His Pro Ser Leu Thr Ser Pro Val Thr Val Glu Trp Arg Ala Arg Ser
            180                 185                 190

Glu Ser Ala Gln Gly Lys Met Met Ser Gly Val Gly Gly Phe Val Leu
```

-continued

```
            195                 200                 205
Gly Leu Leu Phe Val Ala Val Gly Leu Phe Ile Tyr Phe Lys Asn Gln
        210                 215                 220
Lys Gly Arg Pro Ala Leu Gln Pro Thr Gly Leu Leu Ser
225                 230                 235

<210> SEQ ID NO 206
<211> LENGTH: 237
<212> TYPE: PRT
<213> ORGANISM: swine

<400> SEQUENCE: 206

Arg Asp Thr Pro Pro His Phe Leu Phe Leu Gly Lys Ala Glu Cys His
1               5                   10                  15
Phe Phe Asn Gly Thr Glu Arg Val Arg Leu Leu Asp Arg Tyr Phe Tyr
            20                  25                  30
Asn Gly Asp Glu Tyr Val Arg Phe Asp Ser Asp Val Gly Glu Phe Arg
        35                  40                  45
Glu Val Thr Glu Phe Gly Arg Pro Asp Ala Lys Tyr Trp Asn Ser Gln
    50                  55                  60
Lys Asp Phe Met Glu Gln Lys Arg Ala Glu Val Asp Thr Val Cys Arg
65                  70                  75                  80
His Asn Tyr Glu Ile Leu Glu Thr Phe Leu Val Pro Arg Arg Ala Glu
                85                  90                  95
Pro Arg Val Thr Val Tyr Pro Ala Lys Thr Gln Pro Leu Gln His His
            100                 105                 110
Asn Leu Leu Val Cys Ser Val Thr Gly Phe Tyr Pro Gly His Val Glu
        115                 120                 125
Val Arg Trp Phe Arg Asn Gly Gln Glu Glu Ala Ala Gly Val Val Ser
    130                 135                 140
Thr Gly Leu Ile Pro Asn Gly Asp Trp Thr Phe Gln Thr Met Val Met
145                 150                 155                 160
Leu Glu Thr Val Pro Gln Ser Gly Glu Val Tyr Thr Cys Arg Val Glu
                165                 170                 175
His Pro Ser Leu Thr Ser Pro Val Thr Val Glu Trp Arg Ala Arg Ser
            180                 185                 190
Glu Ser Ala Gln Gly Lys Met Met Ser Gly Ile Gly Gly Phe Val Leu
        195                 200                 205
Gly Leu Leu Phe Val Ala Val Gly Leu Phe Ile Tyr Phe Lys Asn Gln
    210                 215                 220
Lys Gly Arg Pro Ala Leu Gln Pro Thr Gly Leu Leu Ser
225                 230                 235

<210> SEQ ID NO 207
<211> LENGTH: 237
<212> TYPE: PRT
<213> ORGANISM: swine

<400> SEQUENCE: 207

Arg Asp Thr Pro Pro His Phe Leu Phe Leu Gly Lys Phe Glu Cys His
1               5                   10                  15
Phe Phe Asn Gly Thr Glu Gln Val Arg Leu Leu Glu Arg Gln Tyr Tyr
            20                  25                  30
Asn Gly Glu Glu Phe Val Arg Phe Asp Ser Asp Val Gly Glu Tyr Arg
        35                  40                  45
Ala Val Thr Glu Leu Gly Arg Pro Asp Ala Lys Asn Tyr Asn Ser Gln
```

```
            50                  55                  60
Lys Asp Leu Leu Glu Gln Arg Arg Ala Glu Val Asp Thr Tyr Cys Arg
 65                  70                  75                  80

His Asn Tyr Arg Thr Ser Asp Thr Phe Leu Val Pro Arg Arg Ala Glu
                 85                  90                  95

Pro Arg Val Thr Val Tyr Pro Ala Lys Thr Gln Pro Leu Gln His His
                100                 105                 110

Asn Leu Leu Val Cys Ser Val Thr Gly Phe Tyr Pro Gly His Val Glu
                115                 120                 125

Val Arg Trp Phe Arg Asn Gly Gln Glu Glu Ala Ala Gly Val Val Ser
                130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
                165                 170                 175

His Pro Ser Leu Thr Ser Pro Val Thr Val Glu Trp Arg Ala Arg Ser
                180                 185                 190

Glu Ser Ala Gln Gly Lys Met Met Ser Gly Ile Gly Gly Phe Val Leu
                195                 200                 205

Gly Leu Leu Phe Val Ala Val Gly Leu Phe Ile Tyr Phe Lys Asn Gln
                210                 215                 220

Lys Gly Arg Pro Ala Leu Gln Pro Thr Gly Leu Leu Ser
225                 230                 235
```

<210> SEQ ID NO 208
<211> LENGTH: 237
<212> TYPE: PRT
<213> ORGANISM: swine

<400> SEQUENCE: 208

```
Arg Asp Thr Pro Pro His Phe Leu Tyr Leu Leu Lys Phe Glu Cys His
 1               5                  10                  15

Phe Phe Asn Gly Thr Glu Arg Val Arg Leu Leu Glu Arg Gln Tyr Tyr
                20                  25                  30

Asn Gly Glu Glu Tyr Val Arg Phe Asp Ser Asp Val Gly Glu Tyr Arg
                35                  40                  45

Ala Val Thr Glu Leu Gly Arg Pro Val Ala Lys Asp Trp Asn Ser Gln
 50                  55                  60

Lys Asp Leu Leu Glu Gln Arg Arg Ala Glu Val Asp Thr Tyr Cys Arg
 65                  70                  75                  80

His Asn Tyr Arg Thr Ser Asp Thr Phe Leu Val Pro Arg Arg Ala Glu
                 85                  90                  95

Pro Arg Val Thr Val Tyr Pro Ala Lys Thr Gln Pro Leu Gln His His
                100                 105                 110

Asn Leu Leu Val Cys Ser Val Thr Gly Phe Tyr Pro Gly His Val Glu
                115                 120                 125

Val Arg Trp Phe Arg Asn Gly Gln Glu Glu Ala Ala Gly Val Val Ser
                130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
                165                 170                 175

His Pro Ser Leu Thr Ser Pro Val Thr Val Glu Trp Arg Ala Arg Ser
                180                 185                 190
```

-continued

Glu Ser Ala Gln Gly Lys Met Met Ser Gly Val Gly Phe Val Leu
         195                 200                 205

Gly Leu Leu Phe Val Ala Val Gly Leu Phe Ile Tyr Phe Lys Asn Gln
         210                 215                 220

Lys Gly Arg Pro Ala Leu Gln Pro Thr Gly Leu Leu Ser
225                 230                 235

<210> SEQ ID NO 209
<211> LENGTH: 237
<212> TYPE: PRT
<213> ORGANISM: swine

<400> SEQUENCE: 209

Arg Asp Thr Pro Pro His Phe Leu His Leu Leu Lys Phe Glu Cys His
1               5                   10                  15

Phe Phe Asn Gly Thr Glu Arg Val Arg Leu Leu Glu Arg Gln Tyr Tyr
                20                  25                  30

Asn Gly Glu Glu Phe Leu Arg Phe Asp Ser Asp Val Gly Glu Tyr Arg
            35                  40                  45

Ala Val Thr Glu Leu Gly Arg Pro Asp Ala Lys Asp Trp Asn Ser Gln
        50                  55                  60

Lys Asp Leu Leu Glu Gln Arg Arg Ala Glu Val Asp Thr Tyr Cys Arg
65                  70                  75                  80

His Asn Tyr Arg Ile Leu Asp Thr Phe Leu Val Pro Arg Arg Ala Glu
                85                  90                  95

Pro Thr Val Thr Val Tyr Pro Ala Lys Thr Gln Pro Leu Gln His His
            100                 105                 110

Asn Leu Leu Val Cys Ser Val Thr Gly Phe Tyr Pro Gly His Val Glu
        115                 120                 125

Val Arg Trp Phe Arg Asn Gly Gln Glu Glu Ala Ala Gly Val Val Ser
    130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
                165                 170                 175

His Pro Ser Leu Thr Ser Pro Val Thr Val Glu Trp Arg Ala Arg Ser
            180                 185                 190

Glu Ser Ala Gln Gly Lys Met Met Ser Gly Ile Gly Gly Phe Val Leu
        195                 200                 205

Gly Leu Leu Phe Val Ala Val Gly Leu Phe Ile Tyr Phe Lys Asn Gln
    210                 215                 220

Lys Gly Arg Pro Ala Leu Gln Pro Thr Gly Leu Leu Ser
225                 230                 235

<210> SEQ ID NO 210
<211> LENGTH: 237
<212> TYPE: PRT
<213> ORGANISM: swine

<400> SEQUENCE: 210

Arg Asp Ile Pro Pro His Phe Leu His Gln Leu Lys Phe Glu Cys His
1               5                   10                  15

Phe Phe Asn Gly Thr Glu Arg Val Arg Leu Leu Gln Arg Asn Cys Tyr
                20                  25                  30

Asn Gly Glu Glu Tyr Val Arg Phe Asp Ser Asp Val Gly Glu Tyr Arg
            35                  40                  45

```
Ala Val Thr Glu Leu Gly Arg Pro Asp Ala Lys Tyr Arg Asn Ser Gln
    50                  55                  60

Lys Asp Leu Leu Glu Gln Arg Ala Ala Val Asp Thr Tyr Cys Arg
65                  70                  75                  80

His Asn Tyr Arg Ile Leu Asp Thr Phe Leu Val Pro Arg Arg Ala Glu
                85                  90                  95

Pro Thr Val Thr Val Tyr Pro Ala Lys Thr Gln Pro Leu Gln His His
            100                 105                 110

Asn Leu Leu Val Cys Ser Val Thr Gly Phe Tyr Pro Gly His Val Glu
            115                 120                 125

Val Arg Trp Phe Arg Asn Gly Gln Glu Glu Ala Ala Gly Val Val Ser
        130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
                165                 170                 175

His Pro Ser Leu Thr Ser Pro Val Thr Val Glu Trp Arg Ala Arg Ser
            180                 185                 190

Glu Ser Ala Gln Gly Lys Met Met Ser Gly Val Gly Phe Val Leu
        195                 200                 205

Gly Leu Leu Phe Val Ala Val Gly Leu Phe Ile Tyr Phe Lys Asn Gln
    210                 215                 220

Lys Gly Arg Pro Ala Leu Gln Pro Thr Gly Leu Leu Ser
225                 230                 235

<210> SEQ ID NO 211
<211> LENGTH: 237
<212> TYPE: PRT
<213> ORGANISM: swine

<400> SEQUENCE: 211

Arg Asp Thr Pro Pro His Phe Leu His Leu Val Lys His Glu Cys Arg
1               5                   10                  15

Phe Phe Asn Gly Thr Glu Arg Val Leu Leu Leu Asp Arg Tyr Phe Tyr
            20                  25                  30

Asn Gly Glu Glu Phe Val Arg Phe Asp Ser Asp Val Gly Glu Phe Arg
        35                  40                  45

Ala Val Thr Glu Leu Gly Arg Pro Asp Ala Lys Tyr Trp Asn Ser Gln
    50                  55                  60

Lys Asp Ile Leu Glu Asp Ser Arg Ala Ser Val Asp Thr Tyr Cys Ile
65                  70                  75                  80

His Asn Tyr Arg Ile Leu Asp Thr Phe Leu Val Pro Arg Arg Ala Glu
                85                  90                  95

Pro Thr Val Thr Val Tyr Pro Ala Lys Thr Gln Pro Leu Gln His His
            100                 105                 110

Asn Leu Leu Val Cys Ser Val Thr Gly Phe Tyr Pro Gly His Val Glu
            115                 120                 125

Val Arg Trp Phe Arg Asn Gly Gln Glu Glu Ala Ala Gly Val Val Ser
        130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
                165                 170                 175

His Pro Ser Leu Thr Ser Pro Val Thr Val Glu Trp Arg Ala Arg Ser
            180                 185                 190
```

```
Glu Ser Ala Gln Gly Lys Met Met Ser Gly Ile Gly Gly Phe Val Leu
            195                 200                 205
Gly Leu Leu Phe Val Ala Val Gly Leu Phe Ile Tyr Phe Lys Asn Gln
            210                 215                 220
Lys Gly Arg Pro Ala Leu Gln Pro Thr Gly Leu Leu Ser
225                 230                 235

<210> SEQ ID NO 212
<211> LENGTH: 237
<212> TYPE: PRT
<213> ORGANISM: swine

<400> SEQUENCE: 212

Arg Asp Ile Pro Pro His Phe Phe Met Gly Lys Ser Glu Cys His
1               5                   10                  15

Phe Phe Asn Gly Thr Glu Arg Val Arg Tyr Leu Leu Lys Tyr Leu Tyr
            20                  25                  30

Asn Gly Glu Glu Phe Val Arg Phe Asp Ser Asp Leu Gly Glu Tyr Arg
            35                  40                  45

Glu Val Thr Glu Leu Gly Arg Pro Asp Ala Lys Tyr Trp Asn Ser Gln
50                  55                  60

Lys Asp Leu Leu Glu Gln Arg Arg Glu Lys Val Asp Thr Tyr Cys Arg
65                  70                  75                  80

His Asn Tyr Gly Val Ser Asp Ser Phe Leu Val Pro Arg Arg Ala Glu
            85                  90                  95

Pro Thr Val Thr Val Tyr Pro Ala Lys Thr Gln Pro Leu Gln His His
            100                 105                 110

Asn Leu Leu Val Cys Ser Val Thr Gly Phe Tyr Pro Gly His Val Glu
            115                 120                 125

Val Arg Trp Phe Arg Asn Gly Gln Glu Glu Ala Ala Gly Val Val Ser
            130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
            165                 170                 175

His Pro Ser Leu Thr Ser Pro Val Thr Val Glu Trp Arg Ala Arg Ser
            180                 185                 190

Glu Ser Ala Gln Gly Lys Met Met Ser Gly Val Gly Gly Phe Val Leu
            195                 200                 205

Gly Leu Leu Phe Val Ala Val Gly Leu Phe Ile Tyr Phe Lys Asn Gln
            210                 215                 220

Lys Gly Arg Pro Ala Leu Gln Pro Thr Gly Leu Leu Ser
225                 230                 235

<210> SEQ ID NO 213
<211> LENGTH: 237
<212> TYPE: PRT
<213> ORGANISM: swine

<400> SEQUENCE: 213

Arg Asp Thr Pro Pro His Phe Leu His Leu Leu Lys Phe Glu Cys His
1               5                   10                  15

Phe Phe Asn Gly Thr Glu Arg Val Arg Leu Leu Glu Arg Gln Tyr Tyr
            20                  25                  30

Asn Gly Glu Glu Phe Val Arg Phe Asp Ser Asp Val Gly Glu Tyr Arg
            35                  40                  45
```

-continued

```
Ala Val Thr Glu Leu Gly Arg Pro Asp Ala Lys Tyr Trp Asn Ser Gln
    50                  55                  60

Lys Asp Leu Leu Glu Gln Arg Ala Glu Val Asp Thr Tyr Cys Arg
 65                  70                  75                  80

His Asn Tyr Arg Ile Leu Asp Thr Phe Leu Val Pro Arg Arg Ala Glu
                 85                  90                  95

Pro Thr Val Thr Val Tyr Pro Ala Lys Thr Gln Pro Leu Gln His His
                100                 105                 110

Asn Leu Leu Val Cys Ser Val Thr Gly Phe Tyr Pro Gly His Val Glu
            115                 120                 125

Val Arg Trp Phe Arg Asn Gly Gln Glu Glu Ala Ala Gly Val Val Ser
    130                 135                 140

Thr Gly Leu Ile Pro Asn Gly Asp Trp Thr Phe Gln Thr Met Val Met
145                 150                 155                 160

Leu Glu Thr Val Pro Gln Ser Gly Glu Val Tyr Ser Cys Arg Val Glu
                165                 170                 175

His Pro Ser Leu Thr Ser Pro Val Thr Val Glu Trp Arg Ala Arg Ser
            180                 185                 190

Glu Ser Ala Gln Gly Lys Met Met Ser Gly Ile Gly Gly Phe Val Leu
        195                 200                 205

Gly Leu Leu Phe Val Ala Val Gly Leu Phe Ile Tyr Phe Lys Asn Gln
    210                 215                 220

Lys Gly Arg Pro Ala Leu Gln Pro Thr Gly Leu Leu Ser
225                 230                 235

<210> SEQ ID NO 214
<211> LENGTH: 232
<212> TYPE: PRT
<213> ORGANISM: swine

<400> SEQUENCE: 214

Glu Asp Ile Ala Ala Asp His Val Ala Ser Tyr Gly Leu Asn Val Tyr
 1               5                  10                  15

Gln Ser Tyr Gly Pro Ser Gly Tyr Tyr Thr His Glu Phe Asp Gly Asp
            20                  25                  30

Glu Glu Phe Tyr Val Asp Leu Gly Lys Lys Glu Thr Val Trp Gln Leu
        35                  40                  45

Pro Leu Phe Ser Lys Phe Arg Ser Phe Asp Pro Gln Gly Ala Leu Arg
    50                  55                  60

Asn Ile Ala Thr Ala Lys His Asn Leu Asn Ile Leu Ile Lys Arg Ser
 65                  70                  75                  80

Asn Asn Thr Ala Ala Val Asn Gln Val Pro Glu Val Thr Val Phe Pro
                 85                  90                  95

Lys Ser Pro Val Met Leu Gly Gln Pro Asn Thr Leu Ile Cys His Val
                100                 105                 110

Asp Asn Ile Phe Pro Pro Val Ile Asn Ile Thr Trp Leu Lys Asn Gly
            115                 120                 125

His Ser Val Thr Glu Gly Phe Ser Glu Thr Ser Phe Leu Ser Lys Asn
    130                 135                 140

Asp His Ser Phe Leu Lys Ile Ser Tyr Leu Thr Phe Leu Pro Ser Asp
145                 150                 155                 160

Asp Asp Phe Tyr Asp Cys Lys Val Glu His Trp Gly Leu Asp Lys Pro
                165                 170                 175

Leu Leu Lys His Trp Glu Pro Glu Ile Pro Ala Pro Met Ser Glu Leu
```

```
                    180                 185                 190
Thr Glu Thr Val Val Cys Ala Leu Gly Leu Ile Val Gly Leu Val Gly
        195                 200                 205

Ile Val Val Gly Thr Val Phe Ile Ile Gln Gly Leu Arg Ser Gly Gly
    210                 215                 220

Pro Ser Arg His Gln Gly Ser Leu
225                 230

<210> SEQ ID NO 215
<211> LENGTH: 232
<212> TYPE: PRT
<213> ORGANISM: swine

<400> SEQUENCE: 215

Glu Asp Ile Ala Ala Asp His Val Ala Ser Tyr Gly Leu Asn Val Tyr
1               5                   10                  15

Gln Ser Tyr Gly Pro Ser Gly Tyr Tyr Thr His Glu Phe Asp Gly Asp
            20                  25                  30

Glu Glu Phe Tyr Val Asp Leu Gly Lys Lys Glu Thr Val Trp Gln Leu
        35                  40                  45

Pro Leu Phe Ser Lys Phe Arg Ser Phe Asp Pro Gln Gly Ala Leu Arg
    50                  55                  60

Asn Ile Ala Thr Ala Lys His Asn Leu Asn Ile Leu Ile Lys Arg Ser
65                  70                  75                  80

Asn Asn Thr Ala Ala Val Asn Gln Val Pro Glu Val Thr Val Phe Pro
                85                  90                  95

Lys Ser Pro Val Met Leu Gly Gln Pro Asn Thr Leu Ile Cys His Val
            100                 105                 110

Asp Asn Ile Phe Pro Pro Val Ile Asn Ile Thr Trp Leu Lys Asn Gly
        115                 120                 125

His Ser Val Thr Glu Gly Phe Ser Glu Thr Ser Phe Leu Ser Lys Asn
    130                 135                 140

Asp His Ser Phe Leu Lys Ile Ser Tyr Leu Thr Phe Leu Pro Ser Asp
145                 150                 155                 160

Asp Asp Phe Tyr Asp Cys Lys Val Glu His Trp Gly Leu Asp Lys Pro
                165                 170                 175

Leu Leu Lys His Trp Glu Pro Glu Ile Pro Ala Pro Met Ser Glu Leu
            180                 185                 190

Thr Glu Thr Val Val Cys Ala Leu Gly Leu Ile Val Gly Leu Val Gly
        195                 200                 205

Ile Val Val Gly Thr Val Phe Ile Ile Gln Gly Leu Arg Ser Gly Gly
    210                 215                 220

Pro Ser Arg His Gln Gly Ser Leu
225                 230

<210> SEQ ID NO 216
<211> LENGTH: 232
<212> TYPE: PRT
<213> ORGANISM: swine

<400> SEQUENCE: 216

Glu Asp Ile Ala Ala Asp His Val Ala Ser Tyr Gly Leu Asn Val Tyr
1               5                   10                  15

Gln Ser Tyr Gly Pro Ser Gly Tyr Tyr Thr His Glu Phe Asp Gly Asp
            20                  25                  30

Glu Glu Phe Tyr Val Asp Leu Gly Lys Lys Glu Thr Val Trp Gln Leu
```

```
                35                  40                  45
Pro Leu Phe Ser Lys Phe Arg Ser Phe Asp Pro Gln Gly Ala Leu Arg
     50                  55                  60

Asn Ile Ala Thr Ala Lys His Asn Leu Asn Ile Leu Ile Lys Arg Ser
 65                  70                  75                  80

Asn Asn Thr Ala Ala Val Asn Gln Val Pro Glu Val Thr Val Phe Pro
                 85                  90                  95

Lys Ser Pro Val Met Leu Gly Gln Pro Asn Thr Leu Ile Cys His Val
                100                 105                 110

Asp Asn Ile Phe Pro Pro Val Ile Asn Ile Thr Trp Leu Lys Asn Gly
            115                 120                 125

His Ser Val Thr Glu Gly Phe Ser Glu Thr Ser Phe Leu Ser Lys Asn
        130                 135                 140

Asp His Ser Phe Leu Lys Ile Ser Tyr Leu Thr Phe Leu Pro Ser Asp
145                 150                 155                 160

Asp Asp Phe Tyr Asp Cys Lys Val Glu His Trp Gly Leu Asp Lys Pro
                165                 170                 175

Leu Leu Lys His Trp Glu Pro Glu Ile Pro Ala Pro Met Ser Glu Leu
            180                 185                 190

Thr Glu Thr Val Val Cys Ala Leu Gly Leu Ile Val Gly Leu Val Gly
        195                 200                 205

Ile Val Val Gly Thr Val Phe Ile Ile Gln Gly Leu Arg Ser Gly Gly
    210                 215                 220

Pro Ser Arg His Gln Gly Ser Leu
225                 230

<210> SEQ ID NO 217
<211> LENGTH: 232
<212> TYPE: PRT
<213> ORGANISM: swine

<400> SEQUENCE: 217

Glu Asp Ile Ala Ala Asp His Val Ala Ser Tyr Gly Leu Asn Val Tyr
 1               5                  10                  15

Gln Ser Tyr Gly Pro Ser Gly Tyr Tyr Thr His Glu Phe Asp Gly Asp
                20                  25                  30

Glu Glu Phe Tyr Val Asp Leu Glu Lys Lys Glu Thr Val Trp Gln Leu
            35                  40                  45

Pro Leu Phe Ser Lys Phe Thr Ser Phe Asp Pro Gln Gly Ala Leu Arg
     50                  55                  60

Asn Ile Ala Thr Ala Lys His Asn Leu Asn Ile Leu Ile Lys Arg Ser
 65                  70                  75                  80

Asn Asn Thr Ala Ala Val Asn Gln Val Pro Glu Val Thr Val Phe Pro
                 85                  90                  95

Lys Ser Pro Val Met Leu Gly Gln Pro Asn Thr Leu Ile Cys His Val
                100                 105                 110

Asp Asn Ile Phe Pro Pro Val Ile Asn Ile Thr Trp Leu Lys Asn Gly
            115                 120                 125

His Ser Val Thr Glu Gly Phe Ser Glu Thr Ser Phe Leu Ser Lys Asn
        130                 135                 140

Asp His Ser Phe Leu Lys Ile Ser Tyr Leu Thr Phe Leu Pro Ser Asp
145                 150                 155                 160

Asp Asp Phe Tyr Asp Cys Lys Val Glu His Trp Gly Leu Asp Lys Pro
                165                 170                 175
```

```
Leu Leu Lys His Trp Glu Pro Glu Ile Pro Ala Pro Met Ser Glu Leu
            180                 185                 190

Thr Glu Thr Val Val Cys Ala Leu Gly Leu Ile Val Gly Leu Val Gly
            195                 200                 205

Ile Val Val Gly Thr Val Phe Ile Ile Gln Gly Leu Arg Ser Gly Gly
        210                 215                 220

Pro Ser Arg His Gln Gly Ser Leu
225                 230

<210> SEQ ID NO 218
<211> LENGTH: 231
<212> TYPE: PRT
<213> ORGANISM: swine

<400> SEQUENCE: 218

Glu Asp Ile Ala Ala Asp His Val Ala Ser Tyr Gly Leu Asn Val Tyr
1               5                   10                  15

Gln Ser Tyr Gly Pro Arg Gly Tyr Tyr Thr His Glu Phe Asp Gly Asp
            20                  25                  30

Glu Gln Phe Tyr Val Asp Leu Glu Lys Lys Glu Thr Val Trp Arg Leu
        35                  40                  45

Pro Leu Phe Ser Glu Phe Thr Ser Phe Asp Pro Gln Gly Ala Leu Arg
    50                  55                  60

Asn Ile Ala Thr Leu Lys His Asn Leu Asn Ile Val Thr Lys Arg Ser
65                  70                  75                  80

Asn Asn Thr Ala Ala Val Asn Lys Val Pro Glu Val Thr Val Phe Ser
                85                  90                  95

Lys Ser Pro Val Ile Leu Gly Gln Pro Asn Thr Leu Ile Cys His Val
            100                 105                 110

Asp Ser Ile Phe Pro Pro Val Ile Asn Ile Thr Trp Leu Lys Asn Gly
        115                 120                 125

His Ser Val Lys Gly Phe Ser Glu Thr Ser Phe Leu Ser Lys Asn Asp
    130                 135                 140

His Ser Phe Leu Lys Ile Ser Tyr Leu Thr Phe Leu Pro Ser Asp Asp
145                 150                 155                 160

Asp Phe Tyr Asp Cys Lys Val Glu His Trp Gly Leu Asp Lys Pro Leu
                165                 170                 175

Leu Lys His Trp Glu Pro Glu Ile Pro Ala Pro Met Ser Glu Leu Thr
            180                 185                 190

Glu Thr Val Val Cys Ala Leu Gly Leu Ile Val Gly Leu Val Gly Ile
        195                 200                 205

Val Val Gly Thr Val Phe Ile Ile Gln Gly Leu Arg Ser Gly Gly Pro
    210                 215                 220

Ser Arg His Gln Gly Ser Leu
225                 230

<210> SEQ ID NO 219
<211> LENGTH: 231
<212> TYPE: PRT
<213> ORGANISM: swine

<400> SEQUENCE: 219

Glu Asp Ile Ala Ala Asp His Val Ala Ser Tyr Gly Leu Asn Val Tyr
1               5                   10                  15

Gln Ser Tyr Gly Pro Arg Gly Tyr Phe Thr His Glu Phe Asp Gly Asp
            20                  25                  30
```

```
Glu Gln Phe Tyr Val Asp Leu Glu Lys Lys Glu Thr Val Trp Arg Leu
            35                  40                  45

Pro Leu Phe Ser Glu Phe Thr Ser Phe Asp Pro Gln Gly Ala Leu Arg
 50                  55                  60

Asn Ile Ala Thr Leu Lys His Asn Leu Asn Ile Val Thr Lys Arg Ser
65                   70                  75                  80

Asn Asn Thr Ala Ala Val Asn Lys Val Pro Glu Val Thr Val Phe Ser
                85                  90                  95

Lys Ser Pro Val Ile Leu Gly Gln Pro Asn Thr Leu Ile Cys His Val
            100                 105                 110

Asp Ser Ile Phe Pro Pro Val Ile Asn Ile Thr Trp Leu Lys Asn Gly
            115                 120                 125

His Ser Val Lys Gly Phe Ser Glu Thr Ser Phe Leu Ser Lys Asn Asp
            130                 135                 140

His Ser Phe Leu Lys Ile Ser Tyr Leu Thr Phe Leu Pro Ser Asp Asp
145                 150                 155                 160

Asp Phe Tyr Asp Cys Lys Val Glu His Trp Gly Leu Asp Lys Pro Leu
                165                 170                 175

Leu Lys His Trp Glu Pro Glu Ile Pro Ala Pro Met Ser Glu Leu Thr
            180                 185                 190

Glu Thr Val Val Cys Ala Leu Gly Leu Ile Val Gly Leu Val Gly Ile
            195                 200                 205

Val Val Gly Thr Val Phe Ile Ile Gln Gly Leu Arg Ser Gly Gly Pro
            210                 215                 220

Ser Arg His Gln Gly Ser Leu
225                 230

<210> SEQ ID NO 220
<211> LENGTH: 231
<212> TYPE: PRT
<213> ORGANISM: swine

<400> SEQUENCE: 220

Glu Asp Ile Ala Ala Asp His Val Ala Ser Tyr Gly Leu Asn Val Tyr
1               5                   10                  15

Gln Ser Tyr Gly Pro Ser Gly Tyr Phe Thr His Glu Phe Asp Gly Asp
            20                  25                  30

Glu Glu Phe Tyr Val Asp Leu Glu Lys Lys Glu Thr Val Trp Arg Leu
            35                  40                  45

Pro Leu Phe Ser Glu Phe Thr Ser Phe Asp Pro Gln Gly Ala Leu Arg
 50                  55                  60

Asn Ile Ala Thr Leu Lys His Asn Leu Asn Ile Val Thr Lys Arg Ser
65                   70                  75                  80

Asn Asn Thr Ala Ala Val Asn Gln Val Pro Glu Val Thr Val Phe Ser
                85                  90                  95

Lys Ser Pro Val Ile Leu Gly Gln Pro Asn Thr Leu Ile Cys His Val
            100                 105                 110

Asp Ser Ile Phe Pro Pro Val Ile Asn Ile Thr Trp Leu Lys Asn Gly
            115                 120                 125

His Ser Val Lys Gly Phe Ser Glu Thr Ser Phe Leu Ser Lys Asn Asp
            130                 135                 140

His Ser Phe Leu Lys Ile Ser Tyr Leu Thr Phe Leu Pro Ser Asp Asp
145                 150                 155                 160

Asp Phe Tyr Asp Cys Lys Val Glu His Trp Gly Leu Asp Lys Pro Leu
                165                 170                 175
```

-continued

```
Leu Lys His Trp Glu Pro Glu Ile Pro Ala Pro Met Ser Glu Leu Thr
            180                 185                 190
Glu Thr Val Val Cys Ala Leu Gly Leu Ile Val Gly Leu Val Gly Ile
        195                 200                 205
Val Val Gly Thr Val Phe Ile Ile Gln Gly Leu Leu Ser Gly Gly Pro
    210                 215                 220
Ser Arg His Gln Gly Ser Leu
225                 230

<210> SEQ ID NO 221
<211> LENGTH: 230
<212> TYPE: PRT
<213> ORGANISM: swine

<400> SEQUENCE: 221

Gly Arg Asp Ser Pro Gln Asp Phe Val Val Gln Phe Lys Gly Glu Cys
1               5                   10                  15
Tyr Phe Tyr Asn Gly Thr Gln Arg Val Trp Ser Val Asp Arg Tyr Ile
            20                  25                  30
Tyr Asn Gln Glu Glu Phe Leu Arg Phe Asp Ser Asp Met Gly Glu Tyr
        35                  40                  45
Arg Ala Val Thr Pro Leu Gly Arg Pro Asp Ala Asp Tyr Leu Asn Gly
    50                  55                  60
Gln Lys Glu Ala Leu Glu Gln Lys Arg Ala Glu Leu Asp Thr Val Cys
65                  70                  75                  80
Lys His Asn Tyr Gln Ile Glu Gly Thr Thr Leu Gln Arg Arg Val
                85                  90                  95
Gln Pro Thr Val Thr Ile Ser Pro Ser Lys Ala Glu Ala Leu Asn His
            100                 105                 110
His Asn Leu Leu Val Cys Ala Val Thr Asp Phe Tyr Pro Ser Gln Val
        115                 120                 125
Lys Val Gln Trp Phe Arg Asn Gly Gln Glu Glu Thr Ala Gly Val Val
    130                 135                 140
Ser Thr Pro Leu Ile Arg Asn Gly Asp Trp Thr Tyr Gln Val Leu Val
145                 150                 155                 160
Met Leu Glu Met Asn Leu Gln Arg Gly Asp Val Tyr Thr Cys Arg Val
                165                 170                 175
Glu His Ser Ser Leu Gln Ser Pro Ile Leu Val Glu Trp Arg Ala Gln
            180                 185                 190
Ser Glu Ser Ala Gln Ser Lys Met Leu Ser Gly Val Gly Gly Phe Val
        195                 200                 205
Leu Gly Leu Ile Phe Leu Gly Leu Gly Leu Phe Ile Arg His Arg Ser
    210                 215                 220
Gln Lys Gly Leu Val Arg
225                 230

<210> SEQ ID NO 222
<211> LENGTH: 230
<212> TYPE: PRT
<213> ORGANISM: swine

<400> SEQUENCE: 222

Gly Arg Asp Ser Pro Gln Asp Phe Val Phe Gln Phe Lys Gly Glu Cys
1               5                   10                  15
Tyr Phe Tyr Asn Gly Thr Gln Arg Val Trp Ser Val Asp Arg Tyr Ile
            20                  25                  30
```

-continued

Tyr Asn Gln Glu Glu Phe Leu Arg Phe Asp Ser Asp Met Gly Glu Tyr
            35                  40                  45

Arg Ala Val Thr Pro Leu Gly Arg Pro Asp Ala Asp Tyr Leu Asn Gly
 50                  55                  60

Gln Lys Glu Ala Leu Glu Gln Lys Arg Ala Glu Leu Asp Thr Val Cys
 65                  70                  75                  80

Lys His Asn Tyr Gln Ile Glu Glu Gly Thr Thr Leu Gln Arg Arg Val
                85                  90                  95

Gln Pro Thr Val Thr Ile Ser Pro Ser Lys Ala Glu Ala Leu Asn His
            100                 105                 110

His Asn Leu Leu Val Cys Ala Val Thr Asp Phe Tyr Pro Ser Gln Val
            115                 120                 125

Lys Val Gln Trp Phe Arg Asn Gly Gln Glu Glu Thr Ala Gly Val Val
            130                 135                 140

Ser Thr Pro Leu Ile Arg Asn Gly Asp Trp Thr Tyr Gln Val Leu Val
145                 150                 155                 160

Met Leu Glu Met Asn Leu Gln Arg Gly Asp Val Tyr Thr Cys Arg Val
                165                 170                 175

Glu His Ser Ser Leu Gln Ser Pro Ile Leu Val Glu Trp Arg Ala Gln
            180                 185                 190

Ser Glu Ser Ala Gln Ser Lys Met Leu Ser Gly Val Gly Gly Phe Val
            195                 200                 205

Leu Gly Leu Ile Phe Leu Gly Leu Gly Leu Phe Ile Arg His Arg Ser
            210                 215                 220

Gln Lys Gly Leu Val Arg
225                 230

<210> SEQ ID NO 223
<211> LENGTH: 230
<212> TYPE: PRT
<213> ORGANISM: swine

<400> SEQUENCE: 223

Gly Arg Asp Ser Pro Gln Asp Phe Val Tyr Gln Phe Lys Phe Glu Cys
1               5                   10                  15

Tyr Phe Phe Asn Gly Thr Gln Arg Val Arg Gly Val Ala Arg Trp Val
                20                  25                  30

Tyr Asn Gln Glu Glu His Val Arg Phe Asp Ser Asp Val Gly Glu Phe
            35                  40                  45

Arg Ala Val Thr Pro Leu Gly Arg Pro Thr Ala Asp Tyr Trp Asn Gly
 50                  55                  60

Gln Lys Asp Val Leu Glu Gln Lys Arg Ala Glu Val Asp Thr Val Cys
 65                  70                  75                  80

Lys His Asn Tyr Gln Ile Glu Glu Gly Thr Thr Leu Gln Arg Arg Val
                85                  90                  95

Gln Pro Thr Val Thr Ile Ser Pro Ser Lys Ala Glu Ala Leu Asn His
            100                 105                 110

His Asn Leu Leu Val Cys Ala Val Thr Asp Phe Tyr Pro Ser Gln Val
            115                 120                 125

Lys Val Gln Trp Phe Arg Asn Gly Gln Glu Glu Thr Ala Gly Val Val
            130                 135                 140

Ser Thr Pro Leu Ile Arg Asn Gly Asp Trp Thr Tyr Gln Val Leu Val
145                 150                 155                 160

Met Leu Glu Met Asn Leu Gln Arg Gly Asp Val Tyr Thr Cys Arg Val 165                 170                 175

Glu His Ser Ser Leu Gln Asn Pro Ile Leu Val Glu Trp Arg Ala Gln
            180                 185                 190

Ser Glu Ser Ala Gln Ser Lys Met Leu Ser Gly Val Gly Gly Phe Val
        195                 200                 205

Leu Gly Leu Ile Phe Leu Gly Leu Gly Leu Phe Ile Arg His Arg Ser
    210                 215                 220

Gln Lys Gly Leu Val Arg
225                 230

<210> SEQ ID NO 224
<211> LENGTH: 230
<212> TYPE: PRT
<213> ORGANISM: swine

<400> SEQUENCE: 224

Gly Arg Asp Ser Pro Gln Asp Phe Val Tyr Gln Phe Lys Phe Glu Cys
1               5                   10                  15

Tyr Phe Tyr Asn Gly Thr Gln Arg Val Arg Leu Val Ala Arg Trp Val
            20                  25                  30

Tyr Asn Arg Glu Glu His Val Arg Phe Asp Ser Asp Val Gly Glu Phe
        35                  40                  45

Arg Ala Val Thr Pro Leu Gly Arg Pro Asp Ala Asp Tyr Trp Asn Gly
    50                  55                  60

Gln Lys Glu Val Leu Glu Gln Lys Arg Ala Glu Leu Asp Thr Val Cys
65                  70                  75                  80

Lys His Asn Tyr Gln Ile Glu Glu Gly Thr Thr Leu Gln Arg Arg Val
                85                  90                  95

Gln Pro Thr Val Thr Ile Ser Pro Ser Lys Ala Glu Ala Leu Asn His
            100                 105                 110

His Asn Leu Leu Val Cys Ala Val Thr Asp Phe Tyr Pro Ser Gln Val
        115                 120                 125

Lys Val Gln Trp Phe Arg Asn Gly Gln Glu Glu Thr Ala Gly Val Val
    130                 135                 140

Ser Thr Pro Leu Ile Arg Asn Gly Asp Trp Thr Tyr Gln Val Leu Val
145                 150                 155                 160

Met Leu Glu Met Asn Leu Gln Arg Gly Asp Val Tyr Thr Cys Arg Val
                165                 170                 175

Glu His Ser Ser Leu Gln Ser Pro Ile Leu Val Glu Trp Arg Ala Gln
            180                 185                 190

Ser Glu Ser Ala Gln Ser Lys Met Leu Ser Gly Val Gly Gly Phe Val
        195                 200                 205

Leu Gly Leu Ile Phe Leu Gly Leu Gly Leu Phe Ile Arg His Arg Ser
    210                 215                 220

Gln Lys Gly Leu Val Arg
225                 230

<210> SEQ ID NO 225
<211> LENGTH: 230
<212> TYPE: PRT
<213> ORGANISM: swine

<400> SEQUENCE: 225

Gly Arg Asp Ser Pro Gln Asp Phe Val Tyr Gln Phe Lys Phe Glu Cys
1               5                   10                  15

Tyr Phe Phe Asn Gly Thr Gln Arg Val Arg Leu Val Thr Arg Tyr Ile

-continued

```
                20                  25                  30
Tyr Asn Gln Glu Glu Tyr Ala Arg Phe Asp Ser Asp Val Gly Glu Tyr
            35                  40                  45
Arg Ala Val Thr Pro Leu Gly Arg Pro Ala Ala Asp Tyr Trp Asn Ser
 50                  55                  60
Gln Lys Asp Ile Leu Glu Gln Thr Arg Ala Glu Leu Asp Thr Val Cys
 65                  70                  75                  80
Lys His Asn Tyr Gln Ile Glu Glu Gly Thr Thr Leu Gln Arg Arg Val
                85                  90                  95
Gln Pro Thr Val Thr Ile Ser Pro Ser Lys Ala Glu Ala Leu Asn His
                100                 105                 110
His Asn Leu Leu Val Cys Ala Val Thr Asp Phe Tyr Pro Ser Gln Val
                115                 120                 125
Lys Val Gln Trp Phe Arg Asn Gly Gln Glu Glu Thr Ala Gly Val Val
            130                 135                 140
Ser Thr Pro Leu Ile Arg Asn Gly Asp Trp Thr Tyr Gln Val Leu Val
145                 150                 155                 160
Met Leu Glu Met Asn Leu Gln Arg Gly Asp Val Tyr Thr Cys Arg Val
                165                 170                 175
Glu His Ser Ser Leu Gln Ser Pro Ile Leu Val Glu Trp Arg Ala Gln
            180                 185                 190
Ser Glu Ser Ala Gln Ser Lys Met Leu Ser Gly Val Gly Gly Phe Val
            195                 200                 205
Leu Gly Leu Ile Phe Leu Gly Leu Gly Leu Phe Ile Arg His Arg Ser
    210                 215                 220
Gln Lys Gly Leu Val Arg
225                 230

<210> SEQ ID NO 226
<211> LENGTH: 230
<212> TYPE: PRT
<213> ORGANISM: swine

<400> SEQUENCE: 226

Gly Arg Asp Ser Pro Gln Asp Phe Val Tyr Gln Phe Lys Phe Glu Cys
 1               5                  10                  15
Tyr Phe Phe Asn Gly Thr Gln Arg Val Arg Leu Leu Thr Arg Tyr Ile
            20                  25                  30
Tyr Asn Gln Glu Glu His Val Arg Phe Asp Ser Asn Val Gly Glu Tyr
            35                  40                  45
Arg Ala Val Thr Pro Leu Gly Arg Pro Asp Ala Asp Tyr Trp Asn Gly
 50                  55                  60
Gln Lys Asp Val Leu Glu Gln Thr Arg Ala Glu Leu Asp Thr Val Cys
 65                  70                  75                  80
Lys His Asn Tyr Gln Ile Glu Glu Gly Thr Thr Leu Gln Arg Arg Val
                85                  90                  95
Gln Pro Thr Val Thr Ile Ser Pro Ser Lys Ala Glu Ala Leu Asn His
                100                 105                 110
His Asn Leu Leu Val Cys Ala Val Thr Asp Phe Tyr Pro Ser Gln Val
                115                 120                 125
Lys Val Gln Trp Phe Arg Asn Gly Gln Glu Glu Thr Ala Gly Val Val
            130                 135                 140
Ser Thr Pro Leu Ile Arg Asn Gly Asp Trp Thr Tyr Gln Val Leu Val
145                 150                 155                 160
```

```
Met Leu Glu Met Asn Leu Gln Arg Gly Asp Val Tyr Thr Cys Arg Val
                165                 170                 175

Glu His Ser Ser Leu Gln Ser Pro Ile Leu Val Glu Trp Arg Ala Gln
            180                 185                 190

Ser Glu Ser Ala Gln Ser Lys Met Leu Ser Gly Val Gly Gly Phe Val
        195                 200                 205

Leu Gly Leu Ile Phe Leu Gly Leu Gly Leu Phe Ile Arg His Arg Ser
    210                 215                 220

Gln Lys Gly Leu Val Arg
225             230

<210> SEQ ID NO 227
<211> LENGTH: 230
<212> TYPE: PRT
<213> ORGANISM: swine

<400> SEQUENCE: 227

Gly Arg Asp Ser Pro Gln Asp Phe Val Tyr Gln Phe Lys Gly Glu Cys
1               5                   10                  15

Tyr Phe Phe Asn Gly Thr Gln Arg Val Arg His Val Thr Arg Tyr Ile
            20                  25                  30

Tyr Asn Gln Glu Glu His Val Arg Phe Asp Ser Asp Val Gly Glu Phe
        35                  40                  45

Arg Ala Val Thr Pro Leu Gly Arg Pro Asp Ala Asp Tyr Trp Asn Gly
    50                  55                  60

Gln Lys Asp Phe Leu Glu Gln Thr Arg Ala Glu Leu Asp Thr Val Cys
65                  70                  75                  80

Lys His Asn Tyr Gln Ile Glu Glu Gly Thr Thr Leu Gln Arg Arg Val
                85                  90                  95

Gln Pro Thr Val Thr Ile Ser Pro Ser Lys Ala Glu Ala Leu Asn His
            100                 105                 110

His Asn Leu Leu Val Cys Ala Val Thr Asp Phe Tyr Pro Ser Gln Val
        115                 120                 125

Lys Val Gln Trp Phe Arg Asn Gly Gln Glu Glu Thr Ala Gly Val Val
    130                 135                 140

Ser Thr Pro Leu Ile Arg Asn Gly Asp Trp Thr Tyr Gln Val Leu Val
145                 150                 155                 160

Met Leu Glu Met Asn Leu Gln Arg Gly Asp Val Tyr Thr Cys Arg Val
                165                 170                 175

Glu His Ser Ser Leu Gln Ser Pro Ile Leu Val Glu Trp Arg Ala Gln
            180                 185                 190

Ser Glu Ser Ala Gln Ser Lys Met Leu Ser Gly Val Gly Gly Phe Val
        195                 200                 205

Leu Gly Leu Ile Phe Leu Gly Leu Gly Leu Phe Ile Arg His Arg Ser
    210                 215                 220

Gln Lys Gly Leu Val Arg
225             230

<210> SEQ ID NO 228
<211> LENGTH: 230
<212> TYPE: PRT
<213> ORGANISM: swine

<400> SEQUENCE: 228

Gly Arg Asp Ser Pro Gln Asp Phe Val Phe Gln Phe Lys Gly Glu Cys
1               5                   10                  15
```

```
Tyr Phe Tyr Asn Gly Thr Gln Arg Val Arg Gly Val Ala Arg Tyr Ile
             20                  25                  30

Tyr Asn Gln Glu Glu His Leu Arg Phe Asp Ser Asp Val Gly Glu Phe
             35                  40                  45

Arg Ala Val Thr Pro Leu Gly Arg Pro Glu Ala Asp Ser Trp Asn Ser
 50                  55                  60

Gln Lys Asp Val Leu Glu Gln Met Arg Ala Glu Val Asp Arg Val Cys
 65                  70                  75                  80

Lys His Asn Tyr Gln Ile Glu Glu Gly Thr Thr Leu Gln Arg Arg Val
                 85                  90                  95

Gln Pro Thr Val Thr Ile Ser Pro Ser Lys Ala Glu Ala Leu Asn His
                100                 105                 110

His Asn Leu Leu Val Cys Ala Val Thr Asp Phe Tyr Pro Ser Gln Val
             115                 120                 125

Lys Val Gln Trp Phe Arg Asn Gly Gln Glu Glu Thr Ala Gly Val Val
         130                 135                 140

Ser Thr Pro Leu Ile Arg Asn Gly Asp Trp Thr Tyr Gln Val Leu Val
145                 150                 155                 160

Met Leu Glu Met Asn Leu Gln Arg Gly Asp Val Tyr Thr Cys Arg Val
                165                 170                 175

Glu His Ser Ser Leu Gln Asn Pro Ile Leu Val Glu Trp Arg Ala Gln
             180                 185                 190

Ser Glu Ser Ala Gln Ser Lys Met Leu Ser Gly Val Gly Gly Phe Val
         195                 200                 205

Leu Gly Leu Ile Phe Leu Gly Leu Gly Leu Phe Ile Arg His Arg Ser
210                 215                 220

Gln Lys Gly Leu Val Arg
225                 230

<210> SEQ ID NO 229
<211> LENGTH: 229
<212> TYPE: PRT
<213> ORGANISM: swine

<400> SEQUENCE: 229

Gly Arg Asp Ser Pro Gln Asp Phe Val Tyr Gln Phe Lys Phe Glu Cys
1               5                  10                  15

Tyr Phe Phe Asn Gly Thr Gln Arg Val Arg Val Ala Arg Tyr Ile Tyr
             20                  25                  30

Asn Gln Glu Glu His Val Arg Phe Asp Ser Asp Val Gly Glu Phe Arg
             35                  40                  45

Ala Val Thr Pro Leu Gly Arg Pro Asp Ala Asp Tyr Trp Asn Gly Gln
 50                  55                  60

Lys Asp Val Leu Glu Gln Lys Arg Ala Glu Leu Asp Thr Val Cys Lys
 65                  70                  75                  80

His Asn Tyr Gln Ile Glu Glu Gly Thr Thr Leu Gln Arg Arg Val Gln
                 85                  90                  95

Pro Thr Val Thr Ile Ser Pro Ser Lys Ala Glu Ala Leu Asn His His
                100                 105                 110

Asn Leu Leu Val Cys Ala Val Thr Asp Phe Tyr Pro Ser Gln Val Lys
             115                 120                 125

Val Gln Trp Phe Arg Asn Gly Gln Glu Glu Thr Ala Gly Val Val Ser
         130                 135                 140

Thr Pro Leu Ile Arg Asn Gly Asp Trp Thr Tyr Gln Val Leu Val Met
145                 150                 155                 160
```

-continued

```
Leu Glu Met Asn Leu Gln Arg Gly Asp Val Tyr Thr Cys Arg Val Glu
            165                 170                 175

His Ser Ser Leu Gln Ser Pro Ile Leu Val Glu Trp Arg Ala Gln Ser
            180                 185                 190

Glu Ser Ala Gln Ser Lys Met Leu Ser Gly Val Gly Gly Phe Val Leu
            195                 200                 205

Gly Leu Ile Phe Leu Gly Leu Gly Leu Phe Ile Arg His Arg Ser Gln
    210                 215                 220

Lys Gly Leu Val Arg
225
```